US012509455B2

(12) United States Patent
Gray et al.

(10) Patent No.: US 12,509,455 B2
(45) Date of Patent: Dec. 30, 2025

(54) IMIDAZOPYRIDINE DERIVATIVES AND AZA-IMIDAZOPYRIDINE DERIVATIVES AS JANUS KINASE 2 INHIBITORS AND USES THEREOF

(71) Applicant: Dana-Farber Cancer Institute, Inc., Boston, MA (US)

(72) Inventors: Nathanael S. Gray, Boston, MA (US); Tinghu Zhang, Brookline, MA (US); Yao Liu, Brookline, MA (US); Zhixiang He, Brookline, MA (US); Mingfeng Hao, Hefei (CN); David Weinstock, Jamaica Plain, MA (US); Loretta Sze-Mun Li, Chicago, IL (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 1086 days.

(21) Appl. No.: 17/291,927

(22) PCT Filed: Nov. 7, 2019

(86) PCT No.: PCT/US2019/060363
§ 371 (c)(1),
(2) Date: May 6, 2021

(87) PCT Pub. No.: WO2020/097400
PCT Pub. Date: May 14, 2020

(65) Prior Publication Data

US 2022/0127260 A1 Apr. 28, 2022
US 2023/0151001 A9 May 18, 2023
US 2023/0391768 A2 Dec. 7, 2023

Related U.S. Application Data

(60) Provisional application No. 62/757,124, filed on Nov. 7, 2018.

(51) Int. Cl.
*C07D 471/04* (2006.01)
*A61K 45/06* (2006.01)
*C07D 487/04* (2006.01)

(52) U.S. Cl.
CPC ............ *C07D 471/04* (2013.01); *A61K 45/06* (2013.01); *C07D 487/04* (2013.01)

(58) Field of Classification Search
CPC ..... C07D 471/04; A61K 45/06; A07D 487/04
See application file for complete search history.

(56) References Cited

U.S. PATENT DOCUMENTS 5,270,148 A 12/1993 Morigaki et al.
5,512,590 A 4/1996 George et al.
5,616,537 A 4/1997 Yokota et al.
5,702,877 A 12/1997 Odenwalder et al.
5,814,633 A 9/1998 Muller et al.
5,852,046 A 12/1998 Lang et al.
5,994,629 A 11/1999 Bojsen et al.
6,329,383 B1 12/2001 Hedgecock et al.
6,346,531 B1 2/2002 Luengo et al.
(Continued)

FOREIGN PATENT DOCUMENTS

CN 1148043 A 4/1997
CN 101239980 A 8/2008
(Continued)

OTHER PUBLICATIONS

Smith et al, "Imidazo[1,2-a]pyridin-6-yl-benzamide analogs as potent RAF inhibitors," Bioorganic & Medicinal Chemistry Letters, vol. 27, Issue 23, 2017, pp. 5221-5224. (Year: 2017).*
(Continued)

*Primary Examiner* — Marcos L Sznaidman
(74) *Attorney, Agent, or Firm* — Nielsen IP Law LLC

(57) ABSTRACT

The present disclosure provides compounds of Formula (I') (e.g., compounds of Formula (I)), and pharmaceutically acceptable salts, solvates, hydrates, polymorphs, cocrystals, tautomers, stereoisomers, isotopically labeled derivatives, and prodrugs thereof. The provided compounds may be kinase (e.g., Janus kinase (JAK), e.g., Janus kinase 2 (JAK2)) inhibitors. Also provided are pharmaceutical compositions and kits including the provided compounds. Further provided are methods of using the provided compounds, pharmaceutical compositions, and kits (e.g., for treating a disease (e.g., proliferative disease) in a subject in need thereof).

(I')

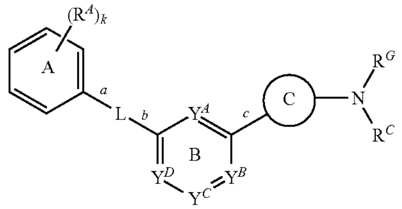

(I)

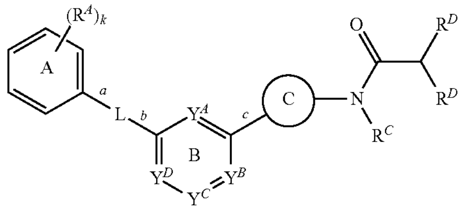

18 Claims, 4 Drawing Sheets

(56) References Cited

U.S. PATENT DOCUMENTS 6,444,816 B1 9/2002 Das et al.
6,552,192 B1 4/2003 Hanus et al.
6,566,372 B1 5/2003 Zhi et al.
6,630,470 B1 10/2003 Luengo et al.
6,743,800 B1 6/2004 Peyman et al.
6,747,016 B1 6/2004 Peyman et al.
7,256,196 B1 8/2007 Sabat et al.
7,531,553 B2 5/2009 Di Pietro et al.
8,114,874 B2 2/2012 Zou et al.
8,293,923 B2 10/2012 Guckian et al.
8,614,330 B2 12/2013 Amiri et al.
8,765,747 B2 7/2014 Choi et al.
8,846,697 B2 9/2014 Carson et al.
9,145,438 B2 9/2015 Chesworth et al.
9,200,020 B2 12/2015 De Jersey et al.
9,284,299 B2 3/2016 Ji et al.
9,505,784 B2 11/2016 Choi et al.
10,017,477 B2 7/2018 Gray et al.
10,766,888 B1 9/2020 Biddle et al.
2001/0056090 A1 12/2001 Aquila et al.
2002/0010159 A1 1/2002 Weigele et al.
2002/0052368 A1 5/2002 Marlowe et al.
2002/0058677 A1 5/2002 Marlowe et al.
2002/0068721 A1 6/2002 Weigele et al.
2002/0094994 A1 7/2002 Bourzat et al.
2002/0120144 A1 8/2002 Akama et al.
2002/0165261 A1 11/2002 Borisy et al.
2002/0173506 A1 11/2002 Clark et al.
2003/0109714 A1 6/2003 Wishart et al.
2003/0187261 A1 10/2003 Havlicek et al.
2003/0199564 A1 10/2003 Fenton et al.
2004/0006117 A1 1/2004 Blume et al.
2004/0034224 A1 2/2004 Hammarstrom et al.
2004/0077633 A1 4/2004 Watson et al.
2004/0082583 A1 4/2004 Cheung et al.
2004/0122237 A1 6/2004 Amiri et al.
2004/0171630 A1 9/2004 Kim et al.
2004/0198725 A1 10/2004 Sun et al.
2005/0049263 A1 3/2005 Kasibhatla et al.
2005/0101647 A1 5/2005 Oda et al.
2005/0137234 A1 6/2005 Bressi et al.
2005/0192287 A1 9/2005 Costales et al.
2005/0209176 A1 9/2005 Meutermans et al.
2005/0239821 A1 10/2005 Neyts et al.
2005/0272765 A1 12/2005 Feng et al.
2005/0282802 A1 12/2005 Kostik et al.
2006/0042026 A1 3/2006 Glenn et al.
2006/0052331 A1 3/2006 Koch et al.
2006/0111362 A1 5/2006 Kira et al.
2006/0116383 A1 6/2006 Bloxham et al.
2006/0148830 A1 7/2006 Terakado et al.
2006/0154977 A1 7/2006 Morand et al.
2006/0160872 A1 7/2006 Norman et al.
2007/0032493 A1 2/2007 Foley et al.
2007/0043043 A1 2/2007 Chen et al.
2007/0049622 A1 3/2007 Dimitroff et al.
2007/0093544 A1 4/2007 Parmee et al.
2007/0105930 A1 5/2007 Parmee et al.
2007/0112048 A1 5/2007 Bavari et al.
2007/0173527 A1 7/2007 Bressi et al.
2007/0197450 A1 8/2007 Fushimi et al.
2007/0219235 A1 9/2007 Mjalli et al.
2007/0249637 A1 10/2007 Collins et al.
2007/0275984 A1 11/2007 Imogai et al.
2008/0008682 A1 1/2008 Chong et al.
2008/0009488 A1 1/2008 Anand et al.
2008/0032936 A1 2/2008 Gai et al.
2008/0058297 A1 3/2008 Ono et al.
2008/0096903 A1 4/2008 Chen et al.
2008/0132501 A1 6/2008 Sun et al.
2008/0161254 A1 7/2008 Green et al.
2008/0194803 A1 8/2008 Sinclair et al.
2008/0221148 A1 9/2008 Ibrahim et al.
2008/0284322 A1 11/2008 Hosokawa et al.
2009/0047249 A1 2/2009 Graupe et al.
2009/0118200 A1 5/2009 Bergman et al.
2009/0140637 A1 6/2009 Hosokawa et al.
2009/0176778 A1 7/2009 Schmitz et al.
2009/0232844 A1 9/2009 Sutton et al.
2009/0233946 A1 9/2009 Krasinski et al.
2009/0278115 A1 11/2009 Hosokawa et al.
2010/0010217 A1 1/2010 Valiante et al.
2010/0029709 A1 2/2010 Menet et al.
2010/0093747 A1 4/2010 Goodhew
2010/0197688 A1 8/2010 Nantermet et al.
2010/0204265 A1 8/2010 Baskaran et al.
2010/0210598 A1 8/2010 Carson et al.
2010/0216810 A1 8/2010 Okaniwa et al.
2010/0249119 A1 9/2010 Hirose et al.
2010/0256188 A1 10/2010 Pfau et al.
2010/0261679 A1 10/2010 Sutton et al.
2010/0267714 A1 10/2010 Jorgensen et al.
2011/0021518 A1 1/2011 Magnuson et al.
2011/0039895 A1 2/2011 Chai et al.
2011/0059962 A1 3/2011 Alekshun et al.
2011/0098280 A1 4/2011 Garcia-Echeverria et al.
2011/0105498 A1 5/2011 Pettus et al.
2011/0117073 A1 5/2011 Singh et al.
2011/0172186 A1 7/2011 Behnke et al.
2011/0237620 A1 9/2011 Okaniwa et al.
2011/0263598 A1 10/2011 Sampson et al.
2011/0281865 A1 11/2011 Muthuppalaniappan et al.
2011/0312935 A1 12/2011 Pfau et al.
2012/0028969 A1 2/2012 Barnes et al.
2012/0115902 A1 5/2012 Pfau et al.
2012/0122930 A1 5/2012 Pfau et al.
2012/0172351 A1 7/2012 Negoro et al.
2012/0202287 A1 8/2012 Adams et al.
2012/0208839 A1 8/2012 Priepke et al.
2012/0214786 A1 8/2012 Priepke et al.
2012/0258967 A1 10/2012 Qiao et al.
2012/0329771 A1 12/2012 Treu et al.
2013/0059851 A1 3/2013 Garraway et al.
2013/0079342 A1 3/2013 Dransfield et al.
2013/0084346 A1 4/2013 Wolkenberg et al.
2013/0090327 A1 4/2013 Hata et al.
2013/0096136 A1 4/2013 Hata et al.
2013/0136782 A1 5/2013 Blackwell et al.
2013/0149717 A1 6/2013 Krause et al.
2013/0165446 A1 6/2013 Fujita et al.
2013/0184240 A1 7/2013 Tonogaki et al.
2013/0184248 A1 7/2013 Grauert et al.
2013/0190320 A1 7/2013 Xu et al.
2013/0224195 A1 8/2013 Costales et al.
2013/0225596 A1 8/2013 Kai et al.
2013/0261125 A1 10/2013 Shipps, Jr. et al.
2013/0310333 A1 11/2013 Chesworth et al.
2013/0345261 A1 12/2013 Waters et al.
2014/0011763 A1 1/2014 Lakshman
2014/0031339 A1 1/2014 Abeywardane et al.
2014/0155379 A1 6/2014 Ho et al.
2014/0194420 A1 7/2014 Kojima et al.
2014/0303102 A1 10/2014 Choe et al.
2014/0303360 A1 10/2014 Schroeder et al.
2014/0364386 A1 12/2014 Choe et al.
2015/0018291 A1 1/2015 Choe et al.
2015/0057309 A1 2/2015 Vakkalanka et al.
2015/0126436 A1 5/2015 Phillips et al.
2015/0133500 A1 5/2015 Tafesse et al.
2015/0152065 A1 6/2015 Brookings et al.
2015/0197497 A1 7/2015 Abeywickrama et al.
2015/0216168 A1 8/2015 Frackenpohl et al.
2015/0243903 A1 8/2015 Zeng et al.
2015/0249221 A1 9/2015 Zeng et al.
2016/0024072 A1 1/2016 Kai et al.
2016/0052922 A1 2/2016 Chesworth et al.
2016/0096804 A1 4/2016 Shuttleworth et al.
2016/0168165 A1 6/2016 Koehler et al.
2016/0176825 A1 6/2016 Gray et al.
2016/0229837 A1 8/2016 Xi et al.
2016/0257641 A1 9/2016 Kobayashi et al.
2016/0297795 A1 10/2016 Heer et al.
2016/0304511 A1 10/2016 Jackson et al.
2016/0304513 A1 10/2016 Deligny et al.

(56) References Cited

U.S. PATENT DOCUMENTS

| | | | |
|---|---|---|---|
| 2017/0044111 | A1 | 2/2017 | Gray et al. |
| 2017/0114078 | A1 | 4/2017 | McGowan et al. |
| 2017/0121349 | A1 | 5/2017 | Kim et al. |
| 2017/0129883 | A1 | 5/2017 | Jackson et al. |
| 2017/0158688 | A1 | 6/2017 | Jackson et al. |
| 2017/0222157 | A1 | 8/2017 | Jatsch et al. |
| 2017/0333398 | A1 | 11/2017 | Kojima et al. |
| 2018/0030453 | A1 | 2/2018 | Zakharenko et al. |
| 2018/0072688 | A1 | 3/2018 | Qian et al. |
| 2018/0079727 | A1 | 3/2018 | Ohyabu et al. |
| 2018/0086725 | A1 | 3/2018 | Kumar et al. |
| 2018/0153877 | A1 | 6/2018 | Azam |
| 2018/0273511 | A1 | 9/2018 | Long |
| 2019/0002442 | A1 | 1/2019 | Zhao et al. |
| 2019/0022074 | A1 | 1/2019 | Hadari et al. |
| 2019/0038603 | A1 | 2/2019 | Jakobsson |
| 2019/0119217 | A1 | 4/2019 | Long et al. |
| 2019/0134042 | A1 | 5/2019 | Miao et al. |
| 2019/0135834 | A1 | 5/2019 | Tamura et al. |
| 2019/0183866 | A1 | 6/2019 | Tamura et al. |
| 2019/0382377 | A1 | 12/2019 | Li et al. |
| 2019/0388426 | A1 | 12/2019 | Nguyen et al. |
| 2020/0039933 | A1 | 2/2020 | Gaisina et al. |
| 2020/0039961 | A1 | 2/2020 | Campbell et al. |
| 2020/0039998 | A1 | 2/2020 | Campbell et al. |
| 2020/0054635 | A1 | 2/2020 | Campbell et al. |
| 2020/0062758 | A1 | 2/2020 | Liu et al. |
| 2020/0101091 | A1 | 4/2020 | Peyrottes et al. |
| 2020/0113901 | A1 | 4/2020 | Campbell et al. |
| 2020/0113907 | A1 | 4/2020 | Hagiwara et al. |
| 2020/0237717 | A1 | 7/2020 | Jensen et al. |
| 2020/0268753 | A1 | 8/2020 | Nguyen et al. |
| 2020/0274072 | A1 | 8/2020 | Kugler |
| 2020/0317642 | A1 | 10/2020 | Campbell et al. |
| 2021/0008046 | A1 | 1/2021 | Bravo et al. |
| 2022/0127246 | A1 | 4/2022 | Gray et al. |
| 2022/0127284 | A1 | 4/2022 | Gray et al. |
| 2023/0148448 | A9 | 5/2023 | Gray et al. |
| 2023/0183204 | A9 | 6/2023 | Gray et al. |

FOREIGN PATENT DOCUMENTS

| | | | | |
|---|---|---|---|---|
| CN | 107383014 | A | 11/2017 | |
| CN | 108689942 | A | 10/2018 | |
| CN | 110092798 | A | 8/2019 | |
| EP | 639573 | A1 | 2/1995 | |
| EP | 3 059 225 | A1 | 8/2016 | |
| EP | 3279187 | A1 | 2/2018 | |
| EP | 3450435 | A1 | 3/2019 | |
| JP | H11-283746 | A | 10/1999 | |
| JP | 2000-299186 | A | 10/2000 | |
| JP | 2004-067629 | A | 3/2004 | |
| JP | 2005-289921 | A | 10/2005 | |
| JP | 2009-149589 | A | 7/2009 | |
| JP | 2016-132649 | A | 7/2016 | |
| KR | 10-2019-0064508 | A | 6/2019 | |
| WO | WO 93/05163 | A1 | 3/1993 | |
| WO | WO 97/11065 | A1 | 3/1997 | |
| WO | WO 99/26932 | A1 | 6/1999 | |
| WO | WO 2001/044259 | A1 | 6/2001 | |
| WO | WO 2002/076960 | A1 | 10/2002 | |
| WO | WO 2003/082272 | A1 | 10/2003 | |
| WO | WO 2004/006849 | A2 | 1/2004 | |
| WO | WO 2004/085425 | A1 | 10/2004 | |
| WO | WO 2004/087153 | A2 | 10/2004 | |
| WO | WO 2005/032548 | A1 | 4/2005 | |
| WO | WO 2005/035526 | A1 | 4/2005 | |
| WO | WO 2005/037273 | A1 | 4/2005 | |
| WO | WO 2006/027365 | A1 | 3/2006 | |
| WO | WO 2006/128129 | A2 | 11/2006 | |
| WO | WO 2006/130469 | A1 | 12/2006 | |
| WO | WO 2007/058628 | A1 | 5/2007 | |
| WO | WO 2007/091950 | A1 | 8/2007 | |
| WO | WO 2007/121484 | A2 | 10/2007 | |
| WO | WO 2008/016666 | A2 | 2/2008 | |
| WO | WO 2008/124145 | A1 | 10/2008 | |
| WO | WO 2008/144062 | A1 | 11/2008 | |
| WO | WO 2008/150015 | A1 | 12/2008 | |
| WO | WO 2009/011775 | A1 | 1/2009 | |
| WO | WO 2009/017954 | A1 | 2/2009 | |
| WO | WO 2009/032694 | A1 | 3/2009 | |
| WO | WO 2009/034386 | A1 | 3/2009 | |
| WO | WO 2009/050228 | A2 | 4/2009 | |
| WO | WO 2009/155565 | A1 | 12/2009 | |
| WO | WO 2010/002492 | A1 | 1/2010 | |
| WO | WO 2010/141796 | A2 | 12/2010 | |
| WO | WO 2010/144909 | A1 | 12/2010 | |
| WO | WO 2011/063908 | A1 * | 6/2011 | ........... C07D 471/04 |
| WO | WO 2011/127833 | A1 | 10/2011 | |
| WO | WO 2012/016133 | A2 | 2/2012 | |
| WO | WO 2013/014162 | A1 | 1/2013 | |
| WO | WO 2013/024078 | A1 | 2/2013 | |
| WO | WO 2014/069426 | A1 | 5/2014 | |
| WO | WO 2014/072435 | A1 | 5/2014 | |
| WO | WO 2014/175330 | A1 | 10/2014 | |
| WO | WO 2015/008861 | A1 | 1/2015 | |
| WO | WO 2015/164614 | A1 | 10/2015 | |
| WO | WO 2016/014576 | A1 | 1/2016 | |
| WO | WO 2016/119700 | A1 | 8/2016 | |
| WO | WO 2017/143014 | A1 | 8/2017 | |
| WO | WO 2017/175068 | A1 | 10/2017 | |
| WO | WO 2018/039557 | A1 | 3/2018 | |
| WO | WO 2018/064498 | A1 | 4/2018 | |
| WO | WO 2018/066545 | A1 | 4/2018 | |
| WO | WO 2018/191146 | A1 | 10/2018 | |
| WO | WO 2018/200786 | A1 | 11/2018 | |
| WO | WO 2018/203099 | A1 | 11/2018 | |
| WO | WO 2018/204765 | A1 | 11/2018 | |
| WO | WO 2019/000683 | A1 | 1/2019 | |
| WO | WO 2019/018119 | A1 | 1/2019 | |
| WO | WO 2019/038683 | A1 | 2/2019 | |
| WO | WO 2019/079596 | A1 | 4/2019 | |
| WO | WO 2019/079607 | A1 | 4/2019 | |
| WO | WO 2019/088159 | A1 | 5/2019 | |
| WO | WO 2019/217838 | A1 | 11/2019 | |
| WO | WO 2020/014599 | A1 | 1/2020 | |
| WO | WO 2020/081450 | A1 | 4/2020 | |
| WO | WO 2020/089455 | A1 | 5/2020 | |
| WO | WO 2020/093905 | A1 | 5/2020 | |
| WO | WO 2020/097396 | A1 | 5/2020 | |
| WO | WO 2020/097398 | A1 | 5/2020 | |
| WO | WO 2020/097400 | A1 | 5/2020 | |
| WO | WO 2020/118045 | A1 | 6/2020 | |
| WO | WO 2020/165907 | A1 | 8/2020 | |
| WO | WO 2020/176597 | A1 | 9/2020 | |
| WO | WO 2020/180768 | A1 | 9/2020 | |
| WO | WO 2020/181050 | A1 | 9/2020 | |
| WO | WO 2020/210481 | A1 | 10/2020 | |
| WO | WO 2020/243457 | A1 | 12/2020 | |
| WO | WO 2021/067682 | A1 | 4/2021 | |
| WO | WO 2021/091575 | A1 | 5/2021 | |
| WO | WO 2021/113557 | A1 | 6/2021 | |
| WO | WO 2021/226261 | A1 | 11/2021 | |
| WO | WO 2022/ 140527 | A1 | 6/2022 | |

OTHER PUBLICATIONS

Lucas MC et al. "Rational design of highly selective spleen tyrosine kinase inhibitors". J Med Chem. Dec. 13, 2012;55(23):10414-23. (Year: 2012).*

Smith et. al. (Bioorganic and Medicinal Letters (2017) 27:5221-5224). (Year: 2017).*

International Search Report and Written Opinion for PCT/US2019/060358, mailed on Mar. 3, 2020.

International Preliminary Report on Patentability for PCT/US2019/060358, mailed on May 20, 2021.

Invitation to Pay Additional Fees for PCT/US2019/060358, mailed on Dec. 27, 2019.

Invitation to Pay Additional Fees for PCT/US2019/060363, mailed on Dec. 27, 2019.

International Search Report and Written Opinion for PCT/US2019/060363, mailed on Mar. 9, 2020.

(56) References Cited

OTHER PUBLICATIONS

International Preliminary Report on Patentability for PCT/US2019/060363, mailed on May 20, 2021.
International Search Report and Written Opinion for PCT/US2019/060360, mailed on Mar. 3, 2020.
International Preliminary Report on Patentability for PCT/US2019/060360, mailed on May 20, 2021.
International Search Report and Written Opinion for PCT/US2020/053922, mailed on Mar. 8, 2021.
Akhtar et al., Therapeutic evolution of benzimidazole derivatives in the last quinquennial period. Eur J Med Chem. Jan. 27, 2017;126:705-753. doi: 10.1016/j.ejmech.2016.12.010. Epub Dec. 5, 2016. PMID: 27951484.
Andraos et al, Modulation of activation-loop phosphorylation by JAK inhibitors is binding mode dependent. Cancer Discov. Jun. 2012;2(6):512-523. doi: 10.1158/2159-8290.CD-11-0324. Epub May 3, 2012. PMID: 22684457; PMCID: PMC5022112.
Berge et al., Pharmaceutical salts. J Pharm Sci. Jan. 1977;66(1):1-19.
Elf et al., Mutant Calreticulin Requires Both Its Mutant C-terminus and the Thrombopoietin Receptor for Oncogenic Transformation. Cancer Discov. Apr. 2016;6(4):368-81. doi: 10.1158/2159-8290.CD-15-1434. Epub Mar. 7, 2016. PMID: 26951227; PMCID: PMC4851866.
Harrison et al., JAK inhibition with ruxolitinib versus best available therapy for myelofibrosis. N Engl J Med. Mar. 1, 2012;366(9):787-98. doi: 10.1056/NEJMoa1110556. PMID: 22375970.
Koppikar et al., Heterodimeric JAK-STAT activation as a mechanism of persistence to JAK2 inhibitor therapy. Nature. Sep. 6, 2012;489(7414):155-9. doi: 10.1038/nature11303. PMID: 22820254; PMCID: PMC3991463.
Roberts et al., Targetable kinase-activating lesions in Ph-like acute lymphoblastic leukemia. N Engl J Med. Sep. 11, 2014;371(11):1005-15. doi: 10.1056/NEJMoa1403088. PMID: 25207766; PMCID: PMC4191900.
Rui et al., Cooperative epigenetic modulation by cancer amplicon genes. Cancer Cell. Dec. 14, 2010;18(6):590-605. doi: 10.1016/j.ccr.2010.11.013. PMID: 21156283; PMCID: PMC3049192.
Rzymski et al., SEL120-34A is a novel CDK8 inhibitor active in AML cells with high levels of serine phosphorylation of STAT1 and STAT5 transactivation domains. Oncotarget. May 16, 2017;8(20):33779-33795. doi: 10.18632/oncotarget.16810. PMID: 28422713; PMCID: PMC5464911.
Shiels et al., Cancer burden in the HIV-infected population in the United States. J Natl Cancer Inst. May 4, 2011;103(9):753-62. doi: 10.1093/jnci/djr076. Epub Apr. 11, 2011. PMID: 21483021; PMCID: PMC3086877.
Smith et al., Imidazo[1,2-a]pyridin-6-yl-benzamide analogs as potent RAF inhibitors. Bioorg Med Chem Lett. Dec. 1, 2017;27(23):5221-5224. doi: 10.1016/j.bmcl.2017.10.047. Epub Oct. 20, 2017. PMID: 29107542.
Verstovsek et al., A double-blind, placebo-controlled trial of ruxolitinib for myelofibrosis. N Engl J Med. Mar. 1, 2012;366(9):799-807. doi: 10.1056/NEJMoa1110557. PMID: 22375971; PMCID: PMC4822164.
Wilen et al., Strategies in optical resolutions. Tetrahedron. 1977;33(21):2725-36.
Wu et al., Activity of the Type II JAK2 Inhibitor CHZ868 in B Cell Acute Lymphoblastic Leukemia. Cancer Cell. Jul. 13, 2015;28(1):29-41. doi: 10.1016/j.ccell.2015.06.005. PMID: 26175414; PMCID: PMC4505625.
International Search Report and Written Opinion for PCT/US2015/027312, mailed Jul. 10, 2015.
International Preliminary Report on Patentability for PCT/US2015/027312, mailed Nov. 3, 2016.
Extended European Search Report for EP 20872304.9, mailed Sep. 25, 2023.
International Preliminary Report on Patentability for PCT/US2020/053922, mailed Apr. 14, 2022.
Arwood et al., New scaffolds for type II JAK2 inhibitors overcome the acquired G993A resistance mutation. Cell Chem Biol. Jun. 15, 2023;30(6):618-631.e12. doi: 10.1016/j.chembiol.2023.05.007. Epub Jun. 7, 2023.
Kong et al., How Does the L884P Mutation Confer Resistance to Type-II Inhibitors of JAK2 Kinase: A Comprehensive Molecular Modeling Study. Sci Rep. Aug. 22, 2017;7(1):9088. doi: 10.1038/s41598-017-09586-3.
Extended European Search Report for EP 19882880.8 mailed Jul. 11, 2022.
International Search Report for PCT/US2021/030926, mailed Sep. 8, 2021.
International Search Report for PCT/US2021/064830, mailed Mar. 25, 2022.
Extended European Search Report for Application No. EP 19882411.2 mailed Jun. 21, 2022.
Aaronson et al., A road map for those who don't know JAK-STAT. Science. May 31, 2002;296(5573):1653-5. doi: 10.1126/science.1071545. PMID: 12040185.
Bundgard, Design of Prodrugs. Amsterdam; New York; Oxford: Elsevier, 1985. 7-9, 21-24.
Choi et al., Development of 'DFG-out' inhibitors of gatekeeper mutant kinases, Bioorganic & Medicinal Chemistry Letters, 22:5297-5302 (2012).
Clark et al., Discovery and Development of Janus Kinase (JAK) Inhibitors for Inflammatory Diseases, J Medicinal Chemistry, J. Med. Chem., 57:5023-5038 (2014).
Dymock et al., Inhibitors of JAK2 and JAK3: an update on the patent literature 2010-2012. Expert Opin Ther Pat. Apr. 2013;23(4):449-501. doi: 10.1517/13543776.2013.765862. Epub Feb. 1, 2013. PMID: 23367873.
Jaffer et al., The emerging role of chemokine receptor CXCR2 in cancer progression, Transl. Cancer Res., 5(Suppl 4):S616-S628 (2016).
Jutzi et al., LSD1 Inhibition Prolongs Survival in Mouse Models of MPN by Selectivity Targeting the Disease Clone, HemaSphere, 2:3, 13 pages (2018).
Leroy et al., Rethinking JAK2 inhibition: towards novel strategies of more specific and versatile janus kinase inhibition, Leukemia, 31(5):1023-1038 (2017).
Levine, JAK-mutant myeloproliferative neoplasms. Curr Top Microbiol Immunol. 2012;355:119-33. doi: 10.1007/82_2011_170. PMID: 21823028.
Li et al., AutoT&T v.2: An Efficient and Versatile Tool for Lead Structure Generation and Optimization. J Chem Inf Model. Feb. 22, 2016;56(2):435-53. doi: 10.1021/acs.jcim.5b00691. Epub Feb. 3, 2016. PMID: 26799148.
Meyer et al., Molecular Pathways: Molecular Basis for Sensitivity and Resistance to JAK Kinase Inhibitors, Clin. Cancer Res., 20(8):2051-2059 (2014).
O'Hare et al., AP24534, a Pan-BCRBL Inhibitor for Chronic Myeloid Leukemia, Potently Inhibits the T315I Mutant and Overcomes Mutation-Based Resistance, Cancer Cell, 16(5):401-412 (2009).
Okaniwa et al., Design and synthesis of novel DFG-out RAF/vascular endothelial growth factor receptor 2 (VEGFR2) inhibitors. 1. Exploration of [5,6]-fused bicyclic scaffolds. J Med Chem. Apr. 12, 2012;55(7):3452-78. doi: 10.1021/jm300126x. Epub Mar. 14, 2012. PMID: 22376051.
O'Shea, J. et al., Janus kinase Inhibitors in autoimmune diseases, Ann Rheum. Dis., 72, 11 pages (2013).
Pandey et al., Cloning of a receptor subunit required for signaling by thymic stromal lymphopoietin. Nat Immunol. Jul. 2000;1(1):59-64. doi: 10.1038/76923. PMID: 10881176.
Ramurthy, S. et al., Design and Synthesis of Orally Bioavailable Benzimidazoles as Raf Kinase Inhibitors, J. Med. Chem., 51:7049-7052 (2008).
Ramurthy, S. et al., Supporting Information Design and Synthesis of Benzimidazoles Amides as Raf Kinase Inibitors, Novartis Institutes of Biomedical Research, 38 pages (2018).
Rodrigues et al., JAK/STAT inhibitors for the treatment of atopic dermatitis, Journal of Dermatological Treatment, 31(1):33-40 (2020).

(56) References Cited

OTHER PUBLICATIONS

Steelman et al., JAK/STAT, Raf/MEK/ERK, PI3K/Akt and BCRBL in cell cycle progression and leukemogenesis. Leukemia. Feb. 2004;18(2):189-218. doi: 10.1038/sj.leu.2403241. PMID: 14737178.
Subramanian, S. et al., Design and Synthesis of Orally Bioavailable Benzimidazole Reverse Amides as Pan RAF Kinase Inhibitors, ACS Med. Chem. Lett., 5:989-992 (2014).
Vainchenker, W. et al., JAK inhibitors for the treatment of myeloproliferative neoplasms and other disorders, F1000 Research, 7(F1000 Faculty Rev), 19 pages (last updated Jan. 17, 2018).
Williams et al., Discovery of RAF265: A Potent mut-B-RAF Inhibitor for the Treatment of Metastatic Melanoma. ACS Med Chem Lett. Aug. 3, 2015;6(9):961-5. doi: 10.1021/ml500526p. PMID: 26396681; PMCID: PMC4569875.
Yuanyuan et al., Design, synthesis, biological evaluation and molecular modeling of novel 1H-pyrazolo [3,4-d] pyrimidine derivatives as BRAFV600Eand VEGFR-2 dual inhibitors, European J Medicinal Chemistry, 155:210-228 (2018).
Yumeen et al., JAK inhibition synergistically potentiates BCL2, BET, HDAC, and proteasome inhibition in advanced CTCL, Blood Advances, 4(10):2213-2226 (2020).
Zhao et al., Exploration of type II binding mode: A privileged approach for kinase inhibitor focused drug discovery? ACS Chem Biol. Jun. 20, 2014;9(6):1230-41. doi: 10.1021/cb500129t. Epub Apr. 29, 2014. PMID: 24730530; PMCID: PMC4068218.
U.S. Appl. No. 17/766,520, filed Apr. 4, 2022, Gray et al.
EP 19882880.8, Jul. 11, 2022, Extended European Search Report.
PCT/US2021/030926, Sep. 8, 2021, International Search Report.
PCT/US2021/064830, Mar. 25, 2022, International Search Report.
EP 19882411.2, Jun. 21, 2022, Extended European Search Report.
Extended European Search Report for EP 19881035.0 mailed Jun. 29, 2022.
PCT/US2015/027312, Jul. 10, 2015, International Search Report and Written Opinion.
PCT/US2015/027312, Nov. 3, 2016, International Preliminary Report on Patentability.
PCT/US2020/053922, Apr. 14, 2022, International Preliminary Report on Patentability.
EP 20872304.9, Sep. 25, 2023, Extended European Search Report.

* cited by examiner (Ruxolitinib)

(CHZ868)

| | IC50 |
|---|---|
| CHZ868 | 1.416e-007 |
| I-2 | 8.066e-008 |
| I-6 | 1.598e-007 |

| | IC50 |
|---|---|
| CHZ868 | 1.209e-007 |
| I-2 | 1.392e-007 |
| I-6 | 1.932e-007 |

| | IC50 |
|---|---|
| CHZ868 | 2.188e-007 |
| I-2 | ~ 1.942e-007 |
| I-6 | 2.769e-007 |

IMIDAZOPYRIDINE DERIVATIVES AND AZA-IMIDAZOPYRIDINE DERIVATIVES AS JANUS KINASE 2 INHIBITORS AND USES THEREOF

RELATED APPLICATIONS

The present application is a national stage filing under 35 U.S.C. § 371 of International PCT Application PCT/US2019/060363, filed Nov. 7, 2019, which claims priority under 35 U.S.C. § 119 (e) to U.S. Provisional Application, U.S. Ser. No. 62/757,124, filed Nov. 7, 2018, each of which is incorporated herein by reference.

BACKGROUND OF THE INVENTION

The JAK-STAT signaling pathway is a chain of interactions between proteins in a cell and is involved in processes such as immunity, cell division, cell death, and tumor formation. The pathway communicates information from chemical signals outside of a cell to the cell The JAK-STAT signaling pathway is a chain of interactions between proteins in a cell and is involved in processes such as immunity, cell division, cell death, and tumor formation. The pathway communicates information from chemical signals outside of a cell to the cell nucleus, resulting in the activation of genes through a process called transcription. There are three key parts of JAK-STAT signaling: Janus kinases (JAKs), Signal Transducer and Activator of Transcription proteins (STATs), and receptors (Aaronson, D. S.; Horvath, C. M. (2002). *Science.* 296 (5573): 1653-5). Disrupted JAK-STAT signaling may lead to a variety of diseases, such as skin conditions, cancers, and disorders affecting the immune system. In particular, activated JAK-STAT signaling plays a critical role in a variety of hematologic neoplasms.

JAK2 V617F is the most commonly observed activating mutation in myeloproliferative neoplasms (MPNs), occurring in approximately 95% of polycythemia vera (PV) cases and 50-60% of essential thrombocythemia (ET) and primary myelofibrosis (PMF) cases (Levine, R. L. *Current topics in microbiology and immunology* 355, 119-133, (2012)). Cases that lack JAK2 mutations are also addicted to JAK2 signaling through activation of thrombopoietin (TPO) receptor signaling by calreticulin (CALR) mutations or other mechanisms (Elf, S. et al. *Cancer discovery* 6, 368-381, (2016)). In addition, approximately 50% of "BCR-ABL-like" B-cell acute lymphoblastic leukemias (B-ALLs) harbor rearrangements of the CRLF2 gene, which requires signaling through JAK2. When treated with conventional chemotherapy, these patients do poorly and there is an urgent need for better therapies. Chromosome 9p amplifications that include PD-L1, PD-L2, and JAK2 occur in nearly all cases of classical Hodgkin's lymphoma and confer dependence on JAK2 signaling (Rui, L. et al. *Cancer Cell* 18, 590-605, (2010)). Similarly, activating mutations in JAK1 and JAK2 occur in a subset of T-cell lymphomas. Thus, there is a broad need for potent and effective JAK2 inhibitors for patients with leukemia and lymphoma.

SUMMARY OF THE INVENTION

Kinases are implicated in a range of disease, including proliferative diseases. Provided herein are compounds of Formula (I'):

(I')

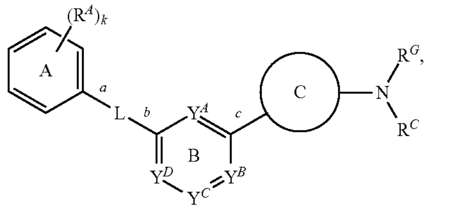

wherein $R^A$, $R^G$, L, $Y^A$, $Y^B$, $Y^C$, $Y^D$, Ring C, $R^C$, $R^D$, and k are as defined herein, and pharmaceutically acceptable salts, solvates, hydrates, polymorphs, co-crystals, tautomers, stereoisomers, isotopically labeled derivatives, and prodrugs thereof. Also provided herein are compounds of Formula (I):

(I)

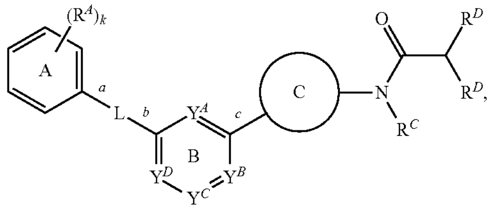

wherein $R^A$, L, $Y^A$, $Y^B$, $Y^C$, $Y^D$, Ring C, $R^C$, $R^D$, and k are as defined herein, and pharmaceutically acceptable salts, solvates, hydrates, polymorphs, co-crystals, tautomers, stereoisomers, isotopically labeled derivatives, and prodrugs thereof. In certain embodiments, a compound described herein is of the formula:

| Compound No. | Compound Formula |
|---|---|
| I-1 | 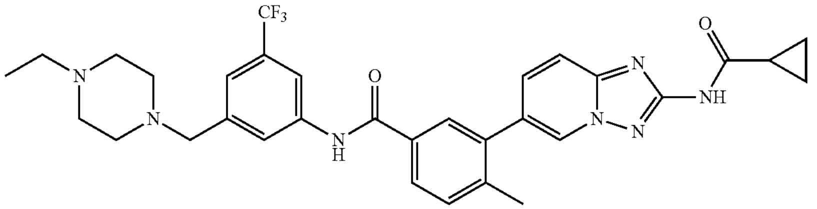 [SMILES: CCN1CCN(Cc2cc(NC(=O)c3ccc(C)c(-c4ccc5nc(NC(=O)C6CC6)nn5c4)c3)cc(C(F)(F)F)c2)CC1] |

-continued
| Compound No. | Compound Formula |
|---|---|
| I-2 | 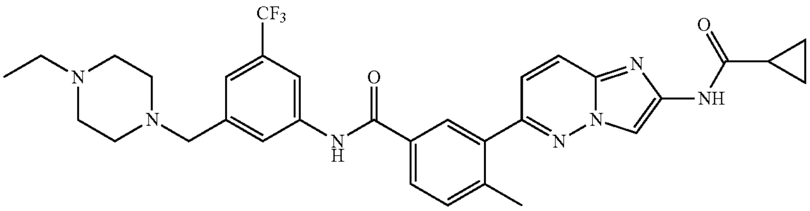 |
| I-3 | 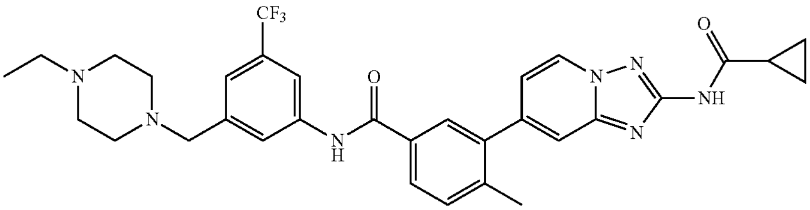 [SMILES: CCN1CCN(Cc2cc(NC(=O)c3ccc(C)c(-c4ccn5nc(NC(=O)C6CC6)nc5c4)c3)cc(C(F)(F)F)c2)CC1] |
| I-4 | 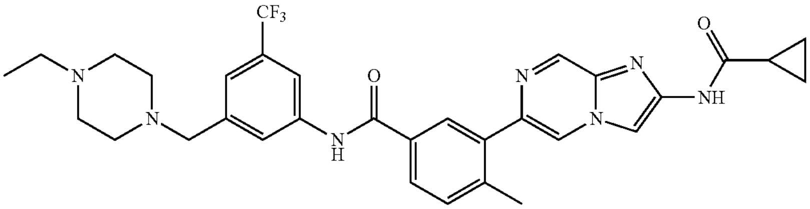 |
| I-5 | 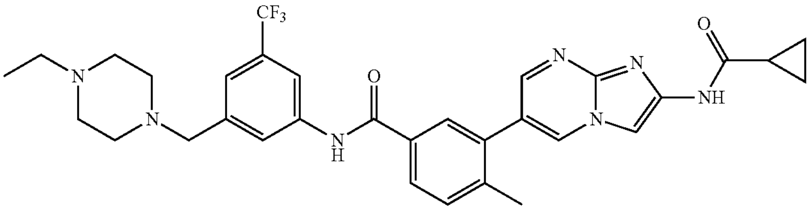 |
| I-6 | 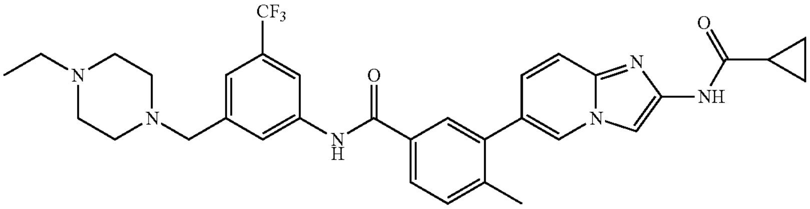 [SMILES: CCN1CCN(Cc2cc(NC(=O)c3ccc(C)c(-c4ccc5nc(NC(=O)C6CC6)cn5c4)c3)cc(C(F)(F)F)c2)CC1] |
| I-7 | 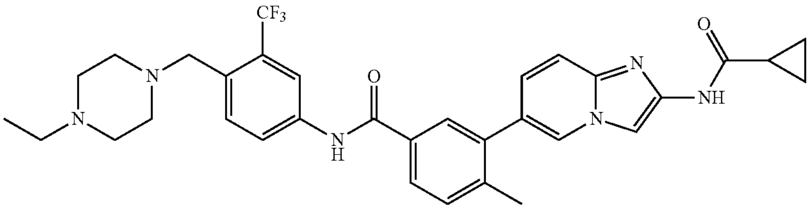 [SMILES: CCN1CCN(Cc2ccc(NC(=O)c3ccc(C)c(-c4ccc5nc(NC(=O)C6CC6)cn5c4)c3)cc2C(F)(F)F)CC1] |
| I-8 | 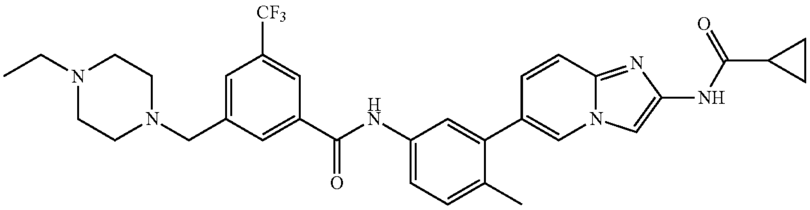 [SMILES: CCN1CCN(Cc2cc(C(=O)Nc3ccc(C)c(-c4ccc5nc(NC(=O)C6CC6)cn5c4)c3)cc(C(F)(F)F)c2)CC1] |

-continued
| Compound No. | Compound Formula |
| --- | --- |
| I-9 | 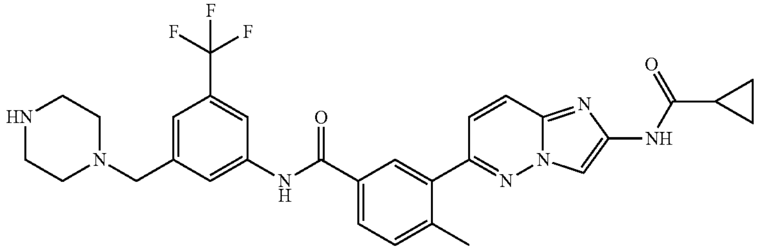 [SMILES: Cc1ccc(C(=O)Nc2cc(CN3CCNCC3)cc(C(F)(F)F)c2)cc1-c1ccc2nc(NC(=O)C3CC3)cn2n1] |
| I-10 | 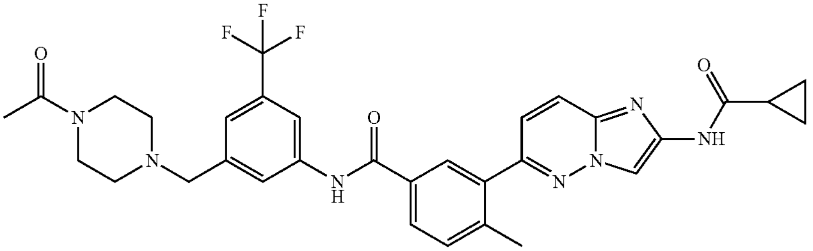 [SMILES: CC(=O)N1CCN(Cc2cc(NC(=O)c3ccc(C)c(-c4ccc5nc(NC(=O)C6CC6)cn5n4)c3)cc(C(F)(F)F)c2)CC1] |
| I-11 | 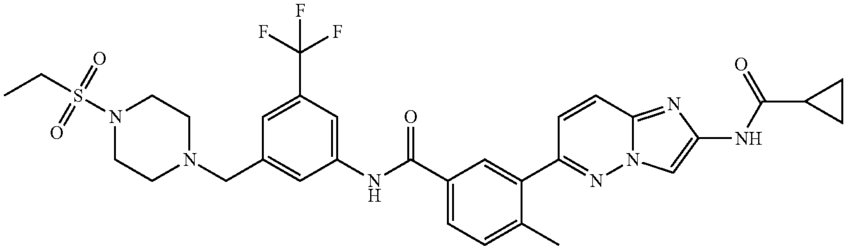 [SMILES: CCS(=O)(=O)N1CCN(Cc2cc(NC(=O)c3ccc(C)c(-c4ccc5nc(NC(=O)C6CC6)cn5n4)c3)cc(C(F)(F)F)c2)CC1] |
| I-12 | 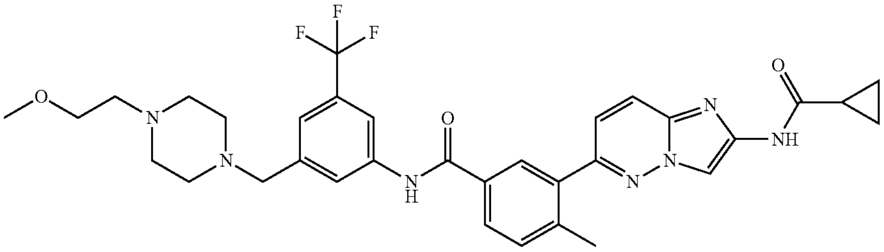 [SMILES: COCCN1CCN(Cc2cc(NC(=O)c3ccc(C)c(-c4ccc5nc(NC(=O)C6CC6)cn5n4)c3)cc(C(F)(F)F)c2)CC1] |
| I-13 | 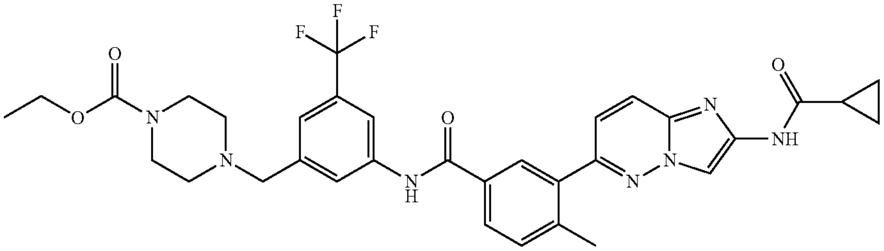 [SMILES: CCOC(=O)N1CCN(Cc2cc(NC(=O)c3ccc(C)c(-c4ccc5nc(NC(=O)C6CC6)cn5n4)c3)cc(C(F)(F)F)c2)CC1] |
| I-14 | 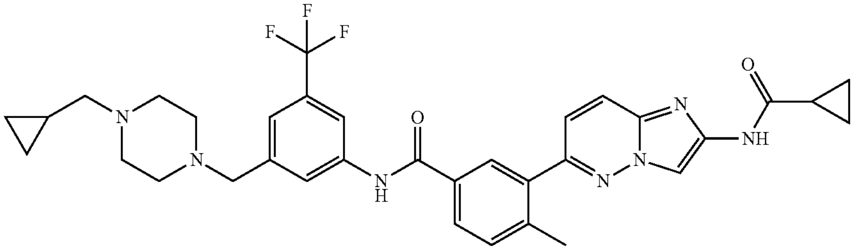 [SMILES: Cc1ccc(C(=O)Nc2cc(CN3CCN(CC4CC4)CC3)cc(C(F)(F)F)c2)cc1-c1ccc2nc(NC(=O)C3CC3)cn2n1] |

-continued
| Compound No. | Compound Formula |
|---|---|
| I-15 | 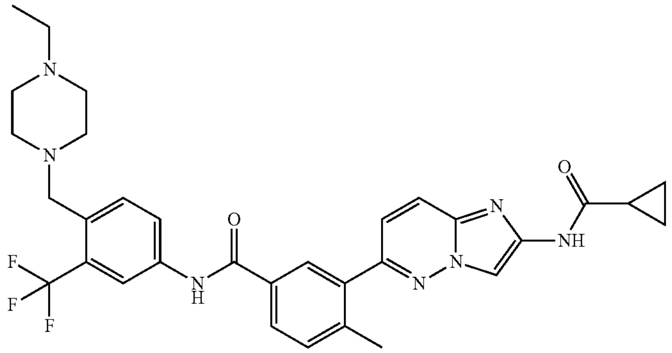 [SMILES: CCN1CCN(Cc2ccc(NC(=O)c3ccc(C)c(-c4ccc5nc(NC(=O)C6CC6)cn5n4)c3)cc2C(F)(F)F)CC1] |
| I-16 | 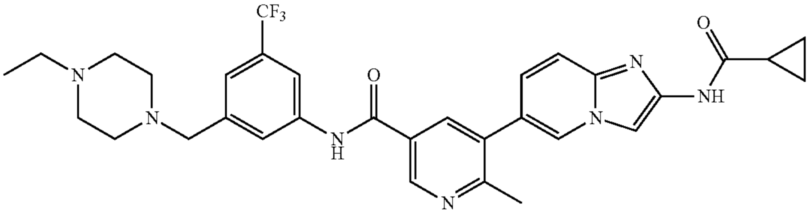 |
| I-17 | 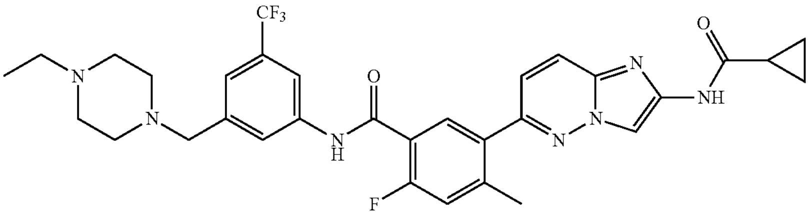 [SMILES: CCN1CCN(Cc2cc(NC(=O)c3cc(-c4ccc5nc(NC(=O)C6CC6)cn5n4)c(C)cc3F)cc(C(F)(F)F)c2)CC1] |
| I-18 | 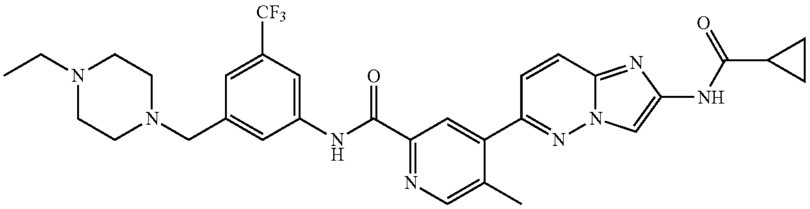 |
| I-19 | 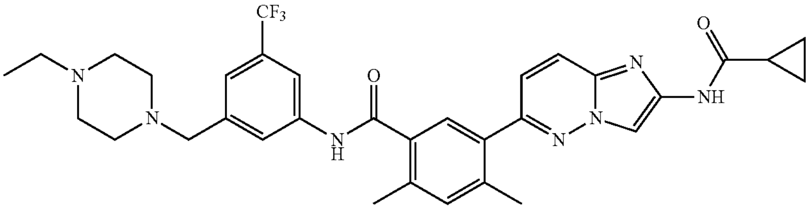 |
| I-20 | 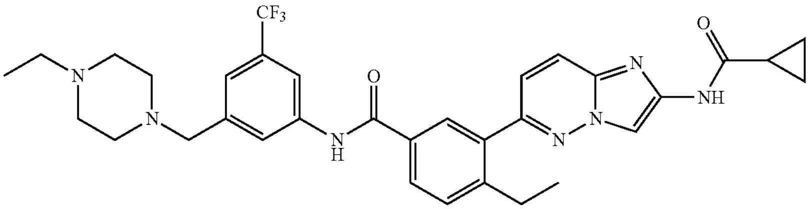 |

-continued
| Compound No. | Compound Formula |
|---|---|
| I-21 | 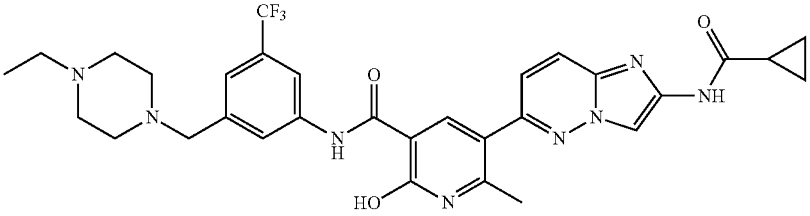 |
| I-22 | 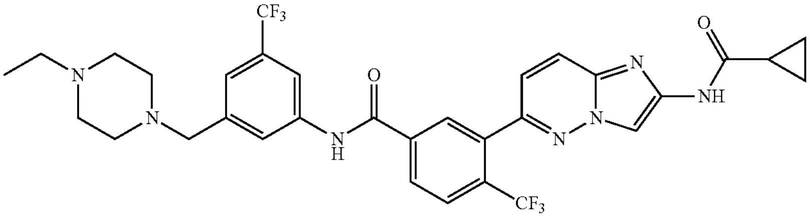 [SMILES: CCN1CCN(Cc2cc(NC(=O)c3ccc(C(F)(F)F)c(-c4ccc5nc(NC(=O)C6CC6)cn5n4)c3)cc(C(F)(F)F)c2)CC1] |
| I-23 | 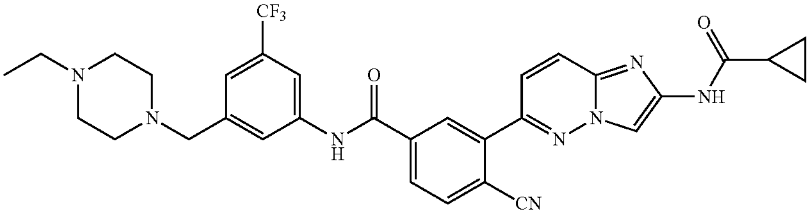 [SMILES: CCN1CCN(Cc2cc(NC(=O)c3ccc(C#N)c(-c4ccc5nc(NC(=O)C6CC6)cn5n4)c3)cc(C(F)(F)F)c2)CC1] |
| I-24 | 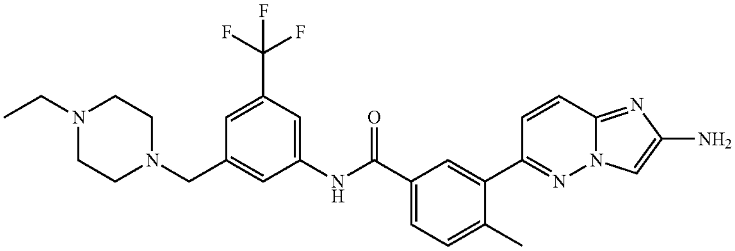 [SMILES: CCN1CCN(Cc2cc(NC(=O)c3ccc(C)c(-c4ccc5nc(N)cn5n4)c3)cc(C(F)(F)F)c2)CC1] |
| I-25 | 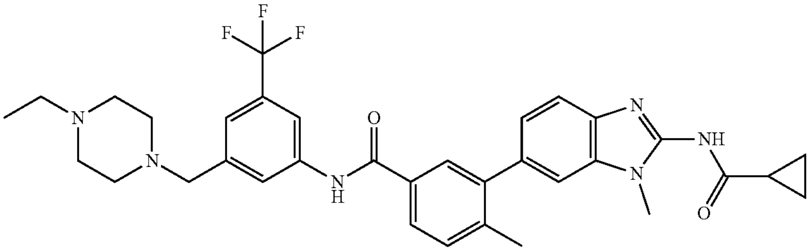 [SMILES: CCN1CCN(Cc2cc(NC(=O)c3ccc(C)c(-c4ccc5nc(NC(=O)C6CC6)n(C)c5c4)c3)cc(C(F)(F)F)c2)CC1] |
| I-26 | 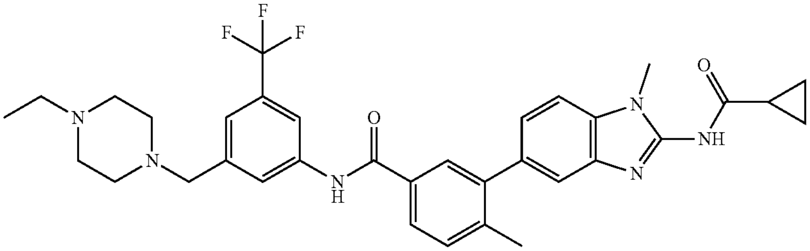 [SMILES: CCN1CCN(Cc2cc(NC(=O)c3ccc(C)c(-c4ccc5c(c4)nc(NC(=O)C4CC4)n5C)c3)cc(C(F)(F)F)c2)CC1] |

-continued

| Compound No. | Compound Formula |
|---|---|
| I-27 | 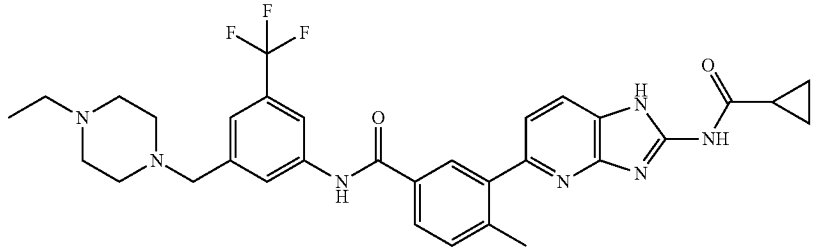 [SMILES: CCN1CCN(Cc2cc(NC(=O)c3ccc(C)c(-c4ccc5[nH]c(NC(=O)C6CC6)nc5n4)c3)cc(C(F)(F)F)c2)CC1] |

or a pharmaceutically acceptable salt, solvate, hydrate, polymorph, co-crystal, tautomer, stereoisomer, isotopically labeled derivative, or prodrug thereof.

The provided compounds may be kinase (e.g., Janus kinase (JAK)) inhibitors, and in certain embodiments, the compounds may be specific or selective for Janus kinase 2 (JAK2) over one or more other kinases. Also provided are pharmaceutical compositions and kits comprising the provided compounds. Also provided are methods of using the provided compounds, pharmaceutical compositions, and kits (e.g., for treating a disease in a subject in need thereof, or inhibiting the activity of a kinase in a subject in need thereof, a biological sample, or a cell).

In one aspect, the present disclosure provides compounds of Formula (I') (e.g., Formula (I)), and pharmaceutically acceptable salts, solvates, hydrates, polymorphs, co-crystals, tautomers, stereoisomers, isotopically labeled derivatives, and prodrugs thereof.

In another aspect, the present disclosure provides pharmaceutical compositions including a compound described herein, and optionally a pharmaceutically acceptable excipient. In certain embodiments, the pharmaceutical composition further comprises an additional pharmaceutical agent. In certain embodiments, the pharmaceutical agent is selected from the group consisting of chemotherapy drugs, epigenetic modifiers, glucocorticoids, biologics, and immunotherapy agents. The pharmaceutical composition may be useful for treating a disease in a subject in need thereof, inhibiting the activity of a kinase in a subject in need thereof, biological sample, or cell, and/or inducing apoptosis in a cell. In certain embodiments, the disease is a proliferative disease. In certain embodiments, the proliferative disease is cancer. In certain embodiments, the proliferative disease is a benign neoplasm, inflammatory disease, autoimmune disease, or pathological angiogenesis. In certain embodiments, the disease is psoriasis, rheumatoid arthritis, polycythemia vera, pancreatic cancer, leukemia, lymphoma, myelofibrosis, myeloproliferative neoplasm, myeloid malignancy, myelodysplastic syndrome, essential thrombocythemia, graft-versus-host disease, alopecia universalis, alopecia, or vitiligo. In certain embodiments, the disease is causing a syndrome of wasting that comprises symptoms of weight loss. In certain embodiments, the disease is a premalignant condition.

Another aspect of the present disclosure relates to methods of inhibiting the activity of a kinase using a compound described herein in a biological sample or subject in need thereof. In certain embodiments, the method involves the selective inhibition of a first kinase (e.g., JAK (e.g., JAK2)) as compared to a second kinase.

The present invention provides methods for administering to a subject in need thereof an effective amount of a compound, or pharmaceutical composition thereof, as described herein. Also described are methods for contacting a biological sample or cell with an effective amount of a compound, or pharmaceutical composition thereof, as described herein. In certain embodiments, a method described herein further includes administering to the subject in need thereof an additional pharmaceutical agent. In certain embodiments, a method described herein further includes contacting the biological sample or cell with an additional pharmaceutical agent.

In yet another aspect, the present invention provides compounds of Formula (I') (e.g., Formula (I)), and pharmaceutically acceptable salts, solvates, hydrates, polymorphs, co-crystals, tautomers, stereoisomers, isotopically labeled derivatives, and prodrugs thereof, and pharmaceutical compositions thereof, for use in the treatment of a disease (e.g., a proliferative disease, such as cancer) in a subject in need thereof.

In yet another aspect, the present invention provides compounds of Formula (I') (e.g., Formula (I)), and pharmaceutically acceptable salts, solvates, hydrates, polymorphs, co-crystals, tautomers, stereoisomers, isotopically labeled derivatives, and prodrugs thereof, and pharmaceutical compositions thereof, for use in the prevention of a disease (e.g., a proliferative disease, such as cancer) in a subject in need thereof.

In another aspect, the present disclosure provides uses of compounds of Formula (I') (e.g., Formula (I)), and pharmaceutically acceptable salts, solvates, hydrates, polymorphs, co-crystals, tautomers, stereoisomers, isotopically labeled derivatives, and prodrugs thereof, and pharmaceutical compositions thereof, in the manufacture of a medicament for treating a disease in a subject in need thereof.

In another aspect, the present disclosure provides uses of compounds of Formula (I') (e.g., Formula (I)), and pharmaceutically acceptable salts, solvates, hydrates, polymorphs, co-crystals, tautomers, stereoisomers, isotopically labeled derivatives, and prodrugs thereof, and pharmaceutical compositions thereof, in the manufacture of a medicament for preventing a disease in a subject in need thereof.

In another aspect, the present disclosure provides methods of preparing a compound of Formula (I') (e.g., Formula (I)), or a pharmaceutically acceptable salt, solvate, hydrate, polymorph, co-crystal, tautomer, stereoisomer, isotopically labeled derivative, or prodrug thereof.

In another aspect, the present disclosure provides kits comprising:

a compound of Formula (I') (e.g., Formula (I)), or a pharmaceutically acceptable salt, solvate, hydrate, polymorph, co-crystal, tautomer, stereoisomer, isotopically labeled derivative, or prodrug thereof, or a pharmaceutical composition thereof; and instructions for using the compound, or a pharmaceutically acceptable salt, solvate, hydrate, polymorph, co-crystal, tautomer, stereoisomer, isotopically labeled derivative, or prodrug thereof, or the pharmaceutical composition.

The details of one or more embodiments of the present disclosure are set forth herein. Other features, objects, and advantages of the present disclosure will be apparent from the Detailed Description, Examples, Figures, and Claims.

Definitions

Definitions of specific functional groups and chemical terms are described in more detail below. The chemical elements are identified in accordance with the Periodic Table of the Elements, CAS version, *Handbook of Chemistry and Physics,* $75^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry,* $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* $3^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC), supercritical fluid chromatography (SFC), and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, Tables of Resolving Agents and Optical Resolutions p. 268 (E.L. Eliel, Ed., Univ. of Notre Dame Press, Notre Dame, IN 1972). The present disclosure additionally encompasses compounds described herein as individual isomers substantially free of other isomers, and alternatively, as mixtures of various isomers.

In a formula, the bond  is a single bond, the dashed line  is a single bond or absent, and the bond 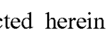 or  is a single or double bond.

Unless otherwise provided, a formula depicted herein includes compounds that do not include isotopically enriched atoms and also compounds that include isotopically enriched atoms. Compounds that include isotopically enriched atoms may be useful as, for example, analytical tools, and/or probes in biological assays.

The term "aliphatic" includes both saturated and unsaturated, nonaromatic, straight chain (i.e., unbranched), branched, acyclic, and cyclic (i.e., carbocyclic) hydrocarbons. In some embodiments, an aliphatic group is optionally substituted with one or more functional groups (e.g., halo, such as fluorine). As will be appreciated by one of ordinary skill in the art, "aliphatic" is intended herein to include alkyl, alkenyl, alkynyl, cycloalkyl, cycloalkenyl, and cycloalkynyl moieties.

When a range of values ("range") is listed, it is intended to encompass each value and sub-range within the range. A range is inclusive of the values at the two ends of the range unless otherwise provided. For example, "an integer between 1 and 4" refers to 1, 2, 3, and 4. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_5$) and the like. Unless otherwise specified, each instance of an alkyl group is independently optionally substituted, e.g., unsubstituted (an "unsubstituted alkyl") or substituted (a "substituted alkyl") with one or more substituents. In certain embodiments, the alkyl group is unsubstituted $C_{1-12}$ alkyl (e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is substituted $C_{1-12}$ alkyl (such as substituted $C_{1-6}$ alkyl, e.g., —$CH_2F$, —$CHF_2$, —$CF_3$, —$CH_2CH_2F$, —$CH_2CHF_2$, —$CH_2CF_3$, or benzyl (Bn)). The attachment point of alkyl may be a single bond (e.g., as in —$CH_3$), double bond (e.g., as in =$CH_2$), or triple bond (e.g., as in ≡CH). The moieties =$CH_2$ and ≡CH are also alkyl.

In some embodiments, an alkyl group is substituted with one or more halogens. "Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$,
—$CF_2CF_3$, —$CF_2CF_2CF_3$, —$CCl_3$, —$CFCl_2$, —$CF_2Cl$, and the like.

"Alkenyl" refers to a radical of a straight-chain or branched hydrocarbon group having from 2 to 20 carbon atoms, one or more (e.g., two, three, or four, as valency permits) carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl (C), and the like. Additional examples of alkenyl include heptenyl ($C_7$), octenyl ($C_5$), octatrienyl ($C_5$), and the like. Unless otherwise specified, each instance of an alkenyl group is independently optionally substituted, e.g., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C═C double bond for which the stereochemistry is not specified (e.g., —CH═$CHCH_3$ or

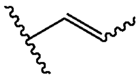
)

may be in the (E)- or (Z)-configuration.

"Alkynyl" refers to a radical of a straight-chain or branched hydrocarbon group having from 2 to 20 carbon atoms, one or more (e.g., two, three, or four, as valency permits) carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, e.g., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 13 ring carbon atoms ("$C_{3-13}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged, or spiro ring system such as a bicyclic system ("bicyclic carbocyclyl"). Carbocyclyl can be saturated, and saturated carbocyclyl is referred to as "cycloalkyl." In some embodiments, carbocyclyl is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl. Carbocyclyl can be partially unsaturated. Carbocyclyl may include zero, one, or more (e.g., two, three, or four, as valency permits) C═C double bonds in all the rings of the carbocyclic ring system that are not aromatic or heteroaromatic. Carbocyclyl including one or more (e.g., two or three, as valency permits) C═C double bonds in the carbocyclic ring is referred to as "cycloalkenyl." Carbocyclyl including one or more (e.g., two or three, as valency permits) C≡C triple bonds in the carbocyclic ring is referred to as "cycloalkynyl." "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, e.g., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl. In certain embodiments, the carbocyclyl is substituted or unsubstituted, 3- to 7-membered, and monocyclic. In certain embodiments, the carbocyclyl is substituted or unsubstituted, 5- to 13-membered, and bicyclic.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 13-membered non-aromatic ring system having ring carbon atoms and 1 to 4 ring heteroatoms, wherein each heteroatom is independently selected from nitrogen, oxygen, and sulfur ("3-13 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system such as a bicyclic system ("bicyclic heterocyclyl"). A heterocyclyl group can be saturated or can be partially unsaturated. Heterocyclyl may include zero, one, or more (e.g., two, three, or four, as valency permits) double bonds in all the rings of the heterocyclic ring system that are not aromatic or heteroaromatic. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, e.g., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl. In certain embodiments, the heterocyclyl is substituted or unsubstituted, 3- to 7-membered, and monocyclic. In certain embodiments, the heterocyclyl is substituted or unsubstituted, 5- to 13-membered, and bicyclic.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include azirdinyl, oxiranyl, or thiiranyl. Exemplary 4-membered heterocyclyl groups containing one heteroatom include azetidinyl, oxetanyl and thietanyl. Exemplary 5-membered heterocyclyl groups containing one heteroatom include tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include dioxolanyl, oxasulfuranyl, disulfuranyl, and oxazolidin-2-one. Exemplary 5-membered heterocyclyl groups containing three heteroatoms include triazolinyl, oxadiazolinyl, and thiadiazolinyl. Exemplary 6-membered heterocyclyl groups containing one heteroatom include piperidinyl, tetrahydropyranyl, dihydropyridinyl, and thianyl. Exemplary 6-membered heterocyclyl groups containing two heteroatoms include piperazinyl, morpholinyl, dithianyl, and dioxanyl. Exemplary 6-membered heterocyclyl groups containing two heteroatoms include triazinanyl. Exemplary 7-membered heterocyclyl groups containing one heteroatom include azepanyl, oxepanyl and thiepanyl. Exemplary 8-membered heterocyclyl groups containing one heteroatom include azocanyl, oxecanyl, and thiocanyl. Exemplary 5-membered heterocyclyl groups fused to a $C_6$ aryl ring (also referred to herein as a 5,6-bicyclic heterocyclic ring) include indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array)

having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, e.g., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 n electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, e.g., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include pyrrolyl, furanyl and thiophenyl. Exemplary 5-membered heteroaryl groups containing two heteroatoms include imidazolyl, pyrazolyl, oxazolyl, isoxazolyl, thiazolyl, and isothiazolyl. Exemplary 5-membered heteroaryl groups containing three heteroatoms include triazolyl, oxadiazolyl, and thiadiazolyl. Exemplary 5-membered heteroaryl groups containing four heteroatoms include tetrazolyl. Exemplary 6-membered heteroaryl groups containing one heteroatom include pyridinyl. Exemplary 6-membered heteroaryl groups containing two heteroatoms include pyridazinyl, pyrimidinyl, and pyrazinyl. Exemplary 6-membered heteroaryl groups containing three or four heteroatoms include triazinyl and tetrazinyl, respectively. Exemplary 7-membered heteroaryl groups containing one heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

In some embodiments, aliphatic, alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X^-$, —$N(OR^{cc})R^{bb}$, —SH, —$SR^{aa}$, —$SSR^{cc}$, —C(═O)$R^{aa}$, —$CO_2H$, —CHO, —$C(OR^{cc})_2$, —$CO_2R^{aa}$, —OC(═O)$R^{aa}$, —$OCO_2R^{aa}$, —C(═O)$N(R^{bb})_2$, —OC(═O)$N(R^{bb})_2$, —$NR^{bb}$C(═O)$R^{aa}$, —$NR^{bb}CO_2R^{aa}$, —$NR^{bb}$C(═O)$N(R^{bb})_2$, —C(═$NR^{bb}$)$R^{aa}$, —C(═$NR^{bb}$)$OR^{aa}$, —OC(═$NR^{bb}$)$R^{aa}$, —OC(═$NR^{bb}$)$OR^{aa}$, —C(═$NR^{bb}$)$N(R^{bb})_2$, —OC(═$NR^{bb}$)$N(R^{bb})_2$, —$NR^{bb}$C(═$NR^{bb}$)$N(R^{bb})_2$, —C(═O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(═O)$R^{aa}$, —OS(═O)$R^{aa}$, —$Si(R^{aa})_3$, —$OSi(R^{aa})_3$, —C(═S)$N(R^{bb})_2$, —C(═O)$SR^{aa}$, —C(═S)$SR^{aa}$, —SC(═S)$SR^{aa}$, —SC(═O)$SR^{aa}$, —OC(═O)$SR^{aa}$, —SC(═O)$OR^{aa}$, —SC(═O)$R^{aa}$, —P(═O)$(R^{aa})_2$, —P(═O)$(OR^{cc})_2$, —OP(═O)$(R^{aa})_2$, —OP(═O)$(OR^{cc})_2$, —P(═O)$(N(R^{bb})_2)_2$, —OP(═O)$(N(R^{bb})_2)_2$, —$NR^{bb}$P(═O)$(R^{aa})_2$, —$NR^{bb}$P(═O)$(OR^{cc})_2$, —$NR^{bb}$P(═O)$(N(R^{bb})_2)_2$, —$P(R^{cc})_2$, —$P(OR^{cc})_2$, —$P(R^{cc})_3{}^+X^-$, —$P(OR^{cc})_3{}^+X^-$, —$P(R^{cc})_4$, —$P(OR^{cc})_4$, —$OP(R^{cc})_2$, —$OP(R^{cc})_3{}^+X^-$, —$OP(OR^{cc})_2$, —$OP(OR^{cc})_3{}^+X^-$, —$OP(R^{cc})_4$, —$OP(OR^{cc})_4$, —$B(R^{aa})_2$, —$B(OR^{cc})_2$, —$BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group ═O, ═S, ═$NN(R^{bb})_2$, ═$NNR^{bb}$C(═O)$R^{aa}$, ═$NNR^{bb}$C(═O)$OR^{aa}$, ═$NNR^{bb}$S(═O)$_2R^{aa}$, ═$NR^{bb}$, or ═$NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —C(═O)$R^{aa}$, —C(═O)$N(R^{cc})_2$, —$CO_2R^{aa}$, —$SO_2R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═O)$(R^{aa})_2$, —P(═O)$(OR^{cc})_2$, —P(═O)$(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —$ON(R^{ff})_2$, —$N(R^{ff})_2$, —$N(R^{ff})_3{}^+X^-$, —$N(OR^{ee})R^{ff}$, —SH, —$SR^{ee}$, —$SSR^{ee}$, —C(═O)$R^{ee}$, —$CO_2H$, —$CO_2R^{ee}$, —OC(═O)$R^{ee}$, —$OCO_2R^{ee}$, —C(═O)$N(R^{ff})_2$, —OC(═O)$N(R^{ff})_2$, —$NR^{ff}$C(═O)$R^{ee}$, —$NR^{ff}CO_2R^{ee}$, —$NR^{ff}$C(═O)$N(R^{ff})_2$, —C(═$NR^{ff}$)$OR^{ee}$, —OC(═$NR^{ff}$)$R^{ee}$, —OC(═$NR^{ff}$)$OR^{ee}$, —C(═$NR^{ff}$)$N(R^{ff})_2$, —OC(═$NR^{ff}$)$N(R^{ff})_2$, —$NR^{ff}$C(═$NR^{ff}$)$N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(═O)$R^{ee}$, —$Si(R^{ee})_3$, —$OSi(R^{ee})_3$, —C(═S)$N(R^{ff})_2$, —C(═O)$SR^{ee}$, —C(═S)$SR^{ee}$, —SC(═S)$SR^{ee}$, —P(═O)$(OR^{ee})_2$, —P(═O)$(R^{ee})_2$, —OP(═O)$(R^{ee})_2$, —OP(═O)$(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form ═O or ═S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3{}^+X^-$, —$NH(C_{1-6}$ alkyl$)_2{}^+X^-$, —$NH_2(C_{1-6}$ alkyl$)^+X^-$, —$NH_3{}^+X^-$, —$N(OC_{1-6}$ alkyl$)(C_{1-6}$ alkyl), —N(OH)$(C_{1-6}$ alkyl), —NH(OH), —SH, —$SC_{1-6}$ alkyl, —$SS(C_{1-6}$ alkyl), —C(═O)$(C_{1-6}$ alkyl), —$CO_2H$, —$CO_2(C_{1-6}$ alkyl), —OC(═O)$(C_{1-6}$ alkyl), —$OCO_2(C_{1-6}$ alkyl), —C(═O)$NH_2$, —C(═O)$N(C_{1-6}$ alkyl$)_2$, —OC(═O)$NH(C_{1-6}$ alkyl), —NHC(═O)$(C_{1-6}$ alkyl), —$N(C_{1-6}$ alkyl)C(═O)$(C_{1-6}$ alkyl), —$NHCO_2(C_{1-6}$ alkyl), —NHC(═O)$N(C_{1-6}$ alkyl$)_2$, —NHC(═O)$NH(C_{1-6}$ alkyl), —NHC(═O)$NH_2$, —C(═NH)$O(C_{1-6}$ alkyl), —OC(═NH)$(C_{1-6}$ alkyl), —OC(═NH)$OC_{1-6}$ alkyl, —C(═NH)$N(C_{1-6}$ alkyl$)_2$, —C(═NH)$NH(C_{1-6}$ alkyl), —C(═NH)$NH_2$, —OC(═NH)$N(C_{1-6}$ alkyl$)_2$, —OC(NH)$NH(C_{1-6}$ alkyl), —OC(NH)$NH_2$, —NHC(NH)$N(C_{1-6}$ alkyl$)_2$, —NHC(═NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl$)_3$-C(═S)$N(C_{1-6}$ alkyl$)_2$, C(═S)$NH(C_{1-6}$ alkyl), C(═S)$NH_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

In certain embodiments, the carbon atom substituents are independently halogen, substituted (e.g., substituted with one or more halogen) or unsubstituted $C_{1-6}$ alkyl, —$OR^{aa}$, —$SR^{aa}$, —N($R^{bb}$)$_2$, —CN, —SCN, —$NO_2$, —C(=O)$R^{aa}$, —$CO_2R^{aa}$, —C(=O)N($R^{bb}$)$_2$, —OC(=O)$R^{aa}$, —$OCO_2R^{aa}$, —OC(=O)N($R^{bb}$)$_2$, —$NR^{bb}$C(=O)$R^{aa}$, —$NR^{bb}CO_2R^{aa}$, or —$NR^{bb}$C(=O)N($R^{bb}$)$_2$. In certain embodiments, the carbon atom substituents are independently halogen, substituted (e.g., substituted with one or more halogen) or unsubstituted $C_{1-6}$ alkyl, —$OR^{aa}$, —$SR^{aa}$, —N($R^{bb}$)$_2$, —CN, —SCN, —$NO_2$, —C(=O)$R^{aa}$, —$CO_2R^{aa}$, —C(=O)N($R^{bb}$)$_2$, —OC(=O)$R^{aa}$, —$OCO_2R^{aa}$, —OC(=O)N($R^{bb}$)$_2$, —$NR^{bb}$C(=O)$R^{aa}$, —$NR^{bb}CO_2R^{aa}$, or —$NR^{bb}$C(=O)N($R^{bb}$)$_2$, wherein $R^{aa}$ is hydrogen, substituted (e.g., substituted with one or more halogen) or unsubstituted $C_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-6}$ alkyl, or a nitrogen protecting group. In certain embodiments, the carbon atom substituents are independently halogen, substituted (e.g., substituted with one or more halogen) or unsubstituted $C_{1-6}$ alkyl, —$OR^{aa}$, —$SR^{aa}$, —N($R^{bb}$)$_2$, —CN, —SCN, or —$NO_2$. In certain embodiments, the carbon atom substituents are independently halogen, substituted (e.g., substituted with one or more halogen moieties) or unsubstituted $C_{1-6}$ alkyl, —$OR^{aa}$, —$SR^{aa}$, —N($R^{bb}$)$_2$, —CN, —SCN, or —$NO_2$, wherein $R^{aa}$ is hydrogen, substituted (e.g., substituted with one or more halogen) or unsubstituted $C_{1-6}$ alkyl, an oxygen protecting group when attached to an oxygen atom, or a sulfur protecting group (e.g., acetamidomethyl, t-Bu, 3-nitro-2-pyridine sulfenyl, 2-pyridine-sulfenyl, or triphenylmethyl) when attached to a sulfur atom; and each $R^{bb}$ is independently hydrogen, substituted (e.g., substituted with one or more halogen) or unsubstituted $C_{1-6}$ alkyl, or a nitrogen protecting group.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quaternary nitrogen atoms. Exemplary nitrogen atom substituents include hydrogen, —OH, —$OR^{aa}$, —N($R^{cc}$)$_2$, —CN, —C(=O)$R^{aa}$, —C(=O)N($R^{cc}$)$_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(=S)N($R^{cc}$)$_2$, —C(=O)$SR^{cc}$, —C(=S)$SR^{cc}$, —P(=O)($OR^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 Rad groups, and wherein $R^{aa}$, $R^{bb}$, $R^{cc}$ and $R^{dd}$ are as defined above.

In certain embodiments, the nitrogen atom substituents are independently substituted (e.g., substituted with one or more halogen) or unsubstituted $C_{1-6}$ alkyl, —C(=O)$R^{aa}$, —$CO_2R^{aa}$, —C(=O)N($R^{bb}$)$_2$, or a nitrogen protecting group. In certain embodiments, the nitrogen atom substituents are independently substituted (e.g., substituted with one or more halogen) or unsubstituted $C_{1-6}$ alkyl, —C(=O)$R^{aa}$, —$CO_2R^{aa}$, —C(=O)N($R^{bb}$)$_2$, or a nitrogen protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the nitrogen atom substituents are independently substituted (e.g., substituted with one or more halogen) or unsubstituted $C_{1-6}$ alkyl or a nitrogen protecting group.

In certain embodiments, the substituent present on a nitrogen atom is a nitrogen protecting group (also referred to as an amino protecting group). Nitrogen protecting groups include —OH, —$OR^{aa}$, —N($R^{cc}$)$_2$, —C(=O)$R^{aa}$, —C(=O)N($R^{cc}$)$_2$, —$CO_2R^{aa}$, —$SO_2R^{aa}$, —C(=$NR^{cc}$)$R^{aa}$, —C(=$NR^{cc}$)$OR^{aa}$, —C(=$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(=S)N($R^{cc}$)$_2$, —C(=O)$SR^{aa}$, —C(=S)$SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Amide nitrogen protecting groups (e.g., —C(=O)$R^{aa}$) include formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine, o-nitrobenzamide, and o-(benzoyloxymethyl)benzamide.

Carbamate nitrogen protecting groups (e.g., —C(═O)OR$^{aa}$) include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Sulfonamide nitrogen protecting groups (e.g., —S(═O)$_2$R$^{aa}$) include p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, a nitrogen protecting group is Bn, Boc, Cbz, Fmoc, trifluoroacetyl, triphenylmethyl, acetyl, or Ts.

In certain embodiments, the oxygen atom substituents are independently substituted (e.g., substituted with one or more halogen) or unsubstituted $C_{1-6}$ alkyl, —C(═O)R$^{aa}$, —CO$_2$R$^{aa}$, —C(═O)N(R$^{bb}$)$_2$, or an oxygen protecting group. In certain embodiments, the oxygen atom substituents are independently substituted (e.g., substituted with one or more halogen) or unsubstituted $C_{1-6}$ alkyl, —C(═O)R$^{aa}$, —CO$_2$R$^{aa}$, —C(═O)N(R$^{bb}$)$_2$, or an oxygen protecting group, wherein R$^{aa}$ is hydrogen, substituted (e.g., substituted with one or more halogen) or unsubstituted $C_{1-6}$ alkyl, or an oxygen protecting group when attached to an oxygen atom; and each R$^{bb}$ is independently hydrogen, substituted (e.g., substituted with one or more halogen) or unsubstituted $C_{1-6}$ alkyl, or a nitrogen protecting group. In certain embodiments, the oxygen atom substituents are independently substituted (e.g., substituted with one or more halogen) or unsubstituted $C_{1-6}$ alkyl or an oxygen protecting group.

In certain embodiments, the substituent present on an oxygen atom is an oxygen protecting group (also referred to herein as an "hydroxyl protecting group"). Oxygen protecting groups include $—R^{aa}$, $—N(R^{bb})_2$, $—C(═O)SR^{aa}$, $—C(═O)R^{aa}$, $—CO_2R^{aa}$, $—C(═O)N(R^{bb})_2$, $—C(═NR^{bb})R^{aa}$, $—C(═NR^{bb})OR^{aa}$, $—C(═NR^{bb})N(R^{bb})_2$, $—S(═O)R^{aa}$, $—SO_2R^{aa}$, $—Si(R^{aa})_3$, $—P(R^{cc})_2$, $—P(R^{aa})_3^+X^-$, $—P(OR^{cc})_2$, $—P(OR^{aa})_3^+X^-$, $—P(═O)(R^{aa})_2$, $—P(═O)(OR^{cc})_2$, and $—P(═O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3rd edition, John Wiley & Sons, 1999, incorporated herein by reference.

Exemplary oxygen protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, an oxygen protecting group is silyl, TBDPS, TBDMS, TIPS, TES, TMS, MOM, THP, t-Bu, Bn, allyl, acetyl, pivaloyl, or benzoyl.

In certain embodiments, the sulfur atom substituents are independently substituted (e.g., substituted with one or more halogen) or unsubstituted $C_{1-6}$ alkyl, $—C(═O)R^{aa}$, $—CO_2R^{aa}$, $—C(═O)N(R^{bb})_2$, or a sulfur protecting group. In certain embodiments, the sulfur atom substituents are independently substituted (e.g., substituted with one or more halogen) or unsubstituted $C_{1-6}$ alkyl, $—C(═O)R^{aa}$, $—CO_2R^{aa}$, $—C(═O)N(R^{bb})_2$, or a sulfur protecting group, wherein $R^{aa}$ is hydrogen, substituted (e.g., substituted with one or more halogen) or unsubstituted $C_{1-6}$ alkyl, or an oxygen protecting group when attached to an oxygen atom; and each $R^{bb}$ is independently hydrogen, substituted (e.g., substituted with one or more halogen) or unsubstituted $C_{1-6}$ alkyl, or a nitrogen protecting group. In certain embodiments, the sulfur atom substituents are independently substituted (e.g., substituted with one or more halogen) or unsubstituted $C_{1-6}$ alkyl or a sulfur protecting group.

In certain embodiments, the substituent present on a sulfur atom is a sulfur protecting group (also referred to as a "thiol protecting group"). Sulfur protecting groups include $—R^{aa}$, $—N(R^{bb})_2$, $—C(═O)SR^{aa}$, $—C(═O)R^{aa}$, $—CO_2R^{aa}$, $—C(═O)N(R^{bb})_2$, $—C(═NR^{bb})R^{aa}$, $—C(═NR^{bb})OR^{aa}$, $—C(═NR^{bb})N(R^{bb})_2$, $—S(═O)R^{aa}$, $—SO_2R^{aa}$, $—Si(R^{aa})_3$, $—P(R^{cc})_2$, $—P(R^{aa})_3^+X^-$, $—P(OR^{cc})_2$, $—P(OR^{aa})_3^+X^-$, $—P(═O)(R^{aa})_2$, $—P(═O)(OR^{cc})_2$, and $—P(═O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

The "molecular weight" of —R, wherein —R is any monovalent moiety, is calculated by subtracting the atomic weight of a hydrogen atom from the molecular weight of the molecule R—H. The "molecular weight" of -L-, wherein -L- is any divalent moiety, is calculated by subtracting the combined atomic weight of two hydrogen atoms from the molecular weight of the molecule H-L-H.

In certain embodiments, the molecular weight of a substituent is lower than 200, lower than 150, lower than 100, lower than 50, or lower than 25 g/mol. In certain embodiments, a substituent consists of carbon, hydrogen, fluorine, chlorine, bromine, iodine, oxygen, sulfur, nitrogen, and/or silicon atoms. In certain embodiments, a substituent consists of carbon, hydrogen, fluorine, chlorine, bromine, and/or iodine atoms. In certain embodiments, a substituent consists of carbon, hydrogen, and/or fluorine atoms. In certain embodiments, a substituent does not comprise one or more, two or more, or three or more hydrogen bond donors. In certain embodiments, a substituent does not comprise one or more, two or more, or three or more hydrogen bond acceptors.

These and other exemplary substituents are described in more detail in the Detailed Description, Examples, Figures, and Claims. The present disclosure is not intended to be limited in any manner by the above exemplary listing of substituents.

"Pharmaceutically acceptable salt" refers to those salts which are, within the scope of sound medical judgment, suitable for use in contact with the tissues of humans and other animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences* (1977) 66:1-19. Pharmaceutically acceptable salts of the compounds describe herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, quaternary salts.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I') (e.g., Formula (I)) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R \cdot 0.5H_2O$)), and polyhydrates (x is a number greater than 1, e.g., dihydrates ($R \cdot 2H_2O$) and hexahydrates ($R \cdot 6H_2O$)).

The term "tautomers" refer to compounds that are interchangeable forms of a particular compound structure, and that vary in the displacement of hydrogen atoms and electrons. Thus, two structures may be in equilibrium through the movement of 7 electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formula (I') (e.g., Formula (I)), which have cleavable groups and become by solvolysis or under physiological conditions the compounds of Formula (I') (e.g., Formula (I)) which are pharmaceutically active in vivo. Such examples include, but are not limited to, ester derivatives and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs, pp.* 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formula (I') (e.g., Formula (I)) may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the subject is a mammal. The subject may be a male or female and at any stage of development. A non-human animal may be a transgenic animal.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration," refers to implanting, absorbing, ingesting, injecting, inhaling, or otherwise introducing a compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound of Formula (I') (e.g., Formula (I)) refers to an amount sufficient to elicit the desired biological response, i.e., treating the condition. As will be appreciated by those of ordinary skill in this art, the effective amount of a compound of Formula (I') (e.g., Formula (I)) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of a compound may reduce the tumor burden or stop the growth or spread of a tumor.

A "therapeutically effective amount" of a compound of Formula (I') (e.g., Formula (I)) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue.

Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary,* 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal or pathological angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases). In certain embodiments, the angiogenesis is pathological angiogenesis.

An "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme arthritis, Guillain-Barré syndrome, Hashimoto's thyroiditis, and cardiomyopathy.

A "protein" or "peptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, or synthetic, or any combination of these.

The term "kinase" refers to any enzyme that catalyzes the addition of phosphate groups to an amino acid residue of a substrate (e.g., a protein or nucleoside). For example, a serine kinase catalyzes the addition of a phosphate group to serine residue in a protein. In certain embodiments, the kinase is a tyrosine kinase. Examples of kinases include, but are not limited to, a Janus kinase (e.g., Janus kinase 1 (JAK1), Janus kinase 2 (JAK2), Janus kinase 3 (JAK3), tyrosine kinase 2 (TYK2)), a CMGC kinase (e.g., a cyclin-dependent kinase (CDK, e.g., CDK1, CDK2, CDK2, CDK4, CDK5, CDK7, CDK8, CDK9, CDK10, CDK11, CDK12, CDK13, CDK14, CDK16, CDK20), a mitogen-activated protein kinase (MAPK, e.g., MAPK1, MAPK3, MAPK4, MAPK6, MAPK7, MAPK8, MAPK9, MAPK10, MAPK11, MAPK12, MAPK13, MAPK14, MAPK15), a glycogen synthase kinase 3 (GSK3, e.g., GSK3a, GSK3P), or a CDC-like kinase (CLK, e.g., CLK1, CLK2, CLK3, CLK4)), an AGC kinase (e.g., protein kinase A (PKA), protein kinase C (PKC), protein kinase G (PKG)), a $Ca^{2+}$/calmodulin-dependent protein kinase (CaM kinase, e.g., a specialized CaM kinase, a multifunctional CaM kinase), a casein kinase 1 (CK1, e.g., CK1alpha, CK1beta 1, CK1gamma 1, CK1gamma 2, CK1gamma 3, CK1delta, CK1epsilon), a STE kinase (e.g., a homolog of yeast Sterile 7, Sterile 11, or Sterile 20 kinase), a tyrosine kinase (TK, e.g., a receptor tyrosine kinase (RTK), a non-receptor tyrosine kinase (nRTK)), and a tyrosine-kinase-like kinase (TKL, e.g., a mixed lineage kinase (MLK), RAF, a serine threonine kinase receptor (STKR), a leucine rich repeat kinase (LRRK), a LIM domain kinase (LIMK), a testis expressed serine kinase (TESK), an IL1 receptor associated kinase (IRAK), a receptor interacting protein kinase (RIPK)).

"Janus kinase" or "JAK" refers to a family of intracellular, nonreceptor tyrosine kinases that transduce cytokine-mediated signals via the JAK-STAT pathway. In certain embodiments, the JAK is Janus kinase 1 (JAK1), Janus kinase 2 (JAK2), Janus kinase 3 (JAK3), or tyrosine kinase 2 (TYK2). The Ensembl entry for the gene that encodes human JAK1 is ENSG00000162434. The Ensembl entry for the gene that encodes human JAK2 is ENSG00000096968. The Ensembl entry for the gene that encodes human JAK3 is ENSG00000105639. The Ensembl entry for the gene that encodes human TYK2 is ENSG00000105397.

BRIEF DESCRIPTION OF THE DRAWINGS

The accompanying drawings, which constitute a part of this specification, illustrate several embodiments of the present disclosure and together with the description, serve to explain the principles of the present disclosure.

DETAILED DESCRIPTION OF CERTAIN EMBODIMENTS OF THE INVENTION

Figure 1:
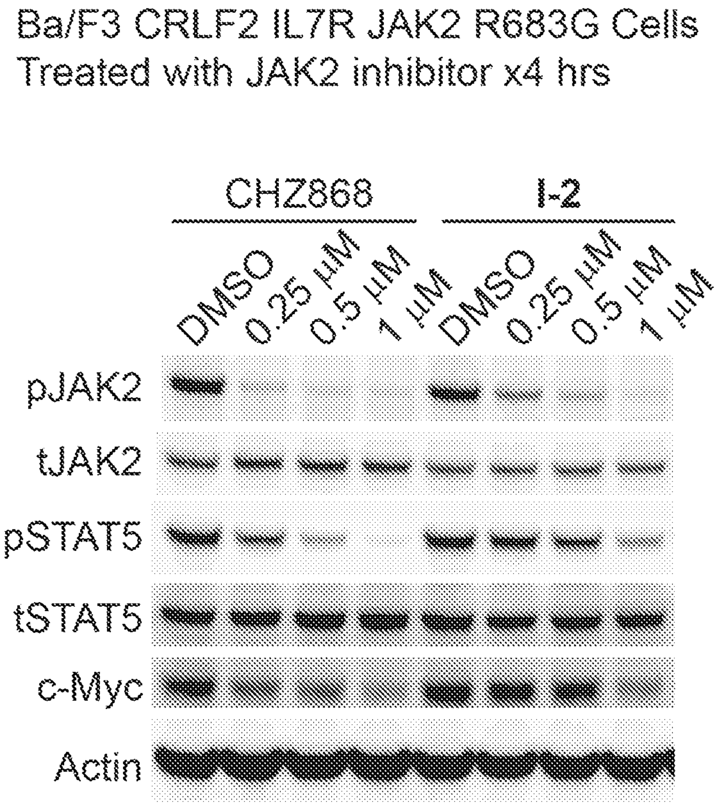
FIG. 1. Ba/F3 CRLF2 IL7R JAK2 R683G cells were treated with various concentrations of the JAK2 inhibitors CHZ868 and Compound I-2. Cell pellets were lysed with Cell Lysis Buffer (Cell Signaling Technology) and then immunoblotting was performed with pJAK2 (#3771), pSTAT5 (#4322), c-Myc (#9402), JAK2 (#3230), STAT5 (#9363 or 94205), and β-actin (#4967 or 12620) antibodies from Cell Signaling Technology.
Figure 1:
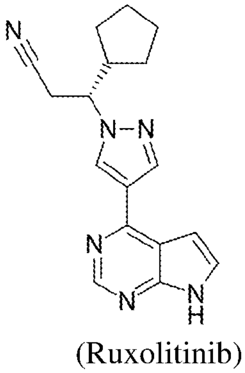
Figure 1:
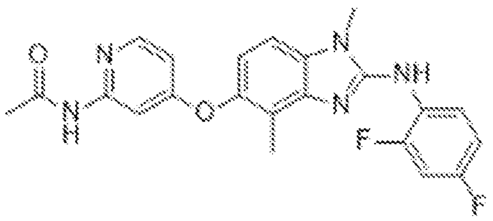

Kinases are implicated in a range of diseases, such as proliferative diseases. Provided herein are compounds of Formula (I') (e.g., Formula (I)), and pharmaceutically acceptable salts, solvates, hydrates, polymorphs, co-crystals, tautomers, stereoisomers, isotopically labeled derivatives, and prodrugs thereof. The provided compounds may be kinase inhibitors. In certain embodiments, the kinase being targeted is a Janus kinase (JAK), ABL1, CDKL2, EPHA4, EPHA8, EPHB2, FLT3, HCK, KIT, LCK, LOK, p38, PDGFRB, RET, SRC, TIE1, CSF1R, DDR1, FLT4, MAP4K2, TRKB, TRKC, CIT, DDR2, HPK1, TIE2, FGR, MAP4K4, TAOK3, MERTK, $CDCl_2L5$, PFTK1, ABL2, CDKL3, or RIPK1. In certain embodiments, the kinase being targeted is JAK (e.g., JAK2). Also provided are pharmaceutical compositions and kits comprising the provided compounds. Further provided are methods of using the provided compounds, pharmaceutical compositions, and kits for treating a disease in a subject in need thereof. In certain embodiments, the disease is a proliferative disease. Further provided are methods of using the provided compounds, pharmaceutical compositions, and kits for inhibiting the activity of a kinase in a subject in need thereof or in a biological sample or cell.

Compounds and Methods of Preparing the Compounds

In one aspect of the invention, provided are compounds of Formula (I'):

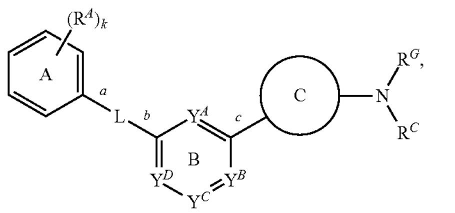

(I')

or a pharmaceutically acceptable salt, solvate, hydrate, polymorph, co-crystal, tautomer, stereoisomer, isotopically labeled derivative, or prodrug thereof, wherein:

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $—OR^1$, $—N(R^1)_2$, $—SR^1$, —CN, —SCN, $—C(=NR^1)R^1$, $—C(=NR^1)OR^1$, $—C(=NR^1)N(R^1)_2$, $—C(=O)R^1$, $—C(=O)OR^1$, $—C(=O)N(R^1)_2$, $—NO_2$, $—NR^1C(=O)R^1$, $—NR^1C(=O)OR^1$, $—NR^1C(=O)N(R^1)_2$, $—OC(=O)R^1$, $—OC(=O)OR^1$, or $—OC(=O)N(R^1)_2$;

each instance of $R^1$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^1$ attached to a nitrogen atom are joined to form a substituted or unsubstituted heterocyclic ring or substituted or unsubstituted heteroaryl ring;

k is 0, 1, 2, 3, 4, or 5;

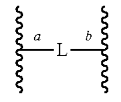

is

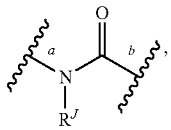, 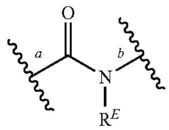, 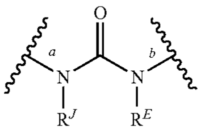,

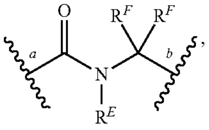, or 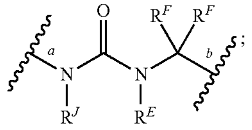;

$R^E$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

or $R^E$ and one instance of $R^B$ are joined to form a substituted or unsubstituted, heterocyclic or heteroaryl ring;

each instance of $R^F$ is independently hydrogen, halogen, or substituted or unsubstituted alkyl;

$R^J$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$Y^A$ is N or $CR^B$;

$Y^B$ is N or $CR^B$;

$Y^C$ is N or $CR^B$;

$Y^D$ is N or $CR^B$;

each instance of $R^B$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^1$, $-N(R^1)_2$, $-SR^1$, $-CN$, $-SCN$, $-C(=NR^1)R^1$, $-C(=NR^1)OR^1$, $-C(=NR^1)N(R^1)_2$, $-C(=O)R^1$, $-C(=O)OR^1$, $-C(=O)N(R^1)_2$, $-NO_2$, $-NR^1C(=O)R^1$, $-NR^1C(=O)OR^1$, $-NR^1C(=O)N(R^1)_2$, $-OC(=O)R^1$, $-OC(=O)OR^1$, or $-OC(=O)N(R^1)_2$;

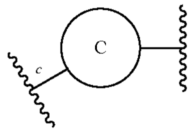

is

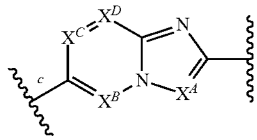, 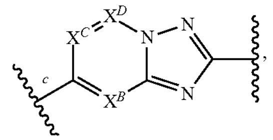,

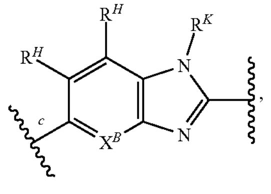, or 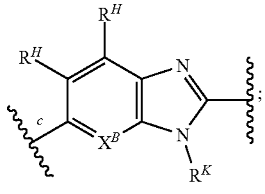;

$X^A$ is N or $CR^H$;

$X^B$ is N or $CR^H$;

$X^C$ is N or $CR^H$;

$X^D$ is N or $CR^H$;

each instance of $R^H$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^1$, $-N(R^1)_2$, $-SR^1$, $-CN$, $-SCN$, $-C(=NR^1)R^1$, $-C(=NR^1)OR^1$, $-C(=NR^1)N(R^1)_2$, $-C(=O)R^1$, $-C(=O)OR^1$, $-C(=O)N(R^1)_2$, $-NO_2$, $-NR^1C(=O)R^1$, $-NR^1C(=O)OR^1$, $-NR^1C(=O)N(R^1)_2$, $-OC(=O)R^1$, $-OC(=O)OR^1$, or $-OC(=O)N(R^1)_2$;

$R^K$ is hydrogen, substituted or unsubstituted alkyl, $-C(=O)R^1$, $-C(=O)OR^1$, $-C(=O)N(R^1)_2$, or a nitrogen protecting group;

$R^C$ is hydrogen, substituted or unsubstituted alkyl, or a nitrogen protecting group;

$R^G$ is

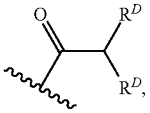

hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-C(=NR^1)R^1$, $-C(=NR^1)OR^1$, $-C(=NR^1)N(R^1)_2$, $-C(=O)R^1$, $-C(=O)OR^1$, $-C(=O)N(R^1)_2$, or a nitrogen protecting group; and each instance of $R^D$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^1$, $-N(R^1)_2$, $-SR^1$, $-CN$, $-SCN$, $-C(=NR^1)R^1$, $-C(=NR^1)OR^1$, $-C(=NR^1)N(R^1)_2$, $-C(=O)R^1$, $-C(=O)OR^1$, $-C(=O)N(R^1)_2$, $-NO_2$, $-NR^1C(=O)R^1$, $-NR^1C(=O)OR^1$, $-NR^1C(=O)N(R^1)_2$, $-OC(=O)R^1$, $-OC(=O)OR^1$, or $-OC(=O)N(R^1)_2$;

or two instances of $R^D$ are joined to form a substituted or unsubstituted, carbocyclic or heterocyclic ring;

provided that when each of $X^A$, $X^B$, $X^C$, and $X^D$ is CH; each of $Y^A$, $Y^B$, $Y^C$, and $Y^D$ is $CR^B$; and

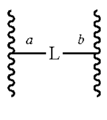

is

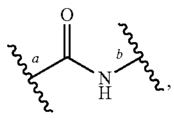 [SMILES: *NC(*)=O], then at least one instance of $R^D$ is not hydrogen and $R^G$ is not —C(=O)$CH_3$; and provided that the compound is not of the formula:

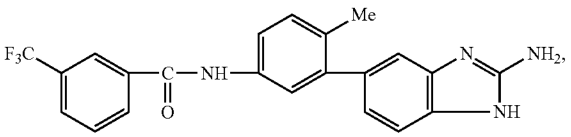 [SMILES: Cc1ccc(NC(=O)c2cccc(C(F)(F)F)c2)cc1-c1ccc2[nH]c(N)nc2c1]

or a pharmaceutically acceptable salt thereof.

In certain embodiments, $R^G$ is

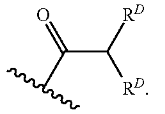

In certain embodiments, $R^G$ is hydrogen. In certain embodiments, $R^G$ is not hydrogen. In certain embodiments, $R^G$ is substituted or unsubstituted alkyl. In certain embodiments, $R^G$ is unsubstituted alkyl. In certain embodiments, $R^G$ is unsubstituted, $C_{1-6}$ alkyl. In certain embodiments, $R^G$ is Me. In certain embodiments, $R^G$ is Et, Pr, or Bu. In certain embodiments, $R^G$ is substituted $C_{1-6}$ alkyl. In certain embodiments, $R^G$ is substituted methyl. In certain embodiments, $R^G$ is substituted ethyl, substituted propyl, or substituted butyl. In certain embodiments, $R^G$ is substituted or unsubstituted alkenyl. In certain embodiments, $R^G$ is substituted or unsubstituted, $C_{2-6}$ alkenyl (e.g., substituted or unsubstituted vinyl or substituted or unsubstituted allyl). In certain embodiments, $R^G$ is substituted or unsubstituted alkynyl. In certain embodiments, $R^G$ is substituted or unsubstituted, $C_{2-6}$ alkynyl (e.g., substituted or unsubstituted ethynyl). In certain embodiments, $R^G$ is substituted or unsubstituted carbocyclyl. In certain embodiments, $R^G$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, $R^G$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, $R^G$ is substituted or unsubstituted heterocyclyl (e.g., substituted or unsubstituted, 3- to 7-membered, monocyclic heterocyclyl). In certain embodiments, $R^G$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, $R^G$ is substituted or unsubstituted aryl. In certain embodiments, $R^G$ is substituted or unsubstituted phenyl. In certain embodiments, $R^G$ is substituted or unsubstituted naphthyl. In certain embodiments, $R^G$ is substituted or unsubstituted heteroaryl. In certain embodiments, $R^G$ is substituted or unsubstituted, 5- to 6-membered, monocyclic heteroaryl. In certain embodiments, $R^G$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, $R^G$ is substituted or unsubstituted pyridinyl, substituted or unsubstituted pyrazinyl, substituted or unsubstituted pyrimidinyl, or substituted or unsubstituted pyridazinyl. In certain embodiments, $R^G$ is —C(=$NR^1$)$R^1$. In certain embodiments, $R^G$ is —C(=$NR^1$)$OR^1$. In certain embodiments, $R^G$ is —C(=$NR^1$)N($R^1$)$_2$. In certain embodiments, $R^G$ is —C(=O)$R^1$. In certain embodiments, $R^G$ is not —C(=O)$R^1$. In certain embodiments, $R^G$ is not —C(=O) (substituted or unsubstituted alkyl). In certain embodiments, $R^G$ is not —C(=O)$CH_3$. In certain embodiments, $R^G$ is —C(=O)$OR^1$. In certain embodiments, $R^G$ is —C(=O)N ($R^1$)$_2$. In certain embodiments, $R^G$ is a nitrogen protecting group (e.g., Bn, Boc, Cbz, Fmoc, trifluoroacetyl, triphenylmethyl, acetyl, or Ts).

In one aspect of the present invention, provided are compounds of Formula (I):

(I)

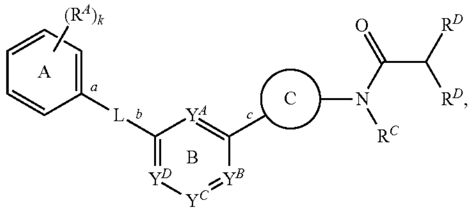

and pharmaceutically acceptable salts, solvates, hydrates, polymorphs, co-crystals, tautomers, stereoisomers, isotopically labeled derivatives, and prodrugs thereof, wherein:

each instance of $R^A$ is independently halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^1$, —N($R^1$)$_2$, —$SR^1$, —CN, —SCN, —C(=$NR^1$)$R^1$, —C(=$NR^1$)$OR^1$, —C(=$NR^1$)N ($R^1$)$_2$, —C(=O)$R^1$, —C(=O)$OR^1$, —C(=O)N($R^1$)$_2$, —$NO_2$, —$NR^1$C(=O)$R^1$, —$NR^1$C(=O)$OR^1$, —$NR^1$C (=O)N($R^1$)$_2$, —OC(=O)$R^1$, —OC(=O)$OR^1$, or —OC (=O)N($R^1$)$_2$;

each instance of $R^1$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^1$ attached to a nitrogen atom are joined to form a substituted or unsubstituted heterocyclic ring or substituted or unsubstituted heteroaryl ring;

k is 0, 1, 2, 3, 4, or 5;

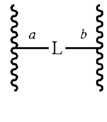

is

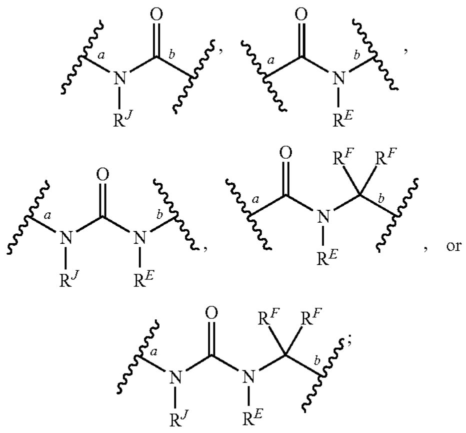

$R^E$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

or $R^E$ and one instance of $R^B$ are joined to form a substituted or unsubstituted, heterocyclic or heteroaryl ring;

each instance of $R^F$ is independently hydrogen, halogen, or substituted or unsubstituted alkyl;

$R^J$ is hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group;

$Y^A$ is N or $CR^B$;

$Y^B$ is N or $CR^B$;

$Y^C$ is N or $CR^B$;

$Y^D$ is N or $CR^B$;

each instance of $R^B$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^1$, $-N(R^1)_2$, $-SR^1$, $-CN$, $-SCN$, $-C(=NR^1)R^1$, $-C(=NR^1)OR^1$, $-C(=NR^1)N(R^1)_2$, $-C(=O)R^1$, $-C(=O)OR^1$, $-C(=O)N(R^1)_2$, $-NO_2$, $-NR^1C(=O)R^1$, $-NR^1C(=O)OR^1$, $-NR^1C(=O)N(R^1)_2$, $-OC(=O)R^1$, $-OC(=O)OR^1$, or $-OC(=O)N(R^1)_2$;

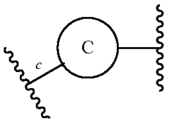

is

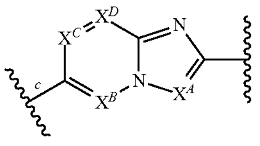

or

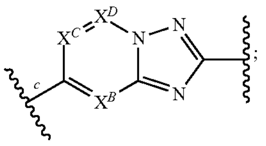

$X^A$ is N or $CR^H$;

$X^B$ is N or $CR^H$;

$X^C$ is N or $CR^H$;

$X^D$ is N or $CR^H$;

each instance of $R^H$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^1$, $-N(R^1)_2$, $-SR^1$, $-CN$, $-SCN$, $-C(=NR^1)R^1$, $-C(=NR^1)OR^1$, $-C(=NR^1)N(R^1)_2$, $-C(=O)R^1$, $-C(=O)OR^1$, $-C(=O)N(R^1)_2$, $-NO_2$, $-NR^1C(=O)R^1$, $-NR^1C(=O)OR^1$, $-NR^1C(=O)N(R^1)_2$, $-OC(=O)R^1$, $-OC(=O)OR^1$, or $-OC(=O)N(R^1)_2$;

$R^C$ is hydrogen, substituted or unsubstituted alkyl, or a nitrogen protecting group; and each instance of $R^D$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{aa}$, $-N(R^1)_2$, $-SR^1$, $-CN$, $-SCN$, $-C(=NR^1)R^1$, $-C(=NR^1)OR^1$, $-C(=NR^1)N(R^1)_2$, $-C(=O)R^1$, $-C(=O)OR^1$, $-C(=O)N(R^1)_2$, $-NO_2$, $-NR^1C(=O)R^1$, $-NR^1C(=O)OR^1$, $-NR^1C(=O)N(R^1)_2$, $-OC(=O)R^1$, $-OC(=O)OR^1$, or $-OC(=O)N(R^1)_2$;

or two instances of $R^D$ are joined to form a substituted or unsubstituted, carbocyclic or heterocyclic ring;

provided that when each of $X^A$, $X^B$, $X^C$, and $X^D$ is CH; each of $Y^A$, $Y^B$, $Y^C$, and $Y^D$ is $CR^B$; and

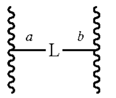

is

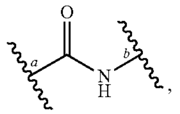 [SMILES: *NC(*)=O]

then at least one instance of $R^D$ is not hydrogen.

is Ring A. In certain embodiments,
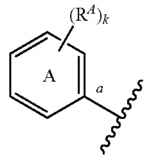
is
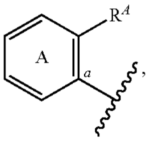,
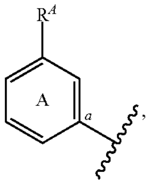, or
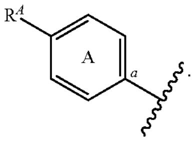.
In certain embodiments,
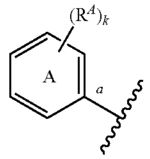
is
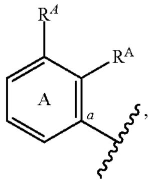,
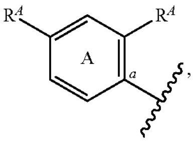,
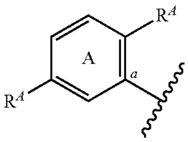,
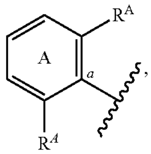,
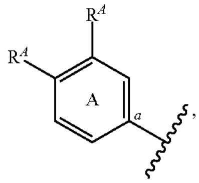, or
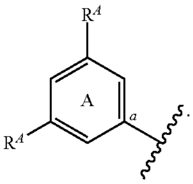.
In certain embodiments
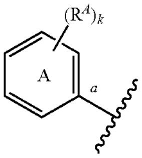
is
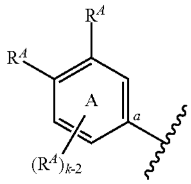
(e.g.,
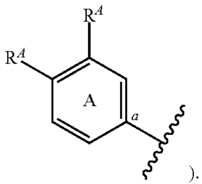
).
In certain embodiments,
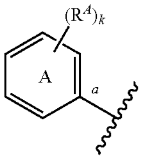
is
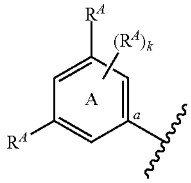
(e.g.,
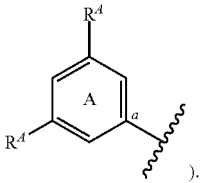
).
In certain embodiments,
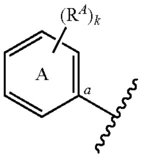
is
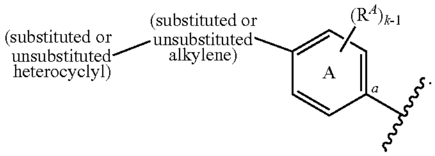.

In certain embodiments,
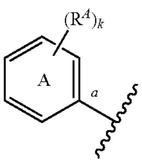
is
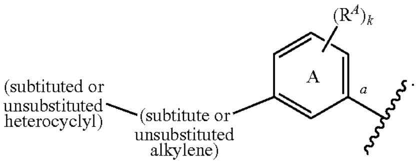
.
In certain embodiments,
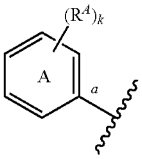
is
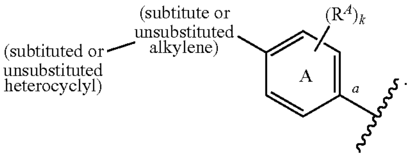
.
In certain embodiments,
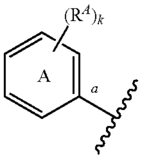
is
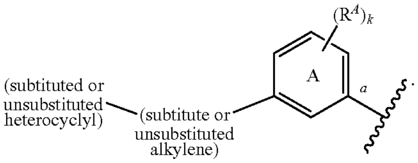
.
In certain embodiments,
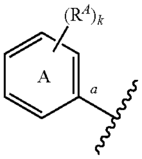
is
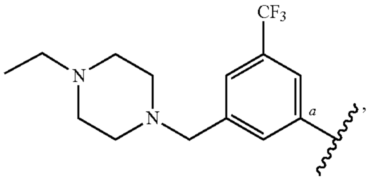
,
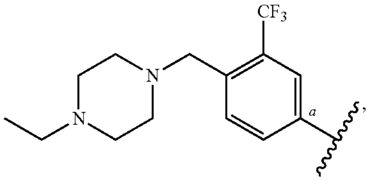
,
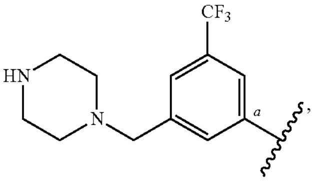
,
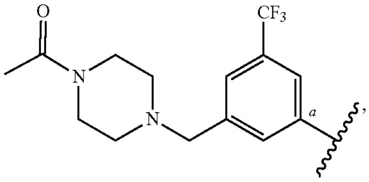
,
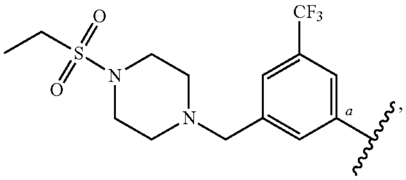
,
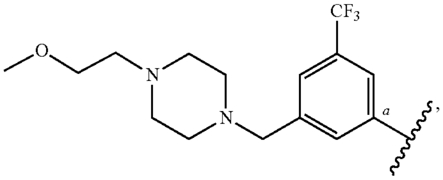
,
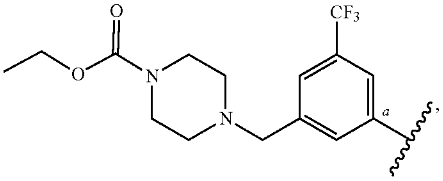
,
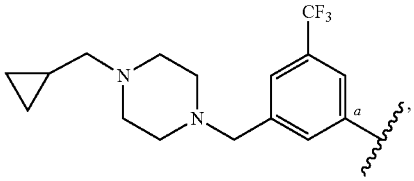
, or -continued

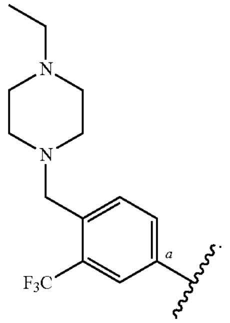 [SMILES: *c1ccc(CN2CCN(CC)CC2)c(C(F)(F)F)c1]

When Formula (I') includes two or more instances of a moiety, unless otherwise provided, any two instances of the moiety may be the same or different from each other.

When Formula (I) includes two or more instances of a moiety, unless otherwise provided, any two instances of the moiety may be the same or different from each other.

In certain embodiments, at least one instance of $R^A$ is halogen (e.g., F, Cl, or Br). In certain embodiments, at least one instance of $R^A$ is substituted alkyl (e.g., alkyl substituted with one or more instances of halogen (e.g., F)). In certain embodiments, at least one instance of $R^A$ is $—CF_3$. In certain embodiments, at least one instance of $R^A$ is -(substituted or unsubstituted alkylene)-(substituted or unsubstituted heterocyclyl). In certain embodiments, at least one instance of $R^A$ is -(substituted or unsubstituted, $C_{1-3}$ alkylene)-(substituted or unsubstituted, monocyclic, 5- or 6-membered heterocyclyl comprising in the heterocyclic system 1 or 2 heteroatoms independently selected from the group consisting of oxygen and nitrogen). In certain embodiments, at least one instance of $R^A$ is -(substituted or unsubstituted, $C_{1-3}$ alkylene)-(substituted or unsubstituted piperazinyl). In certain embodiments, at least one instance of $R^A$ is

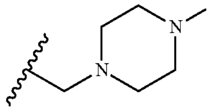
(hydrogen or substituted or unsubstituted alkyl).

In certain embodiments, at least one instance of $R^A$ is

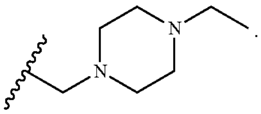 [SMILES: *CN1CCN(CC)CC1]

In certain embodiments, at least one instance of $R^A$ is

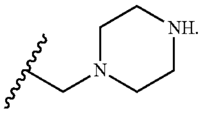 [SMILES: *CN1CCNCC1]

In certain embodiments, at least one instance of $R^A$ is

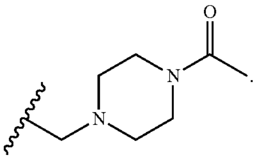 [SMILES: *CN1CCN(C(C)=O)CC1]

In certain embodiments, at least one instance of $R^A$ is

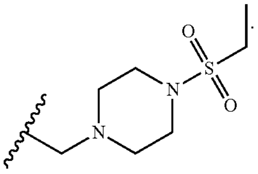 [SMILES: *CN1CCN(S(=O)(=O)CC)CC1]

In certain embodiments, at least one instance of $R^A$ is

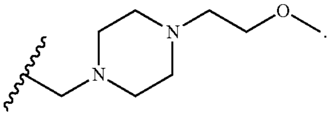 [SMILES: *CN1CCN(CCOC)CC1]

In certain embodiments, at least one instance of $R^A$ is

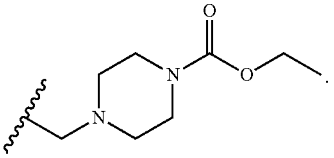 [SMILES: *CN1CCN(C(=O)OCC)CC1]

In certain embodiments, at least one instance of $R^A$ is

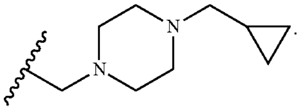 [SMILES: *CN1CCN(CC2CC2)CC1]

In certain embodiments, at least one instance of $R^A$ is unsubstituted alkyl. In certain embodiments, at least one instance of $R^A$ is unsubstituted, $C_{1-6}$ alkyl. In certain embodiments, at least one instance of $R^A$ is Me. In certain embodiments, at least one instance of $R^A$ is Et, Pr, or Bu. In certain embodiments, at least one instance of $R^A$ is substituted $C_{1-6}$ alkyl. In certain embodiments, at least one instance of $R^A$ is substituted methyl. In certain embodiments, at least one instance of $R^A$ is substituted ethyl, substituted propyl, or substituted butyl. In certain embodiments, at least one instance of $R^A$ is substituted or unsubstituted alkenyl. In certain embodiments, at least one instance of $R^A$ is substituted or unsubstituted, $C_{2-6}$ alkenyl (e.g., substituted or unsubstituted vinyl or substituted or unsubstituted allyl). In certain embodiments, at least one instance of $R^A$ is substituted or unsubstituted alkynyl. In certain embodiments, at least one instance of $R^A$ is substituted or unsubstituted, $C_{2-6}$ alkynyl (e.g., substituted or unsubstituted ethynyl). In certain embodiments, at least one instance of $R^A$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, at least one instance of $R^A$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, at least one instance of $R^A$ is substituted or unsubstituted heterocyclyl (e.g., substituted or unsubstituted, 3- to 7-membered, monocyclic heterocyclyl). In certain embodiments, at least one instance of $R^A$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, at least one instance of $R^A$ is substituted or unsubstituted aryl. In certain embodiments, at least one instance of $R^A$ is substituted or unsubstituted phenyl. In certain embodiments, at least one instance of $R^A$ is substituted or unsubstituted naphthyl. In certain embodiments, at least one instance of $R^A$ is substituted or unsubstituted heteroaryl. In certain embodiments, at least one instance of $R^A$ is substituted or unsubstituted, 5- to 6-membered, monocyclic heteroaryl. In certain embodiments, at least one instance of $R^A$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, at least one instance of $R^A$ is substituted or unsubstituted pyridinyl, substituted or unsubstituted pyrazinyl, substituted or unsubstituted pyrimidinyl, or substituted or unsubstituted pyridazinyl. In certain embodiments, at least one instance of $R^A$ is substituted or unsubstituted, 9- to 10-membered, bicyclic heteroaryl. In certain embodiments, at least one instance of $R^A$ is —$OR^1$ (e.g., —OH, —O(substituted or unsubstituted, $C_{1-6}$ alkyl) (e.g., —OMe, —$OCF_3$, —OEt, —OPr, —OBu, or —OBn), or —O(substituted or unsubstituted phenyl) (e.g., —OPh)). In certain embodiments, at least one instance of $R^A$ is —OMe. In certain embodiments, at least one instance of $R^A$ is —$SR^1$ (e.g., —SH, —S(substituted or unsubstituted, $C_{1-6}$ alkyl) (e.g., —SMe, —$SCF_3$, —SEt, —SPr, —SBu, or —SBn), or —S(substituted or unsubstituted phenyl) (e.g., —SPh)). In certain embodiments, at least one instance of $R^A$ is —$N(R^{aa})_2$ (e.g., —$NH_2$, —NH(substituted or unsubstituted, $C_{1-6}$ alkyl) (e.g., —NHMe), or —N(substituted or unsubstituted, $C_{1-6}$ alkyl)-(substituted or unsubstituted, $C_{1-6}$ alkyl) (e.g., —$NMe_2$)). In certain embodiments, at least one instance of $R^A$ is —CN or —SCN. In certain embodiments, at least one instance of $R^A$ is —$NO_2$. In certain embodiments, at least one instance of $R^A$ is —$C(=NR^1)R^1$, —$C(=NR^1)OR^1$, or —$C(=NR^1)N(R^1)_2$. In certain embodiments, at least one instance of $R^A$ is —$C(=O)R^1$ (e.g., —C(=O)(substituted or unsubstituted alkyl) (e.g., —C(=O)Me) or —C(=O)(substituted or unsubstituted phenyl)). In certain embodiments, at least one instance of $R^A$ is —$C(=O)OR^1$ (e.g., —C(=O)OH, —C(=O)O(substituted or unsubstituted alkyl) (e.g., —C(=O)OMe), or —C(=O)O(substituted or unsubstituted phenyl)). In certain embodiments, at least one instance of $R^A$ is —$C(=O)N(R^{aa})_2$ (e.g., —$C(=O)NH_2$, —C(=O)NH(substituted or unsubstituted alkyl) (e.g., —C(=O)NHMe), —C(=O)NH (substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, at least one instance of $R^A$ is —$NR^1C(=O)R^1$ (e.g., —NHC(=O)(substituted or unsubstituted, $C_{1-6}$ alkyl) (e.g., —NHC(=O)Me) or —NHC(=O)(substituted or unsubstituted phenyl)). In certain embodiments, at least one instance of $R^A$ is —$NR^1C(=O)OR^1$. In certain embodiments, at least one instance of $R^A$ is —$NR^1C(=O)N(R^{aa})_2$ (e.g., —NHC(=O)$NH_2$, —NHC(=O)NH(substituted or unsubstituted, $C_{1-6}$ alkyl) (e.g., —NHC(=O)NHMe)). In certain embodiments, at least one instance of $R^A$ is —$OC(=O)R^1$ (e.g., —OC(=O)(substituted or unsubstituted alkyl) or —OC(=O)(substituted or unsubstituted phenyl)), —$OC(=O)OR^1$ (e.g., —OC(=O)O(substituted or unsubstituted alkyl) or —OC(=O)O(substituted or unsubstituted phenyl)), or —$OC(=O)N(R^{aa})_2$ (e.g., —$OC(=O)NH_2$, —OC(=O)NH (substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)).

In certain embodiments, at least one instance of $R^1$ is hydrogen. In certain embodiments, each instance of $R^1$ is hydrogen. In certain embodiments, at least one instance of $R^1$ is not hydrogen. In certain embodiments, no instance of $R^1$ is hydrogen. In certain embodiments, at least one instance of $R^1$ is substituted alkyl (e.g., alkyl substituted with one or more instances of halogen (e.g., F)). In certain embodiments, at least one instance of $R^1$ is unsubstituted alkyl. In certain embodiments, at least one instance of $R^1$ is unsubstituted, $C_{1-6}$ alkyl. In certain embodiments, at least one instance of $R^1$ is Me. In certain embodiments, at least one instance of $R^1$ is Et, Pr, or Bu. In certain embodiments, at least one instance of $R^1$ is substituted $C_{1-6}$ alkyl. In certain embodiments, at least one instance of $R^1$ is substituted methyl. In certain embodiments, at least one instance of $R^1$ is substituted ethyl, substituted propyl, or substituted butyl. In certain embodiments, at least one instance of $R^1$ is substituted or unsubstituted alkenyl. In certain embodiments, at least one instance of $R^1$ is substituted or unsubstituted, $C_{2-6}$ alkenyl (e.g., substituted or unsubstituted vinyl or substituted or unsubstituted allyl). In certain embodiments, at least one instance of $R^1$ is substituted or unsubstituted alkynyl. In certain embodiments, at least one instance of $R^1$ is substituted or unsubstituted, $C_{2-6}$ alkynyl (e.g., substituted or unsubstituted ethynyl). In certain embodiments, at least one instance of $R^1$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, at least one instance of $R^1$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, at least one instance of $R^1$ is substituted or unsubstituted heterocyclyl (e.g., substituted or unsubstituted, 3- to 7-membered, monocyclic heterocyclyl). In certain embodiments, at least one instance of $R^1$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, at least one instance of $R^1$ is substituted or unsubstituted aryl. In certain embodiments, at least one instance of $R^1$ is substituted or unsubstituted phenyl. In certain embodiments, at least one instance of $R^1$ is substituted or unsubstituted naphthyl. In certain embodiments, at least one instance of $R^1$ is substituted or unsubstituted heteroaryl. In certain embodiments, at least one instance of $R^1$ is substituted or unsubstituted, 5- to 6-membered, monocyclic heteroaryl. In certain embodiments, at least one instance of $R^1$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, at least one instance of $R^1$ is substituted or unsubstituted pyridinyl, substituted or unsubstituted pyrazinyl, substituted or unsubstituted pyrimidinyl, or substituted or unsubstituted pyridazinyl. In certain embodiments, at least one instance of $R^1$ is substituted or unsubstituted, 9- to 10-membered, bicyclic heteroaryl. In certain embodiments, at least one instance of $R^1$ is a nitrogen protecting group (e.g., Bn, Boc, Cbz, Fmoc, trifluoroacetyl, triphenylmethyl, acetyl, or Ts) when attached to a nitrogen atom. In certain embodiments, at least one instance of $R^1$ is an oxygen protecting group (e.g., silyl, TBDPS, TBDMS, TIPS, TES, TMS, MOM, THP, t-Bu, Bn, allyl, acetyl, pivaloyl, or benzoyl) when attached to an oxygen atom. In certain embodiments, two instances of $R^1$ are joined to form substituted or unsubstituted heterocyclyl (e.g., substituted or unsubstituted, 3- to 7-membered, monocyclic heterocyclyl). In certain embodiments, two instances of $R^1$ are joined to form substituted or unsubstituted heteroaryl (e.g., substituted or unsubstituted, 5- to 6-membered, monocyclic heteroaryl).

In certain embodiments, k is 0. In certain embodiments, k is 1. In certain embodiments, k is 2. In certain embodiments, k is 3. In certain embodiments, k is 4. In certain embodiments, k is 5.

In certain embodiments,

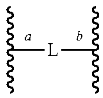

is

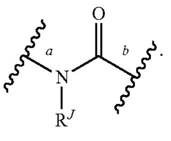

In certain embodiments,

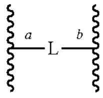

is

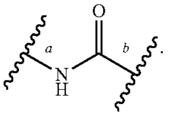

In certain embodiments,

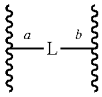

is

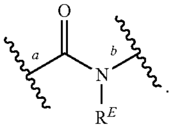

In certain embodiments,

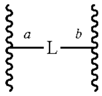

is

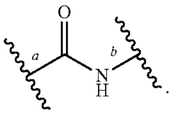 [SMILES: *NC(*)=O]

In certain embodiments,

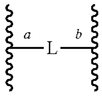

is

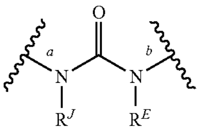

(e.g., 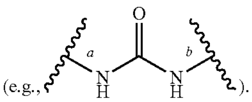).

In certain embodiments,

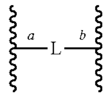

is

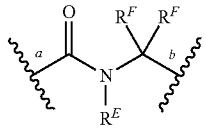

(e.g.,

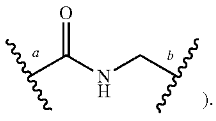

).

In certain embodiments,

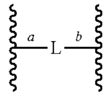

is

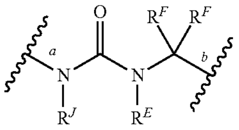

(e.g.,

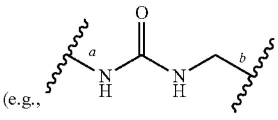

).

In certain embodiments, $R^E$ is hydrogen. In certain embodiments, $R^E$ is substituted or unsubstituted alkyl (e.g., substituted or unsubstituted, $C_{1-6}$ alkyl). In certain embodiments, $R^E$ is Me. In certain embodiments, $R^E$ is Et, Pr, Bu, substituted methyl, substituted ethyl, substituted propyl, or substituted butyl. In certain embodiments, $R^E$ is substituted or unsubstituted phenyl. In certain embodiments, $R^E$ is a nitrogen protecting group (e.g., Bn, Boc, Cbz, Fmoc, trifluoroacetyl, triphenylmethyl, acetyl, or Ts).

In certain embodiments, $R^E$ and one instance of $R^B$ are joined to form a substituted or unsubstituted, heterocyclic or heteroaryl ring. In certain embodiments, $R^E$ and one instance of $R^B$ are joined to form a substituted or unsubstituted, heterocyclic ring (e.g., substituted or unsubstituted, 3- to 7-membered, monocyclic heterocyclic ring). In certain embodiments, $R^E$ and one instance of $R^B$ are joined to form a substituted or unsubstituted, heteroaryl ring (e.g., substituted or unsubstituted, 5- to 6-membered, monocyclic heteroaryl ring).

In certain embodiments, at least one instance of RF is hydrogen. In certain embodiments, each instance of RF is hydrogen. In certain embodiments, at least one instance of $R^F$ is halogen (e.g., F, Cl, or Br). In certain embodiments, at least one instance of $R^F$ is substituted alkyl (e.g., alkyl substituted with one or more instances of halogen (e.g., F)). In certain embodiments, at least one instance of $R^F$ is unsubstituted alkyl. In certain embodiments, at least one instance of $R^F$ is unsubstituted, $C_{1-6}$ alkyl. In certain embodiments, at least one instance of $R^F$ is Me. In certain embodiments, at least one instance of $R^F$ is Et, Pr, or Bu. In certain embodiments, at least one instance of $R^F$ is substituted $C_{1-6}$ alkyl. In certain embodiments, at least one instance of $R^F$ is substituted methyl. In certain embodiments, at least one instance of $R^F$ is substituted ethyl, substituted propyl, or substituted butyl.

In certain embodiments, $R^J$ is hydrogen. In certain embodiments, $R^J$ is substituted or unsubstituted alkyl (e.g., substituted or unsubstituted, $C_{1-6}$ alkyl). In certain embodiments, $R^J$ is Me. In certain embodiments, $R^J$ is Et, Pr, Bu, substituted methyl, substituted ethyl, substituted propyl, or substituted butyl. In certain embodiments, $R^J$ is substituted or unsubstituted phenyl. In certain embodiments, $R^J$ is a nitrogen protecting group (e.g., Bn, Boc, Cbz, Fmoc, trifluoroacetyl, triphenylmethyl, acetyl, or Ts).

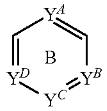

is Ring B. In certain embodiments,

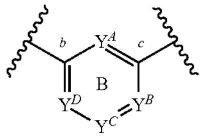

is

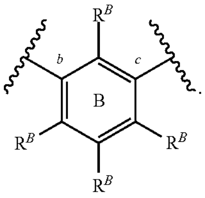

In certain embodiments,

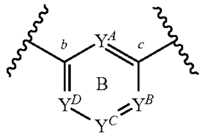

is

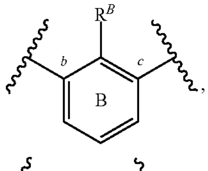

,

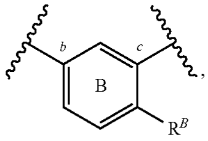

,

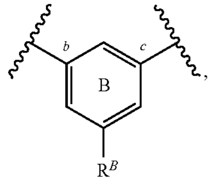

, or

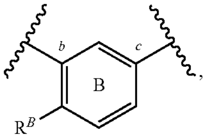

, provided that $R^B$ is not hydrogen. In certain embodiments,

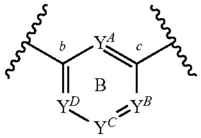

is

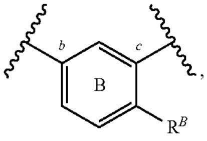, provided that $R^B$ is not hydrogen. In certain embodiments,

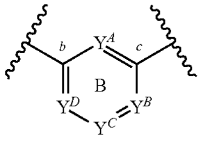

is

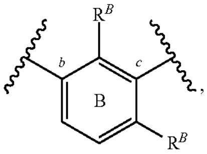, 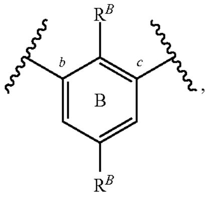, 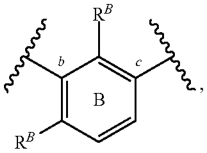, 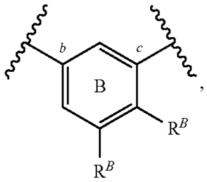, 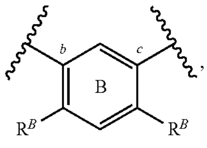, or 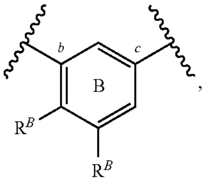, provided that each instance of $R^B$ is not hydrogen. In certain embodiments,

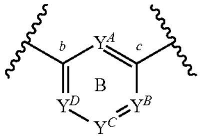

is

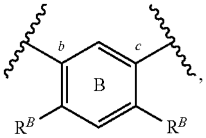, provided that each instance of $R^B$ is not hydrogen. In certain embodiments,

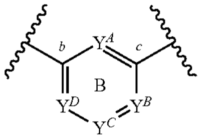

is

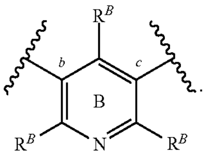.

In certain embodiments,

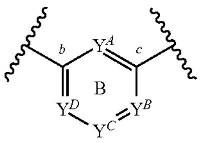

is

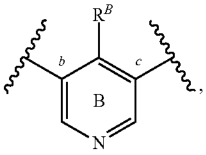, 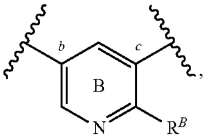, or 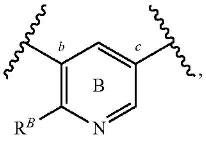, provided that $R^B$ is not hydrogen. In certain embodiments,

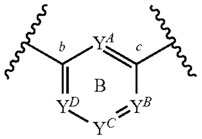

is

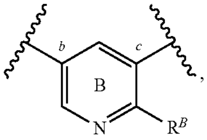

provided that $R^B$ is not hydrogen. In certain embodiments,

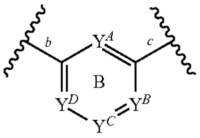

is

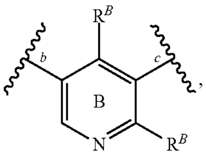,

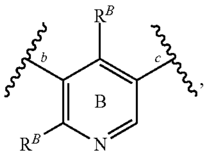, or

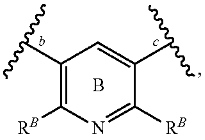, provided that each instance of $R^B$ is not hydrogen. In certain embodiments,

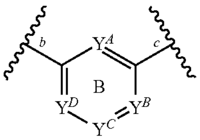

is

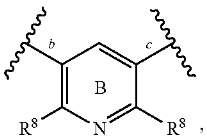, provided that each instance of $R^B$ is not hydrogen. In certain embodiments,

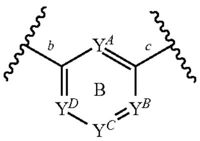

is

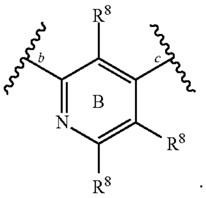.

In certain embodiments,

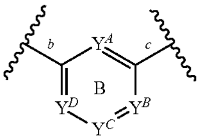

is

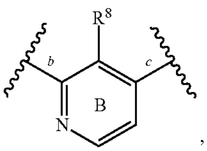,

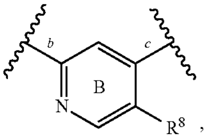, or

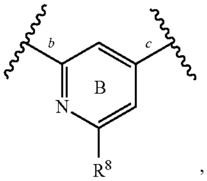, provided that $R^B$ is not hydrogen. In certain embodiments,

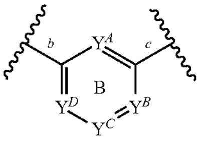

is

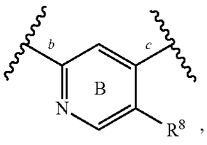, provided that $R^B$ is not hydrogen. In certain embodiments,

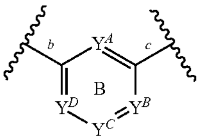

is

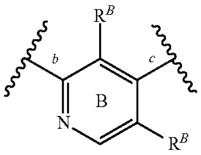
,
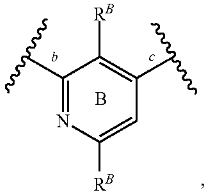
, or
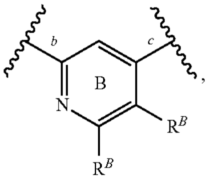
, provided that each instance of $R^B$ is not hydrogen. In certain embodiments,

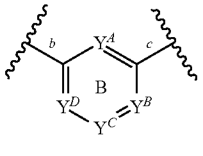

is

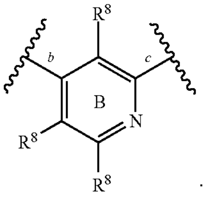
.

In certain embodiments,

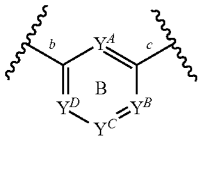

is

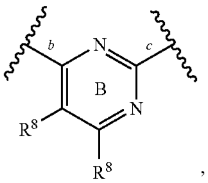
,
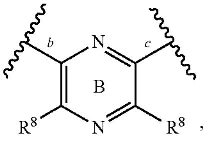
,

-continued

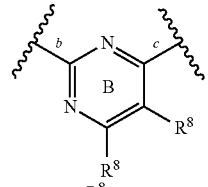
,
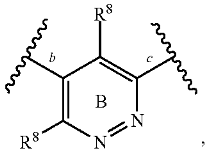
,
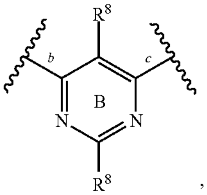
, or
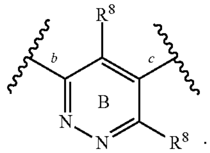
.

In certain embodiments, at least one instance of $R^B$ is hydrogen. In certain embodiments, each instance of $R^B$ is hydrogen. In certain embodiments, at least one instance of $R^B$ is not hydrogen. In certain embodiments, at least one instance of $R^B$ is not hydrogen. In certain embodiments, each instance of $R^B$ is not hydrogen. In certain embodiments, at least one instance of $R^B$ is halogen (e.g., F, Cl, or Br). In certain embodiments, at least one instance of $R^B$ is substituted alkyl (e.g., alkyl substituted with one or more instances of halogen (e.g., F)). In certain embodiments, at least one instance of $R^B$ is $-CF_3$. In certain embodiments, at least one instance of $R^B$ is unsubstituted alkyl. In certain embodiments, at least one instance of $R^B$ is unsubstituted, $C_{1-6}$ alkyl. In certain embodiments, at least one instance of $R^B$ is Me. In certain embodiments, at least one instance of $R^B$ is Et. In certain embodiments, at least one instance of $R^B$ is Pr, or Bu. In certain embodiments, at least one instance of $R^B$ is substituted $C_{1-6}$ alkyl. In certain embodiments, at least one instance of $R^B$ is substituted methyl. In certain embodiments, at least one instance of $R^B$ is substituted ethyl, substituted propyl, or substituted butyl. In certain embodiments, at least one instance of $R^B$ is substituted or unsubstituted alkenyl. In certain embodiments, at least one instance of $R^B$ is substituted or unsubstituted, $C_{2-6}$ alkenyl (e.g., substituted or unsubstituted vinyl or substituted or unsubstituted allyl). In certain embodiments, at least one instance of $R^B$ is substituted or unsubstituted alkynyl. In certain embodiments, at least one instance of $R^B$ is substituted or unsubstituted, $C_{2-6}$ alkynyl (e.g., substituted or unsubstituted ethynyl). In certain embodiments, at least one instance of $R^B$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, at least one instance of $R^B$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, at least one instance of $R^B$ is substituted or unsubstituted heterocyclyl (e.g., substituted or unsubstituted, 3- to 7-membered, monocyclic heterocyclyl). In certain embodiments, at least one instance of $R^B$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, at least one instance of $R^B$ is substituted or unsubstituted aryl. In certain embodiments, at least one instance of $R^B$ is substituted or unsubstituted phenyl. In certain embodiments, at least one instance of $R^B$ is substituted or unsubstituted naphthyl. In certain embodiments, at least one instance of $R^B$ is substituted or unsubstituted heteroaryl. In certain embodiments, at least one instance of $R^B$ is substituted or unsubstituted, 5- to 6-membered, monocyclic heteroaryl. In certain embodiments, at least one instance of $R^B$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, at least one instance of $R^B$ is substituted or unsubstituted pyridinyl, substituted or unsubstituted pyrazinyl, substituted or unsubstituted pyrimidinyl, or substituted or unsubstituted pyridazinyl. In certain embodiments, at least one instance of $R^B$ is substituted or unsubstituted, 9- to 10-membered, bicyclic heteroaryl. In certain embodiments, at least one instance of $R^B$ is —$OR^1$ (e.g., —OH, —O(substituted or unsubstituted, $C_{1-6}$ alkyl) (e.g., —OMe, —$OCF_3$, —OEt, —OPr, —OBu, or —OBn), or —O(substituted or unsubstituted phenyl) (e.g., —OPh)). In certain embodiments, at least one instance of $R^B$ is —OH. In certain embodiments, at least one instance of $R^B$ is —OMe. In certain embodiments, at least one instance of $R^B$ is —$SR^1$ (e.g., —SH, —S(substituted or unsubstituted, $C_{1-6}$ alkyl) (e.g., —SMe, —$SCF_3$, —SEt, —SPr, —SBu, or —SBn), or —S(substituted or unsubstituted phenyl) (e.g., —SPh)). In certain embodiments, at least one instance of $R^B$ is —$N(R^1)_2$ (e.g., —$NH_2$, —NH(substituted or unsubstituted, $C_{1-6}$ alkyl) (e.g., —NHMe), or —N(substituted or unsubstituted, $C_{1-6}$ alkyl)-(substituted or unsubstituted, $C_{1-6}$ alkyl) (e.g., —$NMe_2$)). In certain embodiments, at least one instance of $R^B$ is —CN. In certain embodiments, at least one instance of $R^B$ is —SCN. In certain embodiments, at least one instance of $R^B$ is —$NO_2$. In certain embodiments, at least one instance of $R^B$ is —$C(=NR^1)R^1$, —$C(=NR^1)OR^1$, or —$C(=NR^1)N(R^1)_2$. In certain embodiments, at least one instance of $R^B$ is —$C(=O)R^1$ (e.g., —C(=O)(substituted or unsubstituted alkyl) (e.g., —C(=O)Me) or —C(=O)(substituted or unsubstituted phenyl)). In certain embodiments, at least one instance of $R^B$ is —$C(=O)OR^1$ (e.g., —C(=O)OH, —C(=O)O(substituted or unsubstituted alkyl) (e.g., —C(=O)OMe), or —C(=O)O(substituted or unsubstituted phenyl)). In certain embodiments, at least one instance of $R^B$ is —$C(=O)N(R^1)_2$ (e.g., —$C(=O)NH_2$, —C(=O)NH(substituted or unsubstituted alkyl) (e.g., —C(=O)NHMe), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, at least one instance of $R^B$ is —$NR^1C(=O)R^1$ (e.g., —NHC(=O)(substituted or unsubstituted, $C_{1-6}$ alkyl) (e.g., —NHC(=O)Me) or —NHC(=O)(substituted or unsubstituted phenyl)). In certain embodiments, at least one instance of $R^B$ is —$NR^1C(=O)OR^1$. In certain embodiments, at least one instance of $R^B$ is —$NR^1C(=O)N(R^{aa})_2$ (e.g., —$NHC(=O)NH_2$, —NHC(=O)NH(substituted or unsubstituted, $C_{1-6}$ alkyl) (e.g., —NHC(=O)NHMe)). In certain embodiments, at least one instance of $R^B$ is —$OC(=O)R^1$ (e.g., —OC(=O)(substituted or unsubstituted alkyl) or —OC(=O)(substituted or unsubstituted phenyl)), —$OC(=O)OR^1$ (e.g., —OC(=O)O(substituted or unsubstituted alkyl) or —OC(=O)O(substituted or unsubstituted phenyl)), or —$OC(=O)N(R^1)_2$ (e.g., —$OC(=O)NH_2$, —OC(=O)NH(substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)). In certain embodiments, at least one instance of $R^B$ is halogen, substituted or unsubstituted alkyl, or —$OR^1$.

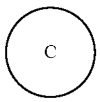

is Ring C. In certain embodiments,

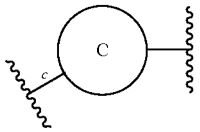

is

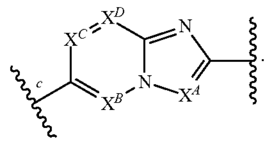

In certain embodiments,

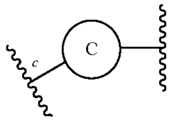

is

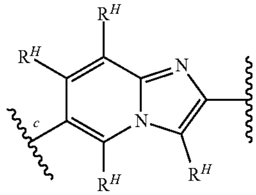
,
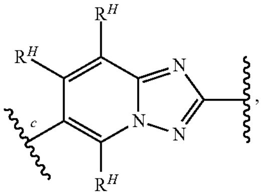
,
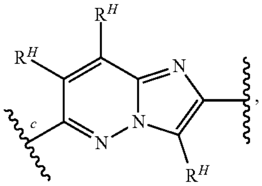
,
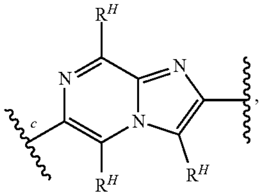
, or
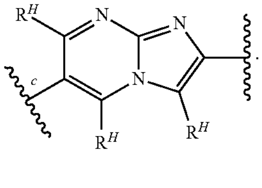

In certain embodiments,
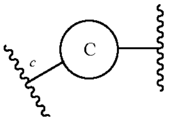
is
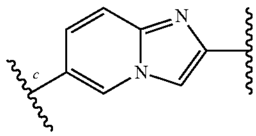,
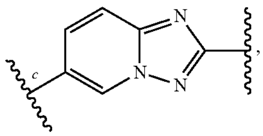,
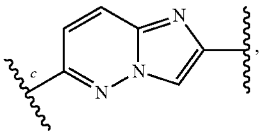,
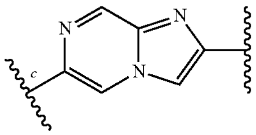, or
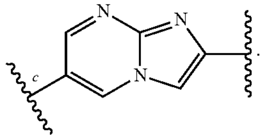.
In certain embodiments,
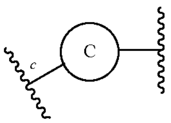
is
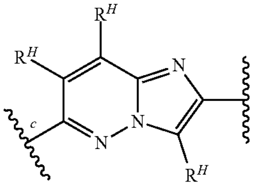
(e.g.,
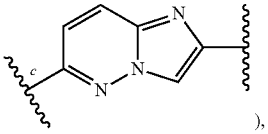
),
In certain embodiments,
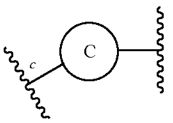
is
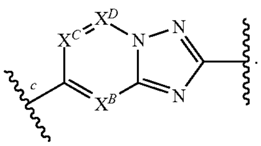.
In certain embodiments,
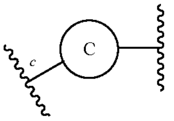
is
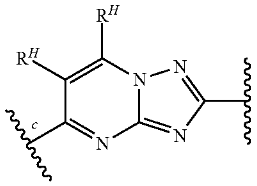
(e.g.,
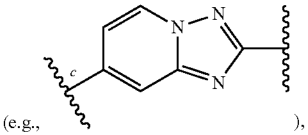
),
In certain embodiments,
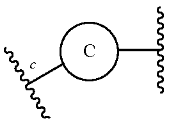
is
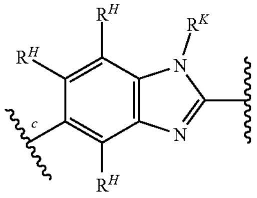
(e.g.,
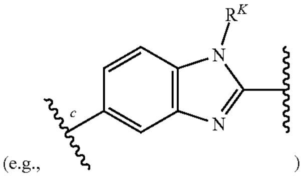
) or
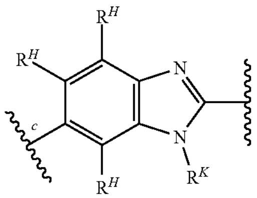
(e.g.,
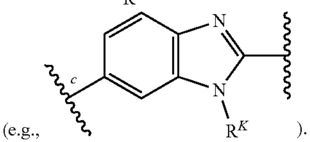
).

In certain embodiments,

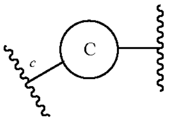

is

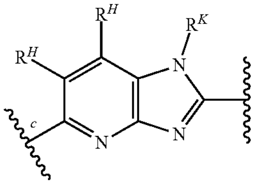

(e.g.,

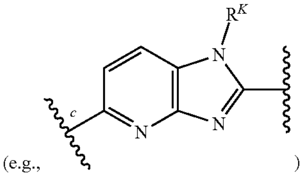

) or

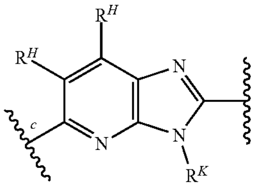

(e.g.,

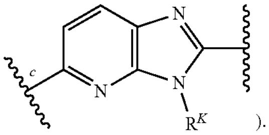

).

In certain embodiments,

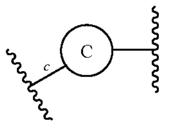

is

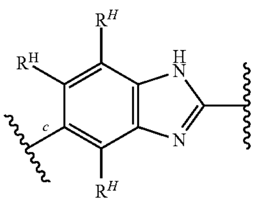

(e.g.,

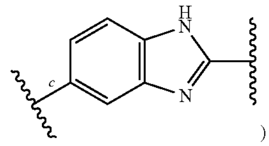

) or

-continued

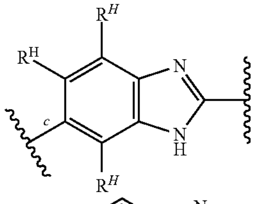

(e.g.,

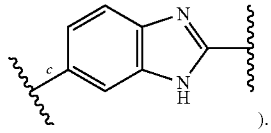

).

In certain embodiments,

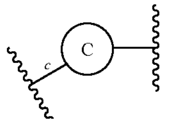

is

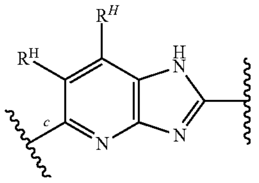

(e.g.,

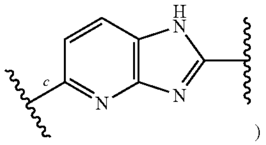

) or

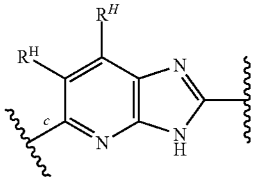

(e.g.,

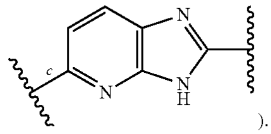

).

In certain embodiments, $R^K$ is hydrogen. In certain embodiments, $R^K$ is substituted or unsubstituted alkyl. In certain embodiments, $R^K$ is hydrogen or substituted or unsubstituted, $C_{1-6}$ alkyl. In certain embodiments, $R^K$ is unsubstituted, $C_{1-6}$ alkyl. In certain embodiments, $R^K$ is Me. In certain embodiments, $R^K$ is Et, Pr, or Bu. In certain embodiments, $R^K$ is substituted $C_{1-6}$ alkyl. In certain embodiments, $R^K$ is substituted methyl. In certain embodiments, $R^K$ is Bn. In certain embodiments, $R^K$ is substituted ethyl, substituted propyl, or substituted butyl. In certain embodiments, $R^K$ is $-C(=O)R^1$. In certain embodiments, $R^K$ is $-C(=O)OR^1$. In certain embodiments, $R^K$ is $-C(=O)N(R^1)_2$. In certain embodiments, $R^K$ is a nitrogen protecting group (e.g., Bn, Boc, Cbz, Fmoc, trifluoroacetyl, triphenylmethyl, acetyl, or Ts).

In certain embodiments, none or only one of $X^A$, $X^B$, $X^C$, and $X^D$ is N.

In certain embodiments, none or only one of $Y^A$, $Y^B$, $Y^C$, and $Y^D$ is N. In certain embodiments, two or more of $Y^A$, $Y^B$, $Y^C$, and $Y^D$ are N.

In certain embodiments, at least one instance of $R^H$ is hydrogen. In certain embodiments, each instance of $R^H$ is hydrogen. In certain embodiments, at least one instance of $R^H$ is not hydrogen. In certain embodiments, each instance of $R^H$ is not hydrogen. In certain embodiments, at least one instance of $R^H$ is halogen (e.g., F, Cl, or Br). In certain embodiments, at least one instance of $R^H$ is substituted alkyl (e.g., alkyl substituted with one or more instances of halogen (e.g., F)). In certain embodiments, at least one instance of $R^H$ is unsubstituted alkyl. In certain embodiments, at least one instance of $R^H$ is unsubstituted, $C_{1-6}$ alkyl. In certain embodiments, at least one instance of $R^H$ is Me. In certain embodiments, at least one instance of $R^H$ is Et, Pr, or Bu. In certain embodiments, at least one instance of $R^H$ is substituted $C_{1-6}$ alkyl. In certain embodiments, at least one instance of $R^H$ is substituted methyl. In certain embodiments, at least one instance of $R^H$ is substituted ethyl, substituted propyl, or substituted butyl. In certain embodiments, at least one instance of $R^H$ is substituted or unsubstituted alkenyl. In certain embodiments, at least one instance of $R^H$ is substituted or unsubstituted, $C_{2-6}$ alkenyl (e.g., substituted or unsubstituted vinyl or substituted or unsubstituted allyl). In certain embodiments, at least one instance of $R^H$ is substituted or unsubstituted alkynyl. In certain embodiments, at least one instance of $R^H$ is substituted or unsubstituted, $C_{2-6}$ alkynyl (e.g., substituted or unsubstituted ethynyl). In certain embodiments, at least one instance of $R^H$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, at least one instance of $R^H$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, at least one instance of $R^H$ is substituted or unsubstituted heterocyclyl (e.g., substituted or unsubstituted, 3- to 7-membered, monocyclic heterocyclyl). In certain embodiments, at least one instance of $R^H$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, at least one instance of $R^H$ is substituted or unsubstituted aryl. In certain embodiments, at least one instance of $R^H$ is substituted or unsubstituted phenyl. In certain embodiments, at least one instance of $R^H$ is substituted or unsubstituted naphthyl. In certain embodiments, at least one instance of $R^H$ is substituted or unsubstituted heteroaryl. In certain embodiments, at least one instance of $R^H$ is substituted or unsubstituted, 5- to 6-membered, monocyclic heteroaryl. In certain embodiments, at least one instance of $R^H$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, at least one instance of $R^H$ is substituted or unsubstituted pyridinyl, substituted or unsubstituted pyrazinyl, substituted or unsubstituted pyrimidinyl, or substituted or unsubstituted pyridazinyl. In certain embodiments, at least one instance of $R^H$ is substituted or unsubstituted, 9- to 10-membered, bicyclic heteroaryl. In certain embodiments, at least one instance of $R^H$ is —$OR^a$ (e.g., —OH, —O(substituted or unsubstituted, $C_{1-6}$ alkyl) (e.g., —OMe, —$OCF_3$, —OEt, —OPr, —OBu, or —OBn), or —O(substituted or unsubstituted phenyl) (e.g., —OPh)). In certain embodiments, at least one instance of $R^H$ is —OMe. In certain embodiments, at least one instance of $R^H$ is —$SR^a$ (e.g., —SH, —S(substituted or unsubstituted, $C_{1-6}$ alkyl) (e.g., —SMe, —$SCF_3$, —SEt, —SPr, —SBu, or —SBn), or —S(substituted or unsubstituted phenyl) (e.g., —SPh)). In certain embodiments, at least one instance of $R^H$ is —$N(R^a)_2$ (e.g., —$NH_2$, —NH(substituted or unsubstituted, $C_{1-6}$ alkyl) (e.g., —NHMe), or —N(substituted or unsubstituted, $C_{1-6}$ alkyl)-(substituted or unsubstituted, $C_{1-6}$ alkyl) (e.g., —$NMe_2$)). In certain embodiments, at least one instance of $R^H$ is —CN or —SCN. In certain embodiments, at least one instance of $R^H$ is —$NO_2$. In certain embodiments, at least one instance of $R^H$ is —$C(=NR^a)R^a$, —$C(=NR^a)OR^a$, or —$C(=NR^a)N(R^a)_2$. In certain embodiments, at least one instance of $R^H$ is —$C(=O)R^a$ (e.g., —C(=O)(substituted or unsubstituted alkyl) (e.g., —C(=O)Me) or —C(=O)(substituted or unsubstituted phenyl)). In certain embodiments, at least one instance of $R^H$ is —$C(=O)OR^a$ (e.g., —C(=O)OH, —C(=O)O(substituted or unsubstituted alkyl) (e.g., —C(=O)OMe), or —C(=O)O(substituted or unsubstituted phenyl)). In certain embodiments, at least one instance of $R^H$ is —$C(=O)N(R^a)_2$ (e.g., —$C(=O)NH_2$, —C(=O)NH(substituted or unsubstituted alkyl) (e.g., —C(=O)NHMe), —C(=O)NH(substituted or unsubstituted phenyl), —C(=O)N(substituted or unsubstituted alkyl)-(substituted or unsubstituted alkyl), or —C(=O)N(substituted or unsubstituted phenyl)-(substituted or unsubstituted alkyl)). In certain embodiments, at least one instance of $R^H$ is —$NR^aC(=O)R^a$(e.g., —NHC(=O)(substituted or unsubstituted, $C_{1-6}$ alkyl) (e.g., —NHC(=O)Me) or —NHC(=O)(substituted or unsubstituted phenyl)). In certain embodiments, at least one instance of $R^H$ is —$NR^aC(=O)OR^a$. In certain embodiments, at least one instance of $R^H$ is —$NR^aC(=O)N(R^a)_2$ (e.g., —$NHC(=O)NH_2$, —NHC(=O)NH(substituted or unsubstituted, $C_{1-6}$ alkyl) (e.g., —NHC(=O)NHMe)). In certain embodiments, at least one instance of $R^H$ is —$OC(=O)R^a$ (e.g., —OC(=O)(substituted or unsubstituted alkyl) or —OC(=O)(substituted or unsubstituted phenyl)), —$OC(=O)OR^a$ (e.g., —OC(=O)O(substituted or unsubstituted alkyl) or —OC(=O)O(substituted or unsubstituted phenyl)), or —$OC(=O)N(R^a)_2$ (e.g., —$OC(=O)NH_2$, —OC(=O)NH(substituted or unsubstituted alkyl), —OC(=O)NH(substituted or unsubstituted phenyl), —OC(=O)N(substituted or unsubstituted alkyl)-(substituted or unsubstituted alkyl), or —OC(=O)N(substituted or unsubstituted phenyl)-(substituted or unsubstituted alkyl)). In certain embodiments, at least one instance of $R^H$ is hydrogen, halogen, substituted or unsubstituted alkyl, or —$OR^1$.

In certain embodiments, $R^C$ is hydrogen. In certain embodiments, $R^C$ is substituted or unsubstituted alkyl (e.g., substituted or unsubstituted, $C_{1-6}$ alkyl). In certain embodiments, $R^C$ is Me. In certain embodiments, $R^C$ is Et, Pr, Bu, substituted methyl, substituted ethyl, substituted propyl, or substituted butyl. In certain embodiments, $R^C$ is a nitrogen protecting group (e.g., Bn, Boc, Cbz, Fmoc, trifluoroacetyl, triphenylmethyl, acetyl, or Ts).

In certain embodiments, when

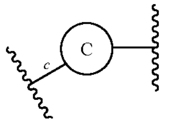

is

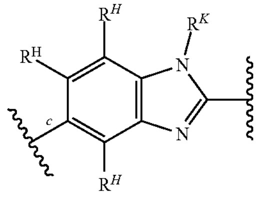

or

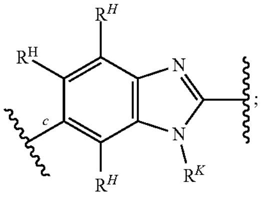

;

each of $Y^A$, $Y^B$, $Y^C$, and $Y^D$ is $CR^B$; and

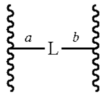

is

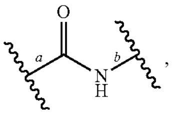 [SMILES: *NC(*)=O]

, then —$N(R^G)(R^C)$ is not —$NH_2$. In certain embodiments, —$N(R^G)(R^C)$ is not —$NH_2$.

In certain embodiments, at least one instance of $R^D$ is hydrogen. In certain embodiments, each instance of $R^D$ is hydrogen. In certain embodiments, at least one instance of $R^D$ is not hydrogen. In certain embodiments, each instance of $R^D$ is not hydrogen. In certain embodiments, at least one instance of $R^D$ is halogen (e.g., F, Cl, or Br). In certain embodiments, at least one instance of $R^D$ is substituted alkyl (e.g., alkyl substituted with one or more instances of halogen (e.g., F)). In certain embodiments, at least one instance of $R^D$ is unsubstituted alkyl. In certain embodiments, at least one instance of $R^D$ is unsubstituted, $C_{1-6}$ alkyl. In certain embodiments, at least one instance of $R^D$ is Me. In certain embodiments, at least one instance of $R^D$ is Et, Pr, or Bu. In certain embodiments, at least one instance of $R^D$ is substituted $C_{1-6}$ alkyl. In certain embodiments, at least one instance of $R^D$ is substituted methyl. In certain embodiments, at least one instance of $R^D$ is substituted ethyl, substituted propyl, or substituted butyl. In certain embodiments, at least one instance of $R^D$ is substituted or unsubstituted alkenyl. In certain embodiments, at least one instance of $R^D$ is substituted or unsubstituted, $C_{2-6}$ alkenyl (e.g., substituted or unsubstituted vinyl or substituted or unsubstituted allyl). In certain embodiments, at least one instance of $R^D$ is substituted or unsubstituted alkynyl. In certain embodiments, at least one instance of $R^D$ is substituted or unsubstituted, $C_{2-6}$ alkynyl (e.g., substituted or unsubstituted ethynyl). In certain embodiments, at least one instance of $R^D$ is substituted or unsubstituted carbocyclyl (e.g., substituted or unsubstituted, monocyclic, 3- to 7-membered carbocyclyl comprising 0, 1, or 2 double bonds in the carbocyclic ring system, as valency permits). In certain embodiments, at least one instance of $R^D$ is substituted or unsubstituted cyclopropyl, substituted or unsubstituted cyclobutyl, substituted or unsubstituted cyclopentyl, substituted or unsubstituted cyclohexyl, or substituted or unsubstituted cycloheptyl. In certain embodiments, at least one instance of $R^D$ is substituted or unsubstituted heterocyclyl (e.g., substituted or unsubstituted, 3- to 7-membered, monocyclic heterocyclyl). In certain embodiments, at least one instance of $R^D$ is substituted or unsubstituted oxetanyl, substituted or unsubstituted tetrahydrofuranyl, substituted or unsubstituted tetrahydropyranyl, substituted or unsubstituted azetidinyl, substituted or unsubstituted pyrrolidinyl, substituted or unsubstituted piperidinyl, substituted or unsubstituted morpholinyl, or substituted or unsubstituted piperazinyl. In certain embodiments, at least one instance of $R^D$ is substituted or unsubstituted aryl. In certain embodiments, at least one instance of $R^D$ is substituted or unsubstituted phenyl. In certain embodiments, at least one instance of $R^D$ is substituted or unsubstituted naphthyl. In certain embodiments, at least one instance of $R^D$ is substituted or unsubstituted heteroaryl. In certain embodiments, at least one instance of $R^D$ is substituted or unsubstituted, 5- to 6-membered, monocyclic heteroaryl. In certain embodiments, at least one instance of $R^D$ is substituted or unsubstituted furanyl, substituted or unsubstituted thienyl, substituted or unsubstituted pyrrolyl, substituted or unsubstituted imidazolyl, substituted or unsubstituted oxazolyl, substituted or unsubstituted isoxazolyl, substituted or unsubstituted thiazolyl, or substituted or unsubstituted isothiazolyl. In certain embodiments, at least one instance of $R^D$ is substituted or unsubstituted pyridinyl, substituted or unsubstituted pyrazinyl, substituted or unsubstituted pyrimidinyl, or substituted or unsubstituted pyridazinyl. In certain embodiments, at least one instance of $R^D$ is substituted or unsubstituted, 9- to 10-membered, bicyclic heteroaryl. In certain embodiments, at least one instance of $R^D$ is —$OR^a$ (e.g., —OH, —O(substituted or unsubstituted, $C_{1-6}$ alkyl) (e.g., —OMe, —$OCF_3$, —OEt, —OPr, —OBu, or —OBn), or —O(substituted or unsubstituted phenyl) (e.g., —OPh)). In certain embodiments, at least one instance of $R^D$ is —OMe. In certain embodiments, at least one instance of $R^D$ is —$SR^a$ (e.g., —SH, —S(substituted or unsubstituted, $C_{1-6}$ alkyl) (e.g., —SMe, —$SCF_3$, —SEt, —SPr, —SBu, or —SBn), or —S(substituted or unsubstituted phenyl) (e.g., —SPh)). In certain embodiments, at least one instance of $R^D$ is —$N(R^a)_2$ (e.g., —$NH_2$, —NH(substituted or unsubstituted, $C_{1-6}$ alkyl) (e.g., —NHMe), or —N(substituted or unsubstituted, $C_{1-6}$ alkyl)-(substituted or unsubstituted, $C_{1-6}$ alkyl) (e.g., —$NMe_2$)). In certain embodiments, at least one instance of $R^D$ is —CN or —SCN. In certain embodiments, at least one instance of $R^D$ is —$NO_2$. In certain embodiments, at least one instance of $R^D$ is —$C(=NR^a)R^a$, —$C(=NR^a)OR^a$, or —$C(=NR^a)N(R^a)_2$. In certain embodiments, at least one instance of $R^D$ is —$C(=O)R^a$ (e.g., —C(=O)(substituted or unsubstituted alkyl) (e.g., —C(=O)Me) or —C(=O)(substituted or unsubstituted phenyl)). In certain embodiments, at least one instance of $R^D$ is —$C(=O)OR^a$ (e.g., —C(=O)OH, —C(=O)O(substituted or unsubstituted alkyl) (e.g., —C(=O)OMe), or —C(=O)O(substituted or unsubstituted phenyl)). In certain embodiments, at least one instance of $R^D$ is —$C(=O)N(R^a)_2$ (e.g., —$C(=O)NH_2$, —C(=O)NH(substituted or unsubstituted alkyl) (e.g., —C(=O)NHMe), —C(=O)NH (substituted or unsubstituted phenyl), —C(═O)N(substituted or unsubstituted alkyl)-(substituted or unsubstituted alkyl), or —C(═O)N(substituted or unsubstituted phenyl)-(substituted or unsubstituted alkyl)). In certain embodiments, at least one instance of $R^D$ is —$NR^aC$(═O)$R^a$(e.g., —NHC(═O)(substituted or unsubstituted, $C_{1-6}$ alkyl) (e.g., —NHC(═O)Me) or —NHC(═O)(substituted or unsubstituted phenyl)). In certain embodiments, at least one instance of $R^D$ is —$NR^aC$(═O)$OR^a$. In certain embodiments, at least one instance of $R^D$ is —$NR^aC$(═O)$N(R^a)_2$ (e.g., —NHC(═O)$NH_2$, —NHC(═O)NH(substituted or unsubstituted, $C_{1-6}$ alkyl) (e.g., —NHC(═O)NHMe)). In certain embodiments, at least one instance of $R^D$ is —OC(═O)$R^a$ (e.g., —OC(═O)(substituted or unsubstituted alkyl) or —OC(═O)(substituted or unsubstituted phenyl)), —OC(═O)$OR^a$ (e.g., —OC(═O)O(substituted or unsubstituted alkyl) or —OC(═O)O(substituted or unsubstituted phenyl)), or —OC(═O)$N(R^a)_2$ (e.g., —OC(═O)$NH_2$, —OC(═O)NH(substituted or unsubstituted alkyl), —OC(═O)NH(substituted or unsubstituted phenyl), —OC(═O)N(substituted or unsubstituted alkyl)-(substituted or unsubstituted alkyl), or —OC(═O)N(substituted or unsubstituted phenyl)-(substituted or unsubstituted alkyl)).

In certain embodiments, two instances of $R^D$ are joined to form a substituted or unsubstituted, carbocyclic or heterocyclic ring. In certain embodiments, two instances of $R^D$ are joined to form a substituted or unsubstituted, carbocyclic ring (e.g., substituted or unsubstituted, monocyclic, 3- to 7-membered carbocyclic ring comprising 0, 1, or 2 double bonds in the carbocyclic ring system, as valency permits). In certain embodiments, two instances of $R^D$ are joined to form a substituted or unsubstituted, cyclopropyl ring (e.g., unsubstituted cyclopropyl ring). In certain embodiments, two instances of $R^D$ are joined to form a substituted or unsubstituted, cyclobutyl ring, substituted or unsubstituted, cyclopentyl ring, substituted or unsubstituted, cyclohexyl ring, or substituted or unsubstituted, cycloheptyl ring. In certain embodiments, two instances of $R^D$ are joined to form a substituted or unsubstituted, heterocyclic ring (e.g., substituted or unsubstituted, 3- to 7-membered, monocyclic heterocyclic ring).

In certain embodiments, the compound is of the formula:

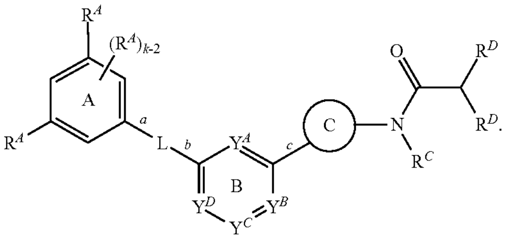

In certain embodiments, the compound is of the formula:

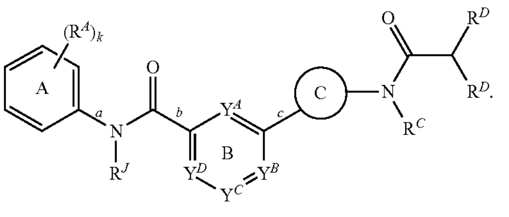

In certain embodiments, the compound is of the formula:

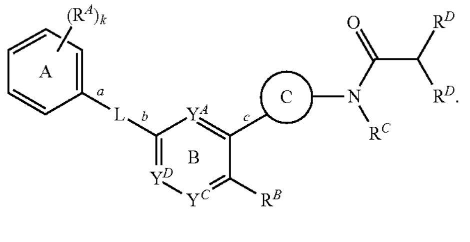

In certain embodiments, the compound is of the formula:

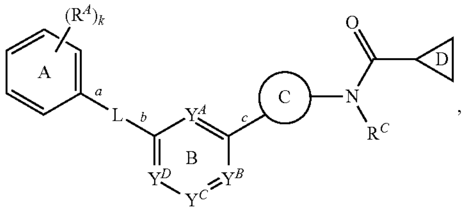

wherein

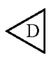

is substituted or unsubstituted.

In certain embodiments, the compound is of the formula:

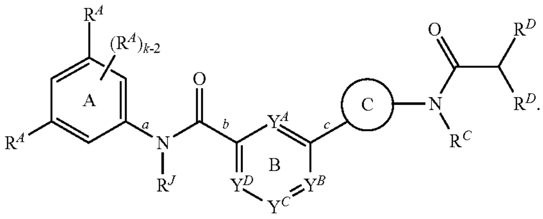

In certain embodiments, the compound is of the formula:

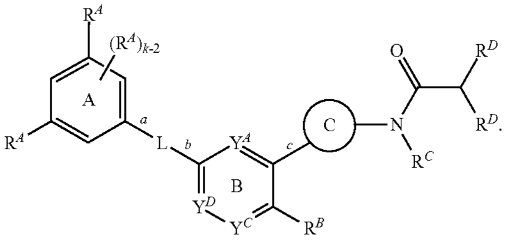

In certain embodiments, the compound is of the formula:

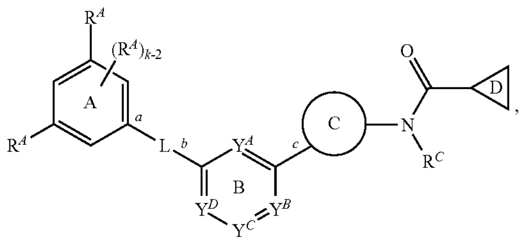

wherein

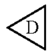

is substituted or unsubstituted.

In certain embodiments, the compound is of the formula:

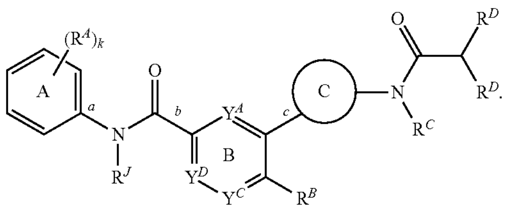

In certain embodiments, the compound is of the formula:

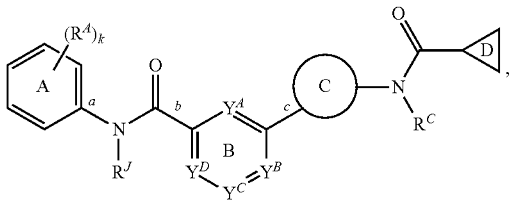

wherein

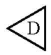

is substituted or unsubstituted.

In certain embodiments, the compound is of the formula:

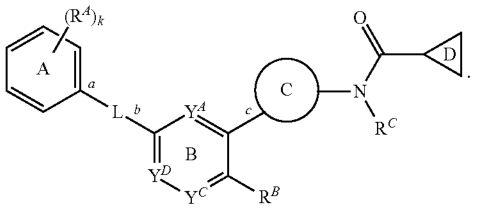

In certain embodiments, the compound is of the formula:

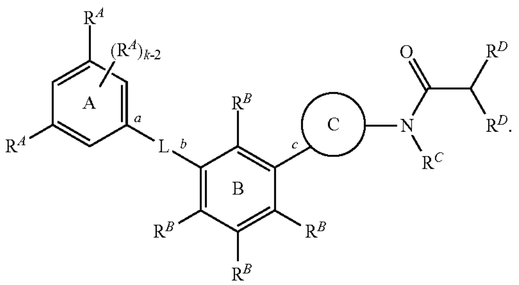

In certain embodiments, the compound is of the formula:

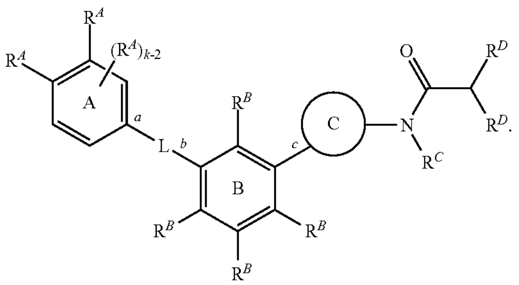

In certain embodiments, the compound is of the formula:

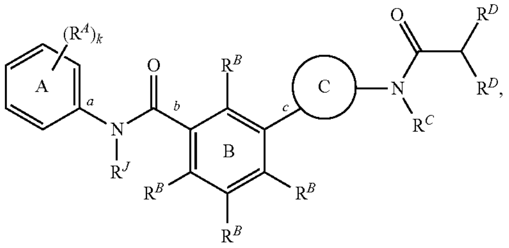

In certain embodiments, the compound is of the formula:

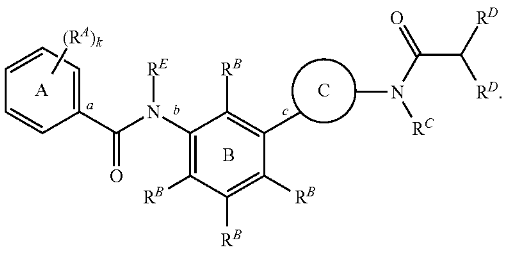

In certain embodiments, the compound is of the formula:

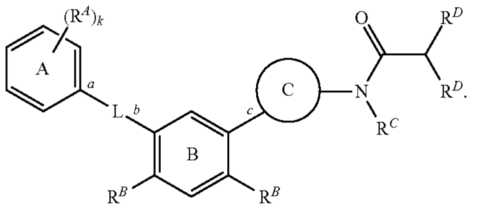

In certain embodiments, the compound is of the formula:

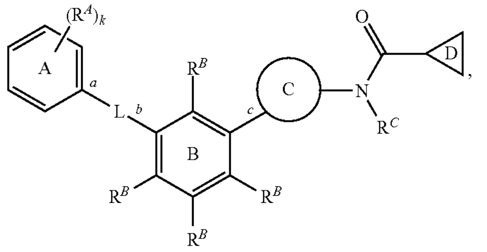

wherein

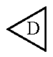

is substituted or unsubstituted.

In certain embodiments, the compound is of the formula:

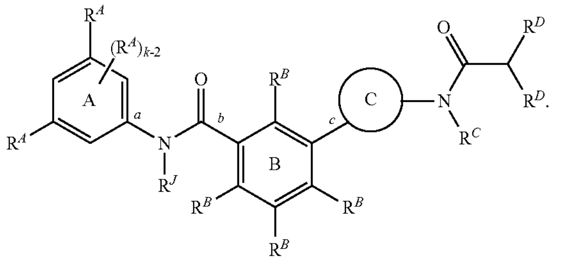

In certain embodiments, the compound is of the formula:

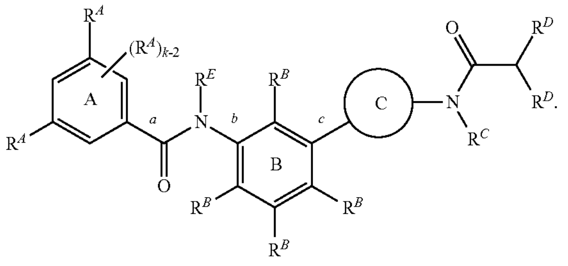

In certain embodiments, the compound is of the formula:

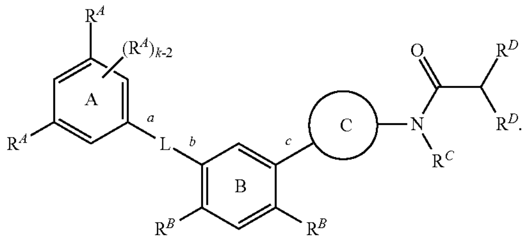

In certain embodiments, the compound is of the formula:

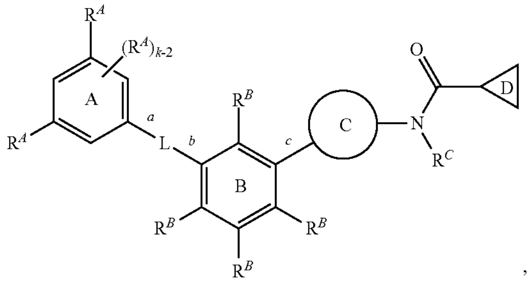

wherein

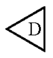

is substituted or unsubstituted.

In certain embodiments, the compound is of the formula:

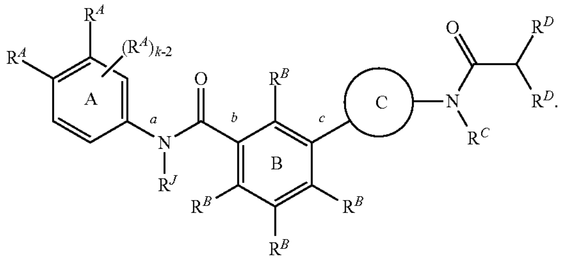

In certain embodiments, the compound is of the formula:

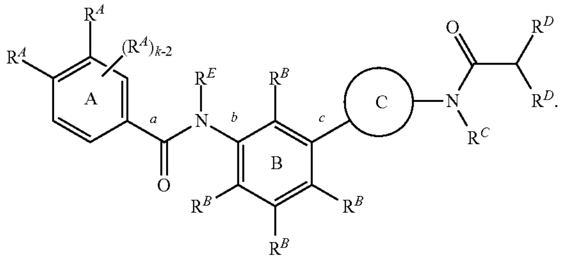

In certain embodiments, the compound is of the formula:

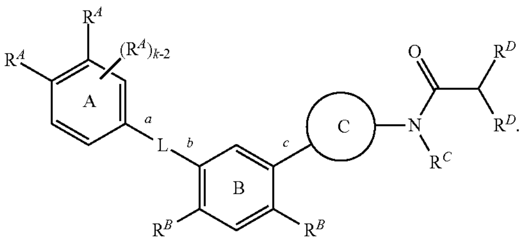

In certain embodiments, the compound is of the formula:

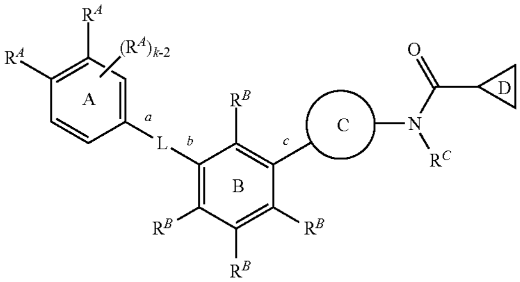

, wherein

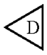

is substituted or unsubstituted.

In certain embodiments, the compound is of the formula:

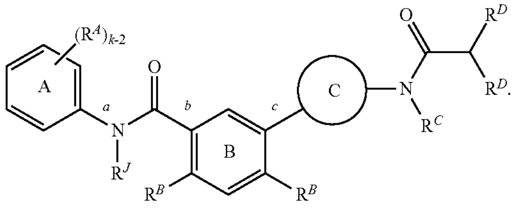

In certain embodiments, the compound is of the formula:

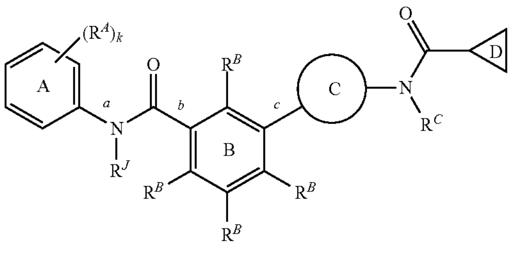

, wherein

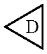

is substituted or unsubstituted.

In certain embodiments, the compound is of the formula:

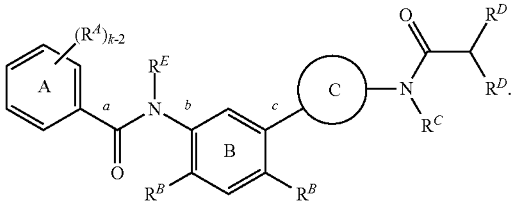

In certain embodiments, the compound is of the formula:

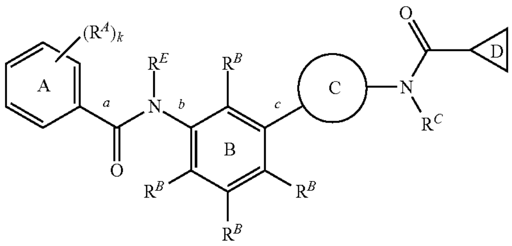

, wherein

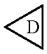

is substituted or unsubstituted.

In certain embodiments, the compound is of the formula:

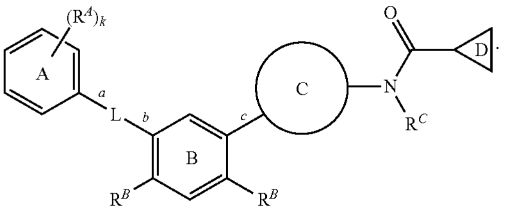

In certain embodiments, the compound is of the formula:

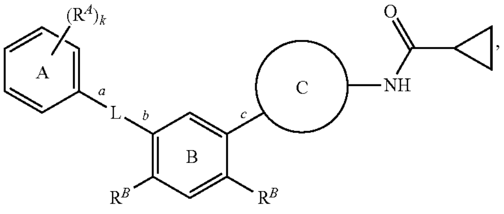

wherein:

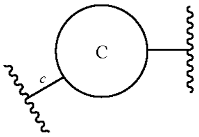

is

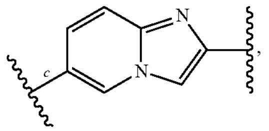

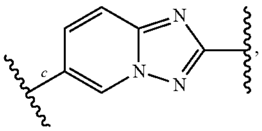

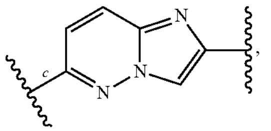

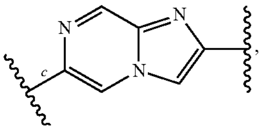

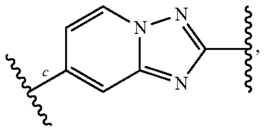

or

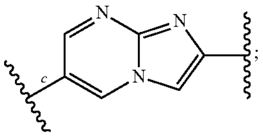

and each instance of $R^B$ is independently hydrogen, halogen, substituted or unsubstituted alkyl, —$OR^1$, or —CN (optionally provided that at least one instance of $R^B$ is not hydrogen).

In certain embodiments, the compound is of the formula:

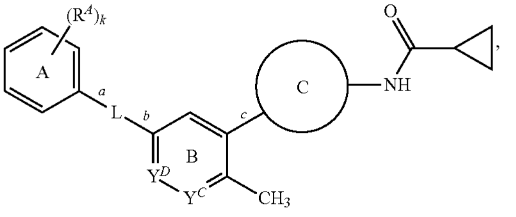

wherein

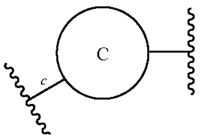

is

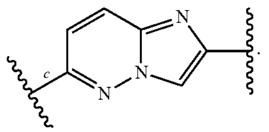

In certain embodiments, the compound is of the formula:

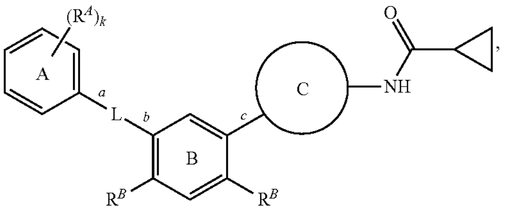

wherein

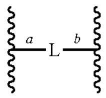

is

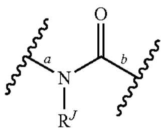

(e.g.,

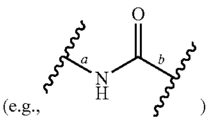

) or

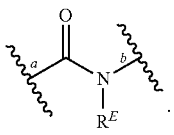

In certain embodiments, the compound is of the formula:

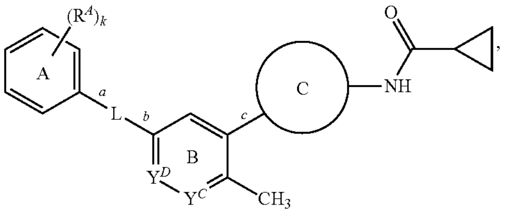

wherein

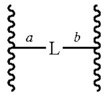

is

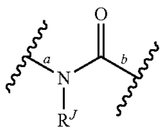

(e.g.,

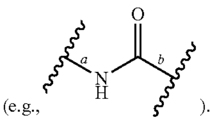

).

In certain embodiments, the compound is of the formula:

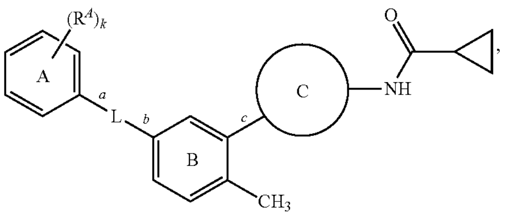

wherein
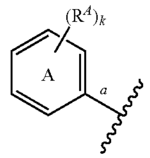
is
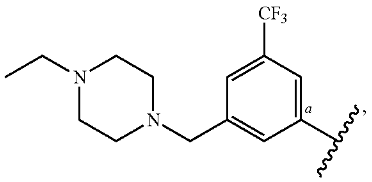
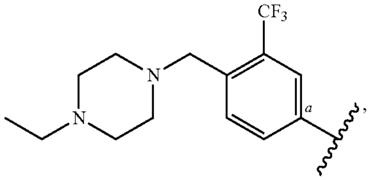
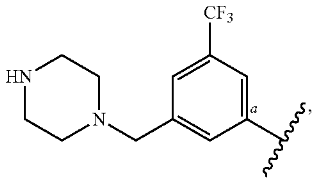
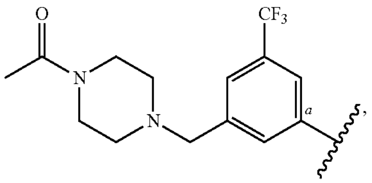
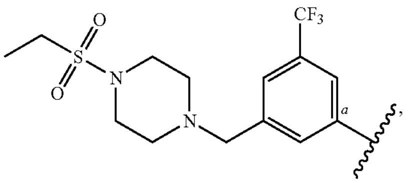
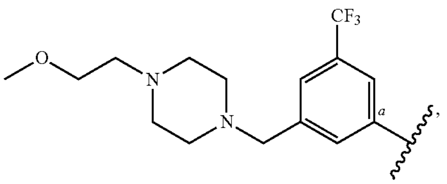
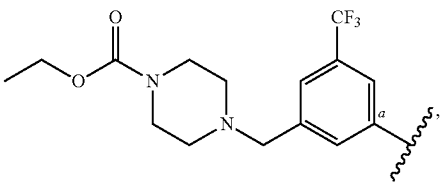
-continued
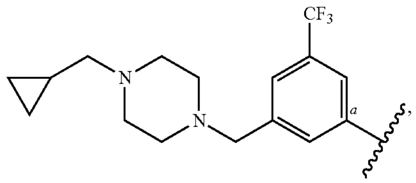
or
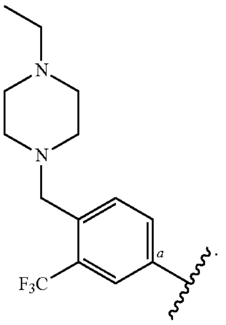 [SMILES: *c1ccc(CN2CCN(CC)CC2)c(C(F)(F)F)c1]
In certain embodiments, the compound is of the formula:
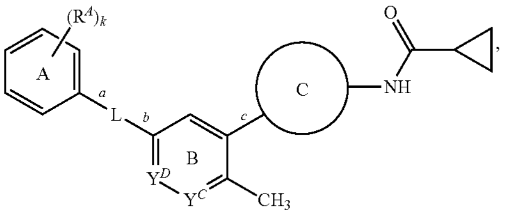
wherein
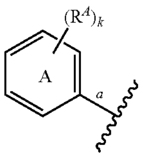
is
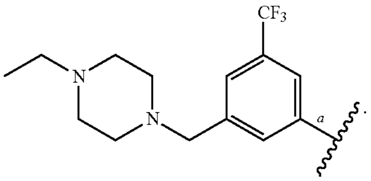 [SMILES: *c1cc(CN2CCN(CC)CC2)cc(C(F)(F)F)c1]

In certain embodiments, the compound is of the formula:
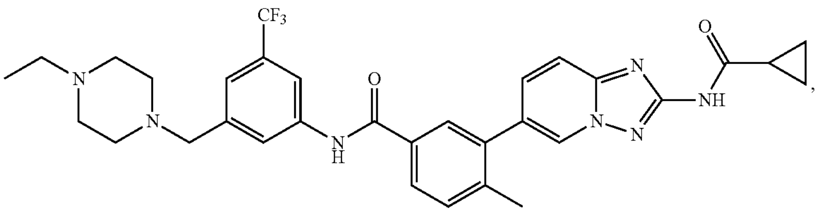,
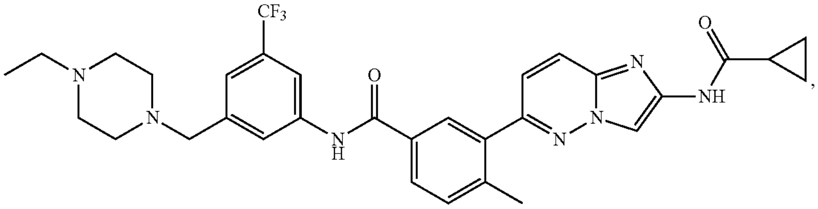,
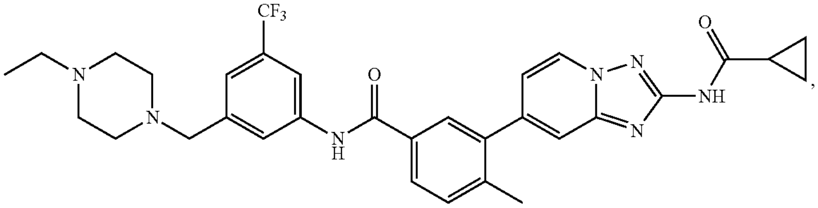,
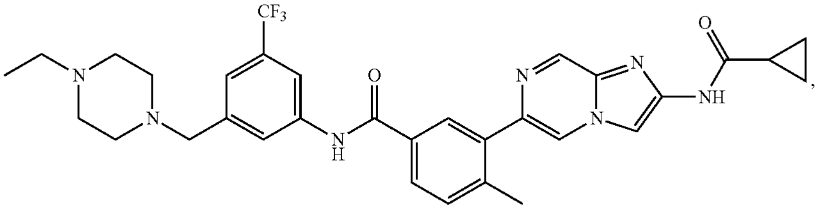,
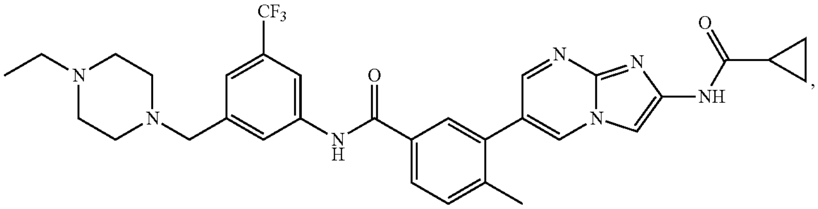,
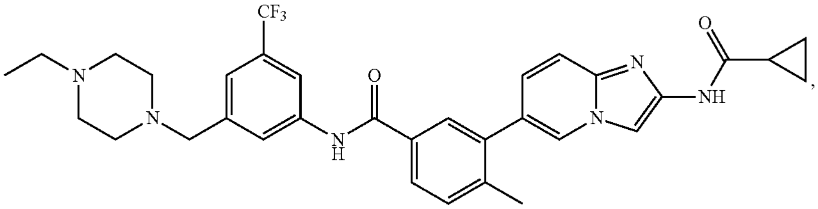,
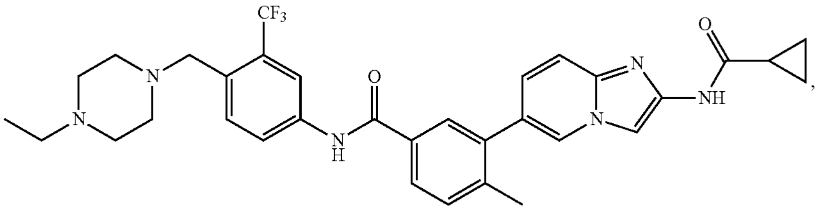,
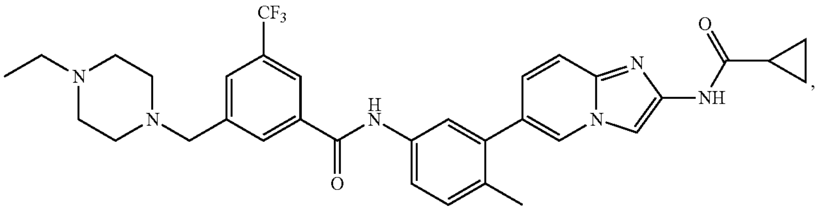, -continued
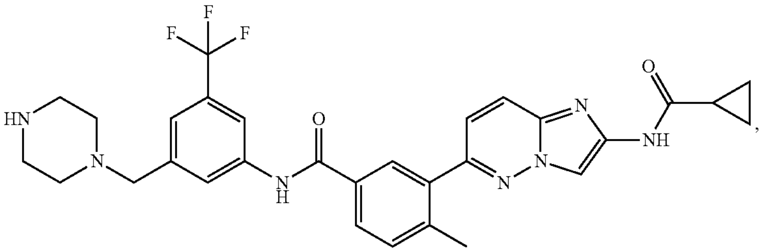
,
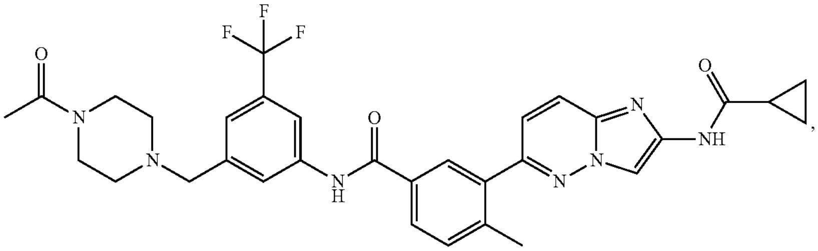
,
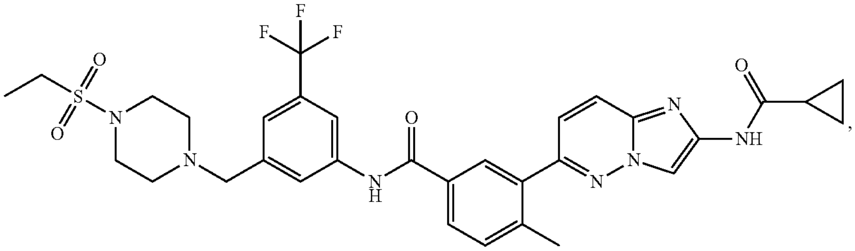
,
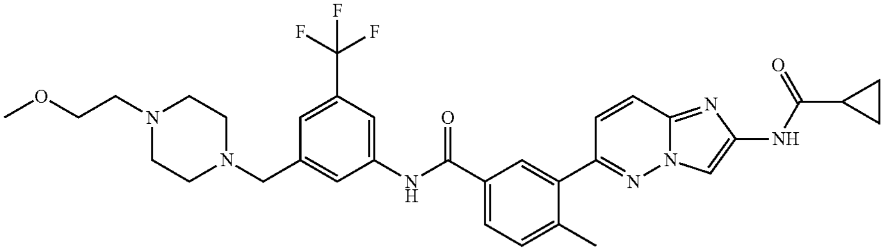
,
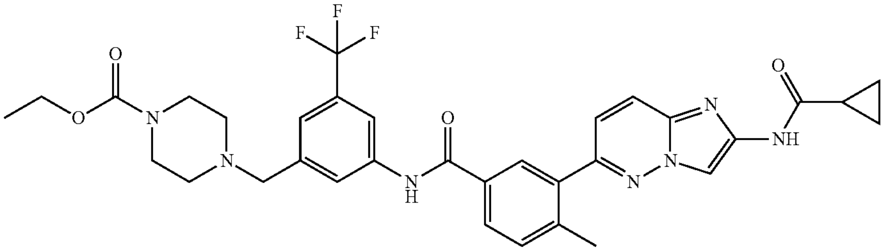
,
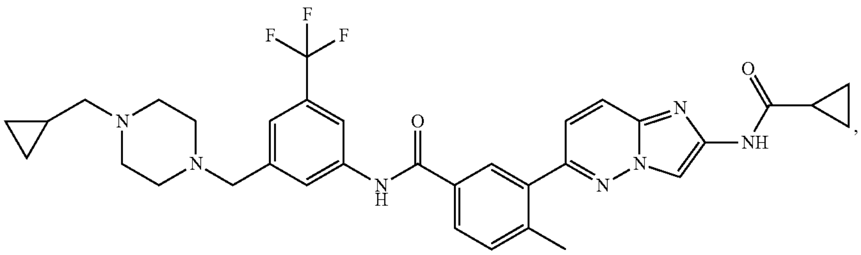
, -continued
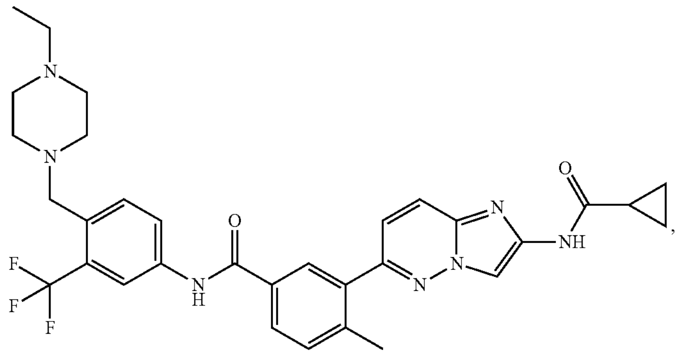
,
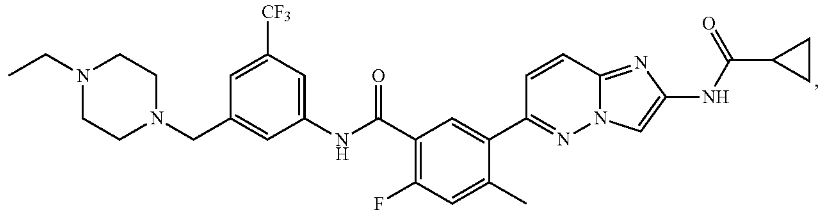
,
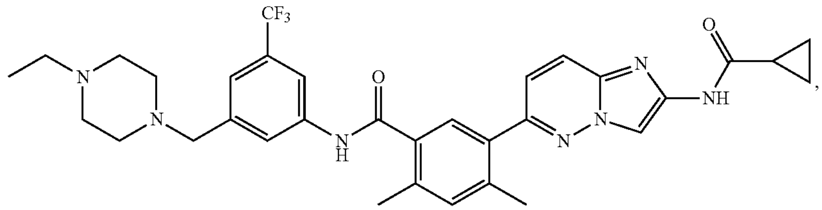
,
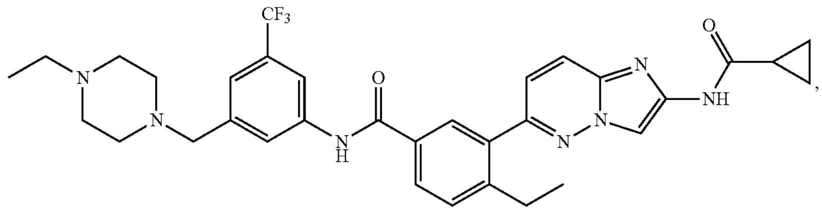
,
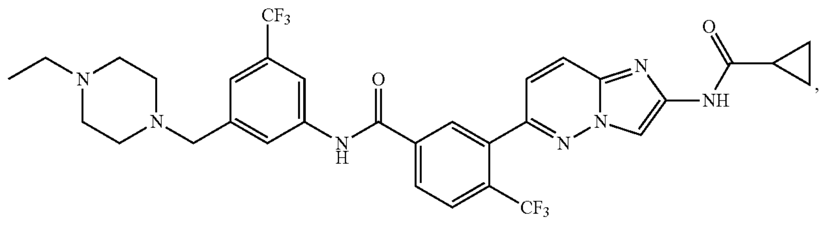
, or
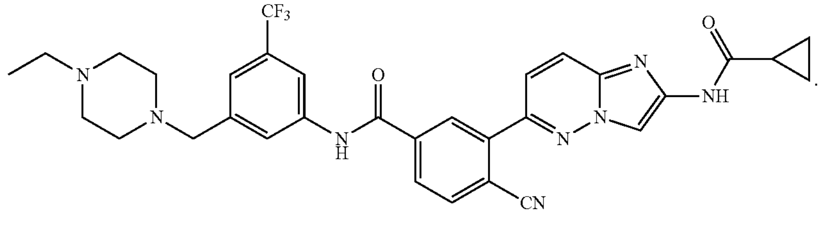
.

In certain embodiments, the compound is of the formula:
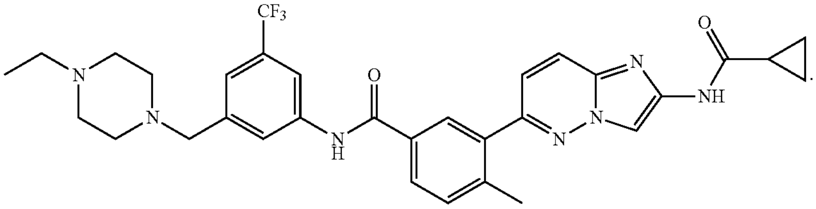 [SMILES: CCN1CCN(Cc2cc(NC(=O)c3ccc(C)c(-c4ccc5nc(NC(=O)C6CC6)cn5n4)c3)cc(C(F)(F)F)c2)CC1]
.
In certain embodiments, the compound is of the formula:
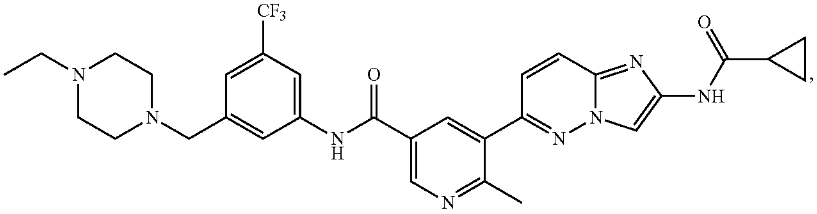
,
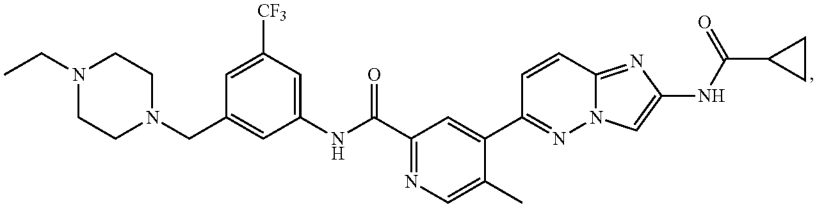
, or
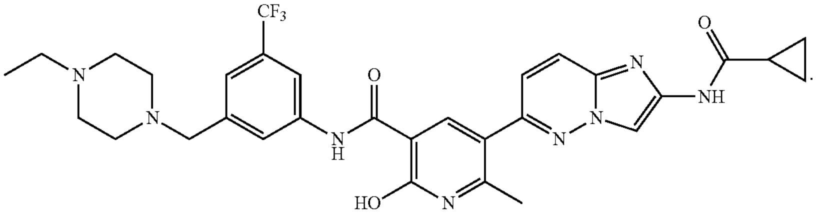
.
In certain embodiments, the compound is of the formula:
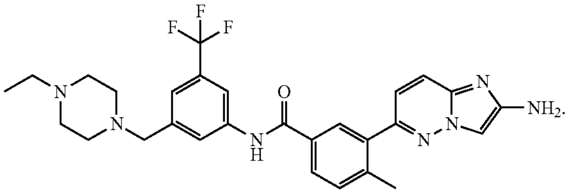 [SMILES: CCN1CCN(Cc2cc(NC(=O)c3ccc(C)c(-c4ccc5nc(N)cn5n4)c3)cc(C(F)(F)F)c2)CC1]
.
In certain embodiments, the compound is of the formula:
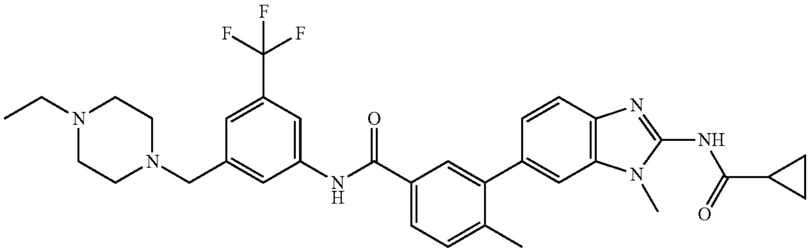
, -continued

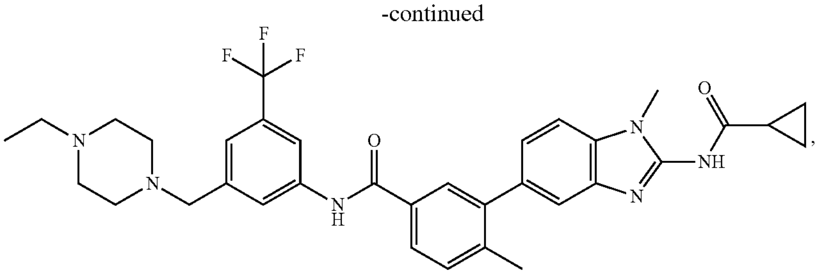

, or

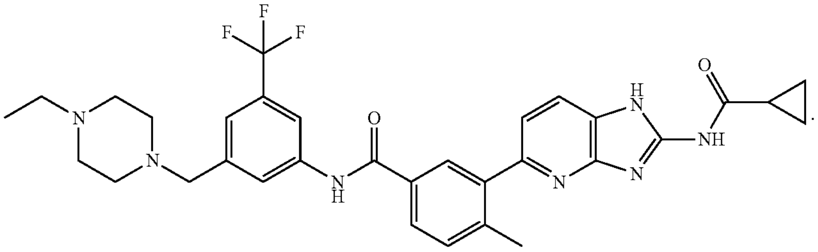

.

In certain embodiments, a provided compound (a compound described herein) is a compound of Formula (I'), or a pharmaceutically acceptable salt, solvate, hydrate, polymorph, co-crystal, tautomer, stereoisomer, isotopically labeled derivative, or prodrug thereof. In certain embodiments, a provided compound is a compound of Formula (I'), or a pharmaceutically acceptable salt, solvate, hydrate, co-crystal, tautomer, stereoisomer, isotopically labeled derivative, or prodrug thereof. In certain embodiments, a provided compound is a compound of Formula (I'), or a pharmaceutically acceptable salt, solvate, hydrate, tautomer, or stereoisomer thereof. In certain embodiments, a provided compound is a compound of Formula (I'), or a pharmaceutically acceptable salt, tautomer, or stereoisomer thereof. In certain embodiments, a provided compound is a compound of Formula (I), or a pharmaceutically acceptable salt thereof. In certain embodiments, a provided compound is a mixture (e.g., a racemic mixture) of enantiomers and/or diastereomers.

In certain embodiments, a provided compound (a compound described herein) is a compound of Formula (I), or a pharmaceutically acceptable salt, solvate, hydrate, polymorph, co-crystal, tautomer, stereoisomer, isotopically labeled derivative, or prodrug thereof. In certain embodiments, a provided compound is a compound of Formula (I), or a pharmaceutically acceptable salt, solvate, hydrate, co-crystal, tautomer, stereoisomer, isotopically labeled derivative, or prodrug thereof. In certain embodiments, a provided compound is a compound of Formula (I), or a pharmaceutically acceptable salt, solvate, hydrate, tautomer, or stereoisomer thereof. In certain embodiments, a provided compound is a compound of Formula (I), or a pharmaceutically acceptable salt, tautomer, or stereoisomer thereof. In certain embodiments, a provided compound is a compound of Formula (I), or a pharmaceutically acceptable salt thereof. In certain embodiments, a provided compound is a mixture (e.g., a racemic mixture) of enantiomers and/or diastereomers.

In certain embodiments, the molecular weight of a provide compound that is not in the form of a salt, solvate, hydrate, co-crystal, or prodrug is lower than 2,000, lower than 1,500, lower than 1,200, lower than 1,000, lower than 800, lower than 700, or lower than 600 g/mol. In certain embodiments, the molecular weight of a provide compound that is not in the form of a salt, solvate, hydrate, co-crystal, or prodrug is lower than 1000 g/mol. In certain embodiments, the molecular weight of a provide compound that is not in the form of a salt, solvate, hydrate, co-crystal, or prodrug is lower than 700 g/mol.

In certain embodiments, a provided compound inhibits a kinase. In certain embodiments, a provided compound inhibits the activity (e.g., aberrant activity (e.g., higher-than-normal activity, increase activity)) of a kinase. In certain embodiments, a provided compound inhibits the overexpression of a kinase. In certain embodiments, the kinase is a JAK, ABL1, CDKL2, EPHA4, EPHA8, EPHB2, FLT3, HCK, KIT, LCK, LOK, p38, PDGFRB, RET, SRC, TIE1, CSF1R, DDR1, FLT4, MAP4K2, TRKB, TRKC, CIT, DDR2, HPK1, TIE2, FGR, MAP4K4, TAOK3, MERTK, $CDCl_2L5$, PFTK1, ABL2, CDKL3, RIPK1, or a combination thereof. In certain embodiments, the kinase is a JAK, ABL1, CDKL2, EPHA4, EPHA8, EPHB2, FLT3, HCK, KIT, LOK, p38, RET, SRC, TIE1, CSF1R, DDR1, FLT4, MAP4K2, TRKB, TRKC, CIT, TIE2, DDR2, FGR, MAP4K4, TAOK3, MERTK, $CDCl_2L5$, PFTK1, CDKL3, RIPK1, or a combination thereof. In certain embodiments, the kinase is a JAK. In certain embodiments, the JAK is JAK1. In certain embodiments, the JAK is JAK2 (e.g., wild type or mutant JAK2). In certain embodiments, the JAK is JAK3. In certain embodiments, the JAK is TYK2. In certain embodiments, the JAK is a human JAK. In certain embodiments, the JAK is a non-human mammal (e.g., dog) JAK. In certain embodiments, the kinase is a wild type kinase. In certain embodiments, the kinase is a mutant kinase. In certain embodiments, a provided compound inhibits a kinase as measured in an assay described herein or known in the art. In certain embodiments, a provided compound inhibits the kinase at an $IC_{50}$ less than or equal to 30 μM, less than or equal to 10 μM, less than or equal to 3 μM, less than or equal to 1 μM, less than or equal to 0.3 μM, or less than or equal to 0.1 μM. In certain embodiments, a provided compound is selective for inhibiting a first kinase over a second kinase, wherein the first and second kinases are different from each other. In certain embodiments, the first kinase is a JAK, ABL1, CDKL2, EPHA4, EPHA8, EPHB2, FLT3, HCK, KIT, LCK, LOK, p38, PDGFRB, RET, SRC, TIE1, CSF1R, DDR1, FLT4, MAP4K2, TRKB, TRKC, CIT, DDR2, HPK1, TIE2, FGR, MAP4K4, TAOK3, MERTK, $CDCl_2L5$, PFTK1, ABL2, CDKL3, RIPK1, or a combination thereof. In certain embodiments, the first kinase is a JAK, ABL1, CDKL2, EPHA4, EPHA8, EPHB2, FLT3, HCK, KIT, LOK, p38, RET, SRC, TIE1, CSF1R, DDR1, FLT4, MAP4K2, TRKB, TRKC, CIT, TIE2, DDR2, FGR, MAP4K4, TAOK3, MERTK, $CDCl_2L5$, PFTK1, CDKL3, RIPK1, or a combination thereof. In certain embodiments, the first kinase is a JAK (e.g., JAK1, JAK2, JAK3, TYK2). In certain embodiments, the first kinase is JAK2. In certain embodiments, the first kinase is JAK3. In certain embodiments, a provided compound is selective for inhibiting the first kinase over the second kinase by at least 2-fold, at least 3-fold, at least 4-fold, at least 5-fold, at least 7-fold, at least 10-fold, at least 20-fold, at least 50-fold, at least 100-fold, at least 300-fold, or at least 1,000-fold (e.g., in an in vitro assay or an assay described herein). In certain embodiments, a provided compound reversibly binds to a kinase. In certain embodiments, a provided compound irreversibly binds to a kinase.

In another aspect, the present disclosure provides methods of preparing a compound described herein. In certain embodiments, the method of preparing is a method described herein (e.g., a method described in Example 1).

Pharmaceutical Compositions, Administration, and Kits

The present disclosure also provides pharmaceutical compositions comprising a compound described herein and optionally a pharmaceutically acceptable excipient. In certain embodiments, the pharmaceutical composition further comprises an additional pharmaceutical agent.

In certain embodiments, the compound described herein is provided in an effective (e.g., effective for inhibiting a kinase, such as a JAK (e.g., JAK2)) amount in the pharmaceutical composition. In certain embodiments, the effective amount is a therapeutically effective amount. In certain embodiments, a therapeutically effective amount is an amount effective for inhibiting a kinase. In certain embodiments, a therapeutically effective amount is an amount effective for treating a disease (e.g., a disease associated with aberrant activity of a kinase (e.g., proliferative disease)). In certain embodiments, a therapeutically effective amount is an amount effective for inhibiting the activity of a kinase and treating a disease (e.g., a disease associated with aberrant activity of a kinase (e.g., proliferative disease)). In certain embodiments, a therapeutically effective amount is an amount effective for inducing apoptosis in a cell (e.g., cancer cell, premalignant cell).

In certain embodiments, the effective amount is an amount effective for inhibiting the activity of a kinase by at least 10%, at least 20%, at least 30%, at least 40%, at least 50%, at least 60%, at least 70%, at least 80%, at least 90%, at least 95%, or at least 98%. In certain embodiments, the effective amount is an amount effective for inhibiting the activity of a kinase by not more than 10%, not more than 20%, not more than 30%, not more than 40%, not more than 50%, not more than 60%, not more than 70%, not more than 80%, not more than 90%, not more than 95%, or not more than 98%.

In certain embodiments, the subject is an animal. The animal may be of either sex and may be at any stage of development. In certain embodiments, the subject described herein is a human (e.g., an adult, juvenile, or child). In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a dog. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the subject is a genetically engineered animal. In certain embodiments, the subject is a transgenic animal (e.g., transgenic mice, transgenic pigs). In certain embodiments, the subject is a fish or reptile.

In certain embodiments, the biological sample or cell (e.g., the biological sample or cell being contacted with a compound or pharmaceutical composition described herein) is in vitro. In certain embodiments, the biological sample or cell is in vivo or ex vivo. In certain embodiments, the biological sample or cell is a malignant cell or premalignant cell.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample or cell, any two doses of the multiple doses include different or substantially the same amounts of a compound described herein. In certain embodiments, when multiple doses are administered to a subject or applied to a biological sample or cell, the frequency of administering the multiple doses to the subject or applying the multiple doses to the biological sample or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample or cell is one dose per day. In certain embodiments, the frequency of administering the multiple doses to the subject or applying the multiple doses to the biological sample or cell is two doses per day. In certain embodiments, the frequency of administering the multiple doses to the subject or applying the multiple doses to the biological sample or cell is three doses per day. In certain embodiments, when multiple doses are administered to a subject or applied to a biological sample or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject or cell. In certain embodiments, the duration between the first dose and last dose of the multiple doses is three months, six months, or one year. In certain embodiments, the duration between the first dose and last dose of the multiple doses is the lifetime of the subject or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inhibiting the activity of a kinase (e.g., JAK) in a subject, biological sample, or cell), improve bioavailability, improve safety, reduce drug resistance, reduce and/or modify metabolism, inhibit excretion, and/or modify distribution in a subject, biological sample, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, cancer, inflammatory disease, autoimmune disease, genetic disease, hematological disease, neurological disease, painful condition, psychiatric disorder, or metabolic disorder) or premalignant condition. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, cytotoxic chemotherapeutic agents, epigenetic modifiers, glucocorticoids, immunotherapeutic agents, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase *Erwinia Chrysanthemi*), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TK1258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055, BEZ235, BGT226, XL765, PF-4691502, GDC0980, SF1126, and OSI-027), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the additional pharmaceutical agent is a cytotoxic chemotherapeutic agent (e.g., gemcitabine, cytarabine, daunorubicin, doxorubicin, vincristine, 1-asparaginase, cyclophosphamide, or etoposide). In certain embodiments, the additional pharmaceutical agent is an epigenetic modifier such as azacitidine or romidepsin. In certain embodiments, the additional pharmaceutical agent is ruxolitinib, BBT594, CHZ868, CYT387, or BMS911543. In certain embodiments, the additional pharmaceutical agent is an inhibitor of a tyrosine kinase. In some embodiments, the additional pharmaceutical agent is a topoisomerase inhibitor, a MCL1 inhibitor, a BCL-2 inhibitor, a BCL-xL inhibitor, a BRD4 inhibitor, a BRCA1 inhibitor, BRCA2 inhibitor, HER1 inhibitor, HER2 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-(((R)-1-methoxypropan-2-yl)amino)cyclohexyl)amino)-[2,4'-bipyridin]-6-yl)amino)methyl)tetrahydro-2H-pyran-4-carbonitrile, JIB04, or cisplatin. In certain embodiments, the additional pharmaceutical agent is a binder or inhibitor of a kinase (e.g., JAK, ABL1, CDKL2, EPHA4, EPHA8, EPHB2, FLT3, HCK, KIT, LCK, LOK, p38, PDGFRB, RET, SRC, TIE1, CSF1R, DDR1, FLT4, MAP4K2, TRKB, TRKC, CIT, DDR2, HPK1, TIE2, FGR, MAP4K4, TAOK3, MERTK, $CDCl_2L5$, PFTK1, ABL2, CDKL3, RIPK1, or a combination thereof). In certain embodiments, the additional pharmaceutical agent is an antibody or a fragment thereof (e.g., monoclonal antibody). In certain embodiments, the additional pharmaceutical agent is a tyrosine kinase inhibitor. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the additional pharmaceutical agent is a glucocorticoid (e.g., cortisol, cortisone, prednisone, methylprednisolone, dexamethasone, betamethasone, triamcinolone, fludrocortisone acetate, or deoxycorticosterone acetate). In certain embodiments, the additional therapy is an immunotherapy (e.g., an immunotherapeutic monoclonal antibody). In certain embodiments, the additional pharmaceutical agent is an immunomodulator. In certain embodiments, the additional pharmaceutical agent is an immune checkpoint inhibitor. In certain embodiments, the additional pharmaceutical agent is a programmed cell death 1 protein (PD-1) inhibitor. In certain embodiments, the additional pharmaceutical agent is a programmed cell death 1 protein ligand 1 (PD-L1) inhibitor. In certain embodiments, the additional pharmaceutical agent is a cytotoxic T-lymphocyte-associated protein 4 (CTLA-4) inhibitor. In certain embodiments, the additional pharmaceutical agent is a T-cell immunoglobulin domain and mucin domain 3 (TIM3) inhibitor, lymphocyte activation gene-3 (LAG3) inhibitor, V-set domain-containing T-cell activation inhibitor 1 (VTCN1 or B7-H4) inhibitor, cluster of differentiation 276 (CD276 or B7-H3) inhibitor, B and T lymphocyte attenuator (BTLA) inhibitor, galectin-9 (GAL9) inhibitor, checkpoint kinase 1 (Chk1) inhibitor, adenosine A2A receptor (A2AR) inhibitor, indoleamine 2,3-dioxygenase (IDO) inhibitor, killer-cell immunoglobulin-like receptor (KIR) inhibitor, or V-domain Ig suppressor of T cell activation (VISTA) inhibitor. In certain embodiments, the PD-1 inhibitor is nivolumab, pidilizumab, pembrolizumab, MEDI-0680, REGN2810, or AMP-224. In certain embodiments, the PD-L1 inhibitor is atezolizumab, durvalumab, BMS-936559, avelumab, or CA-170. In certain embodiments, the CTLA-4 inhibitor is ipilimumab or tremelimumab. In certain embodiments, the compounds described herein or pharmaceutical compositions can be administered in combination with an anti-cancer therapy including, but not limited to, surgery, radiation therapy, and transplantation (e.g., stem cell transplantation, bone marrow transplantation).

Also encompassed by the present disclosure are kits (e.g., pharmaceutical packs). In certain embodiments, the kit comprises a compound or pharmaceutical composition described herein, and instructions for using the compound or pharmaceutical composition. In certain embodiments, the kit comprises a first container, wherein the first container includes the compound or pharmaceutical composition. In some embodiments, the kit further comprises a second container. In certain embodiments, the second container includes an excipient (e.g., an excipient for dilution or suspension of the compound or pharmaceutical composition). In certain embodiments, the second container includes an additional pharmaceutical agent. In some embodiments, the kit further comprises a third container. In certain embodiments, the third container includes an additional pharmaceutical agent. In some embodiments, the compound or pharmaceutical composition included in the first container and the excipient or additional pharmaceutical agent included in the second container are combined to form one unit dosage form. In some embodiments, the compound or pharmaceutical composition included in the first container, the excipient included in the second container, and the additional pharmaceutical agent included in the third container are combined to form one unit dosage form. In certain embodiments, each of the first, second, and third containers is independently a vial, ampule, bottle, syringe, dispenser package, tube, or inhaler.

In certain embodiments, the instructions are for administering the compound or pharmaceutical composition to a subject (e.g., a subject in need of treatment or prevention of a disease described herein). In certain embodiments, the instructions are for contacting a biological sample or cell with the compound or pharmaceutical composition. In certain embodiments, the instructions comprise information required by a regulatory agency, such as the U.S. Food and Drug Administration (FDA) or the European Agency for the Evaluation of Medicinal Products (EMA). In certain embodiments, the instructions comprise prescribing information.

Methods of Use and Uses

The present disclosure provides methods of modulating (e.g., inhibiting or increasing) the activity (e.g., aberrant activity, such as increased or decreased activity) of a kinase (e.g., JAK (e.g., JAK2)). The present disclosure provides methods of modulating (e.g., inhibiting or increasing) the activity (e.g., undesired or aberrant activity, such as increased activity (e.g., activity above normal levels) or decreased activity (e.g., activity below normal levels)), of a kinase in a subject, biological sample, or cell. The present disclosure also provides methods for the treatment of a range of diseases and conditions, such as diseases and conditions associated with undesired or aberrant activity (e.g., increased activity) or overexpression of a kinase. In certain embodiments, the diseases include proliferative diseases, musculoskeletal diseases, genetic diseases, hematological diseases, neurological diseases, painful conditions, psychiatric disorders, metabolic disorders, benign neoplasms, diseases associated with angiogenesis, inflammatory diseases, autoinflammatory diseases, autoimmune diseases, and premalignant conditions.

In another aspect, the present disclosure provides methods of treating a disease in a subject in need thereof, the method comprising administering to the subject in need thereof an effective amount (e.g., therapeutically effective amount) of a compound described herein or a pharmaceutical composition described herein.

In another aspect, the present disclosure provides methods of preventing a disease in a subject in need thereof, the method comprising administering to the subject in need thereof an effective amount (e.g., prophylactically effective amount) of a compound described herein or a pharmaceutical composition described herein.

In another aspect, the present disclosure provides methods of inhibiting the activity of a kinase in a subject in need thereof, the method comprising administering to the subject in need thereof an effective amount of a compound described herein or a pharmaceutical composition described herein.

In another aspect, the present disclosure provides methods of inhibiting the activity of a kinase in a biological sample (e.g., an in vitro biological sample), the method comprising contacting the biological sample with an effective amount of a compound described herein or a pharmaceutical composition described herein.

In another aspect, the present disclosure provides methods of inhibiting the activity of a kinase in a cell (e.g., an in vitro cell), the method comprising contacting the cell with an effective amount of a compound described herein or a pharmaceutical composition described herein.

Without wishing to be bound by any particular theory, in certain embodiments the compounds described herein are able to bind (e.g., covalently modify) the kinase being inhibited. In certain embodiments, a compound described herein is able to bind (e.g., covalently modify) to the kinase. In certain embodiments, the kinase is JAK. In certain embodiments, the kinase is JAK2. In certain embodiments, the kinase is JAK3. In certain embodiments, the kinase is JAK1. In certain embodiments, the kinase is TYK2.

In certain embodiments, provided are methods of decreasing the activity of a kinase (e.g., JAK (e.g., JAK2)) in a subject, biological sample, or cell by at least about 1%, at least about 3%, at least about 10%, at least about 20%, at least about 30%, at least about 40%, at least about 50%, at least about 60%, at least about 70%, at least about 80%, or at least about 90%. In certain embodiments, the activity of a kinase in a subject, biological sample, or cell is decreased by at least about 1%, at least about 3%, at least about 10%, at least about 20%, at least about 30%, at least about 40%, at least about 50%, at least about 60%, at least about 70%, at least about 80%, or at least about 90%. In some embodiments, the activity of a kinase in a subject, biological sample, or cell is selectively inhibited by the method. In some embodiments, the activity of a kinase (e.g., JAK2) in a subject, biological sample, or cell is selectively decreased by a compound or pharmaceutical composition described herein.

A disease, including proliferative disease, may be associated with aberrant or undesired activity of a kinase, and/or overexpression of the kinase. Aberrant or undesired activity of a kinase may be an increased or a decreased level of activity of the kinase. Proliferative diseases are sometimes associate with abnormal levels of JAK activity, frequently through increased or decreased JAK activation. Inhibition of the activity of JAK2 would be expected to inhibit phosphorylation. In certain embodiments, JAK2 is not overexpressed, but the activity of JAK2 is increased. In certain embodiments, JAK2 is overexpressed, and the activity of JAK2 is increased. The compounds and pharmaceutical compositions described herein may inhibit the activity of JAK2 and be useful in treating and/or preventing diseases, such as diseases associated with the aberrant, increased, or undesired activity of a kinase, overactivation of the kinase, and/or overexpression of the kinase.

JAK1 has been implicated in the signaling of the common gamma chain (γc) of type I cytokine receptors, to elicit signals from the IL-2 receptor family (e.g. IL-2R, IL-7R, IL-9R and IL-15R), the IL-4 receptor family (e.g. IL-4R and IL-13R), the gp130 receptor family (e.g. IL-6R, IL-11R, LIF-R, OSM-R, cardiotrophin-1 receptor (CT-1R), ciliary neurotrophic factor receptor (CNTF-R), and neurotrophin-1 receptor (NNT-1R) and Leptin-R.

JAK2 has been implicated in signaling by members of the type II cytokine receptor family (e.g. interferon receptors), the GM-CSF receptor family (IL-3R, IL-5R and GM-CSF-R), the gp130 receptor family (e.g., IL-6R), and the single chain receptors (e.g. Epo-R, Tpo-R, GH-R, PRL-R). JAK3 has been implicated in the signaling of the common gamma chain (γc) of the type I cytokine receptor family (e.g. IL-2R, IL-4R, IL-7R, IL-9R, IL-15R, and IL-21R). TYK2 has been implicated in the signaling of IFN-α, IL-6, IL-10, and IL-12.

Ruxolitinib, a dual JAK1 and JAK2 inhibitor, first gained FDA approval for treatment of myelofibrosis in 2011. While the phase III Controlled Myelofibrosis Study with Oral JAK Inhibitor (COMFORT-I and -II) trials showed that the medication can reduce abnormal splenomegaly and constitutional symptoms, the majority of patients did not achieve a molecular response with reduced mutant allele burden, and improvement in survival was minimal (Harrison, C. et al. *N Engl J Med* 366, 787-798, (2012); Koppikar, P. et al. *Nature* 489, 155-159, (2012); Verstovsek, S. et al. *N Engl J Med* 366, 799-807, (2012)). Thus, there is a significant unmet medical need in the MPN population. Ruxolitinib has essentially no activity (IC50>20 μM) against cell lines or patient-derived xenografts from patients with CRLF2-rearranged B-ALL, but it can induce remarkable remissions in the rare subset of leukemias with TEL-JAK2 fusions (Roberts, K. G. et al. *N Engl J Med* 371, 1005-1015, (2014)). A major advance in this field came from the Levine laboratory, which demonstrated that persistent JAK2 signaling in the presence of an ATP-competitive type I JAK2 inhibitor, such as ruxolitinib, may result from heterodimerization and trans-phosphorylation of JAK2 with JAK1 or TYK2 (Koppikar, P. et al. *Nature* 489, 155-159, (2012)). This helps explain the commonly observed phenomenon that activation loop phosphorylation of JAK2 increases in the presence of type I JAK2 inhibitors. In the setting of JAK2 fusions, obligate homodimerization between TEL domains prevents heterodimerization, and thus these leukemias remain sensitive to type I inhibitors. Of note, CRLF2 signaling involves heterodimerization with the IL7Rα subunit and signaling through JAK2 (bound to CRLF2) and JAK1 (bound to IL7Rα) (Pandey, A. et al. *Nat Immunol* 1, 59-64 (2000)). Thus, persistent trans-phosphorylation of JAK2 is likely to explain the resistance of these B-ALLs to type I JAK2 inhibitors (Wu, S. C. et al. *Cancer Cell* 28, 29-41, (2015)).

Type II inhibitors lock the kinase domain in a closed conformation and therefore should overcome trans-phosphorylation of JAK2 by JAK1 or TYK2. In fact, the Levine lab demonstrated that BBT594, a type II inhibitor initially developed to target BCR-ABL T315I (Andraos, R. et al. *Cancer discovery* 2, 512-523, (2012)), abrogated persistent JAK2 signaling in myeloid cells refractory to treatment with a type I JAK2 inhibitor (Koppikar, P. et al. *Nature* 489, 155-159, (2012)). BBT594 has limitations in potency and selectivity for JAK2, and its pharmacokinetic properties preclude in vivo use. Mining the Novartis database for type II kinase inhibitors and cellular screening in JAK2 V617F-mutant SET2 cells to identify compounds that inhibit JAK2 and STAT5 phosphorylation revealed arylamino-benzimidazoles, originally described as RAF kinase inhibitors (Shiels, M. S. et al., *Journal of the National Cancer Institute* 103, 753-762, (2011)), as a starting point for drug design. Medicinal chemistry efforts led to the development of CHZ868, the first type II JAK2 inhibitor amenable to in vivo testing in transgenic and xenograft mouse models (Wu, S. C. et al., *Cancer cell* 28, 29-41, (2015)).

In certain embodiments, the disease (e.g., the disease to be treated or prevented by a method described herein) is associated with the increased activity of a kinase (e.g., JAK (e.g., JAK2)). In certain embodiments, the disease is associated with overexpression of a kinase (e.g., JAK (e.g., JAK2)). In certain embodiments, the disease is a proliferative disease. In certain embodiments, the disease is cancer. In certain embodiments, the cancer is a JAK-STAT-dependent cancer.

In certain embodiments, the cancer is a hematological malignancy. In certain embodiments, the proliferative disease is a leukemia. In certain embodiments, the proliferative disease is chronic lymphocytic leukemia (CLL). In certain embodiments, the proliferative disease is acute lymphoblastic leukemia (ALL). In certain embodiments, the proliferative disease is T-cell acute lymphoblastic leukemia (T-ALL). In certain embodiments, the proliferative disease is chronic myelogenous leukemia (CML). In certain embodiments, the proliferative disease is acute myelogenous leukemia (AML). In certain embodiments, the proliferative disease is acute monocytic leukemia (AMoL). In certain embodiments, the proliferative disease is lymphoma. In some embodiments, the proliferative disease is Burkitt's lymphoma. In certain embodiments, the proliferative disease is a Hodgkin's lymphoma. In certain embodiments, the proliferative disease is a non-Hodgkin's lymphoma. In certain embodiments, the cancer is essential thrombocythemia.

In certain embodiments, the cancer is a myeloma. In certain embodiments, the cancer is multiple myeloma. In certain embodiments, the cancer is myelofibrosis, myeloproliferative neoplasm, myeloid malignancy, or polycythemia vera.

In certain embodiments, the cancer is an adenocarcinoma. In certain embodiments, the cancer is a blastoma. In certain embodiments, the cancer is a carcinoma. In certain embodiments, the cancer is a sarcoma. In certain embodiments, the cancer is brain cancer. In certain embodiments, the cancer is pancreatic cancer.

In some embodiments, the disease is a benign neoplasm.

In certain embodiments, the disease is an inflammatory disease.

In some embodiments, the disease is an autoinflammatory disease. In certain embodiments, the autoimmune disease is psoriasis, rheumatoid arthritis, graft-versus-host disease, alopecia, alopecia universalis, or vitiligo.

In certain embodiments, the disease is myelodysplastic syndrome.

In certain embodiments, the disease is causing a syndrome of wasting that comprises weight loss as a symptom.

In certain embodiments, the disease is a premalignant condition (e.g., clonal hematopoiesis).

In certain embodiments, the method described herein superior (e.g., showing improved safety and/or therapeutic effects) or comparable to existing therapy (e.g., chemotherapy).

In certain embodiments, the biological sample or cell (e.g., the biological sample or cell being contacted with a compound or pharmaceutical composition described herein) is in vitro. In certain embodiments, the biological sample or cell is in vivo. In certain embodiments, the biological sample or cell is ex vivo.

In certain embodiments, the cell is a malignant cell (e.g., cancer cell). In certain embodiments, the cell is a malignant blood cell. In certain embodiments, the cell is a malignant bone marrow cell. In certain embodiments, the cell is an adenocarcinoma cell, blastoma cell, carcinoma cell, or sarcoma cell. In certain embodiments, the cell is a pre-malignant cell (e.g., pre-cancerous cell).

In certain embodiments, the method described herein further comprises administering to the subject in need thereof an additional therapy. In certain embodiments, the additional therapy is an additional pharmaceutical agent described herein. In certain embodiments, the additional therapy is a cytotoxic chemotherapy (e.g., gemcitabine, cytarabine, daunorubicin, doxorubicin, vincristine, l-asparaginase, cyclophosphamide, or etoposide). In certain embodiments, the additional therapy is an epigenetic modifier (e.g., azacitidine or romidepsin). In certain embodiments, the additional therapy is a glucocorticoid. In certain embodiments, the additional therapy is an immunotherapy (e.g., an immunotherapeutic monoclonal antibody). In some embodiments, the additional pharmaceutical agent is etoposide, obatoclax, or navitoclax, and optionally the disease is breast cancer, e.g., triple-negative breast cancer, HER2 positive breast cancer, HER2 negative breast cancer, ER-positive breast cancer, ER-negative breast cancer, or ER/PR-positive breast cancer. In some embodiments, the additional pharmaceutical agent is etoposide, JIB04, or cisplatin, and optionally the disease is Ewing's sarcoma. In some embodiments, the additional pharmaceutical agent is JQ1 or NVP2, and optionally the disease is leukemia, e.g., acute myelogenous leukemia, myeloblastic leukemia, promyelocytic leukemia, myelomonocytic leukemia, monocytic leukemia, monoblastic leukemia, or megakaryoblastic leukemia.

In yet another aspect, the present invention provides compounds and pharmaceutical compositions described herein for use in the treatment of a disease (e.g., a proliferative disease, such as cancer) in a subject in need thereof.

In yet another aspect, the present invention provides compounds and pharmaceutical compositions described herein for use in the prevention of a disease (e.g., a proliferative disease, such as cancer) in a subject in need thereof.

In another aspect, the present disclosure provides compounds and pharmaceutical compositions described herein for use in inhibiting the activity of a kinase in a subject in need thereof.

In another aspect, the present disclosure provides compounds and pharmaceutical compositions described herein for use in inhibiting the activity of a kinase in a biological sample (e.g., an in vivo or ex vivo biological sample).

In another aspect, the present disclosure provides compounds and pharmaceutical compositions described herein for use in inhibiting the activity of a kinase in a cell (e.g., an in vivo or ex vivo cell).

In another aspect, the present disclosure provides uses of compounds and pharmaceutical compositions described herein in the manufacture of a medicament for treating a disease in a subject in need thereof.

In another aspect, the present disclosure provides uses of compounds and pharmaceutical compositions described herein in the manufacture of a medicament for preventing a disease in a subject in need thereof.

The compounds, pharmaceutical compositions, and kits described herein may synergistically augment inhibition of a kinase (e.g., JAK (e.g., JAK2)) induced by the additional pharmaceutical agent(s) in the biological sample or subject. Thus, the combination of the compounds, pharmaceutical compositions, or kits with additional pharmaceutical agent (s) may be useful in treating diseases resistant to a treatment using the additional pharmaceutical agent(s) without the compounds, pharmaceutical compositions, or kits described herein.

EXAMPLES

In order that the present disclosure described herein may be more fully understood, the following examples are set forth. The synthetic and biological examples described in this application are offered to illustrate the compounds, pharmaceutical compositions, uses, kits, and methods provided herein and are not to be construed in any way as limiting their scope.

Example 1. Preparation of the Compounds of the Present Disclosure

Unless otherwise noted, reagents and solvents were used as received from commercial suppliers. Proton nuclear magnetic resonance spectra were obtained on a Bruker AVANCE spectrometer at 400 MHz or 500 MHz for proton. Spectra are given in ppm (δ) and coupling constants, J, are reported in Hertz. The solvent peak was used as the reference peak for proton spectra. LC-MS spectra were obtained on Waters UPLC or Agilent 1100 HPLC LC-MS ion trap electrospray ionization (ESI) mass spectrometer.

Intermediate B

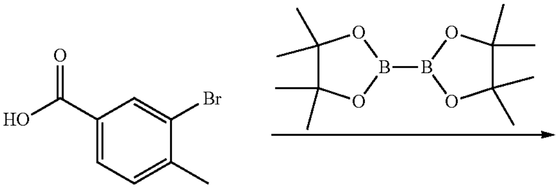

Int-B-1

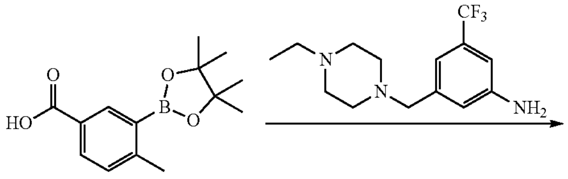

Int-B-2

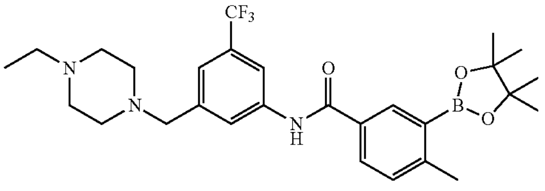

Int-B 4-methyl-3-(4,4,5,5-tetramethyl-1,3,2-dioxaborolan-2-yl)benzoic acid

The mixture of 3-bromo-4-methylbenzoic acid (1 g, 4.65 mmol, 1.0 eq), 4,4,4',4',5,5,5',5'-octamethyl-2,2'-bi(1,3,2-dioxaborolane) (2.362 g, 9.3 mmol, 2.0 eq), Pd(dppf)$Cl_2$ (0.339 g, 0.465 mmol, 0.1 eq) and $CH_3COOK$ (1.367 g, 13.95 mmol, 3.0 eq) in 20 mL of DMSO was stirred at 100° C. for 16 h. After cooling to room temperature, 100 mL of water and HCl was added to adjust pH=2. The mixture was then extracted with ethyl acetate (EA) (100 mL×3). And the organic phase was washed with saturated brine (50 mL×2), dried over anhydrous sodium sulfate, and thereafter concentrated to give target compound as a yellow solid (650 mg, 53%). LCMS (m/z): 263 $[M+H]^+$.

N-(3-((4-ethylpiperazin-1-yl)methyl)-5-(trifluoromethyl)phenyl)-4-methyl-3-(4,4,5,5-tetramethyl-1,3,2-dioxaborolan-2-yl)benzamide (Int-B)

The mixture of 4-methyl-3-(4,4,5,5-tetramethyl-1,3,2-dioxaborolan-2-yl)benzoic acid (500 mg, 1.9 mmol, 1.2 eq), 3-((4-ethylpiperazin-1-yl)methyl)-5-(trifluoromethyl)aniline (1 eq), EDCI (726 mg, 3.8 mmol, 2.0 eq), DMAP (463 mg, 3.8 mmol, 2.0 eq) in 10 mL of DMF, was stirred at 50° C. for 16 h. After dilution with 100 mL of water, the mixture was then extracted with EA (100 mL×3). The organic phase was washed with saturated brine (50 mL×2). After evaporation of organic solvent, the crude residue was purified by flash column chromatography with petroleum ether (PE)/EA=1:10 to give the target compound as a brown solid (520 mg, 51%). LCMS (m/z): 532.0 $[M+H]^+$.

Compound I-5

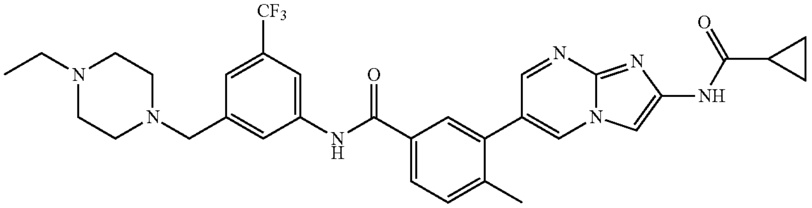 [SMILES: CCN1CCN(Cc2cc(NC(=O)c3ccc(C)c(-c4cnc5nc(NC(=O)C6CC6)cn5c4)c3)cc(C(F)(F)F)c2)CC1]

3-(2-(cyclopropanecarboxamido)imidazo[1,2-a]pyrimidin-6-yl)-N-(3-((4-ethylpiperazin-1-yl)methyl)-5-(trifluoromethyl)phenyl)-4-methylbenzamide

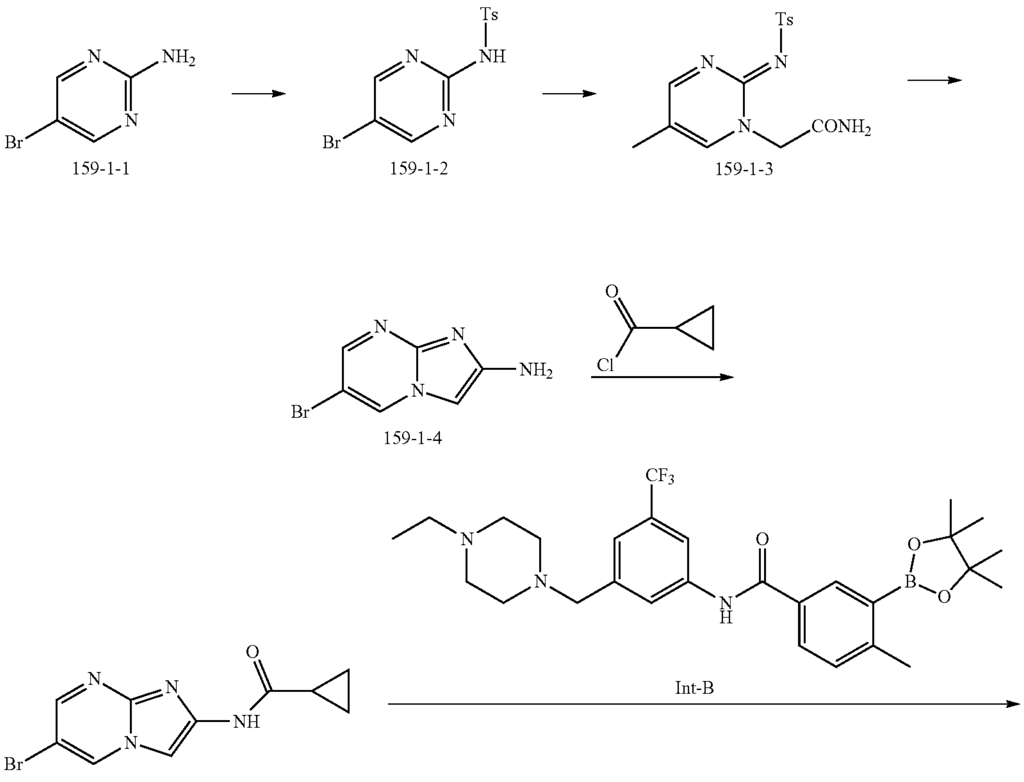

159-1-1 159-1-2 159-1-3 159-1-4 159-1-5 Int-B

-continued

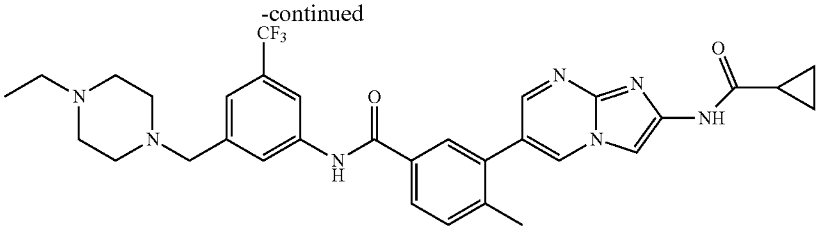

I-5

N-(5-bromopyrimidin-2-yl)-4-methylbenzenesulfonamide

The mixture of 5-bromopyrimidin-2-amine (3.6 g, 20.689 mmol, 1.0 eq), TsCl (4.717 g, 24.827 mmol, 1.2 eq), in 25 mL pyridine was stirred at 90° C. for 12 h. After cooling to room temperature, the mixture was added with 250 mL of water. The solid was collected by filtrated and air dried to give target compound as off-white solid (4 g, 59%). LCMS (m/z): 328 $[M+H]^+$.

2-(5-bromo-2-(tosylimino)pyrimidin-1(2H)-yl)acetamide

The mixture of N-(5-bromopyrimidin-2-yl)-4-methylbenzenesulfonamide (1.6 g, 4.875 mmol, 1.0 eq), 2-bromoacetamide (807 mg, 5.853 mmol, 1.2 eq) and DIPEA (755 mg, 5.853 mmol, 1.2 eq) in 20 mL of DMF was stirred at room temperature overnight. 250 mL of water was then added. The precipitated solid was collected by filtrated and air dried to give target compound as off-white solid (0.9 g, 48%). LCMS (m/z): 384.8 $[M+H]^+$.

6-bromoimidazo[1,2-a]pyrimidin-2-amine

A mixture of 2-(5-bromo-2-(tosylimino)pyrimidin-1(2H)-yl)acetamide (700 mg, 1.818 mmol) in 4 mL $(CF_3SO_2)_2O$ and 8 mL of DCM was stirred at 50° C. for 16 h. Then the mixture was cooled to room temperature. The solid was collected by filtrated and washed with PE to give the product as light yellow solid: (0.3 g, 77%). LCMS (m/z): 214.8 $[M+H]^+$.

N-(6-bromoimidazo[1,2-a]pyrazin-2-yl)cyclopropanecarboxamide

The mixture of 6-bromoimidazo[1,2-a]pyrimidin-2-amine (200 mg, 0.9389 mmol, 1.0 eq) and DIPEA (363 mg, 0.2816 mmol, 3.0 eq) in 6 mL THF was added cyclopropanecarbonyl chloride (107 mg, 1.0328 mmol, 1.1 eq) in 2 mL of THF. Then the mixture was stirred for 12 h. The solvent was removed under reduced pressure. 80 mL of $H_2O$ was added and the mixture was extracted with ethyl acetate (100 mL×3). The combined organic phase was washed with saturated brine, dried over $Na_2SO_4$. The crude product was purified by Combi-flash (PE/EA=10/1 to 100%) to give the product as a light yellow solid (90 mg, 34%). LCMS (m/z): 280.9 $[M+H]^+$.

3-(2-(cyclopropanecarboxamido)imidazo[1,2-a]pyrimidin-6-yl)-N-(3-((4-ethylpiperazin-1-yl)methyl)-5-(trifluoromethyl)phenyl)-4-methylbenzamide (Compound I-5)

The mixture of N-(6-bromoimidazo[1,2-a]pyrimidin-2-yl)cyclopropanecarboxamide (90 mg, 0.32 mmol, 1.0 eq), N-(3-((4-ethylpiperazin-1-yl)methyl)-5-(trifluoromethyl)phenyl)-4-methyl-3-(4,4,5,5-tetramethyl-1,3,2-dioxaborolan-2-yl)benzamide (255 mg, 0.48 mmol, 1.5 eq), $Pd(PPh_3)_4$ (37 mg, 0.032 mmol, 0.1 eq) and $Na_2CO_3$ (68 mg, 0.64 mmol, 2.0 eq) in 4 mL of DMF was stirred for 12 h at 100° C. in a sealed tube. The mixture was cooled to r.t. and filtrated. The solvent was evaporated and purified by Prep-HPLC to give the product as a white solid (10 mg, 5.2%). LCMS (m/z): 606.0 $[M+H]^+$.

Compound I-4

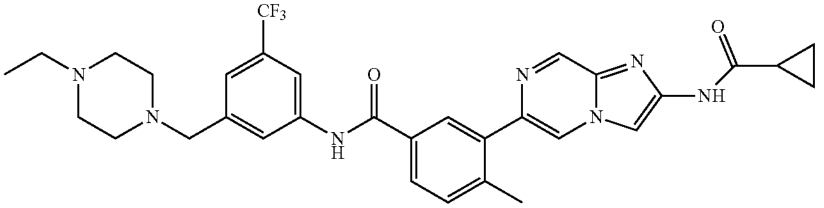 [SMILES: CCN1CCN(Cc2cc(NC(=O)c3ccc(C)c(-c4cn5cc(NC(=O)C6CC6)nc5cn4)c3)cc(C(F)(F)F)c2)CC1]

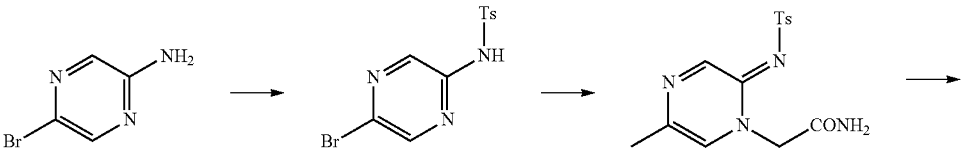

148-1-1 148-1-2 148-1-3

-continued

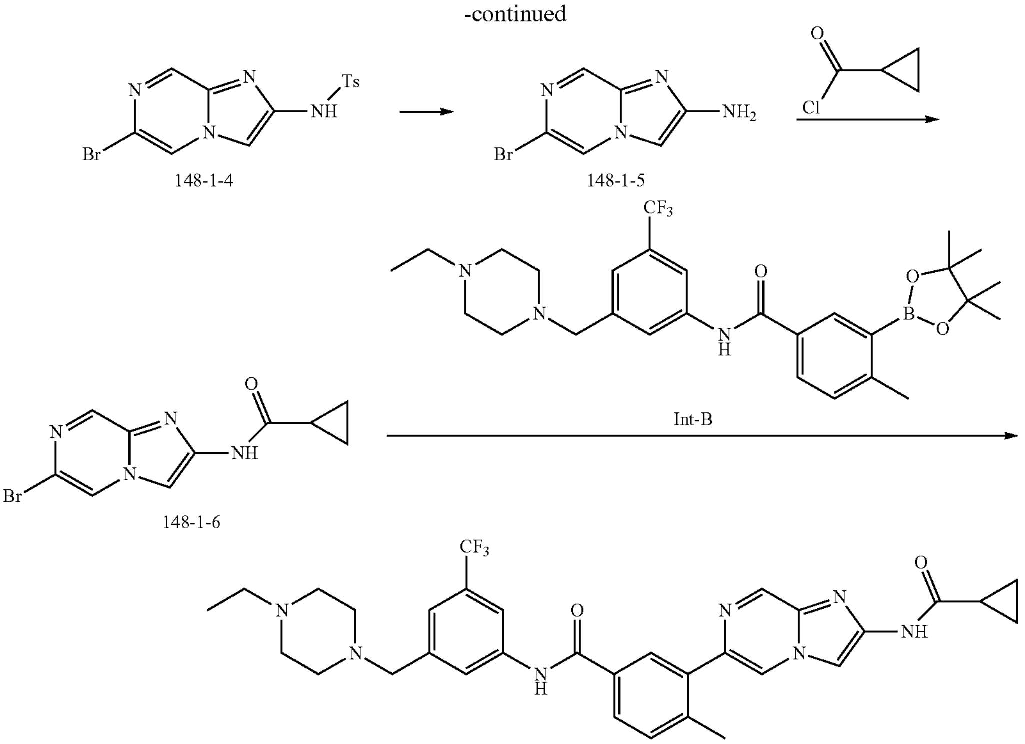

148-1-4

148-1-5

148-1-6

Int-B

I-4

N-(5-bromopyrazin-2-yl)-4-methylbenzenesulfonamide

The mixture of 5-bromopyrazin-2-amine (3.6 g, 20.689 mmol, 1.0 eq) and TsCl (4.717 g, 24.827 mmol, 1.2 eq) in 25 mL pyridine was stirred at 90° C. for 12 h. After cooling to room temperature, 250 mL of water was then added. The precipitated solid was collected by filtrated to give target compound as off-white solid (3.2 g, 47%). LCMS (m/z): 328 $[M+H]^+$.

2-(5-bromo-2-(tosylimino)pyrazin-1(2H)-yl)acetamide

The mixture of N-(5-bromopyrazin-2-yl)-4-methylbenzenesulfonamide (1.6 g, 4.875 mmol, 1.0 eq), 2-bromoacetamide (807 mg, 5.853 mmol, 1.2 eq) and DIPEA (755 mg, 5.853 mmol, 1.2 eq) in 20 mL of DMF was stirred at room temperature overnight. Water (250 mL) was then added and the product was precipitated as off-white solid (0.8 g, 42%). LCMS (m/z): 385 $[M+H]^+$.

N-(6-bromoimidazo[1,2-a]pyrazin-2-yl)-4-methylbenzenesulfonamide

A mixture of 2-(5-bromo-2-(tosylimino)pyrazin-1(2H)-yl)acetamide (700 mg, 1.818 mmol) in 8 mL of $(CF_3SO_2)_2O$ and 16 mL of DCM was stirred at 50° C. for 16 h. Then the mixture was cooled down to room temperature and the solvent was removed under reduced pressure. The residue was then diluted with 80 mL of $H_2O$ and the mixture was extracted with ethyl acetate (100 mL×3). The combined organic phase was washed with saturated brine, dried over $Na_2SO_4$ and concentrated. The crude product was purified by flash column chromatography with PE/EA=1:3 to give the product as a white solid: (0.3 g, 45%). LCMS (m/z): 366.8 $[M+H]^+$.

6-bromoimidazo[1,2-a]pyrazin-2-amine

A mixture of N-(6-bromoimidazo[1,2-a]pyrazin-2-yl)-4-methylbenzenesulfonamide (200 mg, 0.544 mmol) in 3 mL of $H_2SO_4$ was stirred at room temperature for 16 h. Then the mixture was diluted with 80 mL of $H_2O$. Then aq. NaOH was added to adjust pH=9. The resulted mixture was extracted with ethyl acetate (50 mL×3). The combined organic phase was washed with saturated brine, dried over $Na_2SO_4$ and concentrated. The crude product was used in the next step directly (0.12 g, 83%). LCMS (m/z): 214.8 $[M+H]^+$.

N-(6-bromoimidazo[1,2-a]pyrazin-2-yl)cyclopropanecarboxamide

To a mixture of 6-bromoimidazo[1,2-a]pyrazin-2-amine (70 mg, 0.328 mmol, 1.0 eq) and DIPEA (85 mg, 0.656 mmol, 2.0 eq) in 4 mL THF was added cyclopropanecarbonyl chloride (41 mg, 0.394 mmol, 1.2 eq) in 2 mL of THF. Then the mixture was stirred for 12 h. The solvent was removed under reduced pressure and the residue was diluted with 80 mL of $H_2O$. The mixture was extracted with ethyl acetate (100 mL×3). The combined organic phase was washed with saturated brine and dried over $Na_2SO_4$. The crude product was used in the next step directly (70 mg, 75%). LCMS (m/z): 280.9 $[M+H]^+$.

3-(2-(cyclopropanecarboxamido)imidazo[1,2-a]pyrazin-6-yl)-N-(3-((4-ethylpiperazin-1-yl)methyl)-5-(trifluoromethyl)phenyl)-4-methylbenzamide The mixture of N-(6-bromoimidazo[1,2-a]pyrazin-2-yl)cyclopropanecarboxamide (35 mg, 0.12455 mmol, 1.0 eq), N-(3-((4-ethylpiperazin-1-yl)methyl)-5-(trifluoromethyl)

phenyl)-4-methyl-3-(4,4,5,5-tetramethyl-1,3,2-dioxaborolan-2-yl)benzamide (132 mg, 0.2491 mmol, 2.0 eq), $Pd(PPh_3)_4$ (15 mg, 0.012455 mmol, 0.2 eq) and $Na_2CO_3$ (26 mg, 0.2491 mmol, 2.0 eq) in 4 mL of DMF was stirred for 12 h at 100° C. in a sealed tube. The mixture was cooled to room temperature and filtrated. The solvent was concentrated and purified by Prep-HPLC to give the product as a white solid (10 mg, 13%). LCMS (m/z): 606.0 $[M+H]^+$.
Compound I-8
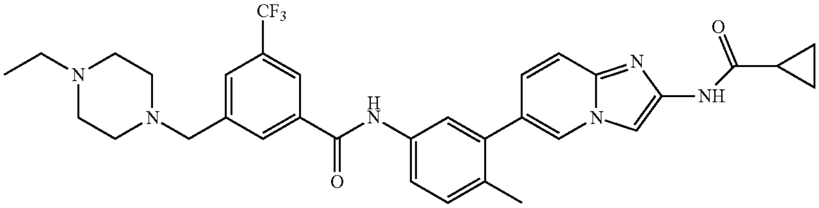
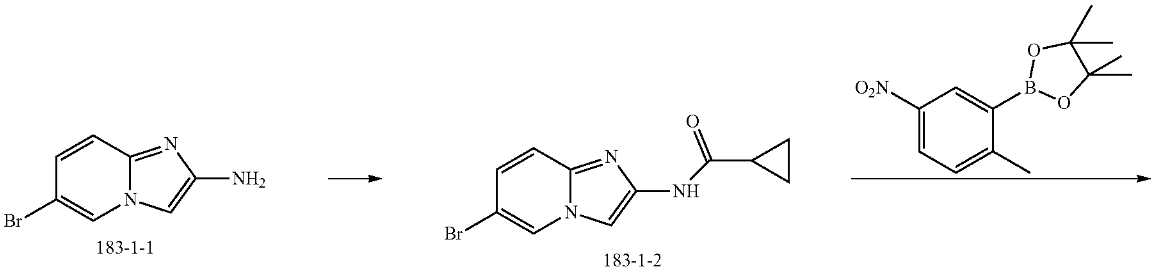
183-1-1
183-1-2
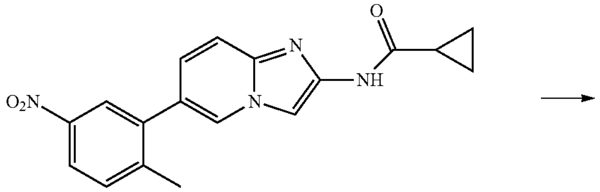
183-1-3
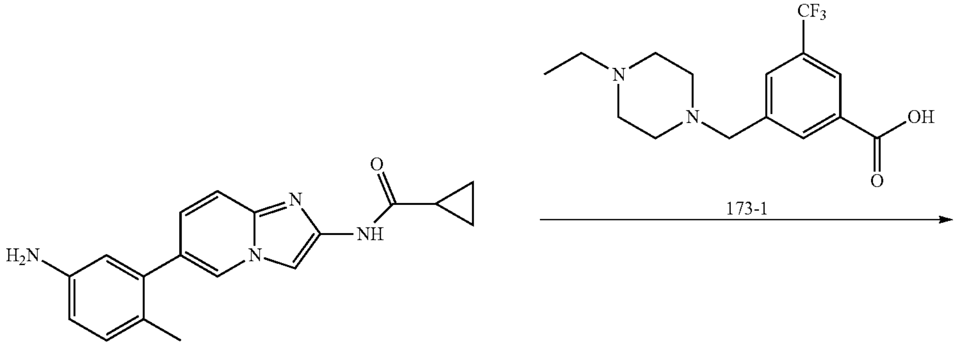
173-1
183-1-4
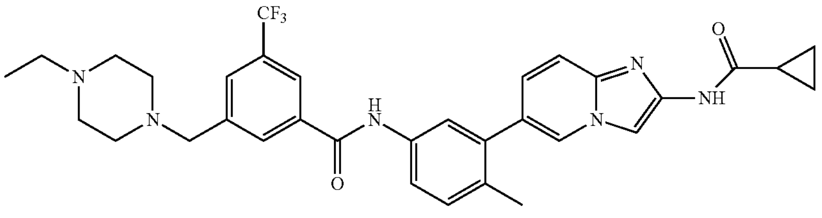 [SMILES: CCN1CCN(Cc2cc(C(=O)Nc3ccc(C)c(-c4ccc5nc(NC(=O)C6CC6)cn5c4)c3)cc(C(F)(F)F)c2)CC1]
I-8

N-(6-bromoimidazo[1,2-a]pyridin-2-yl)cyclopropanecarboxamide

To a mixture of 6-bromoimidazo[1,2-a]pyridin-2-amine (360 mg, 1.7 mmol, 1.0 eq) and TEA (258 mg, 2.55 mmol, 1.5 eq) in 6 mL of DCM was added cyclopropanecarbonyl chloride (204 mg, 1.96 mmol, 1.15 eq) in 2 mL of DCM at 0° C. Then the mixture was stirred at rt for 12 h. The solvent was removed under reduced pressure and the residue was diluted with 80 mL of $H_2O$. The resulted mixture was extracted with ethyl acetate (100 mL×3). The combined organic phase was washed with saturated brine, dried over $Na_2SO_4$. The crude product was purified by silica-gel (hexane:ethyl acetate=4:1 to 1:1 to give the product as a light yellow solid (340 mg, 63%). LCMS (m/z): 280 $[M+H]^+$.

N-(6-(2-methyl-5-nitrophenyl)imidazo[1,2-a]pyridin-2-yl)cyclopropanecarboxamide

The mixture of N-(6-bromoimidazo[1,2-a]pyridin-2-yl) cyclopropanecarboxamide (340 mg, 1.2 mmol, 1.0 eq), 4,4,5,5-tetramethyl-2-(2-methyl-5-nitrophenyl)-1,3,2-dioxaborolane (383 mg, 1.46 mmol, 1.2 eq), $Pd(PPh_3)Cl_2$ (126 mg, 0.18 mmol, 0.15 eq) and sat. $Na_2CO_3$ aq. (3 mL) in 6 mL of dioxane was stirred for 12 h at 100° C. under $N_2$. The mixture was cooled down to room temperature and after filtration, the solvent was removed. The residue was purified by silica-gel (hexane:ethyl acetate=4:1 to 1:1) to give the product as a light yellow solid (190 mg, 47%). LCMS (m/z): 337 $[M+H]^+$.

N-(6-(5-amino-2-methylphenyl)imidazo[1,2-a]pyridin-2-yl)cyclopropanecarboxamide

The mixture of N-(6-(2-methyl-5-nitrophenyl)imidazo[1,2-a]pyridin-2-yl)cyclopropane carboxamide (190 mg, 0.56 mmol), Pd/C (30 mg) in MeOH (10 mL) was stirred at r.t under $H_2$ (1 atm) for 16 h. The solution was then filtered, concentrated to remove the solvent to give the product (light brown solid, 130 mg, 76%). LCMS: 307 (M+H)+.

N-(3-(2-(cyclopropanecarboxamido)imidazo[1,2-a]pyridin-6-yl)-4-methylphenyl)-3-((4-ethyl piperazin-1-yl)methyl)-5-(trifluoromethyl)benzamide To a mixture of N-(6-(5-amino-2-methylphenyl)imidazo[1,2-a]pyridin-2-yl)cyclopropane carboxamide (35 mg, 0.11 mmol), 3-((4-ethylpiperazin-1-yl)methyl)-5-(trifluoromethyl) benzoic acid (36 mg, 0.11 mmol) in DCM (4 mL) was added EDCI (32 mg, 0.165 mmol), HOBt (22 mg, 0.165 mmol) and DIPEA (0.1 mL). The reaction mixture was stirred at rt overnight. After completion, the mixture was extracted with EA (50 mL×3). The organic phase was washed with brine (20 mL×3), dried with $Na_2SO_4$, filtered, concentrated to remove the solvent and the residue was purified by prep-HPLC to obtain Compound I-8 (white solid, 4 mg, yield 6%). LCMS (m/z): 605 $[M+H]^+$.

$^1H$ NMR (500 MHz, DMSO-$d_6$) δ 11.15 (s, 1H), 10.54 (s, 1H), 8.65 (s, 1H), 8.28 (s, 1H), 8.24 (s, 1H), 8.13 (s, 1H), 7.93 (s, 1H), 7.80-7.70 (m, 2H), 7.65-7.51 (m, 1H), 7.35 (m, 2H), 3.49 (s, 2H), 3.21-2.88 (m, 6H), 2.64-2.41 (m, 4H), 2.27 (s, 3H), 1.96 (s, 1H), 1.20 (t, J=7.3 Hz, 3H), 0.91-0.76 (m, 4H).

Compound I-6

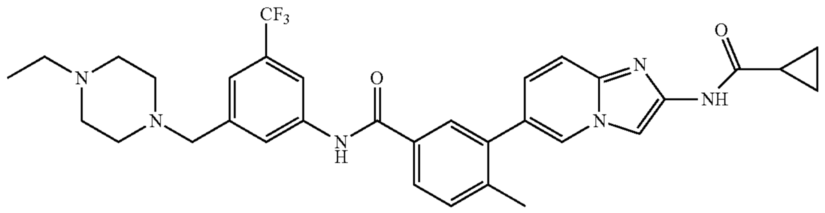 [SMILES: CCN1CCN(Cc2cc(NC(=O)c3ccc(C)c(-c4ccc5nc(NC(=O)C6CC6)cn5c4)c3)cc(C(F)(F)F)c2)CC1]

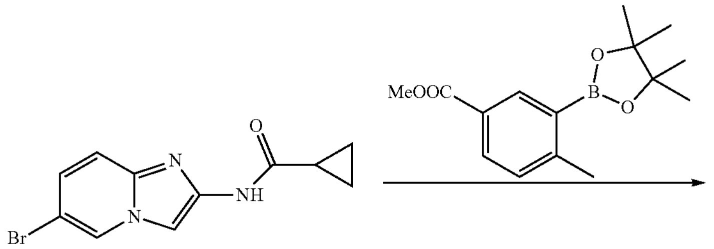

183-1-2

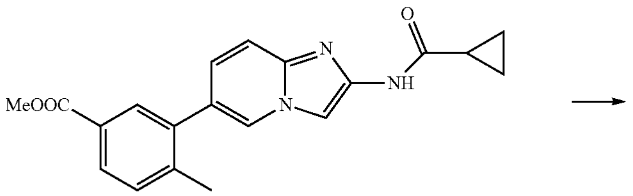

185-1-1

-continued

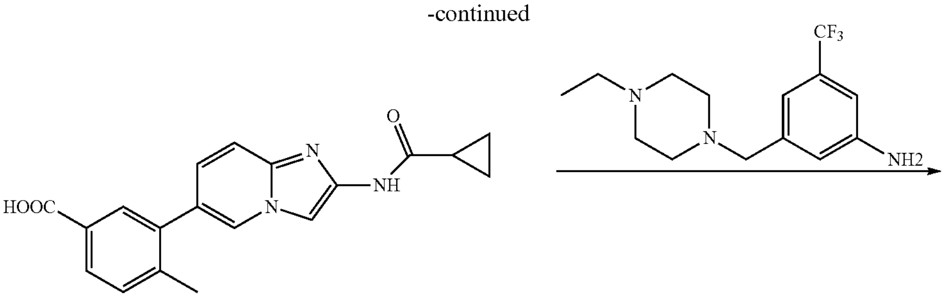

185-1-2

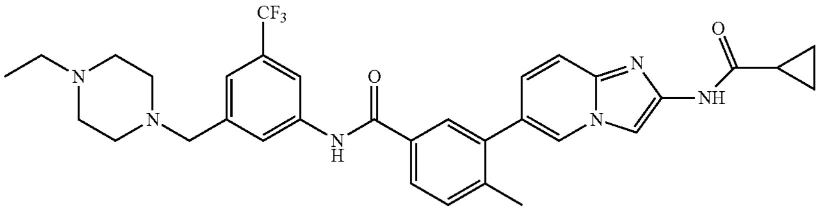

I-6

Methyl 3-(2-(cyclopropanecarboxamido)imidazo[1,2-a]pyridin-6-yl)-4-methylbenzoate The mixture of N-(6-bromoimidazo[1,2-a]pyridin-2-yl) cyclopropanecarboxamide (30 mg, 0.11 mmol, 1.0 eq), methyl 4-methyl-3-(4,4,5,5-tetramethyl-1,3,2-dioxaborolan-2-yl) benzoate (36 mg, 0.13 mmol, 1.2 eq), $Pd(PPh_3)Cl_2$ (12 mg, 0.016 mmol, 0.15 eq) and sat. $Na_2CO_3$ aq. (2 mL) in 4 mL of dioxane was stirred for 8 h at 100° C. under $N_2$. The mixture was cooled down to room temperature and filtered. The solvent was then removed and the crude was purified with silica-gel (hexane:ethyl acetate=4:1) to give the product as a light yellow solid (30 mg, 78%). LCMS (m/z): 350 $[M+H]^+$.

3-(2-(cyclopropanecarboxamido)imidazo[1,2-a]pyridin-6-yl)-4-methylbenzoic acid To a solution of methyl 3-(2-(cyclopropanecarboxamido) imidazo[1,2-a]pyridin-6-yl)-4-methylbenzoate (30 mg, 0.086 mmol) in THF (2 mL) was add 1 mL of 3 N LiOH aqueous solution. The reaction mixture was stirred at rt overnight and then purified by prep-HPLC ($C_{18}$ column, $CH_3CN/H_2O$, containing 0.05% $NH_4HCO_3$) after removing the solvent to give the target compound (white solid, 21 mg, yield 73%). LCMS (m/z): 335 $[M+H]^+$.

3-(2-(cyclopropanecarboxamido)imidazo[1,2-a]pyridin-6-yl)-N-(3-((4-ethylpiperazin-1-yl)methyl)-5-(trifluoromethyl)phenyl)-4-methylbenzamide To a mixture of 3-(2-(cyclopropanecarboxamido)imidazo [1,2-a]pyridin-6-yl)-4-methyl benzoic acid (15 mg, 0.045 mmol), 3-((4-ethylpiperazin-1-yl)methyl)-5-(trifluoromethyl) aniline (14 mg, 0.049 mmol) in DMF (0.5 mL) was added HATU (26 mg, 0.067 mmol) and DIPEA (18 mg, 0.135 mmol). The reaction mixture was stirred at rt overnight. After completion, the mixture was extracted with EA (50 mL×3). The organic phase was washed with brine (20 mL×3), dried with $Na_2SO_4$, filtered, concentrated, and the residue was purified by prep-HPLC to obtain Compound I-6 (white solid, 10.6 mg, yield 39%). LCMS (m/z): 605 $[M+H]^+$. $^1H$ NMR (500 MHz, DMSO-$d_6$) δ 11.24 (s, 1H), 10.60 (s, 1H), 8.76-8.73 (m, 1H), 8.20-8.12 (m, 3H), 8.06-7.97 (m, 2H), 7.65 (m, 1H), 7.58 (m, 1H), 7.52-7.44 (m, 2H), 3.85 (m, 2H), 3.54 (m, 2H), 3.26-2.90 (m, 8H), 2.42 (s, 3H), 2.09-1.90 (m, 1H), 1.24 (t, J=7.3 Hz, 3H), 0.89 (d, J=6.2 Hz, 4H).

Compound I-7

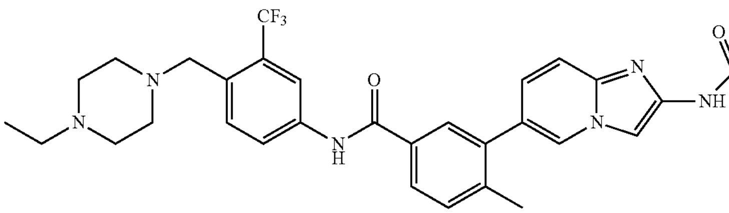

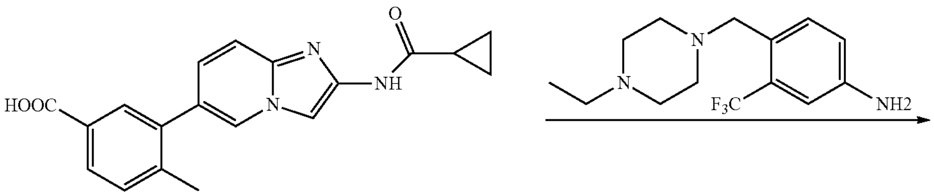

185-1-2

-continued

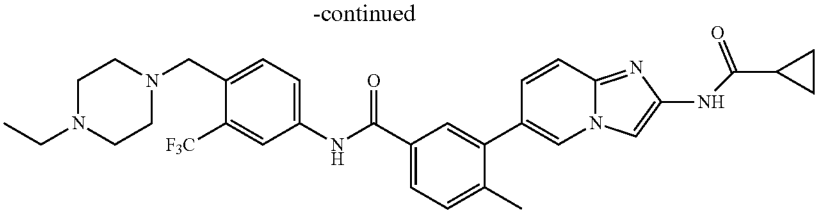

I-7

3-(2-(cyclopropanecarboxamido)imidazo[1,2-a]pyridin-6-yl)-N-(4-((4-ethylpiperazin-1-yl)methyl)-3-(trifluoromethyl)phenyl)-4-methylbenzamide Compound I-7 is prepared by using the similar procedure as Compound I-6, changing 3-((4-ethylpiperazin-1-yl) methyl)-5-(trifluoromethyl)aniline to 4-((4-ethylpiperazin-1-yl) methyl)-3-(trifluoromethyl) aniline. LCMS (m/z): 605 $[M+H]^+$. $^1H$ NMR (500 MHz, DMSO-$d_6$) δ 11.20 (s, 1H), 10.53 (s, 1H), 8.71 (s, 1H), 8.22 (d, J=2.2 Hz, 1H), 8.12 (m, 2H), 7.97 (m, 2H), 7.72 (d, J=8.5 Hz, 1H), 7.61 (d, J=9.1 Hz, 1H), 7.54 (d, J=8.3 Hz, 1H), 7.44 (dd, J=9.1, 1.8 Hz, 1H), 3.70 (s, 2H), 3.47 (m, 2H), 3.20-3.11 (m, 2H), 2.98 (m, 4H), 2.38 (m, 5H), 1.95 (q, J=6.3 Hz, 1H), 1.21 (t, J=7.3 Hz, 3H), 0.85 (d, J=6.2 Hz, 4H).

Compound I-2

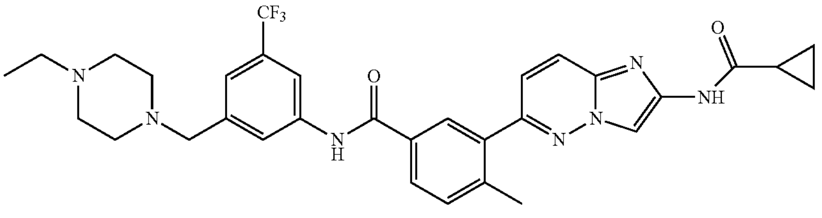 [SMILES: CCN1CCN(Cc2cc(NC(=O)c3ccc(C)c(-c4ccc5nc(NC(=O)C6CC6)cn5n4)c3)cc(C(F)(F)F)c2)CC1]

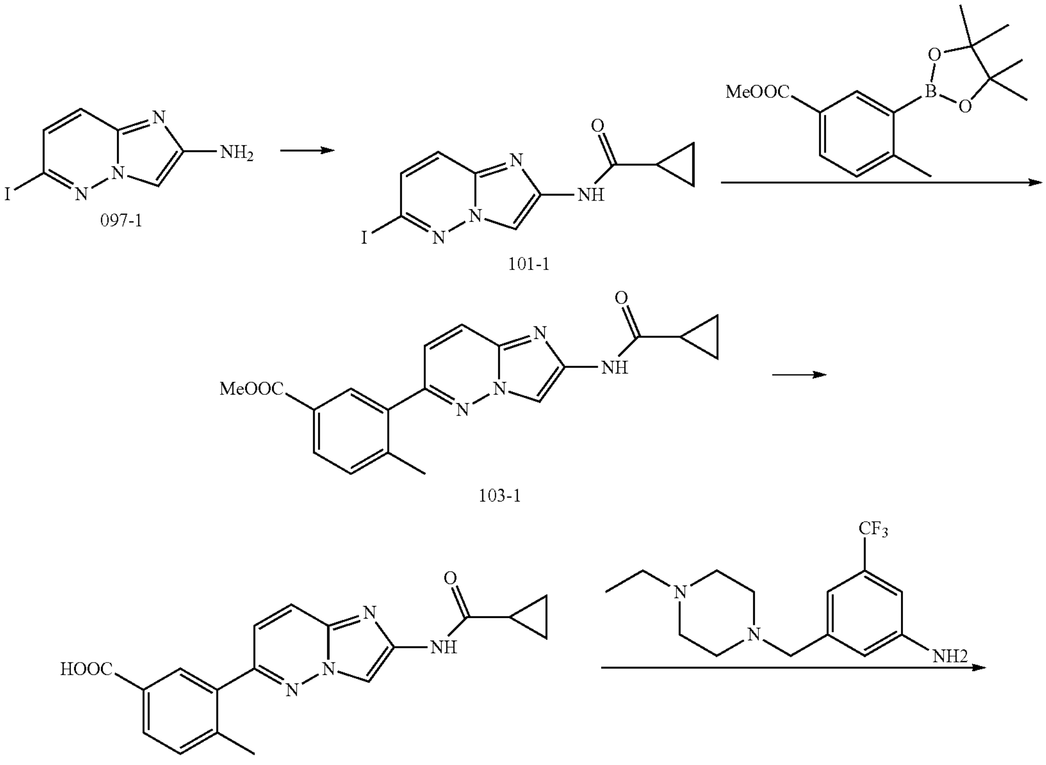

097-1

101-1

103-1

104-1

-continued

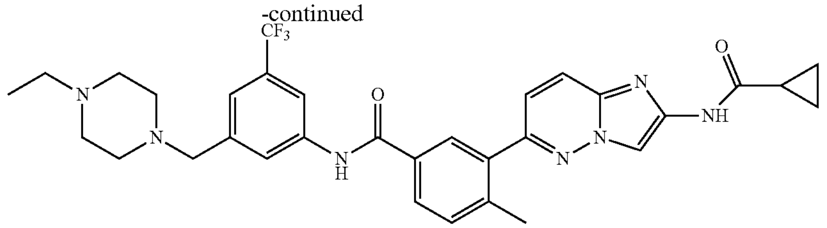

I-2

N-(6-iodoimidazo[1,2-b]pyridazin-2-yl)cyclopropanecarboxamide

To a mixture of 6-iodoimidazo[1,2-b]pyridazin-2-amine (180 mg, 0.69 mmol, 1.0 eq) and DIPEA (180 mg, 1.38 mmol, 2 eq) in DCM (6 mL) was added cyclopropanecarbonyl chloride (80 mg, 0.76 mmol, 1.1 eq) at 0° C. Then the mixture was stirred at rt for 12 h. The solvent was removed under reduced pressure and the residue was then diluted with $H_2O$ (80 mL). The resulted solution was extracted with ethyl acetate (100 mL×3). The combined organic phase was washed with brine and dried over $Na_2SO_4$. The crude product was purified by silica gel (hexane:ethyl acetate=4:1 to 1:1)) to give the product as a light yellow solid (68 mg, 30%). LCMS (m/z): 329 $[M+H]^+$.

Methyl 3-(2-(cyclopropanecarboxamido)imidazo[1,2-b]pyridazin-6-yl)-4-methylbenzoate The mixture of N-(6-iodoimidazo[1,2-b]pyridazin-2-yl) cyclopropanecarboxamide (68 mg, 0.21 mmol, 1.0 eq), methyl 4-methyl-3-(4,4,5,5-tetramethyl-1,3,2-dioxaborolan-2-yl) benzoate (70 mg, 0.25 mmol, 1.2 eq), $Pd(PPh_3)Cl_2$ (17 mg, 0.021 mmol, 0.1 eq) and $Cs_2CO_3$ (140 mg, 0.42 mmol) in dioxane (4 mL)/water (0.4 mL) was stirred for 8 h at 100° C. under $N_2$. The mixture was cooled down to room temperature and the filtered. The solvent was removed under reduced pressure and the crude was purified by silica gel (hexane:ethyl acetate=3:1) give the product as a light yellow solid (70 mg, 95%). LCMS (m/z): 351 $[M+H]^+$.

3-(2-(cyclopropanecarboxamido)imidazo[1,2-b]pyridazin-6-yl)-4-methylbenzoic acid To a solution of methyl 3-(2-(cyclopropanecarboxamido) imidazo[1,2-b]pyridazin-6-yl)-4-methylbenzoate (70 mg, 0.2 mmol) in THF (2 mL) was add 1 mL of 3 N LiOH aqueous solution. The reaction mixture was stirred at rt overnight and the product then purified by prep-HPLC (Cis column, $CH_3CN/H_2O$, containing 0.05% $NH_4HCO_3$) to obtain the target compound (white solid, 40 mg, yield 60%). LCMS (m/z): 336 $[M+H]^+$.

3-(2-(cyclopropanecarboxamido)imidazo[1,2-b]pyridazin-6-yl)-N-(3-((4-ethylpiperazin-1-yl)methyl)-5-(trifluoromethyl)phenyl)-4-methylbenzamide To a mixture of 3-(2-(cyclopropanecarboxamido)imidazo [1,2-b]pyridazin-6-yl)-4-methyl benzoic acid (17 mg, 0.05 mmol) in THF (1 mL) was added oxalyl chloride (8.5 μL, 0.1 mmol), and drops of DMF at 0° C. The reaction solution was stirred at 0° C. for 1 h. Then the THF and excess oxalyl chloride were removed under reduced pressure. The residue was re-dissolved in DCM (3 mL). 3-((4-ethylpiperazin-1-yl)methyl)-5-(trifluoromethyl) aniline (17 mg, 0.06 mmol) in DMF (0.5 mL) and DIPEA (0.03 mL) were then added. The reaction mixture was stirred at rt overnight. After completion, the mixture was extracted with DCM (50 mL×3). The organic phase was washed with brine (20 mL×3), dried with $Na_2SO_4$, filtered, concentrated and the residue was purified by prep-HPLC to obtain the product (white solid, 10.6 mg, yield 35%). LCMS (m/z): 606 $[M+H]^+$. $^1H$ NMR (500 MHz, DMSO-$d_6$) δ 11.21 (s, 1H), 10.55 (s, 1H), 8.29 (s, 1H), 8.18 (s, 1H), 8.13-8.07 (m, 2H), 8.05-7.98 (m, 2H), 7.56 (d, J=8.1 Hz, 1H), 7.46 (d, J=9.3 Hz, 1H), 7.35 (s, 1H), 3.54 (s, 2H), 2.49-2.23 (m, 12H), 1.97 (m, 1H), 1.23 (s, 1H), 0.97 (t, J=7.2 Hz, 3H), 0.90-0.80 (m, 4H).

Compound I-15

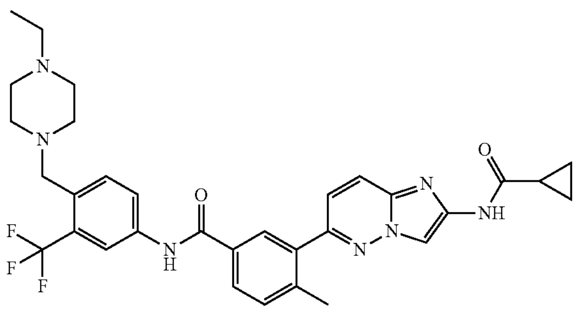 [SMILES: CCN1CCN(Cc2ccc(NC(=O)c3ccc(C)c(-c4ccc5nc(NC(=O)C6CC6)cn5n4)c3)cc2C(F)(F)F)CC1]

3-(2-(cyclopropanecarboxamido)imidazo[1,2-b]pyridazin-6-yl)-N-(4-((4-ethylpiperazin-1-yl)methyl)-3-(trifluoromethyl)phenyl)-4-methylbenzamide Compound I-15 is prepared by using the similar procedure with Compound I-2, except that 4-((4-ethylpiperazin-1-yl) methyl)-3-(trifluoromethyl) aniline was used in the last step. LCMS (m/z): 606 $[M+H]^+$.

Compound I-1

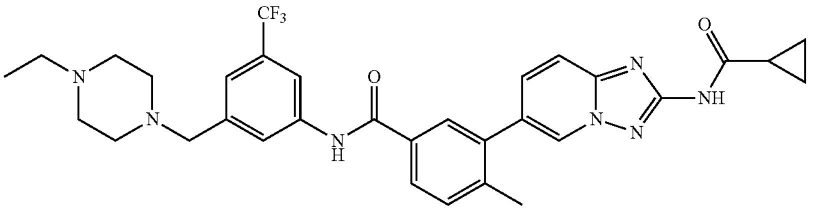 [SMILES: CCN1CCN(Cc2cc(NC(=O)c3ccc(C)c(-c4ccc5nc(NC(=O)C6CC6)nn5c4)c3)cc(C(F)(F)F)c2)CC1]

3-(2-(cyclopropanecarboxamido)-[1,2,4]triazolo[1,5-a]pyridin-6-yl)-N-(3-((4-ethylpiperazin-1-yl)methyl)-5-(trifluoromethyl)phenyl)-4-methylbenzamide Compound I-1 is prepared by using the same procedure as for Compound I-2, except that 6-bromo-[1,2,4]triazolo[1,5-a] pyridin-2-amine was used in the first step. LCMS: 606 (M+H)+. $^1$H NMR (500 MHz, DMSO-$d_6$) δ 11.04 (s, 1H), 10.44 (s, 1H), 8.93 (s, 1H), 8.10 (s, 1H), 7.98-7.93 (m, 2H), 7.90 (dd, J=7.9, 1.9 Hz, 1H), 7.47 (d, J=8.0 Hz, 1H), 7.74-7.65 (m, 2H), 7.30 (s, 1H), 3.51 (s, 2H), 2.44 (m, 9H), 2.32 (s, 3H), 2.00 (s, 1H), 1.19-1.15 (m, 1H), 0.98 (t, J=7.1 Hz, 3H), 0.86-0.65 (m, 4H).

Compound I-3

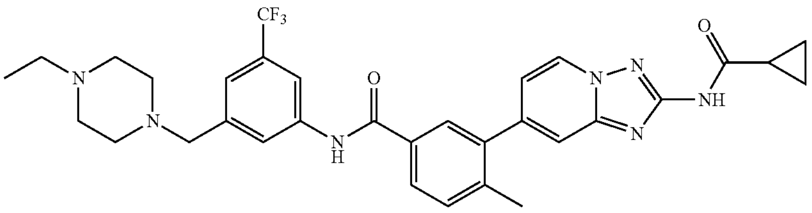 [SMILES: CCN1CCN(Cc2cc(NC(=O)c3ccc(C)c(-c4ccn5nc(NC(=O)C6CC6)nc5c4)c3)cc(C(F)(F)F)c2)CC1]

3-(2-(cyclopropanecarboxamido)-[1,2,4]triazolo[1,5-a]pyridin-7-yl)-N-(3-((4-ethylpiperazin-1-yl)methyl)-5-(trifluoromethyl)phenyl)-4-methylbenzamide Compound I-3 is prepared by using the same procedure as for Compound I-2, except that 7-bromo[1,2,4]triazolo[1,5-a]pyridin-2-amine was used in the first step. LCMS: 606 $(M+H)^+$. 1H NMR (500 MHz, DMSO-d6) δ 11.13 (s, 1H), 10.54 (s, 1H), 8.85 (d, J=6.9 Hz, 1H), 8.11 (t, J=1.9 Hz, 1H), 7.95 (d, J=7.7 Hz, 3H), 7.70 (t, J=1.3 Hz, 1H), 7.53 (d, J=7.9 Hz, 1H), 7.37 (s, 1H), 7.21 (dd, J=6.9, 1.9 Hz, 1H), 3.62-3.47 (m, 6H), 2.77-2.25 (m, 9H), 1.02 (t, J=7.2 Hz, 4H), 0.93-0.69 (m, 4H).

Compound I-16

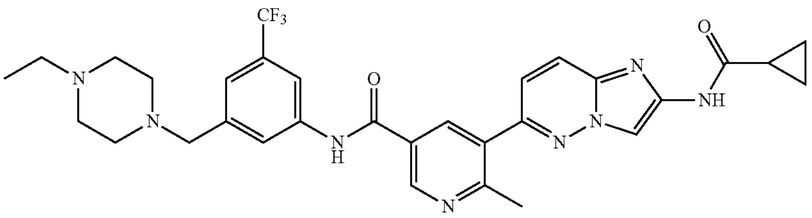 [SMILES: CCN1CCN(Cc2cc(NC(=O)c3cnc(C)c(-c4ccc5nc(NC(=O)C6CC6)cn5n4)c3)cc(C(F)(F)F)c2)CC1]

5-(2-(cyclopropanecarboxamido)imidazo[1,2-b]pyridazin-6-yl)-N-(3-((4-ethylpiperazin-1-yl)methyl)-5-(trifluoromethyl)phenyl)-6-methylnicotinamide Compound I-16 is prepared by using the same procedure as for Compound I-2, except that methyl 6-methyl-5-(4,4,5,5-tetramethyl-1,3,2-dioxaborolan-2-yl)nicotinate was used in the second step. LCMS: 607 (M+H)+. $^1$H NMR (500 MHz, DMSO-$d_6$) δ 11.26 (s, 1H), 10.78 (s, 1H), 9.14 (d, J=2.2 Hz, 1H), 8.47 (d, J=2.2 Hz, 1H), 8.33 (s, 1H), 8.16 (d, J=9.3 Hz, 2H), 8.04 (s, 1H), 7.55 (d, J=9.3 Hz, 1H), 7.41 (s, 1H), 3.60 (s, 2H), 3.17 (d, J=3.4 Hz, 2H), 2.66 (s, 3H), 2.04-1.93 (m, 1H), 1.07 (s, 3H), 0.88-0.70 (m, 4H).

Compound I-17

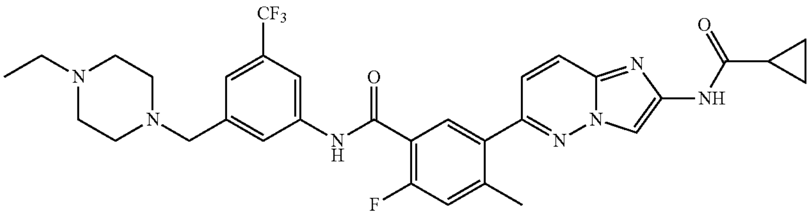 [SMILES: CCN1CCN(Cc2cc(NC(=O)c3cc(-c4ccc5nc(NC(=O)C6CC6)cn5n4)c(C)cc3F)cc(C(F)(F)F)c2)CC1]

5-(2-(cyclopropanecarboxamido)imidazo[1,2-b]pyridazin-6-yl)-N-(3-((4-ethylpiperazin-1-yl)methyl)-5-(trifluoromethyl)phenyl)-2-fluoro-4-methylbenzamide Compound I-17 is prepared by using the same procedure as for Compound I-2, except that methyl 2-fluoro-4-methyl-5-(4,4,5,5-tetramethyl-1,3,2-dioxaborolan-2-yl)benzoate was used in the second step. LCMS: 624 (M+H)+. $^1$H NMR (500 MHz, DMSO-$d_6$) δ 11.23 (s, 1H), 10.79 (s, 1H), 8.28 (s, 1H), 8.10-8.06 (m, 2H), 7.98 (s, 1H), 7.82 (d, J=7.3 Hz, 1H), 7.48-7.38 (m, 3H), 3.65 (s, 2H), 3.51 (s, 2H), 2.45 (s, 3H), 1.99 (ddd, J=12.5, 7.3, 5.2 Hz, 1H), 1.17 (s, 3H), 0.89-0.75 (m, 4H).

Compound I-18

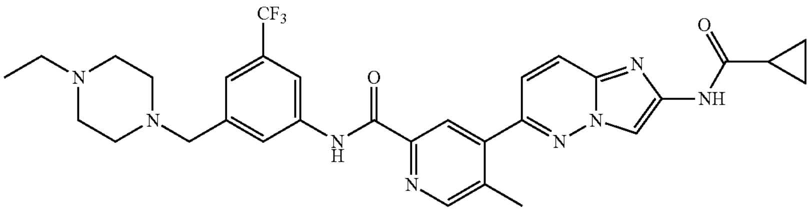 [SMILES: CCN1CCN(Cc2cc(NC(=O)c3cc(-c4ccc5nc(NC(=O)C6CC6)cn5n4)c(C)cn3)cc(C(F)(F)F)c2)CC1]

4-(2-(cyclopropanecarboxamido)imidazo[1,2-b]pyridazin-6-yl)-N-(3-((4-ethylpiperazin-1-yl)methyl)-5-(trifluoromethyl)phenyl)-5-methylpicolinamide Compound I-18 is prepared by using the same procedure as for Compound I-2, except that ethyl 5-methyl-4-(4,4,5,5-tetramethyl-1,3,2-dioxaborolan-2-yl)picolinate was used in the second step. LCMS: 607 (M+H)+. $^1$H NMR (500 MHz, DMSO-$d_6$) δ 11.28 (s, 1H), 11.05 (s, 1H), 8.80 (s, 1H), 8.33 (d, J=9.0 Hz, 2H), 8.24 (d, J=9.2 Hz, 2H), 8.16 (d, J=9.3 Hz, 1H), 7.55 (d, J=9.3 Hz, 1H), 7.43 (s, 1H), 3.67 (s, 2H), 3.51 (s, 2H), 2.54 (s, 3H), 2.00 (ddt, J=12.5, 8.1, 3.5 Hz, 1H), 1.18 (s, 3H), 0.89-0.83 (m, 4H).

Compound I-19

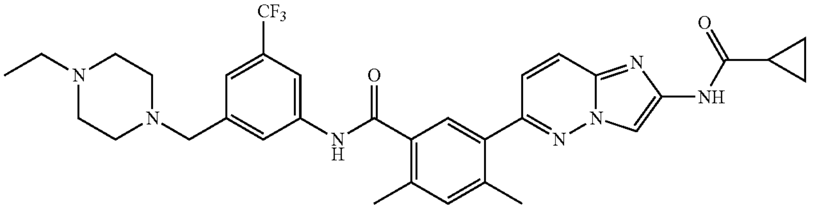 [SMILES: CCN1CCN(Cc2cc(NC(=O)c3cc(-c4ccc5nc(NC(=O)C6CC6)cn5n4)c(C)cc3C)cc(C(F)(F)F)c2)CC1]

5-(2-(cyclopropanecarboxamido)imidazo[1,2-b]pyridazin-6-yl)-N-(3-((4-ethylpiperazin-1-yl)methyl)-5-(trifluoromethyl)phenyl)-2,4-dimethylbenzamide Compound I-19 is prepared by using the same procedure as for Compound I-2, except that methyl 2,4-dimethyl-5-(4,4,5,5-tetramethyl-1,3,2-dioxaborolan-2-yl)benzoate was used in the second step. LCMS: 620 (M+H)+. $^1$H NMR (500 MHz, DMSO-$d_6$) δ 11.20 (s, 1H), 10.64 (s, 1H), 8.27 (s, 1H), 8.12 (s, 1H), 8.07 (d, J=9.3 Hz, 1H), 7.95 (s, 1H), 7.65 (s, 1H), 7.44 (d, J=9.3 Hz, 1H), 7.37 (s, 1H), 7.35 (s, 1H), 3.59 (s, 2H), 3.51 (s, 2H), 2.46 (s, 3H), 2.41 (s, 3H), 1.98 (hept, J=5.2 Hz, 1H), 1.07 (s, 3H), 0.85 (td, J=5.2, 2.2 Hz, 4H).

Compound I-20

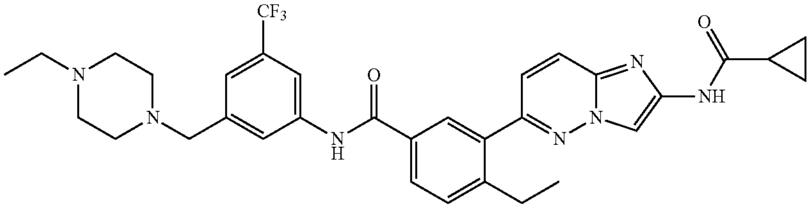 [SMILES: CCc1ccc(C(=O)Nc2cc(CN3CCN(CC)CC3)cc(C(F)(F)F)c2)cc1-c1ccc2nc(NC(=O)C3CC3)cn2n1]

3-(2-(cyclopropanecarboxamido)imidazo[1,2-b]pyridazin-6-yl)-4-ethyl-N-(3-((4-ethylpiperazin-1-yl)methyl)-5-(trifluoromethyl)phenyl)benzamide Compound I-20 is prepared by using the same procedure as for Compound I-2, except that methyl 4-ethyl-3-(4,4,5,5-tetramethyl-1,3,2-dioxaborolan-2-yl)benzoate was used in the second step. LCMS: 620 (M+H)+. $^1$H NMR (500 MHz, DMSO-$d_6$) δ 11.23 (s, 1H), 10.55 (s, 1H), 8.29 (s, 1H), 8.18 (s, 1H), 8.12 (d, J=9.3 Hz, 1H), 8.07 (d, J=7.5 Hz, 2H), 8.02 (s, 1H), 7.60 (d, J=8.0 Hz, 1H), 7.42 (d, J=9.2 Hz, 1H), 7.36 (s, 1H), 3.56 (s, 2H), 3.33 (s, 2H), 2.76 (q, J=7.5 Hz, 2H), 2.42 (s, 3H), 1.99 (ddd, J=12.6, 7.3, 5.2 Hz, 1H), 1.04-0.95 (m, 3H), 0.89-0.77 (m, 4H).

Compound I-21

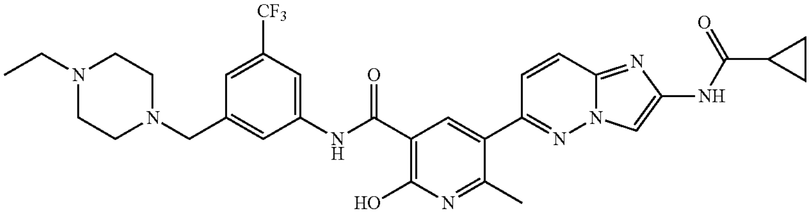 [SMILES: CCN1CCN(Cc2cc(NC(=O)c3cc(-c4ccc5nc(NC(=O)C6CC6)cn5n4)c(C)nc3O)cc(C(F)(F)F)c2)CC1]

5-(2-(cyclopropanecarboxamido)imidazo[1,2-b]pyridazin-6-yl)-N-(3-((4-ethylpiperazin-1-yl)methyl)-5-(trifluoromethyl)phenyl)-2-hydroxy-6-methylnicotinamide Compound I-21 is prepared by using the same procedure as for Compound I-2, except that methyl 2-hydroxy-6-methyl-5-(4,4,5,5-tetramethyl-1,3,2-dioxaborolan-2-yl)nicotinate was used in the second step. LCMS: 623 (M+H)+. $^1$H NMR (500 MHz, DMSO-$d_6$) δ 12.22 (s, 1H), 11.21 (s, 1H), 8.57 (s, 1H), 8.28 (s, 1H), 8.20 (s, 1H), 8.07 (d, J=9.3 Hz, 1H), 7.74 (s, 1H), 7.43 (d, J=9.3 Hz, 1H), 7.38 (s, 1H), 3.58 (s, 2H), 3.32 (s, 2H), 2.43 (s, 3H), 2.02-1.95 (m, 1H), 1.01 (t, J=7.1 Hz, 3H), 0.89-0.78 (m, 4H).

Compound I-22

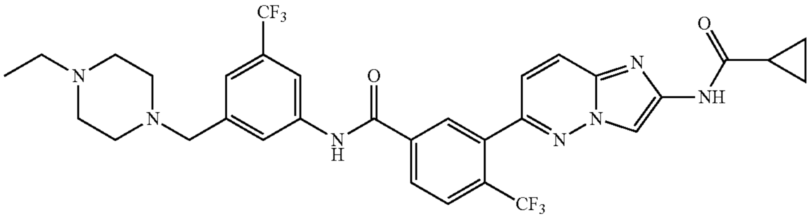 [SMILES: CCN1CCN(Cc2cc(NC(=O)c3ccc(C(F)(F)F)c(-c4ccc5nc(NC(=O)C6CC6)cn5n4)c3)cc(C(F)(F)F)c2)CC1]

3-(2-(cyclopropanecarboxamido)imidazo[1,2-b]pyridazin-6-yl)-N-(3-((4-ethylpiperazin-1-yl)methyl)-5-(trifluoromethyl)phenyl)-4-(trifluoromethyl)benzamide Compound I-22 is prepared by using the same procedure as for Compound I-2, except that Methyl 3-(4,4,5,5-tetramethyl-1,3,2-dioxaborolan-2-yl)-4-(trifluoromethyl)benzoate was used in the second step. LCMS: 660 $[M+H]^+$. $^1$H NMR (500 MHz, DMSO-$d_6$) δ 11.27 (s, 1H), 10.81 (s, 1H), 8.31 (d, J=8.9 Hz, 1H), 8.30-8.26 (m, 2H), 8.19-8.13 (m, 2H), 8.02 (s, 1H), 7.45-7.37 (m, 2H), 3.58 (d, J=2.9 Hz, 2H), 3.33 (s, 2H), 2.45 (s, 3H), 1.99 (tt, J=7.2, 5.4 Hz, 1H), 1.02 (s, 3H), 0.86 (dd, J=6.2, 3.0 Hz, 4H).

Compound I-23

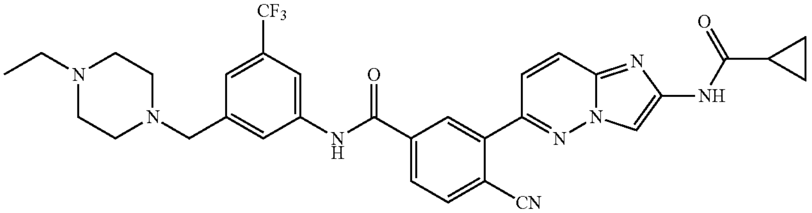 [SMILES: CCN1CCN(Cc2cc(NC(=O)c3ccc(C#N)c(-c4ccc5nc(NC(=O)C6CC6)cn5n4)c3)cc(C(F)(F)F)c2)CC1]

4-cyano-3-(2-(cyclopropanecarboxamido)imidazo[1,2-b]pyridazin-6-yl)-N-(3-((4-ethylpiperazin-1-yl)methyl)-5-(trifluoromethyl)phenyl)benzamide Compound I-23 is prepared by using the same procedure as for Compound I-2, except that Methyl 4-cyano-3-(4,4,5,5-tetramethyl-1,3,2-dioxaborolan-2-yl)benzoate was used in the second step. LCMS: 617 $[M+H]^+$. $^1$H NMR (500 MHz, DMSO-$d_6$) δ 11.32 (s, 1H), 10.86 (s, 1H), 8.49 (s, 1H), 8.35 (s, 1H), 8.28-8.24 (m, 3H), 8.18 (s, 1H), 8.03 (s, 1H), 7.77 (d, J=9.3 Hz, 1H), 7.42 (s, 1H), 3.59 (s, 2H), 3.32 (s, 2H), 2.44-2.36 (m, 3H), 2.00 (s, 1H), 1.01 (s, 3H), 0.86 (dd, J=7.1, 4.6 Hz, 4H).

Compound I-9 and Compound I-10
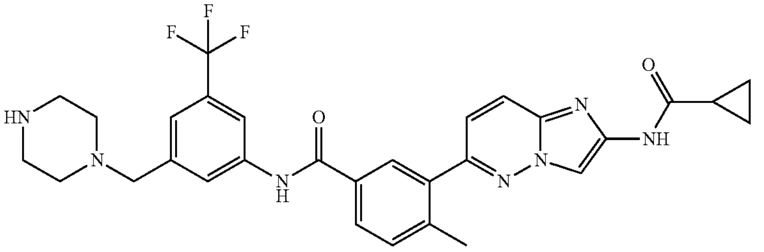
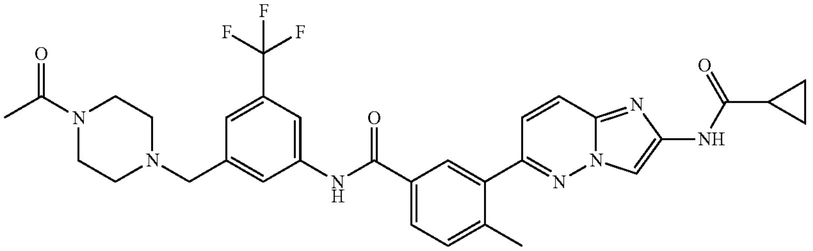
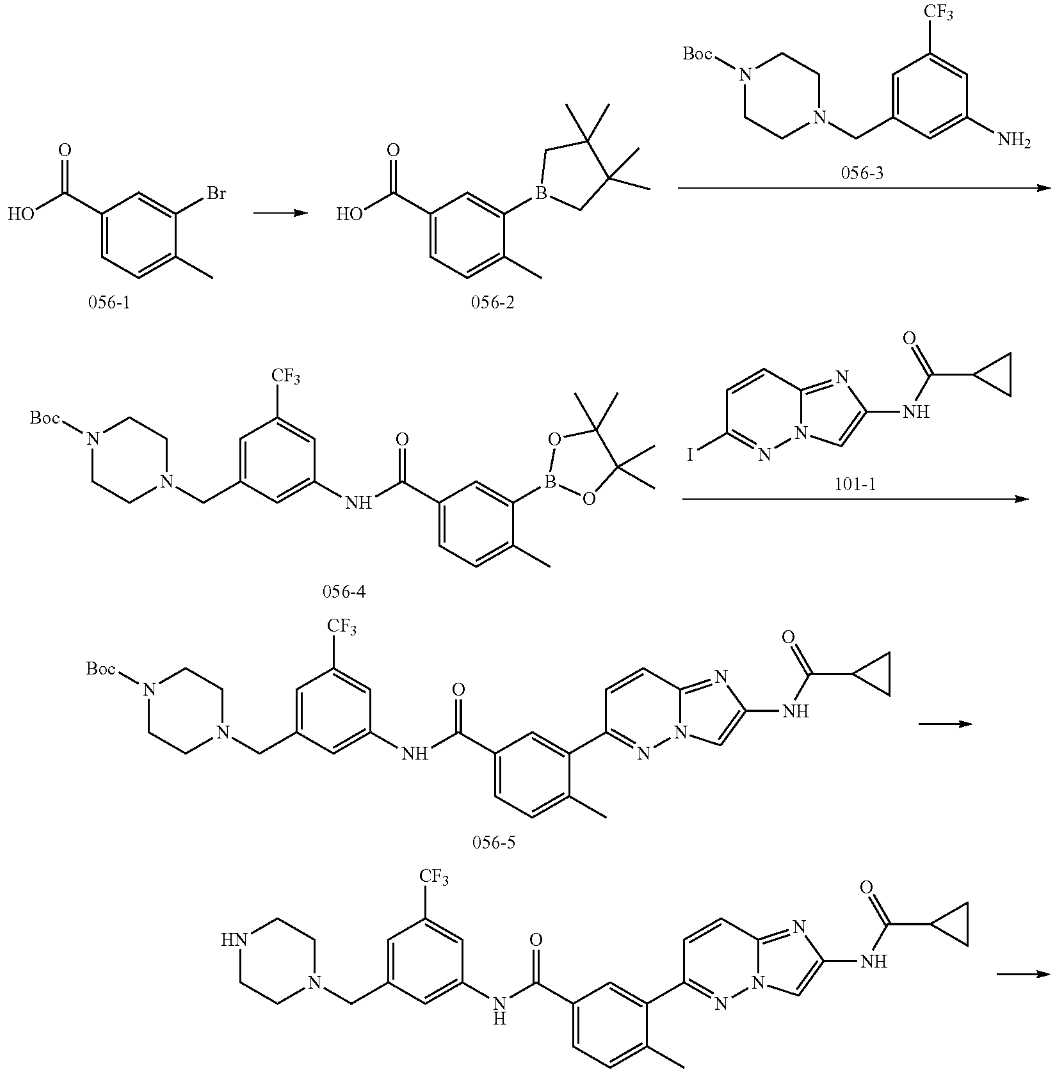

-continued

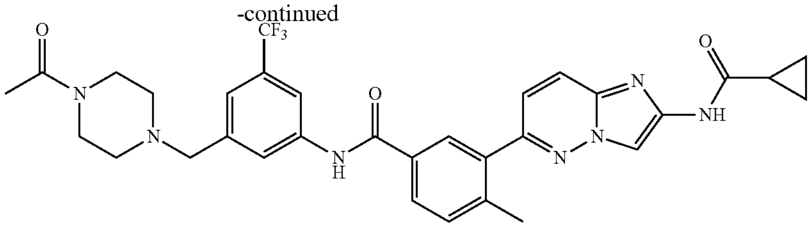

I-10

4-methyl-3-(4,4,5,5-tetramethyl-1,3,2-dioxaborolan-2-yl)benzoic acid

The mixture of 3-bromo-4-methylbenzoic acid (4957 mg, 23.052 mmol), 4,4,4',4',5,5,5',5'-octamethyl-2,2'-bi(1,3,2-dioxaborolane) (11707 mg, 46.104 mmol), Pd(dppf)$Cl_2$ (1687 mg, 2.305 mmol), $CH_3COOK$ (6787 mg, 69.156 mmol) and DMSO (50 mL) was purged with $N_2$ and then was stirred at 100° C. for 16 h. The solution was cooled down to room temperature and water (10 mL) and aqueous HCl was added to adjust pH=1. The resulted solution was extracted with ethyl acetate (200 mL×3). The organic phase was washed with saturated brine (200 mL×3), dried over $Na_2SO_4$ and concentrated to provide the crude product which was used directly in the next step. LCMS (m/z): 263.0 $[M+H]^+$.

tert-butyl 4-(3-(4-methyl-3-(4,4,5,5-tetramethyl-1,3,2-dioxaborolan-2-yl)benzamido)-5-(trifluoromethyl)benzyl)piperazine-1-carboxylate A mixture of 4-methyl-3-(4,4,5,5-tetramethyl-1,3,2-dioxaborolan-2-yl)benzoic acid (2030 mg, 7.746 mmol), tert-butyl 4-(3-amino-5-(trifluoromethyl)benzyl)piperazine-1-carboxylate (2320 mg, 6.455 mmol), EDCI (2475 mg, 12.910 mmol), DMAP (1577 mg, 12.910 mmol) and DMF (30 mL) was stirred at 50° C. for 16 h. The solution was cooled down to room temperature and was extracted with ethyl acetate. The organic layer was washed with brine. The combined organic layer was dried over $Na_2SO_4$ and purified by silica gel (PE:EA=5:1), obtained 842 mg as yellow solid. LCMS (m/z): 604.4, $[M+H]^+$.

tert-butyl 4-(3-(3-(2-(cyclopropanecarboxamido)imidazo[1,2-b]pyridazin-6-yl)-4-methyl benzamido)-5-(trifluoromethyl)benzyl)piperazine-1-carboxylate A mixture of tert-butyl 4-(3-(4-methyl-3-(4,4,5,5-tetramethyl-1,3,2-dioxaborolan-2-yl) benzamido)-5-(trifluoromethyl)benzyl)piperazine-1-carboxylate (1255 mg, 2.080 mmol), N-(6-iodoimidazo[1,2-b]pyridazine-2-yl)cyclopropanecarboxamide (682 mg, 2.080 mmol), Pd(dppf)$Cl_2$ (304 mg, 0.416 mmol), $Na_2CO_3$ (441 mg, 4.160 mmol) and DMF (15 mL) was purged by $N_2$ and then was stirred at 105° C. for 16 h. The reaction solution was then cooled down to room temperature and then extracted with ethyl acetate. The organic layer was washed with brine and dried over $Na_2SO_4$. The solvent was then removed under reduced pressure and the crude product was directly used in the next step. LCMS (m/z): 678, $[M+H]^+$.

3-(2-(cyclopropanecarboxamido)imidazo[1,2-b]pyridazin-6-yl)-4-methyl-N-(3-(piperazin-1-ylmethyl)-5-(trifluoromethyl)phenyl)benzamide A mixture of tert-butyl 4-(3-(3-(2-(cyclopropanecarboxamido)imidazo[1,2-b]pyridazine-6-yl)-4-methylbenzamido)-5-(trifluoromethyl)benzyl)piperazine-1-carboxylate (1040 mg, 1.535 mmol), TFA (2 mL) and DCM (5 mL) was stirred at rt for 3 h. After completion, the solution was concentrated and the crude was purified by HPLC to provide Compound I-9. LCMS (m/z): 578.0, $[M+H]^+$. $^1$H NMR (400 MHz, DMSO-$d_6$) δ 11.22 (s, 1H), 10.62 (s, 1H), 8.72 (s, 1H), 8.30 (s, 1H), 8.19-8.08 (m, 4H), 8.03 (dd, J=8.0, 2.0 Hz, 1H), 7.58 (d, J=8.1 Hz, 1H), 7.50-7.42 (m, 2H), 3.88 (s, 2H), 3.18 (s, 4H), 2.81 (s, 4H), 2.45 (s, 3H), 1.98 (m, 1H), 0.88-0.81 (m, 4H).

N-(3-((4-acetylpiperazin-1-yl)methyl)-5-(trifluoromethyl)phenyl)-3-(2-(cyclopropanecarboxamido)imidazo[1,2-b]pyridazin-6-yl)-4-methylbenzamide To a mixture of 3-(2-(cyclopropanecarboxamido)imidazo[1,2-b]pyridazin-6-yl)-4-methyl-N-(3-(piperazin-1-ylmethyl)-5-(trifluoromethyl)phenyl)benzamide (80 mg, 0.139 mmol), DIEA (0.5 mL) and DCM (2 mL) was added acetyl chloride (13 mg, 0.167 mmol). The solution was stirred at rt for 0.5 h and then concentrated under reduced pressure. The crude was diluted with ethyl acetate (50 mL) and then washed with brine. The combined organic layer was dried over $Na_2SO_4$. The crude was purified by prep-HPLC to provide Compound I-10 (19.0 mg, isolated yield 22%). LCMS (m/z): 620.0, $[M+H]^+$ 0.310.5 $[½ M+H]^+$. $^1$H NMR (400 MHz, DMSO) δ 11.23 (s, 1H), 10.58 (s, 1H), 8.29 (s, 1H), 8.20 (s, 1H), 8.12 (d, J=9.2 Hz, 2H), 8.04 (s, 2H), 7.57 (d, J=2 Hz, 1H), 7.48 (d, J=9.2 Hz, 1H), 7.38 (s, 1H), 3.58 (s, 1H), 3.44 (d, J=4.4 Hz, 4H), 2.44 (s, 3H), 2.39 (t, J=4.4 Hz, 2H), 2.34 (t, J=4.8 Hz, 2H), 1.97 (s, 4H), 0.84 (t, J=3.8 Hz, 4H).

Compound I-11

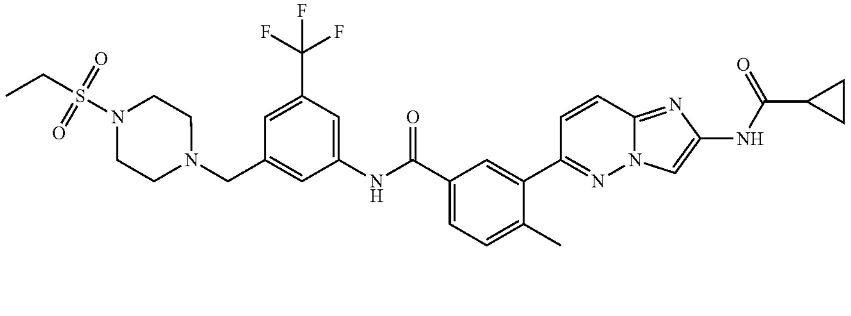 [SMILES: CCS(=O)(=O)N1CCN(Cc2cc(NC(=O)c3ccc(C)c(-c4ccc5nc(NC(=O)C6CC6)cn5n4)c3)cc(C(F)(F)F)c2)CC1]

3-(2-(cyclopropanecarboxamido)imidazo[1,2-b]pyridazin-6-yl)-N-(3-((4-(ethylsulfonyl)piperazin-1-yl)methyl)-5-(trifluoromethyl)phenyl)-4-methylbenzamide Compound I-11 is prepared by using the same procedure as for Compound I-10. Ethanesulfonyl chloride was used in last step. LCMS (m/z): 670.0, [M+H]$^+$.

Compound I-12

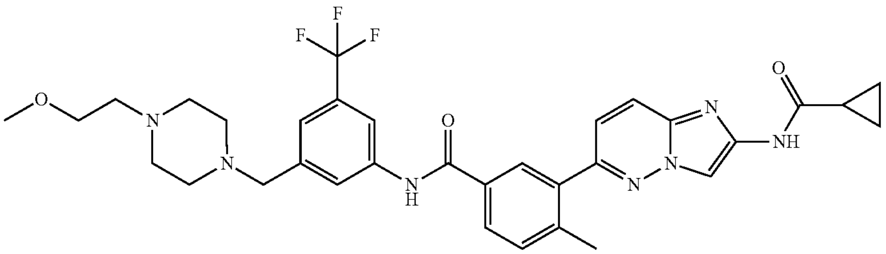 [SMILES: COCCN1CCN(Cc2cc(NC(=O)c3ccc(C)c(-c4ccc5nc(NC(=O)C6CC6)cn5n4)c3)cc(C(F)(F)F)c2)CC1]

3-(2-(cyclopropanecarboxamido)imidazo[1,2-b]pyridazin-6-yl)-N-(3-((4-(2-methoxyethyl)piperazin-1-yl)methyl)-5-(trifluoromethyl)phenyl)-4-methylbenzamide Compound I-12 is prepared by using the similar procedure as for Compound I-10. 1-chloro-2-methoxyethane was used in last step. LCMS (m/z): 636.0, [M+H]$^+$.

Compound I-13

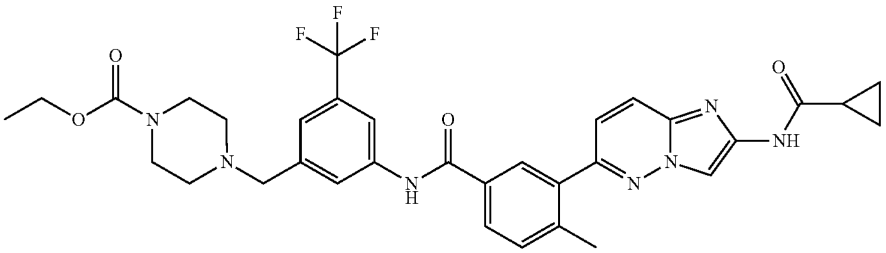 [SMILES: CCOC(=O)N1CCN(Cc2cc(NC(=O)c3ccc(C)c(-c4ccc5nc(NC(=O)C6CC6)cn5n4)c3)cc(C(F)(F)F)c2)CC1]

ethyl 4-(3-(3-(2-(cyclopropanecarboxamido)imidazo[1,2-b]pyridazin-6-yl)-4-methylbenzamido)-5-(trifluoromethyl)benzyl)piperazine-1-carboxylate Compound I-13 is prepared by using the same procedure as for Compound I-10. Ethyl carbonochloridate was used in the last step. LCMS (m/z): 650.0, [M+H]$^+$.

Compound I-14

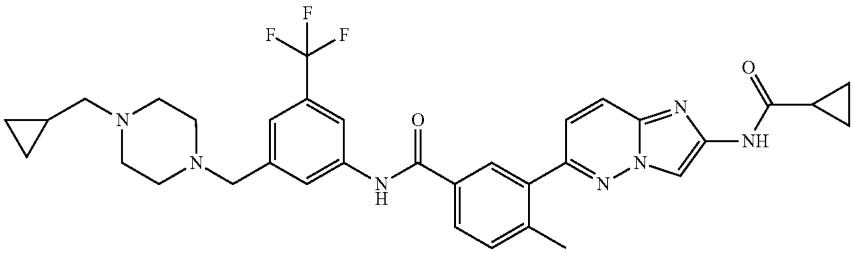 [SMILES: Cc1ccc(C(=O)Nc2cc(CN3CCN(CC4CC4)CC3)cc(C(F)(F)F)c2)cc1-c1ccc2nc(NC(=O)C3CC3)cn2n1]

3-(2-(cyclopropanecarboxamido)imidazo[1,2-b]pyridazin-6-yl)-N-(3-((4-(cyclopropylmethyl)piperazin-1-yl)methyl)-5-(trifluoromethyl)phenyl)-4-methylbenzamide Compound I-14 is prepared by using the similar procedure as for Compound I-10. (chloromethyl)cyclopropane was used in last step. LCMS (m/z): 632.0, $[M+H]^+$.

Compound I-24

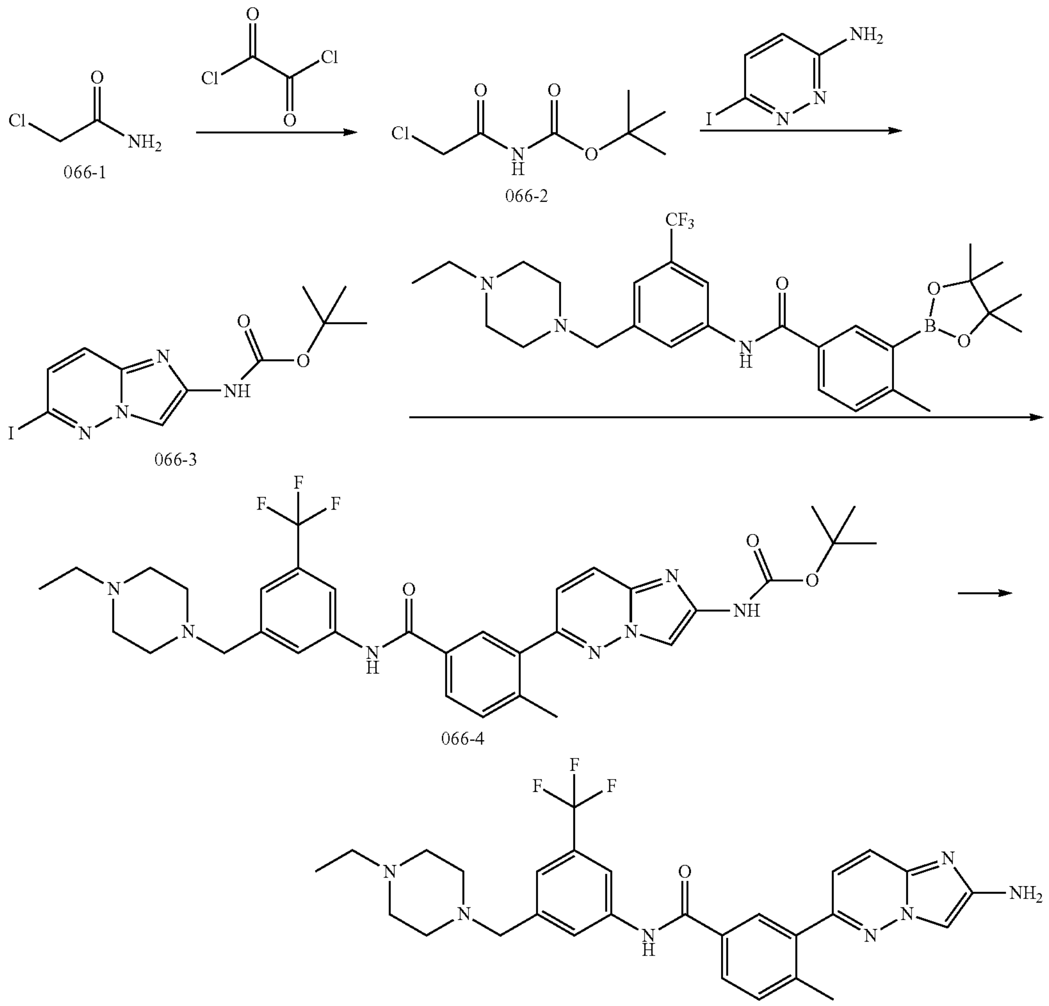

066-1

066-2

066-3

066-4

I-24

Tert-butyl (2-chloroacetyl)carbamate

To a solution of 2-chloroacetamide (10.0 g, 0.11 mol) in DCE (50 mL) was added drop wise oxalyl dichloride (11 mL, 0.13 mol) at 0° C. The mixture was heated at 80° C. for 3 hours, and then cooled down to 0° C. A solution of t-BuOH (15 mL, 0.16 mmol) in DCE (10 mL) was added to the above mixture and stirred at 0° C. for 20 minutes. The reaction mixture was quenched with saturated $NaHCO_3$solution (100 mL) and extracted with DCM (60 mL×3). The combined organic layer was washed with water (120 mL×3), dried over anhydrous $Na_2SO_4$, filtered and concentrated to give the product as off-white solid (11 g, yield 53.12%). LCMS (m/z): 216.0 $[M+H]^+$. $^1H$ NMR (400 MHz, $CDCl_3$) δ (ppm): 7.75 (s, 1H), 4.47 (s, 2H), 1.51 (s, 9H).

Tert-butyl (6-iodoimidazo[1,2-b]pyridazin-2-yl)carbamate

To a solution of 6-iodopyridazin-3-amine (7.0 g, 0.03 mmol) in DMAc (70 mL) was added tert-butyl (2-chloroacetyl)carbamate (9.8 g, 0.05 mmol) and $Na_2HPO_4$ (11.2 g, 0.08 mmol). The reaction mixture was heated to 100° C. for 3 hours. After cooled down to 20° C. the mixture was poured into water (300 mL), the resulting precipitate was collected by filtration, washed with EtOAc and dried under reduced pressure to afford the product as yellow solid (6 g, yield 52.6%). LCMS (m/z): 360.9 $[M+H]^+$.

Tert-butyl (6-(5-((3-((4-ethylpiperazin-1-yl) methyl)-5-(trifluoromethyl) phenyl) carbamoyl)-2-methylphenyl) imidazo[1, 2-b]pyridazin-2-yl)carbamate The mixture of N-(3-((4-ethylpiperazin-1-yl)methyl)-5-(trifluoromethyl)phenyl)-4-methyl-3-(4,4,5,5-tetramethyl-1,3,2-dioxaborolan-2-yl)benzamide (1.5 g, 0.27 mmol), tert-butyl (6-iodoimidazo[1,2-b]pyridazin-2-yl)carbamate (1.1 g, 0.30 mmol), $Pd(Ph_3P)_4$ (0.2 g, 0.015 mmol) and $Na_2CO_3$ (0.9 g, 0.84 mmol) in DMSO (30 mL) and water (3 mL) was heated at 80° C. for 18 hours. The reaction mixture was cooled down to 20° C. and poured into water (300 mL), the resulting precipitate was collected by filtration, washed with water and dried under reduced pressure to afford the desired compound as grey solid (1.2 g, yield 66.7%). LCMS (m/z): 638.4 $[M+H]^+$.

3-(2-aminoimidazo [1, 2-b] pyridazin-6-yl)-N-(3-((4-ethylpiperazin-1-yl) methyl)-5-(trifluoro methyl) phenyl)-4-methylbenzamide To a solution of tert-butyl (6-(5-((3-((4-ethylpiperazin-1-yl) methyl)-5-(trifluoromethyl) phenyl) carbamoyl)-2-methylphenyl) imidazo[l, 2-b]pyridazin-2-yl)carbamate (1.0 g, 1.5 mmol) in DCM (15 mL) was added TFA (3 mL). The mixture was stirred at 20° C. for 2 h. The reaction mixture was diluted with EtOAc (50 mL) and neutralized with saturated $Na_2CO_3$ solution. The organic phase was separated, the aqueous phase was re-extracted with EtOAc (20 mL×3). The combined organic layers were washed with brine (60 mL×3), dried over anhydrous $Na_2SO_4$, filtered and concentrated under reduced pressure, the residue was purified by Combi-flash (Biotage, Silica gel column, 40 g, 40 mL/min, 10% MeOH in DCM) to afford the crude product as a brown solid (0.76 g, yield 90.5%; purity: 73.2%). 50 mg of product was further purified by preparative HPLC (reverse phase, C-18, 40 g, from 0%~95% B in A, B: $CH_3CN$, A: 0.05% $NH_4HCO_3$ in water, collection wavelength: 214 nm) to afford the product as a white solid (0.02 g, yield 40%). LCMS (m/z): 538.4 $[M+H]^+$. 1H NMR (400 MHz, $CD_3OD$) δ (ppm) 8.11 (s, 1H), 8.06 (d, J=1.7 Hz, 1H), 7.98 (dd, J=8.0, 1.9 Hz, 1H), 7.94 (s, 1H), 7.74 (d, J=9.1 Hz, 1H), 7.52 (d, J=8.1 Hz, 1H), 7.45 (s, 2H), 7.25 (d, J=9.1 Hz, 1H), 3.63 (s, 2H), 2.87-2.24 (m, 13H), 1.12 (t, J=7.2 Hz, 3H).

Compound I-25

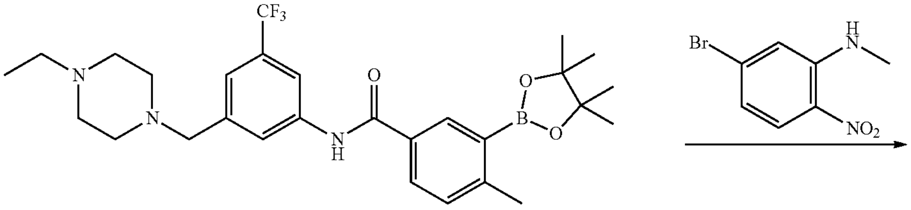

Int-B

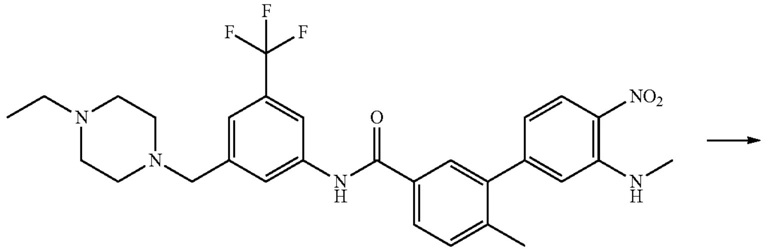

082-1

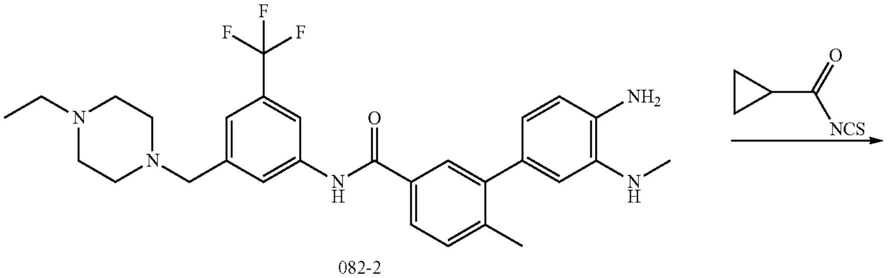

082-2

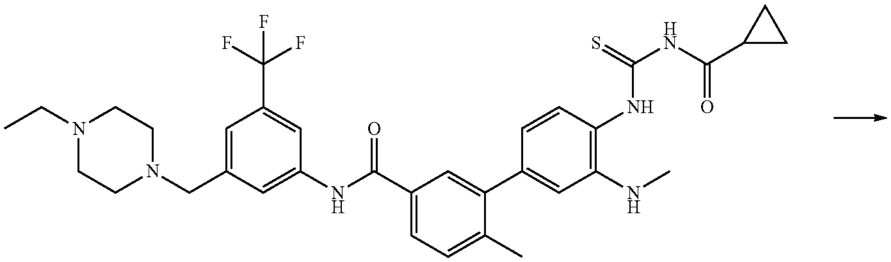

082-3

-continued

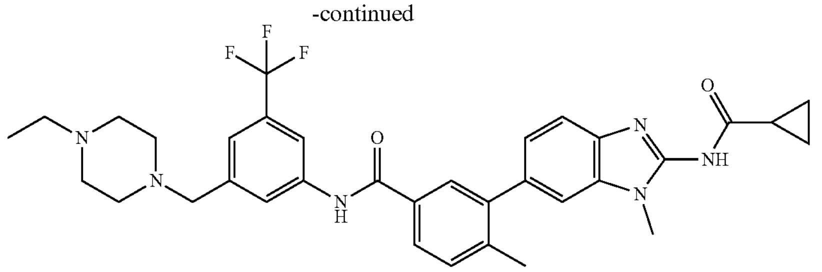

I-25

N-(3-((4-ethylpiperazin-1-yl)methyl)-5-(trifluoromethyl)phenyl)-6-methyl-3'-(methylamino)-4'-nitro-[1,1'-biphenyl]-3-carboxamide A mixture of N-(3-((4-ethylpiperazin-1-yl)methyl)-5-(trifluoromethyl)phenyl)-4-methyl-3-(4,4,5,5-tetramethyl-1,3,2-dioxaborolan-2-yl)benzamide (250.0 mg, 0.47 mmol), 5-bromo-N-methyl-2-nitroaniline (115.0 mg, 0.49 mmol), $Pd(dppf)Cl_2$ (23.0 mg, 0.03 mmol), Brettphos (20.0 mg, 0.03 mmol) and $K_3PO_4$ (0.5 g, 2.40 mmol) in DMSO (9 mL) and water (1 mL) was heated at 100° C. with stirring for 2 h. The reaction mixture was partitioned between EtOAc (20 mL) and water (20 mL), the organic phase was separated, the aqueous phase was re-extracted with EtOAc (10 mL). The combined organic layers were washed with brine (20 mL×3), dried over anhydrous $Na_2SO_4$, filtered, and concentrated under reduced pressure. The residue was purified by Combi-flash (silica gel, eluting with EA in PE (Biotage, 25 mL/min, EA in PE 0%~100%, 20 min, UV 254 280), then 10% MeOH (in DCM) in DCM 0%~100%, 10 min; 100%, 16 min, UV 254 280) to afford the desired product as brown solid (0.2 g, yield 76.5%; purity: 84.6% (214 nm); 100.0% (254 nm)). LCMS (m/z): 556.3 $[M+H]^+$.

4'-amino-N-(3-((4-ethylpiperazin-1-yl)methyl)-5-(trifluoromethyl)phenyl)-6-methyl-3'-(methylamino)-[1,1'-biphenyl]-3-carboxamide To a mixture of N-(3-((4-ethylpiperazin-1-yl)methyl)-5-(trifluoromethyl)phenyl)-6-methyl-3'-(methylamino)-4'-nitrobiphenyl-3-carboxamide (0.2 g, 0.36 mmol) and Pd/C (10%, 0.2 g) in MeOH (12 mL) was added ammonium formate (0.14 g, 2.16 mmol). The mixture was heated at 70° C. with stirring for 1 h. The reaction mixture was cooled down to 20° C. and filtered through CELITE. The filter cake was washed with MeOH (10 mL×3). The combined filtrate and washing was concentrated and purified by Combi-flash (Biotage, Silica gel column, 25 g, 30 mL/min, 10% MeOH (in DCM) in DCM 0%~100%, 20 min; 100%, 10 min, UV 254 280) to afford the desired product as brown solid (0.14 g, yield 73.9%; purity: 69.9% (214 nm); 74.9% (254 nm)). LCMS (m/z): 526.3 $[M+H]^+$.

4'-(3-(cyclopropanecarbonyl)thioureido)-N-(3-((4-ethylpiperazin-1-yl)methyl)-5-(trifluoromethyl)phenyl)-6-methyl-3'-(methylamino)-[1,1'-biphenyl]-3-carboxamide A mixture of 4'-amino-N-(3-((4-ethylpiperazin-1-yl)methyl)-5-(trifluoromethyl)phenyl)-6-methyl-3'-(methylamino)biphenyl-3-carboxamide (130.0 mg, 0.52 mmol) and cyclopropanecarbonyl isothiocyanate (31.5 mg, 0.25 mmol) in THF (5 mL) was stirred at 20° C. for 1 h. The reaction mixture was used directly in the next step without any workup (about 0.16 g, yield 95%; purity: 40.7% (214 nm); 49.1% (254 nm)). LCMS (m/z): 653.3 $[M+H]^+$.

3-(2-(cyclopropanecarboxamido)-1-methyl-1H-benzo[d]imidazol-6-yl)-N-(3-((4-ethylpiperazin-1-yl)methyl)-5-(trifluoromethyl)phenyl)-4-methylbenzamide To the above solution of crude 4'-(3-cyclopropanecarbonylthioureido)-N-(3-((4-ethylpiperazin-1-yl)methyl)-5-(trifluoromethyl)phenyl)-6-methyl-3'-(methylamino) biphenyl-3-carboxamide (0.13 g, 0.12 mol) in THF (5 mL) was added EDCI (0.13 g, 0.60 mmol), the mixture was stirred at 50° C. for 3 h. After cooled down to rt the mixture was partitioned between EtOAc (20 mL) and water (30 mL), the organic phase was separated, the aqueous phase was re-extracted with EtOAc (20 mL×2). The combined organic layers were washed with brine (50 mL×3), dried over anhydrous $Na_2SO_4$, filtered, and concentrated under reduced pressure. The residue was purified by Combi-flash (Biotage, Silica gel column, 25 g, 30 mL/min, MeOH in DCM 0%~6%, 30 min, UV 254 280) to give the crude product as brown solid, which was further purified by Combi-flash (reverse phase, C-18, 40 g, from 0%~95% B in A, B: $CH_3CN$, A: 0.05% $NH_4HCO_3$ in water, collection wavelength: 214 nm) to give the product as a white solid (0.05 g, yield 41.7%; purity: 100% (214 nm); 100% (254 nm)). LCMS (m/z): 619.3 $[M+H]^+$. $^1H$ NMR (400 MHz, $CD_3OD$) δ (ppm) 8.11 (s, 1H), 7.91 (dd, J=15.9, 6.7 Hz, 3H), 7.68-7.54 (m, 1H), 7.49 (d, J=7.7 Hz, 2H), 7.44 (s, 1H), 7.30 (d, J=8.8 Hz, 1H), 3.72 (s, 3H), 3.64 (s, 2H), 2.74-2.42 (m, 9H), 2.39 (s, 4H), 2.01-1.81 (m, 1H), 1.12 (t, J=7.2 Hz, 3H), 1.09-1.02 (m, 2H), 1.02-0.89 (m, 2H).

Compound I-26

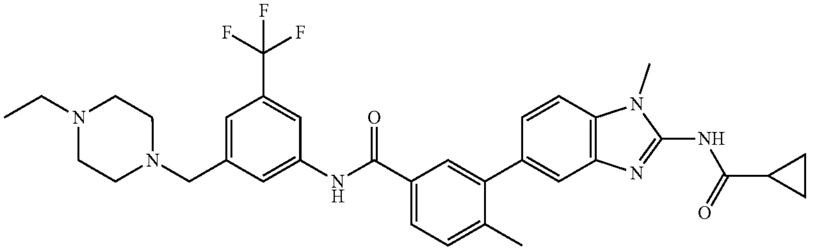 [SMILES: CCN1CCN(Cc2cc(NC(=O)c3ccc(C)c(-c4ccc5c(c4)nc(NC(=O)C4CC4)n5C)c3)cc(C(F)(F)F)c2)CC1]

3-(2-(cyclopropanecarboxamido)-1-methyl-1H-benzo[d]imidazol-5-yl)-N-(3-((4-ethylpiperazin-1-yl)methyl)-5-(trifluoromethyl)phenyl)-4-methylbenzamide I-26 was prepared by using the similar procedure with I-25, changing 5-bromo-N-methyl-2-nitroaniline to 4-bromo-N-methyl-2-nitroaniline in the first step. LCMS (m/z): 619.3 $[M+H]^+$. $^1H$ NMR (400 MHz, $CD_3OD$) δ (ppm) 8.11 (s, 1H), 7.94 (s, 1H), 7.91-7.85 (m, 2H), 7.60-7.52 (m, 2H), 7.52-7.46 (m, 1H), 7.44 (s, 1H), 7.34 (dd, J=8.3 Hz, 1.2 Hz, 1H), 3.74 (s, 3H), 3.64 (s, 2H), 2.82-2.52 (m, 6H), 2.48 (dd, J=14.5, 7.3 Hz, 3H), 2.37 (s, 4H), 1.99-1.82 (m, 1H), 1.12 (t, J=7.2 Hz, 3H), 1.10-1.02 (m, 2H), 1.02-0.78 (m, 2H).

Compound I-27

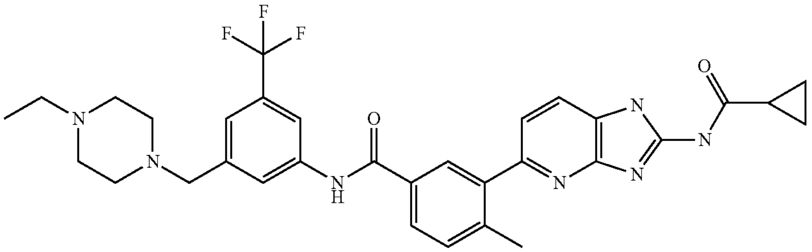 [SMILES: CCN1CCN(Cc2cc(NC(=O)c3ccc(C)c(-c4ccc5[nH]c(NC(=O)C6CC6)nc5n4)c3)cc(C(F)(F)F)c2)CC1]

3-(2-(cyclopropanecarboxamido)-1H-imidazo[4,5-b]pyridin-5-yl)-N-(3-((4-ethylpiperazin-1-yl)methyl)-5-(trifluoromethyl)phenyl)-4-methylbenzamide I-27 was prepared by using the similar procedure with I-25, changing 5-bromo-N-methyl-2-nitroaniline to 6-bromo-2-nitropyridin-3-amine in the first step. LCMS (m/z): 606.2 $[M+H]^+$. $^1H$ NMR (400 MHz, $CD_3OD$) δ (ppm) 8.11 (s, 1H), 8.04 (d, J=1.6 Hz, 1H), 7.97-7.91 (m, 3H), 7.50 (d, J=8.0 Hz, 1H), 7.44 (s, 1H), 7.38 (d, J=7.6 Hz, 1H), 3.64 (s, 2H), 2.80-2.40 (m, 13H), 2.02-1.91 (m, 1H), 1.13 (t, J=7.2 Hz, 3H), 1.15-1.10 (m, 2H), 1.07-0.98 (m, 2H).

Example 2. Biochemical Assay of the Compounds of the Present Disclosure

The JAK2 Z-Lyte biochemical assay was performed according to manufacturer's instructions (Life Technologies).

TABLE 1
| Biochemical $IC_{50}$ by a commercial JAK2 Z-Lyte assay from Invitrogen. | | |
|---|---|---|
| Compound No. | Compound Formula | JAK2 Z-lyte $IC_{50}$ (nM) |
| I-1 | 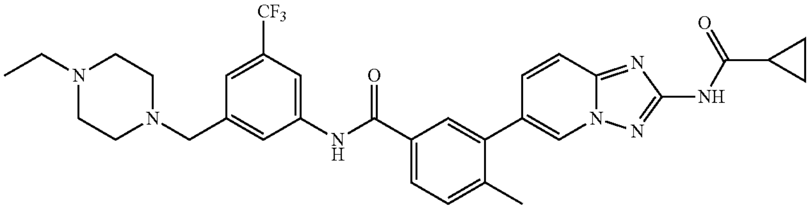 [SMILES: CCN1CCN(Cc2cc(NC(=O)c3ccc(C)c(-c4ccc5nc(NC(=O)C6CC6)nn5c4)c3)cc(C(F)(F)F)c2)CC1] | 508 |
| I-2 | 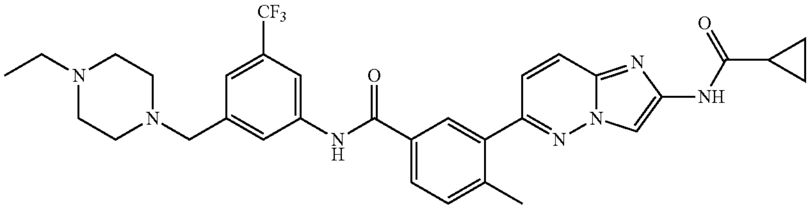 | 190 |
| I-3 | 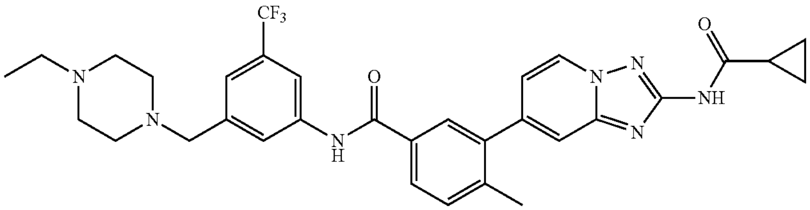 [SMILES: CCN1CCN(Cc2cc(NC(=O)c3ccc(C)c(-c4ccn5nc(NC(=O)C6CC6)nc5c4)c3)cc(C(F)(F)F)c2)CC1] | 981 |
| I-4 | 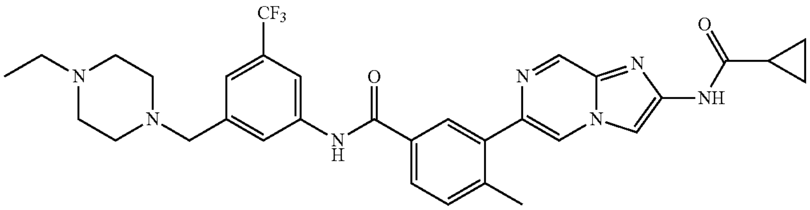 | 950 |
| I-5 | 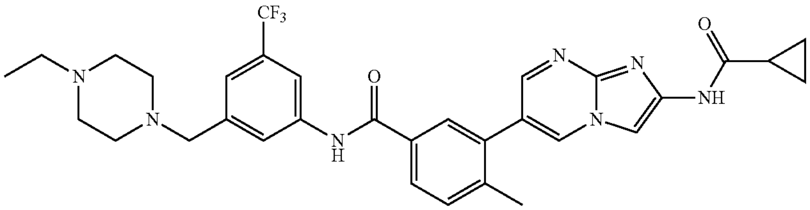 | 9.51E+03 |
| I-6 | 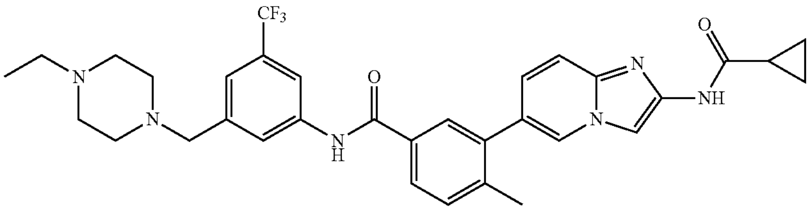 [SMILES: CCN1CCN(Cc2cc(NC(=O)c3ccc(C)c(-c4ccc5nc(NC(=O)C6CC6)cn5c4)c3)cc(C(F)(F)F)c2)CC1] | 284 |
| I-7 | 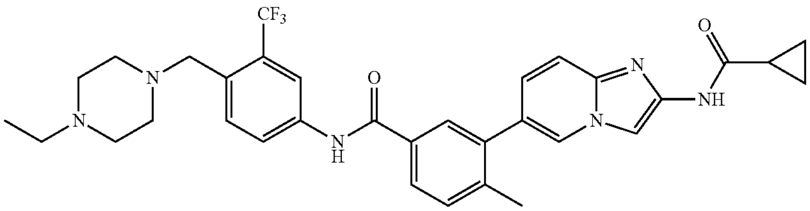 [SMILES: CCN1CCN(Cc2ccc(NC(=O)c3ccc(C)c(-c4ccc5nc(NC(=O)C6CC6)cn5c4)c3)cc2C(F)(F)F)CC1] | 672 |

TABLE 1-continued
| Biochemical $IC_{50}$ by a commercial JAK2 Z-Lyte assay from Invitrogen. | | |
|---|---|---|
| Compound No. | Compound Formula | JAK2 Z-lyte $IC_{50}$ (nM) |
| I-8 | 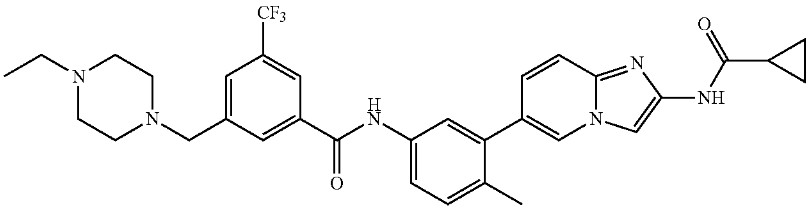 [SMILES: CCN1CCN(Cc2cc(C(=O)Nc3ccc(C)c(-c4ccc5nc(NC(=O)C6CC6)cn5c4)c3)cc(C(F)(F)F)c2)CC1] | 824 |
| I-9 | 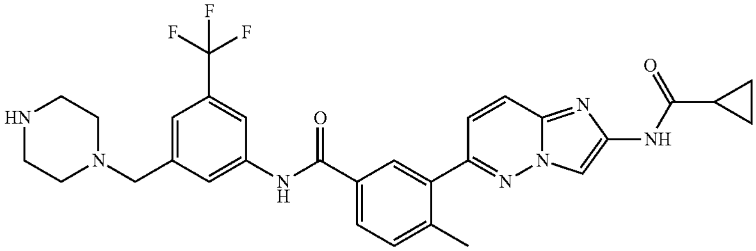 [SMILES: Cc1ccc(C(=O)Nc2cc(CN3CCNCC3)cc(C(F)(F)F)c2)cc1-c1ccc2nc(NC(=O)C3CC3)cn2n1] | 301 |
| I-10 | 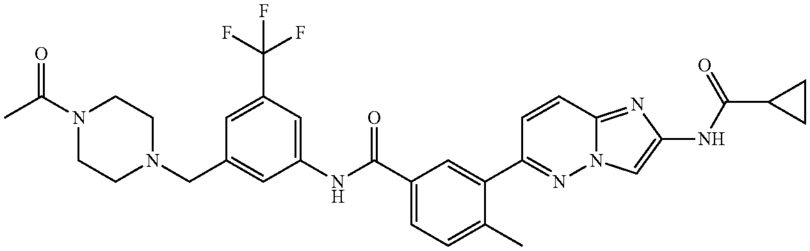 [SMILES: CC(=O)N1CCN(Cc2cc(NC(=O)c3ccc(C)c(-c4ccc5nc(NC(=O)C6CC6)cn5n4)c3)cc(C(F)(F)F)c2)CC1] | 1.35E+03 |
| I-11 | 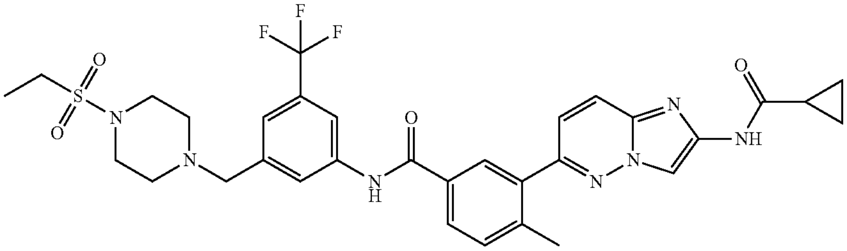 [SMILES: CCS(=O)(=O)N1CCN(Cc2cc(NC(=O)c3ccc(C)c(-c4ccc5nc(NC(=O)C6CC6)cn5n4)c3)cc(C(F)(F)F)c2)CC1] | 2.62E+03 |
| I-12 | 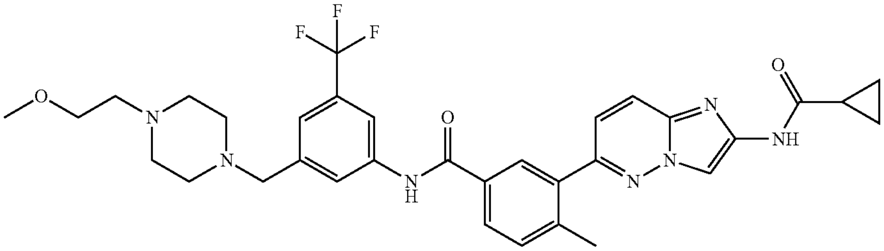 [SMILES: COCCN1CCN(Cc2cc(NC(=O)c3ccc(C)c(-c4ccc5nc(NC(=O)C6CC6)cn5n4)c3)cc(C(F)(F)F)c2)CC1] | 1.82E+03 |
| I-13 | 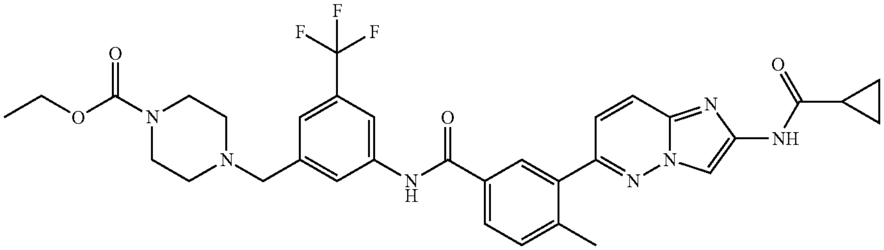 [SMILES: CCOC(=O)N1CCN(Cc2cc(NC(=O)c3ccc(C)c(-c4ccc5nc(NC(=O)C6CC6)cn5n4)c3)cc(C(F)(F)F)c2)CC1] | 3180 |

TABLE 1-continued
| Compound No. | Compound Formula | JAK2 Z-lyte $IC_{50}$ (nM) |
|---|---|---|
| | Biochemical $IC_{50}$ by a commercial JAK2 Z-Lyte assay from Invitrogen. | |
| I-14 | 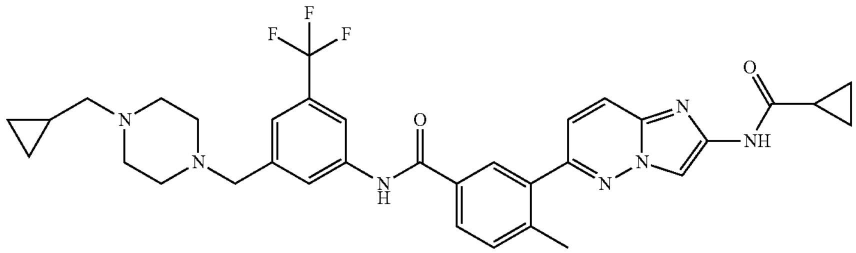 [SMILES: Cc1ccc(C(=O)Nc2cc(CN3CCN(CC4CC4)CC3)cc(C(F)(F)F)c2)cc1-c1ccc2nc(NC(=O)C3CC3)cn2n1] | 772 |
| I-15 | 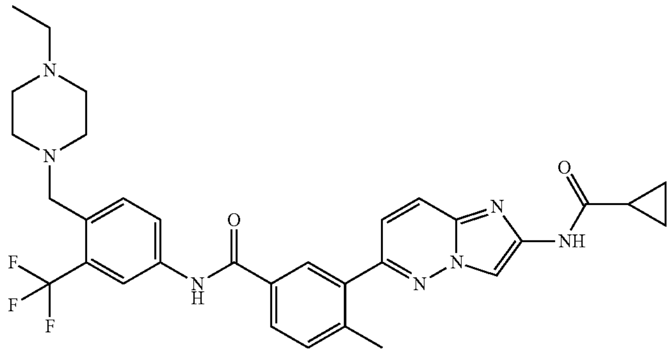 [SMILES: CCN1CCN(Cc2ccc(NC(=O)c3ccc(C)c(-c4ccc5nc(NC(=O)C6CC6)cn5n4)c3)cc2C(F)(F)F)CC1] | 1.1E+03 |
| I-16 | 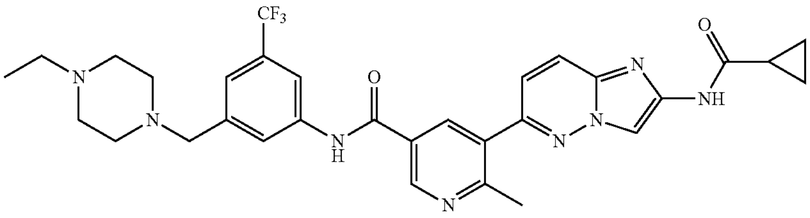 [SMILES: CCN1CCN(Cc2cc(NC(=O)c3cnc(C)c(-c4ccc5nc(NC(=O)C6CC6)cn5n4)c3)cc(C(F)(F)F)c2)CC1] | 486 |
| I-17 | 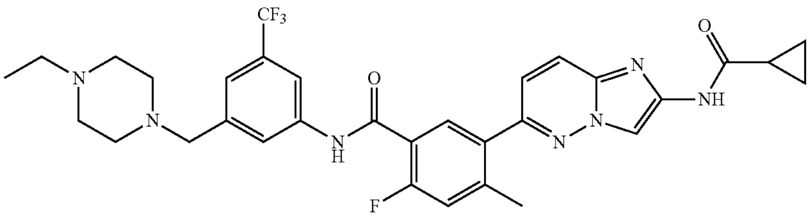 [SMILES: CCN1CCN(Cc2cc(NC(=O)c3cc(-c4ccc5nc(NC(=O)C6CC6)cn5n4)c(C)cc3F)cc(C(F)(F)F)c2)CC1] | 934 |
| I-18 | 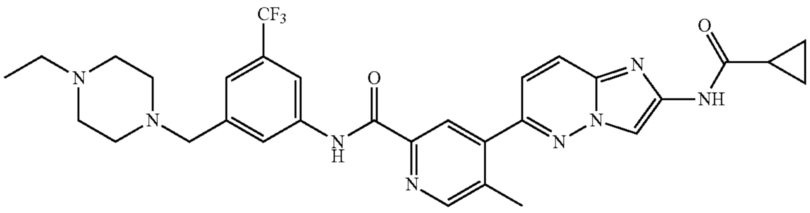 | 985 |
| I-19 | 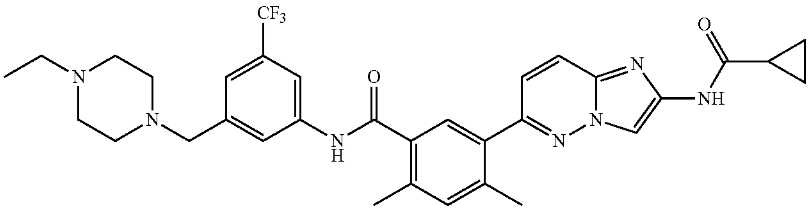 [SMILES: CCN1CCN(Cc2cc(NC(=O)c3cc(-c4ccc5nc(NC(=O)C6CC6)cn5n4)c(C)cc3C)cc(C(F)(F)F)c2)CC1] | 8.76E+03 |

TABLE 1-continued
Biochemical $IC_{50}$ by a commercial JAK2 Z-Lyte assay from Invitrogen.
| Compound No. | Compound Formula | JAK2 Z-lyte $IC_{50}$ (nM) |
|---|---|---|
| I-20 | 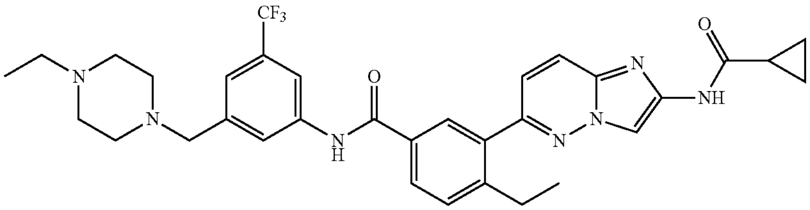 [SMILES: CCc1ccc(C(=O)Nc2cc(CN3CCN(CC)CC3)cc(C(F)(F)F)c2)cc1-c1ccc2nc(NC(=O)C3CC3)cn2n1] | 399 |
| I-21 | 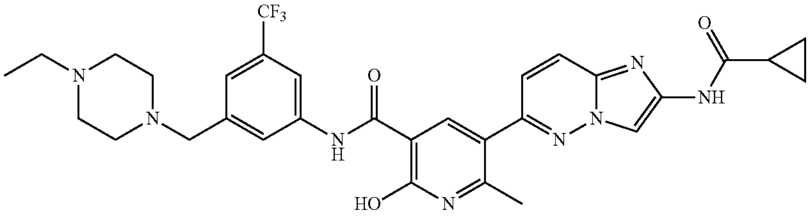 [SMILES: CCN1CCN(Cc2cc(NC(=O)c3cc(-c4ccc5nc(NC(=O)C6CC6)cn5n4)c(C)nc3O)cc(C(F)(F)F)c2)CC1] | >10E+03 |
| I-22 | 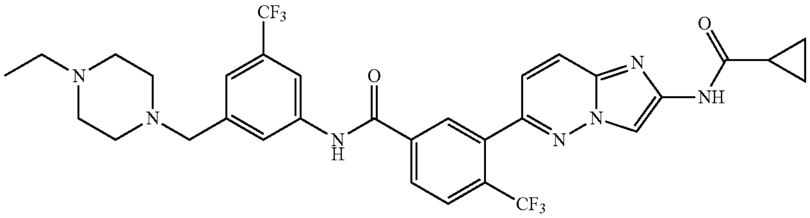 [SMILES: CCN1CCN(Cc2cc(NC(=O)c3ccc(C(F)(F)F)c(-c4ccc5nc(NC(=O)C6CC6)cn5n4)c3)cc(C(F)(F)F)c2)CC1] | 1.9E+03 |
| I-23 | 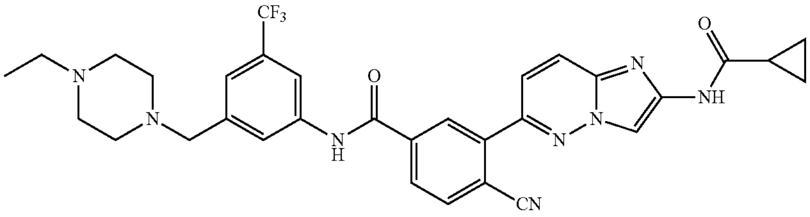 | 5.12E+03 |
| I-24 | 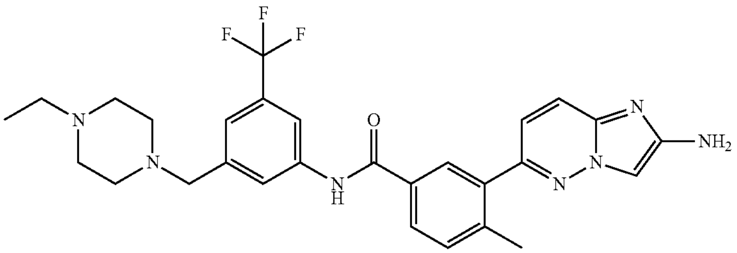 [SMILES: CCN1CCN(Cc2cc(NC(=O)c3ccc(C)c(-c4ccc5nc(N)cn5n4)c3)cc(C(F)(F)F)c2)CC1] | >3.33E+03 |
| I-25 | 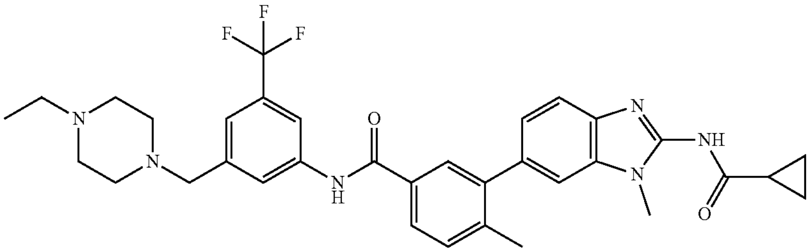 [SMILES: CCN1CCN(Cc2cc(NC(=O)c3ccc(C)c(-c4ccc5nc(NC(=O)C6CC6)n(C)c5c4)c3)cc(C(F)(F)F)c2)CC1] | 7.02E+03 |

TABLE 1-continued

Biochemical $IC_{50}$ by a commercial JAK2 Z-Lyte assay from Invitrogen.

| Compound No. | Compound Formula | JAK2 Z-lyte $IC_{50}$ (nM) |
|---|---|---|
| I-26 | 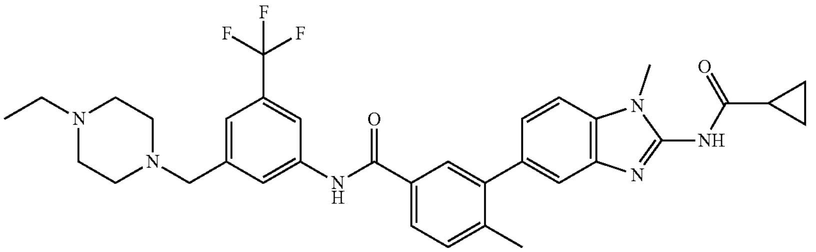 [SMILES: CCN1CCN(Cc2cc(NC(=O)c3ccc(C)c(-c4ccc5c(c4)nc(NC(=O)C4CC4)n5C)c3)cc(C(F)(F)F)c2)CC1] | >10E+03 |
| I-27 | 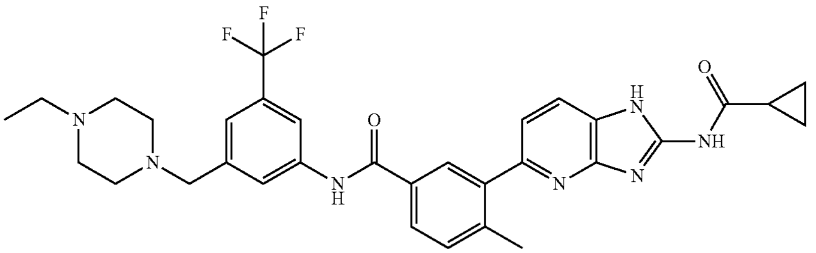 [SMILES: CCN1CCN(Cc2cc(NC(=O)c3ccc(C)c(-c4ccc5[nH]c(NC(=O)C6CC6)nc5n4)c3)cc(C(F)(F)F)c2)CC1] | 1.53E+03 |

Example 3. Western-Blot Assay of the Compounds of the Present Disclosure

Figure 2:
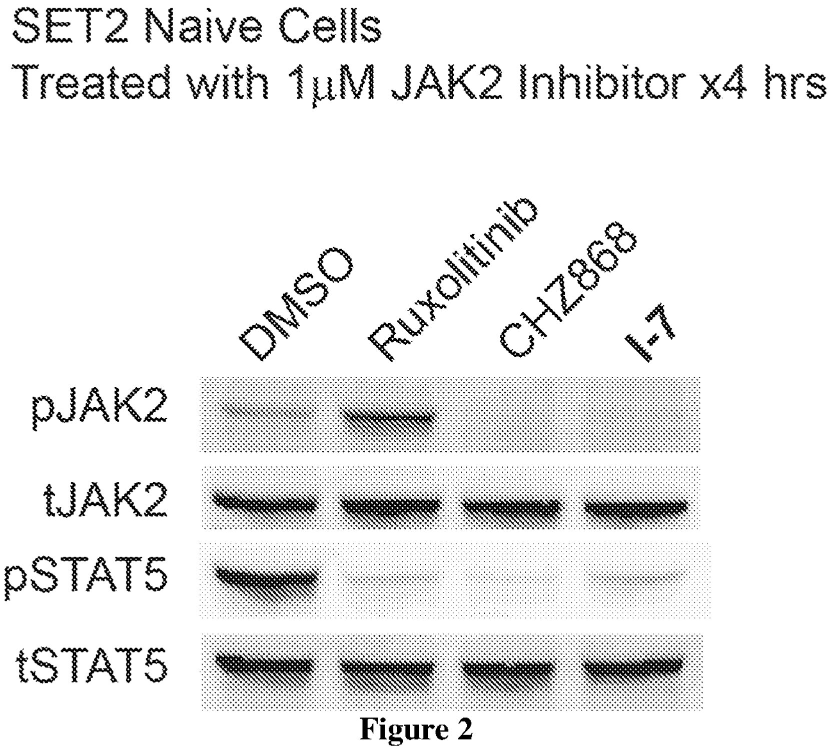
FIG. 2. SET2 Naïve cells were treated with 1 μM concentration of the JAK2 inhibitors Ruxolitinib, CHZ868, and Compound I-7. Cell pellets were lysed with Cell Lysis Buffer (Cell Signaling Technology) and then immunoblotting was performed with pJAK2 (#3771), pSTAT5 (#4322), JAK2 (#3230), and STAT5 (#9363 or 94205) antibodies from Cell Signaling Technology.
Figure 3:
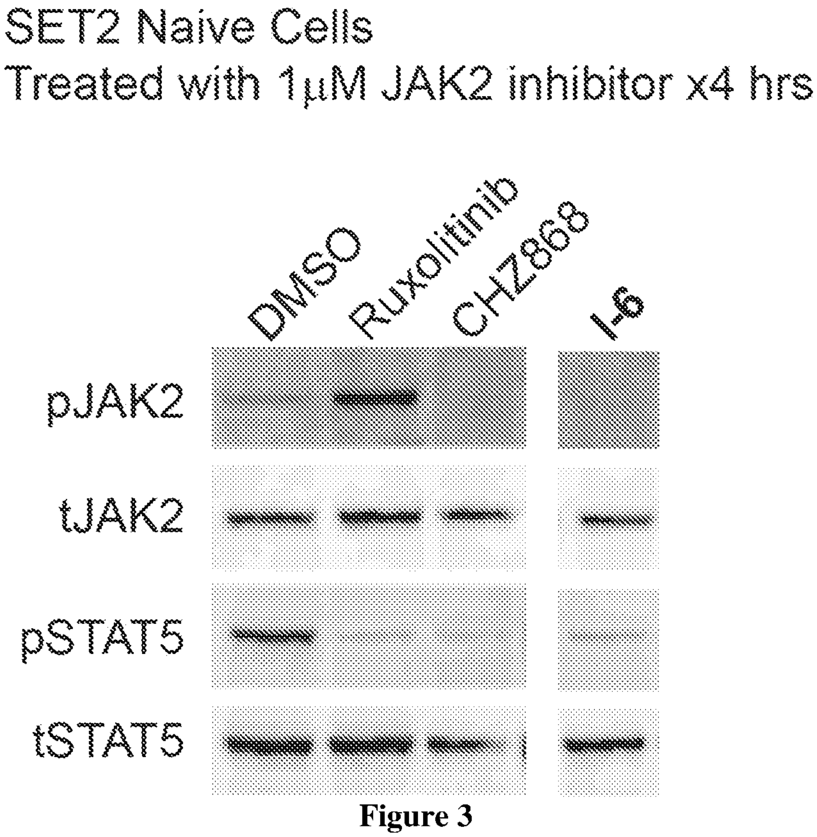
FIG. 3. SET2 Naïve cells were treated with 1 μM concentration of the JAK2 inhibitors Ruxolitinib, CHZ868, and Compound I-6. Cell pellets were lysed with Cell Lysis Buffer (Cell Signaling Technology) and then immunoblotting was performed with pJAK2 (#3771), pSTAT5 (#4322), JAK2 (#3230), and STAT5 (#9363 or 94205) antibodies from Cell Signaling Technology.

For Western blot analyses, cells were treated with the indicated concentrations of JAK2 inhibitor for 4 hours. Cell pellets were lysed with Cell Lysis Buffer (Cell Signaling Technology) and then immunoblotting was performed with pJAK2 (#3771), pSTAT5 (#4322), c-Myc (#9402), JAK2 (#3230), STAT5 (#9363 or 94205), and β-actin (#4967 or 12620) antibodies from Cell Signaling Technology. Exemplary results are shown in FIGS. 1 to 3.

Example 4. Cellular Assay of the Compounds of the Present Disclosure

Figure 4:
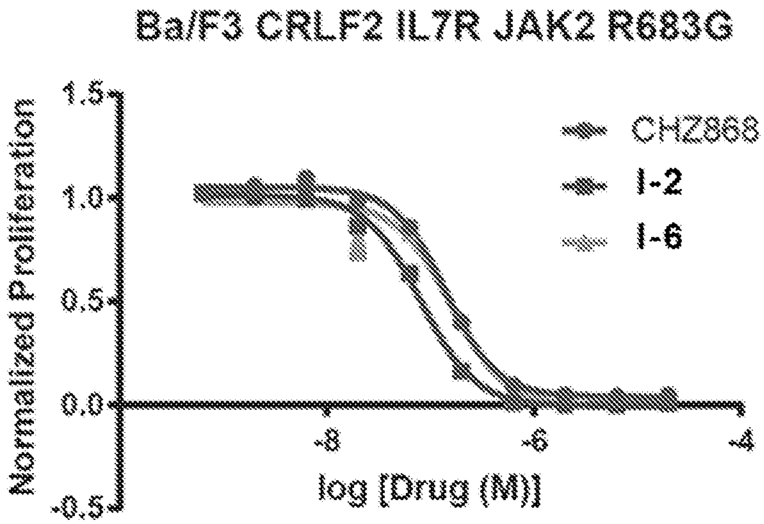
FIG. 4. Ba/F3 CRLF2 IL7R JAK2 R683G cells were plated at a density of $0.1\times10^6$/mL followed by the addition of the JAK2 inhibitor CHZ868, Compound I-2, or Compound I-6, or vehicle (DMSO) control. After 48 hrs (Ba/F3 cells), 25 μL of a 1:2 dilution of the CellTiter-Glo Luminescent Cell Viability Assay reagent (Promega) was added to each well, and the plates were read by the 2104 EnVision Multilabel Reader (PerkinElmer). "[Drug (M)]" refers to the concentration of the JAK2 inhibitor in molar.
Figure 5:
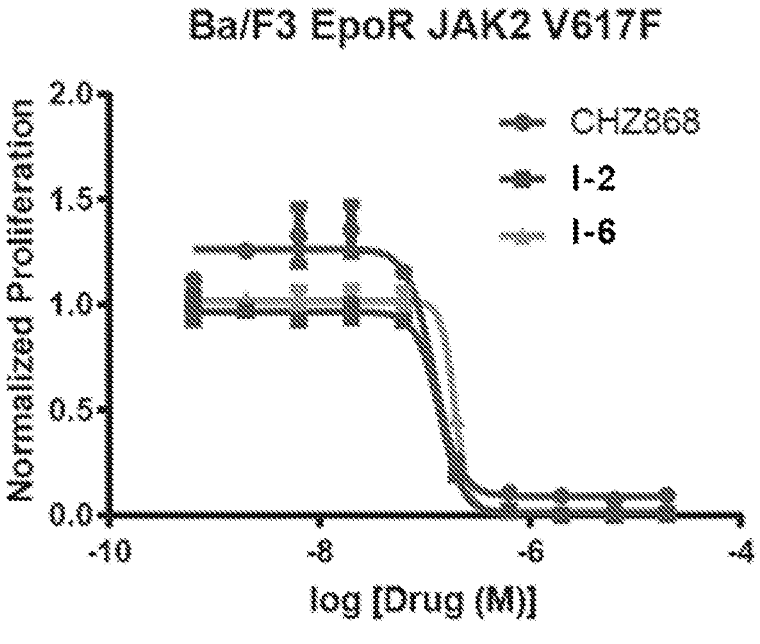
FIG. 5. Ba/F3 EpoR JAK2 V617F cells were plated at a density of $0.1\times10^6$/mL followed by the addition of the JAK2 inhibitor CHZ868, Compound I-2, or Compound I-6, or vehicle (DMSO) control. After 48 hrs (Ba/F3 cells), 25 μL of a 1:2 dilution of the CellTiter-Glo Luminescent Cell Viability Assay reagent (Promega) was added to each well, and the plates were read by the 2104 EnVision Multilabel Reader (PerkinElmer). "[Drug (M)]" refers to the concentration of the JAK2 inhibitor in molar.
Figure 6:
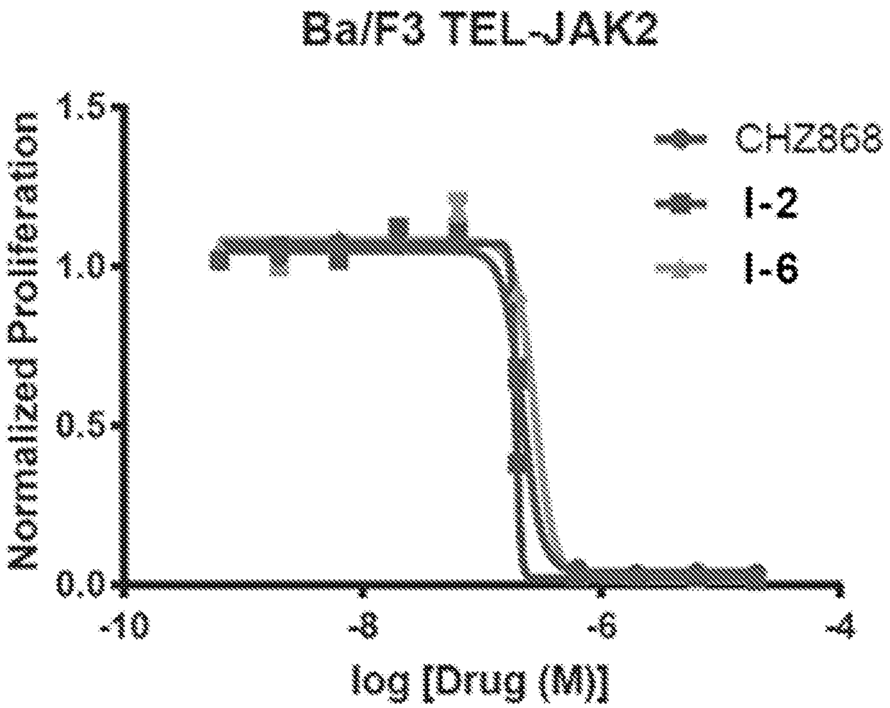
FIG. 6. Ba/F3 TEL-JAK2 cells were plated at a density of $0.1\times10^6$/mL followed by the addition of the JAK2 inhibitor CHZ868, Compound I-2, or Compound I-6, or vehicle (DMSO) control. After 48 hrs (Ba/F3 cells), 25 μL of a 1:2 dilution of the CellTiter-Glo Luminescent Cell Viability Assay reagent (Promega) was added to each well, and the plates were read by the 2104 EnVision Multilabel Reader (PerkinElmer). "[Drug (M)]" refers to the concentration of the JAK2 inhibitor in molar.

For the cell viability assays, Ba/F3 cells were plated at a density of $0.1\times10^6$/mL followed by the addition of JAK2 inhibitor or vehicle (DMSO) control. After 48 hrs, 25 μL of CellTiter-Glo Luminescent Cell Viability Assay (Promega) was added to each well and plates were read by the 2104 EnVision Multilabel Reader (PerkinElmer). Exemplary results are shown in FIGS. 4 to 6.

Example 5. In Vitro Profiling of Compound I-2 Using DiscoveRx KINOMEscan®

In vitro profiling of Compound I-2 (1 μM) was performed using the DiscoveRx KINOMEscan® platform. Exemplary results are shown in Table 2. Table 2 shows that Compound I-2 was more selective for JAK3 over JAK2, JAK1, and TYK2.

TABLE 2

Ambit KINOMEscan ® of Compound I-2 at 1 μM as percent of control

| Kinase | I-2 |
|---|---|
| ABL1(F317I)-nonphosphorylated | 0 |
| ABL1(F317L)-nonphosphorylated | 0 |
| ABL1(H396P)-nonphosphorylated | 0 |
| ABL1(Q252H)-nonpho sphorylated | 0 |
| ABL1(T315I)-nonphosphorylated | 0 |
| ABL1(Y253F)-phosphorylated | 0 |
| ABL1-nonphosphorylated | 0 |
| CDKL2 | 0 |
| EPHA4 | 0 |
| EPHA8 | 0 |
| EPHB2 | 0 |
| FLT3(N841I) | 0 |
| HCK | 0 |
| JAK3(JH1domain-catalytic) | 0 |
| KIT | 0 |
| KIT(A829P) | 0 |
| KIT(L576P) | 0 |
| KIT(V559D) | 0 |
| LCK | 0 |
| LOK | 0 |
| p38-gamma | 0 |
| PDGFRB | 0 |
| RET | 0 |
| SRC | 0 |
| TIE1 | 0 |
| CSF1R | 0.05 |
| DDR1 | 0.05 |
| FLT4 | 0.05 |
| MAP4K2 | 0.05 |
| RET(M918T) | 0.05 |
| RET(V804M) | 0.05 |
| TRKB | 0.05 |
| TRKC | 0.05 |
| ABL1-phosphorylated | 0.1 |
| CIT | 0.1 |
| DDR2 | 0.1 |
| HPK1 | 0.1 |
| TIE2 | 0.1 |
| FGR | 0.15 |

TABLE 2-continued

| Ambit KINOMEscan ® of Compound I-2 at 1 μM as percent of control | |
|---|---|
| Kinase | I-2 |
| MAP4K4 | 0.15 |
| RET(V804L) | 0.15 |
| TAOK3 | 0.2 |
| MERTK | 0.25 |
| ABL1(H396P)-phosphorylated | 0.3 |
| CDC2L5 | 0.3 |
| ABL1(Q252H)-phosphorylated | 0.35 |
| PFTK1 | 0.35 |
| ABL2 | 0.4 |
| CDKL3 | 0.4 |
| RIPK1 | 0.45 |
| ABL1(E255K)-phosphorylated | 0.5 |

TABLE 3

| Ambit KINOMEscan at of compounds I-2 and I-6 at 1 μM as percent of control | | |
|---|---|---|
| Kinase | I-2 | I-6 |
| AAKI | 100 | 89 |
| ABL1(E255K)-phosphorylated | 0.5 | 0.65 |
| ABL1(F317I)-nonphosphorylated | 0 | 0 |
| ABL1(F317I)-phosphorylated | 5.1 | 9.4 |
| ABL1(F317L)-nonphosphorylated | 0 | 0 |
| ABL1(F317L)-phosphorylated | 1.1 | 1.3 |
| ABL1(H396P)-nonphosphorylated | 0 | 0 |
| ABL1(H396P)-phosphorylated | 0.3 | 0.25 |
| ABL1(M351T)-phosphorylated | 0.8 | 0.5 |
| ABL1(Q252H)-nonphosphorylated | 0 | 0.15 |
| ABL1(Q252H)-phosphorylated | 0.35 | 0.6 |
| ABL1(T315I)-nonphosphorylated | 0 | 0 |
| ABL1(T315I)-phosphorylated | 1.4 | 2.2 |
| ABL1(Y253F)-phosphorylated | 0 | 0.1 |
| ABL1-nonphosphorylated | 0 | 0.1 |
| ABL1-phosphorylated | 0.1 | 0.1 |
| ABL2 | 0.4 | 0.4 |
| ACVR1 | 100 | 100 |
| ACVR1B | 99 | 94 |
| ACVR2A | 63 | 100 |
| ACVR2B | 96 | 100 |
| ACVRL1 | 91 | 92 |
| ADCK3 | 97 | 96 |
| ADCK4 | 75 | 91 |
| AKT1 | 90 | 90 |
| AKT2 | 100 | 98 |
| AKT3 | 8 | 94 |
| ALK | 8.7 | 16 |
| ALK(C1156Y) | 30 | 29 |
| ALK(L1196M) | 9.9 | 21 |
| AMPK-alpha1 | 99 | 90 |
| AMPK-alpha2 | 99 | 99 |
| ANKK1 | 100 | 100 |
| ARK5 | 94 | 100 |
| ASK1 | 97 | 100 |
| ASK2 | 99 | 64 |
| AURKA | 64 | 94 |
| AURKB | 97 | 80 |

TABLE 3-continued

| Ambit KINOMEscan at of compounds I-2 and I-6 at 1 μM as percent of control | | |
|---|---|---|
| Kinase | I-2 | I-6 |
| AURKC | 84 | 91 |
| AXL | 2.1 | 3.9 |
| BIKE | 96 | 100 |
| BLK | 0.75 | 0.2 |
| BMPR1A | 99 | 92 |
| BMPR1B | 84 | 86 |
| BMPR2 | 100 | 100 |
| BMX | 65 | 42 |
| BRAF | 11 | 21 |
| BRAF(V600E) | 1.7 | 5.9 |
| BRK | 100 | 91 |
| BRSK1 | 100 | 96 |
| BRSK2 | 93 | 71 |
| BTK | 68 | 87 |
| BUB1 | 100 | 97 |
| CAMK1 | 92 | 95 |
| CAMK1B | 49 | 97 |
| CAMK1D | 97 | 93 |
| CAMK1G | 85 | 100 |
| CAMK2A | 100 | 100 |
| CAMK2B | 100 | 100 |
| CAMK2D | 100 | 92 |
| CAMK2G | 94 | 95 |
| CAMK4 | 94 | 96 |
| CAMKK1 | 12 | 53 |
| CAMKK2 | 28 | 41 |
| CASK | 86 | 85 |
| CDC2L1 | 44 | 33 |
| CDC2L2 | 27 | 34 |
| CDC2L5 | 0.3 | 0.75 |
| CDK11 | 0.6 | 2.7 |
| CDK2 | 7 | 60 |
| CDK3 | 5.7 | 40 |
| CDK4 | 46 | 36 |
| CDK4-cyclinD1 | 19 | 17 |
| CDK4-cyclinD3 | 41 | 64 |
| CDK5 | 6.6 | 52 |
| CDK7 | 0.55 | 1 |
| CDK8 | 4.8 | 3 |
| CDK9 | 14 | 13 |
| CDKL1 | 40 | 77 |
| CDKL2 | 0 | 0.8 |
| CDKL3 | 0.4 | 0 |
| CDKL5 | 95 | 100 |
| CHEK1 | 100 | 100 |
| CHEK2 | 90 | 93 |
| CIT | 0.1 | 0.35 |
| CLK1 | 7.9 | 20 |
| CLK2 | 48 | 100 |
| CLK3 | 79 | 84 |
| CLK4 | 11 | 28 |
| CSF1R | 0.05 | 0 |
| CSF1R-autoinhibited | 25 | 49 |
| CSK | 39 | 21 |
| CSNK1A1 | 73 | 100 |
| CSNK1A1L | 100 | 97 |
| CSNK1D | 100 | 100 |
| CSNK1E | 86 | 93 |
| CSNK1G1 | 100 | 96 |
| CSNK1G2 | 92 | 100 |
| CSNK1G3 | 96 | 92 |
| CSNK2A1 | 98 | 100 |
| CSNK2A2 | 94 | 100 |
| CTK | 38 | 31 |
| DAPK1 | 100 | 100 |
| DAPK2 | 94 | 100 |
| DAPK3 | 93 | 100 |
| DCAMKL1 | 90 | 84 |
| DCAMKL2 | 98 | 100 |
| DCAMKL3 | 91 | 96 |
| DDR1 | 0.05 | 0.15 |
| DDR2 | 0.1 | 0 |
| DLK | 15 | 26 |
| DMPK | 87 | 100 |
| DMPK2 | 87 | 100 |

TABLE 3-continued

Ambit KINOMEscan at of compounds I-2 and I-6 at 1 μM as percent of control

| Kinase | I-2 | I-6 |
|---|---|---|
| DRAK1 | 100 | 94 |
| DRAK2 | 89 | 98 |
| DYRK1A | 92 | 100 |
| DYRK1B | 62 | 87 |
| DYRK2 | 95 | 92 |
| EGFR | 31 | 24 |
| EGFR(E746-A750del) | 29 | 25 |
| EGFR(G719C) | 53 | 46 |
| EGFR(G719S) | 45 | 35 |
| EGFR(L747-E749del, A750P) | 14 | 18 |
| GFR(L747-S752del, P753S | 19 | 12 |
| EGFR(L747-T751del, Sins) | 29 | 12 |
| EGFR(L858R) | 76 | 71 |
| EGFR(L858R, T790M) | 100 | 59 |
| EGFR(L861Q) | 82 | 54 |
| EGFR(S752-I759del) | 80 | 65 |
| EGFR(T790M) | 15 | 15 |
| EIF2AK1 | 100 | 92 |
| EPHA1 | 44 | 38 |
| EPHA2 | 1.8 | 0.15 |
| EPHA3 | 41 | 34 |
| EPHA4 | 0 | 0 |
| EPHA5 | 2.3 | 2.5 |
| EPHA6 | 5.2 | 0.75 |
| EPHA7 | 3.3 | 2 |
| EPHA8 | 0 | 0 |
| EPHB1 | 0.65 | 0.25 |
| EPHB2 | 0 | 0 |
| EPHB3 | 30 | 35 |
| EPHB4 | 1.3 | 0 |
| EPHB6 | 78 | 64 |
| ERBB2 | 82 | 71 |
| ERBB3 | 100 | 93 |
| ERBB4 | 71 | 53 |
| ERK1 | 95 | 100 |
| ERK2 | 100 | 100 |
| ERK3 | 89 | 100 |
| ERK4 | 96 | 100 |
| ERK5 | 95 | 92 |
| ERK8 | 2.2 | 3.1 |
| ERN1 | 84 | 78 |
| FAK | 1.9 | 7.9 |
| FER | 29 | 6 |
| FES | 12 | 0.95 |
| FGFR1 | 77 | 57 |
| FGFR2 | 67 | 57 |
| FGFR3 | 86 | 89 |
| FGFR3 (G697C) | 87 | 69 |
| FGFR4 | 100 | 100 |
| FGR | 0.15 | 0 |
| FLT1 | 3.2 | 3.2 |
| FLT3 | 1 | 2.5 |
| FLT3 (D835H) | 2.2 | 2 |
| FLT3 (D835V) | 5.3 | 7.7 |
| FLT3 (D835Y) | 23 | 27 |
| FLT3 (ITD) | 1.6 | 1.4 |
| FLT3 (ITD, D835V) | 61 | 76 |
| FLT3 (ITD, F691L) | 12 | 34 |
| FLT3 (K663Q) | 5.6 | 4.2 |
| FLT3 (N841I) | 0 | 0 |
| FLT3 (R834Q) | 1.5 | 2.1 |
| FLT3-autoinhibited | 56 | 58 |
| FLT4 | 0.05 | 0.3 |
| FRK | 3.9 | 3.2 |
| FYN | 4.1 | 3.7 |
| GAK | 99 | 93 |
| GCN2 (Kin.Dom.2, S808G) | 82 | 97 |
| GRK1 | 91 | 93 |
| GRK2 | 94 | 63 |
| GRK3 | 87 | 90 |
| GRK4 | 81 | 98 |

TABLE 3-continued

Ambit KINOMEscan at of compounds I-2 and I-6 at 1 μM as percent of control

| Kinase | I-2 | I-6 |
|---|---|---|
| GRK7 | 100 | 97 |
| GSK3A | 43 | 68 |
| GSK3B | 93 | 100 |
| HASPIN | 87 | 64 |
| HCK | 0 | 0.05 |
| HIPK1 | 62 | 96 |
| HIPK2 | 93 | 94 |
| HIPK3 | 56 | 98 |
| HIPK4 | 32 | 55 |
| HPK1 | 0.1 | 0.75 |
| HUNK | 80 | 96 |
| ICK | 50 | 68 |
| IGF1R | 0.7 | 11 |
| IKK-alpha | 53 | 63 |
| IKK-beta | 50 | 80 |
| IKK-epsilon | 80 | 87 |
| INSR | 0.85 | 3.2 |
| INSRR | 0.55 | 3.8 |
| IRAK1 | 18 | 29 |
| IRAK3 | 90 | 93 |
| IRAK4 | 26 | 33 |
| ITK | 1.4 | 5.8 |
| JAK1 (JH1domain-catalytic) | 19 | 20 |
| JAK1 (JH2domainpseudokinase) | 100 | 72 |
| JAK2(JH1domain-catalytic | 7.9 | 6.5 |
| JAK3(JH1domain-catalyti) | 0 | 0 |
| JNK1 | 96 | 96 |
| JNK2 | 46 | 27 |
| JNK3 | 85 | 93 |
| KIT | 0 | 0 |
| KIT(A829P) | 0 | 12 |
| KIT(D816H) | 38 | 29 |
| KIT(D816V) | 32 | 22 |
| KIT(L576P) | 0 | 1.8 |
| KIT(V559D) | 0 | 0.05 |
| KIT(V559D, T670I) | 6.6 | 5.5 |
| KIT(V559D, V654A) | 6.1 | 7.4 |
| KIT-autoinhibited | 79 | 85 |
| LATS1 | 87 | 85 |
| LATS2 | 79 | 85 |
| LCK | 0 | 0.1 |
| LIMK1 | 87 | 96 |
| LIMK2 | 96 | 100 |
| LKB1 | 73 | 100 |
| LOK | 0 | 0 |
| LRRK2 | 100 | 87 |
| LRRK2(G2019S) | 84 | 100 |
| LTK | 3.3 | 2 |
| LYN | 0.55 | 0.6 |
| LZK | 48 | 100 |
| MAK | 11 | 22 |
| MAP3K1 | 97 | 94 |
| MAP3K15 | 55 | 95 |
| MAP3K2 | 28 | 78 |
| MAP3K3 | 48 | 56 |
| MAP3K4 | 89 | 81 |
| MAP4K2 | 0.05 | 0.2 |
| MAP4K3 | 3.4 | 19 |
| MAP4K4 | 0.15 | 0.75 |
| MAP4K5 | 0.7 | 3.2 |
| MAPKAPK2 | 72 | 96 |
| MAPKAPK5 | 72 | 100 |
| MARK1 | 91 | 77 |
| MARK2 | 96 | 78 |
| MARK3 | 94 | 95 |
| MARK4 | 84 | 80 |
| MAST1 | 94 | 95 |
| MEK1 | 92 | 94 |
| MEK2 | 95 | 95 |
| MEK3 | 71 | 87 |
| MEK4 | 98 | 71 |

TABLE 3-continued

Ambit KINOMEscan at of compounds I-2 and I-6 at 1 μM as percent of control

| Kinase | I-2 | I-6 |
|---|---|---|
| MEK5 | 21 | 17 |
| MEK6 | 94 | 95 |
| MELK | 95 | 100 |
| MERTK | 0.25 | 0.25 |
| MET | 9.7 | 14 |
| MET(M1250T) | 9.9 | 42 |
| MET(Y1235D) | 8.7 | 8.9 |
| MINK | 0.6 | 2.4 |
| MKK7 | 84 | 100 |
| MKNK1 | 76 | 91 |
| MKNK2 | 87 | 82 |
| MLCK | 93 | 85 |
| MLK1 | 75 | 94 |
| MLK2 | 72 | 62 |
| MLK3 | 76 | 82 |
| MRCKA | 91 | 100 |
| MRCKB | 100 | 100 |
| MST1 | 30 | 60 |
| MST1R | 83 | 100 |
| MST2 | 50 | 97 |
| MST3 | 85 | 92 |
| MST4 | 92 | 100 |
| MTOR | 78 | 91 |
| MUSK | 0.6 | 2.1 |
| MYLK | 65 | 79 |
| MYLK2 | 92 | 83 |
| MYLK4 | 96 | 100 |
| MYO3A | 85 | 66 |
| MYO3B | 80 | 49 |
| NDR1 | 100 | 85 |
| NDR2 | 98 | 59 |
| NEK1 | 95 | 97 |
| NEK10 | 75 | 62 |
| NEK11 | 65 | 89 |
| NEK2 | 84 | 100 |
| NEK3 | 100 | 96 |
| NEK4 | 28 | 15 |
| NEK5 | 89 | 100 |
| NEK6 | 100 | 100 |
| NEK7 | 99 | 91 |
| NEK9 | 100 | 92 |
| NIK | 100 | 72 |
| NIM1 | 99 | 88 |
| NLK | 95 | 100 |
| OSR1 | 99 | 100 |
| p38-alpha | 8.4 | 26 |
| p38-beta | 60 | 62 |
| p38-delta | 41 | 32 |
| p38-gamma | 0 | 9.4 |
| PAK1 | 81 | 78 |
| PAK2 | 93 | 70 |
| PAK3 | 82 | 66 |
| PAK4 | 96 | 96 |
| PAK6 | 95 | 97 |
| PAK7 | 73 | 98 |
| PCTK1 | 16 | 28 |
| PCTK2 | 1.8 | 1.3 |
| PCTK3 | 4.8 | 27 |
| PDGFRA | 1.1 | 1.2 |
| PDGFRB | 0 | 0 |
| PDPK1 | 89 | 83 |
| PFCDPK1(P.falciparum) | 84 | 88 |
| PFPK5(P.falciparum) | 91 | 77 |
| PFTAIRE2 | 0.9 | 3.6 |
| PFTK1 | 0.35 | 2.4 |
| PHKG1 | 99 | 93 |
| PHKG2 | 93 | 98 |
| PIK3C2B | 100 | 100 |
| PIK3C2G | 92 | 95 |
| PIK3CA | 78 | 96 |
| PIK3CA(C420R) | 85 | 95 |
| PIK3CA(E542K) | 96 | 100 |
| PIK3CA(E545A) | 91 | 100 |
| PIK3CA(E545K) | 99 | 93 |
| PIK3CA(H1047L) | 89 | 68 |

TABLE 3-continued

Ambit KINOMEscan at of compounds I-2 and I-6 at 1 μM as percent of control

| Kinase | I-2 | I-6 |
|---|---|---|
| PIK3CA(H1047Y) | 82 | 92 |
| PIK3CA(I800L) | 100 | 91 |
| PIK3CA(M1043I) | 100 | 73 |
| PIK3CA(Q546K) | 76 | 94 |
| PIK3CB | 100 | 94 |
| PIK3CD | 100 | 69 |
| PIK3CG | 99 | 92 |
| PIK4CB | 97 | 96 |
| PIKFYVE | 93 | 100 |
| PIM1 | 90 | 93 |
| PIM2 | 96 | 97 |
| PIM3 | 90 | 89 |
| PIP5K1A | 100 | 100 |
| PIP5K1C | 85 | 94 |
| PIP5K2B | 93 | 86 |
| PIP5K2C | 5.7 | 46 |
| PKAC-alpha | 75 | 97 |
| PKAC-beta | 92 | 78 |
| PKMYT1 | 100 | 100 |
| PKN1 | 98 | 98 |
| PKN2 | 77 | 100 |
| PKNB (M.tuberculosis) | 78 | 91 |
| PLK1 | 98 | 100 |
| PLK2 | 90 | 96 |
| PLK3 | 100 | 100 |
| PLK4 | 81 | 95 |
| PRKCD | 40 | 48 |
| PRKCE | 86 | 83 |
| PRKCH | 86 | 100 |
| PRKCI | 66 | 100 |
| PRKCQ | 27 | 74 |
| PRKD1 | 93 | 87 |
| PRKD2 | 97 | 100 |
| PRKD3 | 100 | 90 |
| PRKG1 | 100 | 87 |
| PRKG2 | 100 | 99 |
| PRKR | 97 | 95 |
| PRKX | 100 | 100 |
| PRP4 | 87 | 100 |
| PYK2 | 3.2 | 4.1 |
| QSK | 92 | 83 |
| RAF1 | 13 | 18 |
| RET | 0 | 0 |
| RET (M918T) | 0.05 | 0 |
| RET (V804L) | 0.15 | 0 |
| RET (V804M) | 0.05 | 0 |
| RIOK1 | 100 | 95 |
| RIOK2 | 100 | 94 |
| RIOK3 | 100 | 90 |
| RIPK1 | 0.45 | 0.75 |
| RIPK2 | 89 | 35 |
| RIPK4 | 98 | 100 |
| RIPK5 | 89 | 100 |
| ROCK1 | 86 | 100 |
| ROCK2 | 82 | 94 |
| ROS1 | 52 | 59 |
| RPS6KA1 (Kin.Dom.1-Nterminal) | N/A | N/A |
| RPS6KA1 (Kin.Dom.2-C-terminal) | N/A | N/A |
| RPS6KA2 (Kin.Dom.1-N-terminal) | N/A | N/A |
| RPS6KA2 (Kin.Dom.2-C-terminal) | N/A | N/A |
| RPS6KA3 (Kin.Dom.1-N-terminal) | N/A | N/A |
| RPS6KA4 (Kin.Dom.1-N-terminal) | 50 | 66 |
| RPS6KA4 (Kin.Dom.2-C-terminal) | 79 | 100 |
| RPS6KA5 (Kin.Dom.1-N-terminal) | 73 | 66 |
| RPS6KA5 (Kin.Dom.2-C-terminal) | 100 | 98 |

TABLE 3-continued

| Ambit KINOMEscan at of compounds I-2 and I-6 at 1 μM as percent of control | | |
|---|---|---|
| Kinase | I-2 | I-6 |
| RPS6KA6 (Kin.Dom.1-N-terminal) | N/A | N/A |
| RPS6KA6 (Kin.Dom.2-C-terminal) | N/A | N/A |
| RSK1 (Kin.Dom.1-N-terminal) | 97 | 100 |
| RSK1 (Kin.Dom.2-C-terminal) | 100 | 96 |
| RSK2 (Kin.Dom.1-N-terminal) | 88 | 78 |
| RSK2 (Kin.Dom.2-C-terminal) | 78 | 100 |
| RSK3 (Kin.Dom.1-N-terminal) | 100 | 95 |
| RSK3 (Kin.Dom.2-C-terminal) | 98 | 89 |
| RSK4 (Kin.Dom.1-N-terminal) | 93 | 87 |
| RSK4 (Kin.Dom.2-C-terminal) | 94 | 77 |
| S6K1 | 52 | 49 |
| SBK1 | 99 | 97 |
| SGK | 83 | 92 |
| SgK110 | 75 | 57 |
| SGK2 | 87 | 76 |
| SGK3 | 100 | 100 |
| SIK | 100 | 100 |
| SIK2 | 100 | 100 |
| SLK | 1.6 | 2.4 |
| SNARK | 100 | 100 |
| SNRK | 84 | 99 |
| SRC | 0 | 0 |
| SRMS | 86 | 79 |
| SRPK1 | 85 | 57 |
| SRPK2 | 73 | 100 |
| SRPK3 | 92 | 83 |
| STK16 | 90 | 95 |
| STK33 | 70 | 100 |
| STK35 | 69 | 59 |
| STK36 | 66 | 100 |
| STK39 | 74 | 93 |
| SYK | 1.9 | 0.65 |
| TAK1 | 1.1 | 2.7 |
| TAOK1 | 3.9 | 4.5 |
| TAOK2 | 8.6 | 7.6 |
| TAOK3 | 0.2 | 0.9 |
| TBK1 | 75 | 96 |
| TEC | 100 | 100 |
| TESK1 | 100 | 97 |
| TGFBR1 | 94 | 100 |
| TGFBR2 | 90 | 86 |
| TIE1 | 0 | 4 |
| TIE2 | 0.1 | 0.25 |
| TLK1 | 100 | 97 |
| TLK2 | 100 | 98 |
| TNIK | 16 | 14 |
| TNK1 | 63 | 31 |
| TNK2 | 100 | 99 |
| TNNI3K | 56 | 36 |
| TRKA | 0.75 | 0 |
| TRKB | 0.05 | 0 |
| TRKC | 0.05 | 0.05 |
| TRPM6 | 93 | 78 |
| TSSK1B | 96 | 76 |
| TSSK3 | 100 | 91 |
| TTK | 83 | 83 |
| TXK | 16 | 19 |
| TYK2(JH1domain-catalytic) | 54 | 41 |
| TYK2(JH2domainpseudokia | 80 | 95 |
| TYR | 26 | 47 |
| ULK | 89 | 100 |
| ULK2 | 100 | 100 |
| ULK3 | 97 | 100 |
| VEGFR2 | 1.4 | 2 |
| VPS34 | 91 | 93 |
| VRK2 | 88 | 92 |
| WEE1 | 94 | 100 |
| WEE2 | 100 | 95 |
| WNK1 | 100 | 100 |
| WNK2 | 72 | 57 |
| WNK3 | 92 | 83 |
| WNK4 | 75 | 100 |
| YANK1 | 93 | 93 |
| YANK2 | 91 | 100 |
| YANK3 | 91 | 100 |
| YES | 4.7 | 1.6 |
| YSK1 | 61 | 100 |
| YSK4 | 30 | 29 |
| ZAK | 2.3 | 6.2 |
| ZAP70 | 66 | 30 |

EQUIVALENTS AND SCOPE

In the claims articles such as “a,” “an,” and “the” may mean one or more than one unless indicated to the contrary or otherwise evident from the context. Claims or descriptions that include “or” between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms “comprising” and “containing” are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I'):

(I')

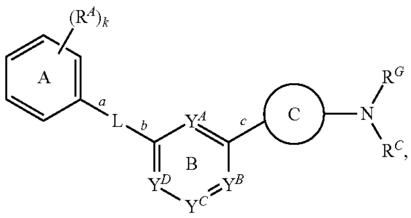

or a pharmaceutically acceptable salt, solvate, hydrate, polymorph, co-crystal, tautomer, or stereoisomer thereof, wherein:

each instance of $R^A$ is independently halogen or substituted or unsubstituted alkyl;

each instance of $R^1$ is independently hydrogen or substituted or unsubstituted alkyl;

k is 0, 1, or 2;

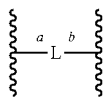

is

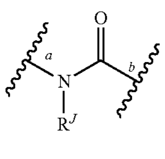 or 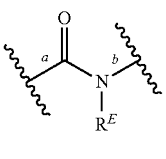;

$R^E$ is hydrogen;

$R^J$ is hydrogen;

$Y^A$ is N or $CR^B$;

$Y^B$ is N or $CR^B$;

$Y^C$ is N or $CR^B$;

$Y^D$ is N or $CR^B$; provided that no more than one of $Y^A$, $Y^B$, $Y^C$, and $Y^D$ is N;

each instance of RB is independently hydrogen, halogen, substituted or unsubstituted alkyl, —$OR^1$, or —CN;

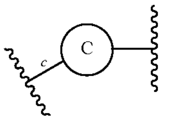

is

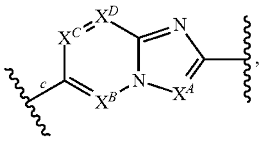, 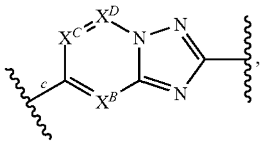,

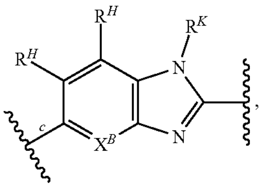, or 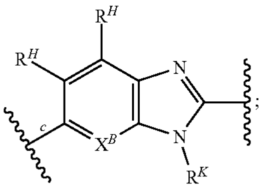;

$X^A$ is N or $CR^H$, $X^B$ is N or $CR^H$, $X^C$ is N or $CR^H$;

$X^D$ is N or $CR^H$; provided that no more than one of $X^A$, $X^B$, $X^C$ and $X^D$ is N;

each instance of $R^H$ is independently hydrogen;

$R^K$ is hydrogen or substituted or unsubstituted alkyl;

$R^C$ is hydrogen;

$R^G$ is

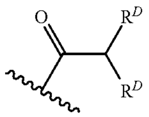

or hydrogen; and each instance of $R^D$ is independently substituted or unsubstituted carbocyclyl;

or two instances of $R^D$ are joined together to form a substituted or unsubstituted; carbocyclic ring;

provided that the compound is not of the formula:

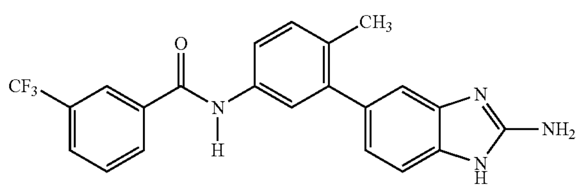 [SMILES: Cc1ccc(NC(=O)c2cccc(C(F)(F)F)c2)cc1-c1ccc2[nH]c(N)nc2c1]

2. The compound of claim 1, wherein the compound is of Formula (I):

(I)

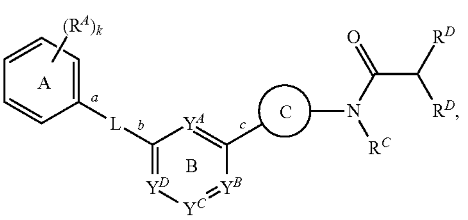

or a pharmaceutically acceptable salt, solvate, hydrate, polymorph, co-crystal, tautomer, or stereoisomer thereof, wherein:

each instance of $R^A$ is independently halogen or substituted or unsubstituted alkyl;

each instance of $R^1$ is independently hydrogen or substituted or unsubstituted alkyl;

k is 0, 1, or 2;

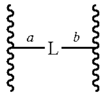

is

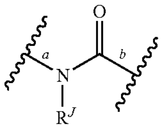

or

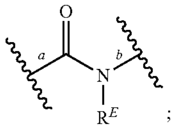

;

$R^E$ is hydrogen;

$R^J$ is hydrogen;

$Y^A$ is N or $CR^B$;

$Y^B$ is N or $CR^B$;

$Y^C$ is N or $CR^B$;

$Y^D$ is N or $CR^B$; provided that no more than one of $Y^A$, $Y^B$, $Y^C$, and $Y^D$ is N;

each instance of RB is independently hydrogen, halogen, substituted or unsubstituted alkyl, —$OR^1$, or —CN;

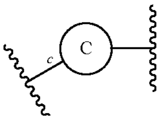

is

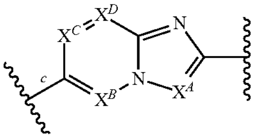

or

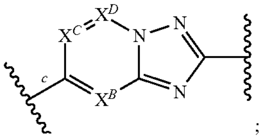

;

$X^A$ is N or $CR^H$;

$X^B$ is N or $CR^H$;

$X^C$ is N or $CR^H$;

$X^D$ is N or $CR^H$; provided that no more than one of $X^A$, $X^B$, $X^C$ and $X^D$ is N;

each instance of $R^H$ is independently hydrogen;

$R^C$ is hydrogen; and each instance of $R^D$ is independently substituted or unsubstituted carbocyclyl;

or two instances of $R^D$ are joined together to form a substituted or unsubstituted, carbocyclic ring.

3. The compound of claim 1, or a pharmaceutically acceptable salt, solvate, hydrate, tautomer, or stereoisomer thereof, wherein

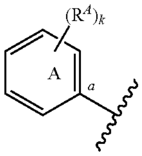

is

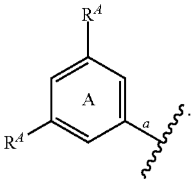

.

4. The compound of claim 1, or a pharmaceutically acceptable salt, solvate, hydrate, tautomer, or stereoisomer thereof, wherein one instance of $R^A$ is—(substituted or unsubstituted alkylene) (substituted or unsubstituted heterocyclyl).

5. The compound of claim 3, or a pharmaceutically acceptable salt, solvate, hydrate, tautomer, or stereoisomer thereof, wherein one instance of $R^A$ is—(substituted or unsubstituted, $C_{1-3}$ alkylene)-(substituted or unsubstituted piperazinyl) and the other instance of $R^A$ is —$CF_3$.

6. The compound of claim 1, or a pharmaceutically acceptable salt, solvate, hydrate, tautomer, or stereoisomer thereof, wherein k is 2.

7. The compound of claim 1, or a pharmaceutically acceptable salt, solvate, hydrate, tautomer, or stereoisomer thereof, wherein

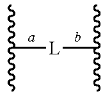

is

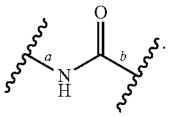 [SMILES: *NC(*)=O]

.

8. The compound of claim 1, or a pharmaceutically acceptable salt, solvate, hydrate, tautomer, or stereoisomer thereof, wherein

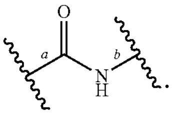 [SMILES: *NC(*)=O]

is

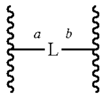

9. The compound of claim 1, or a pharmaceutically acceptable salt, solvate, hydrate, tautomer, or stereoisomer thereof, wherein

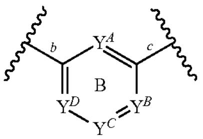

is

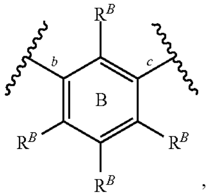

,

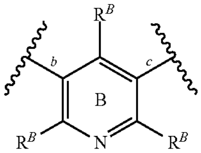

, or

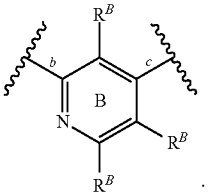

.

10. The compound of claim 1, or a pharmaceutically acceptable salt, solvate, hydrate, tautomer, or stereoisomer thereof, wherein at least one instance of $R^B$ is halogen, substituted or unsubstituted alkyl, or —$OR^1$.

11. The compound of claim 1, or a pharmaceutically acceptable salt, solvate, hydrate, tautomer, or stereoisomer thereof, wherein at least one instance of $R^B$ is substituted or unsubstituted methyl.

12. The compound of claim 1, or a pharmaceutically acceptable salt, solvate, hydrate, tautomer, or stereoisomer thereof, wherein

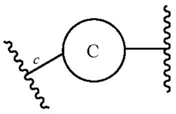

is

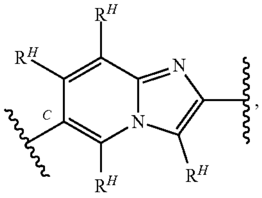

,

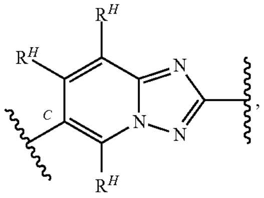

,

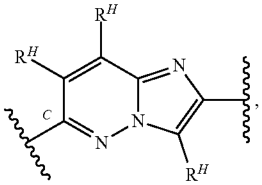

,

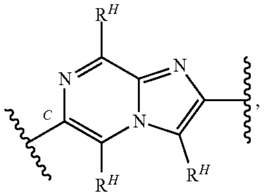

,

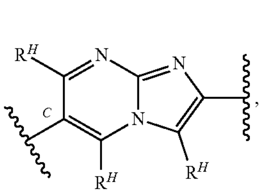

,

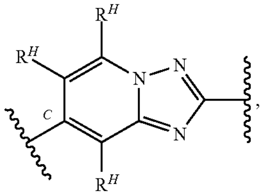

,

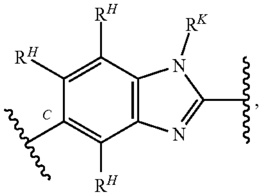

,

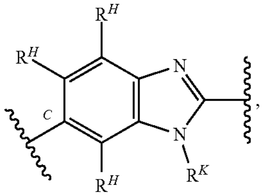

,

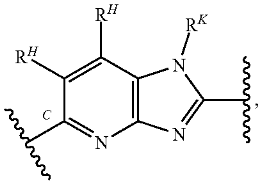

, or

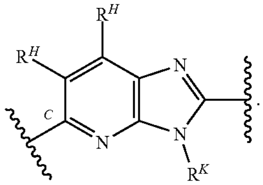

.

13. The compound of claim 1, or a pharmaceutically acceptable salt, solvate, hydrate, tautomer, or stereoisomer thereof, wherein $R^K$ is hydrogen or substituted or unsubstituted $C_{1-6}$ alkyl.

14. The compound of claim 1, or a pharmaceutically acceptable salt, solvate, hydrate, tautomer, or stereoisomer thereof, wherein two instances of $R^D$ are joined to form a substituted or unsubstituted carbocyclic ring.

15. The compound of claim 2, or a pharmaceutically acceptable salt, solvate, hydrate, tautomer, or stereoisomer thereof, wherein the compound is of the formula:

(I-1)

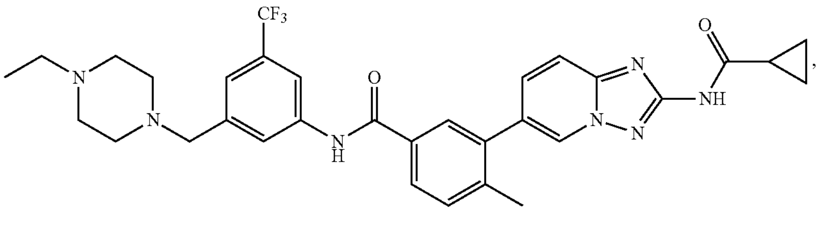

,

-continued
(I-2)
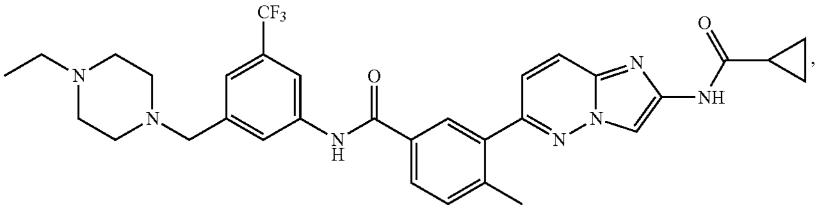
(I-3)
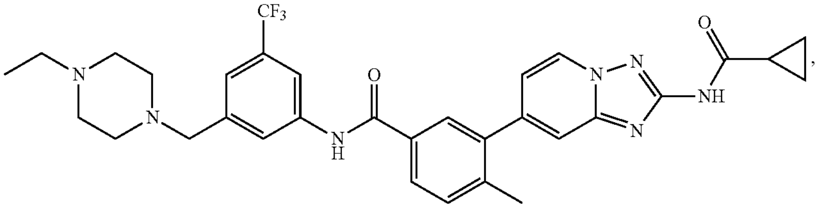
(I-4)
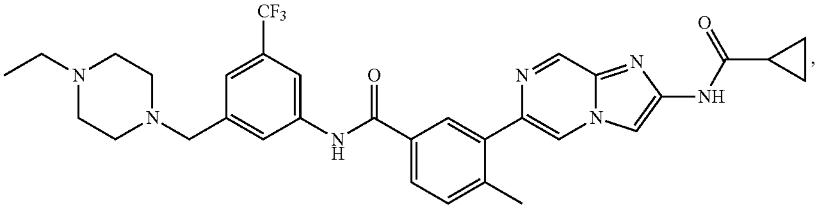
(I-5)
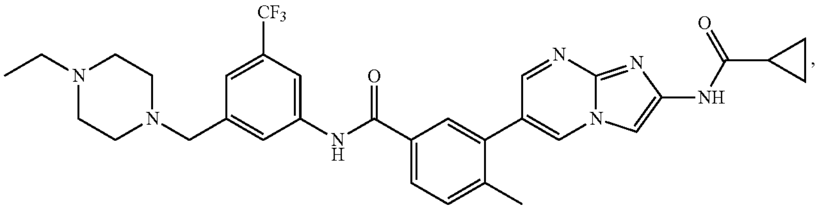
(I-6)
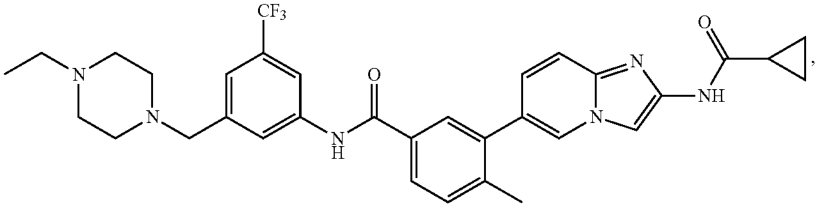
(I-7)
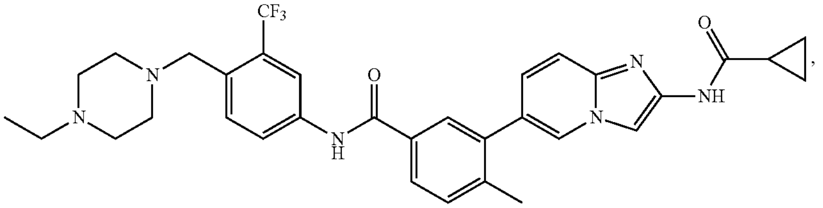
(I-8)
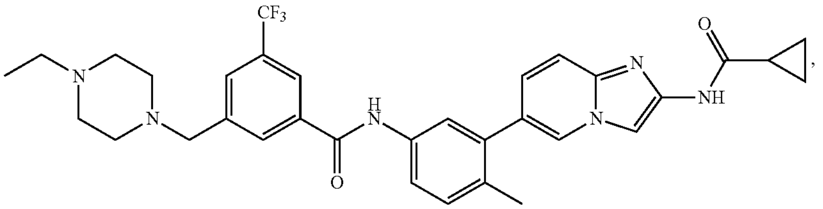

-continued
(I-9)
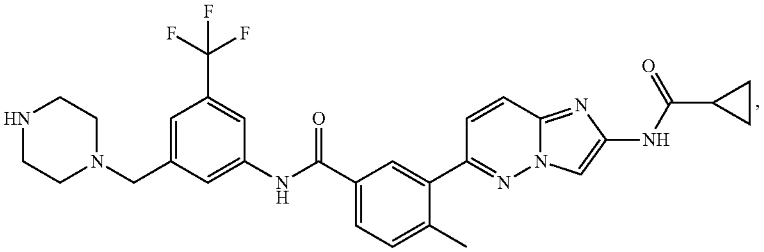
(I-10)
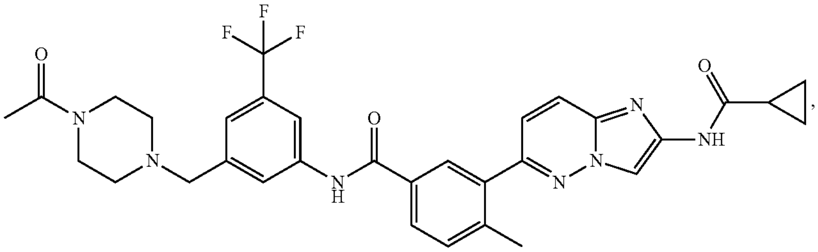
(I-11)
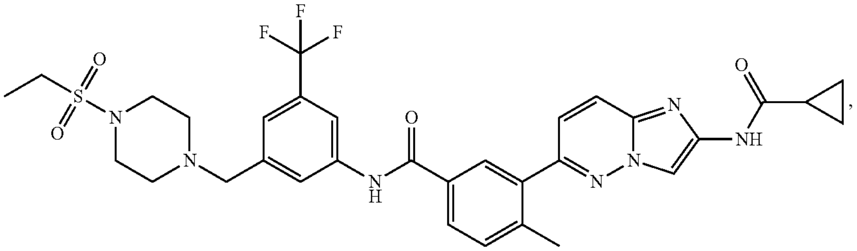
(I-12)
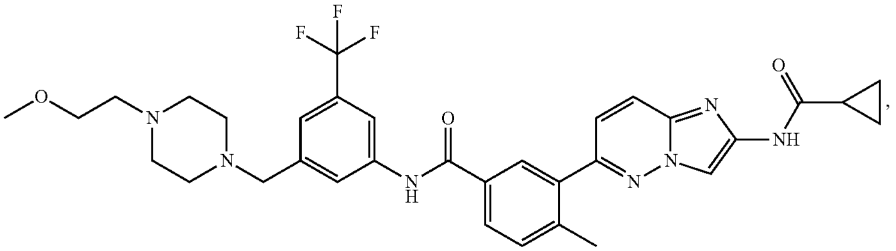
(I-13)
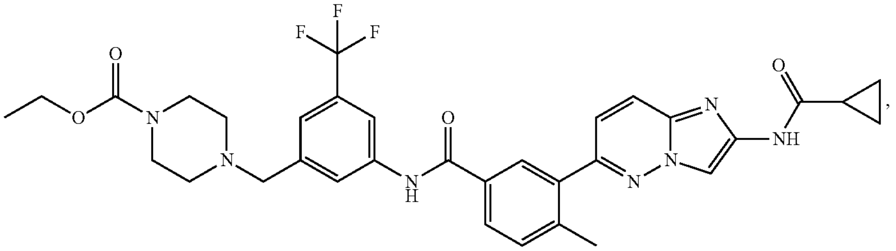
(I-14)
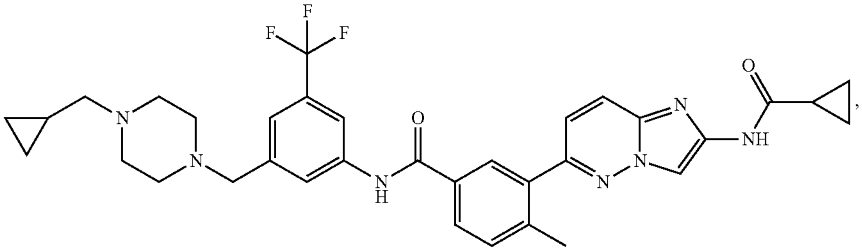

-continued
(I-15)
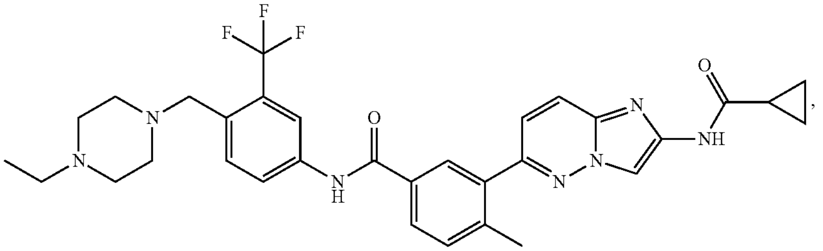
(I-17)
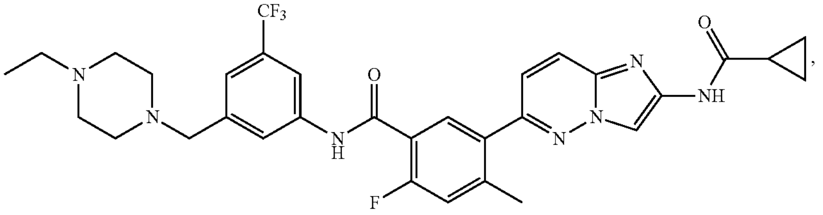
(I-19)
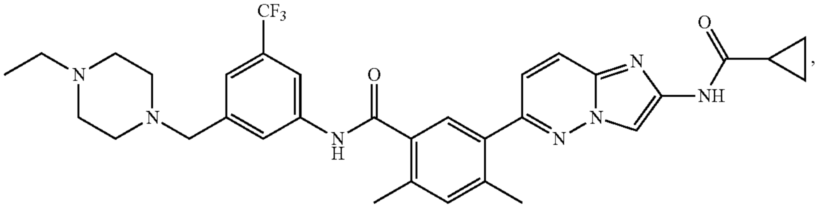
(I-20)
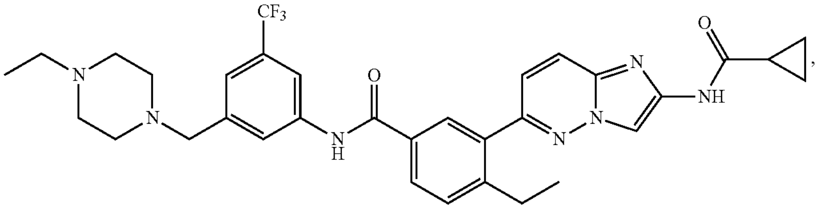
(I-22)
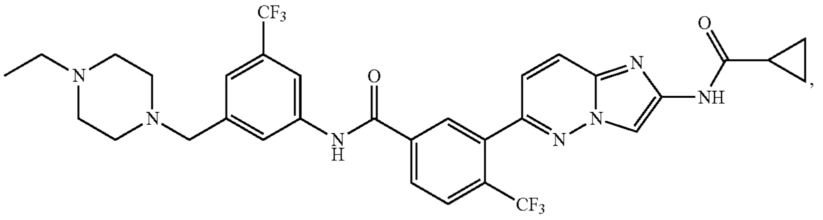
(I-23)
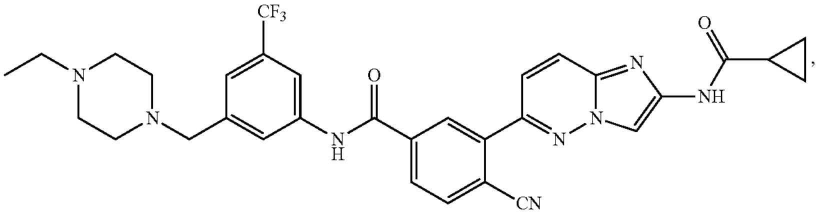
(I-16)
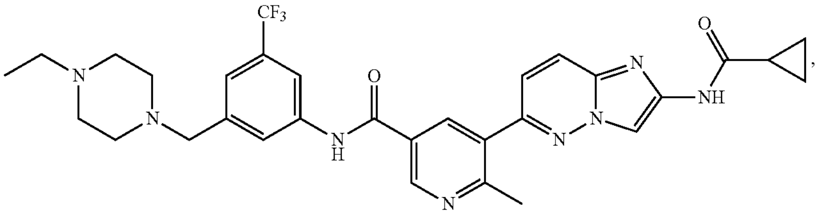

-continued
(I-18)
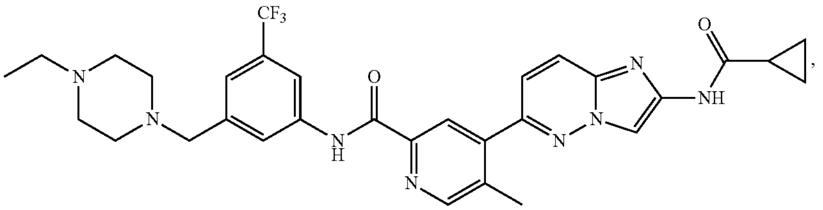
(I-21)
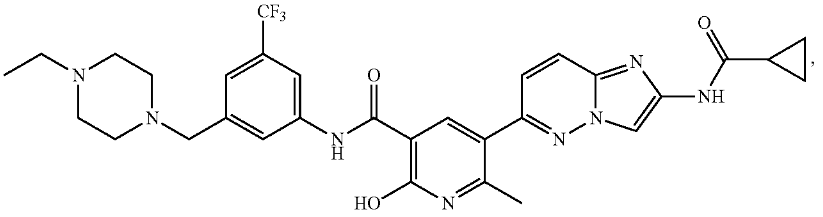
(I-24)
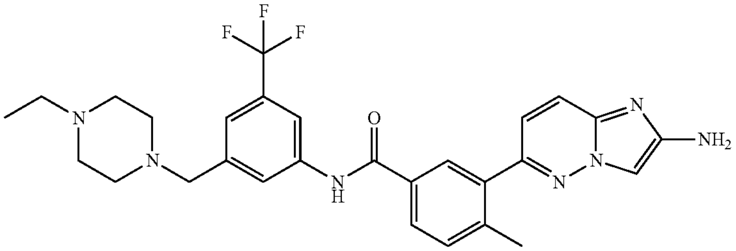
(I-25)
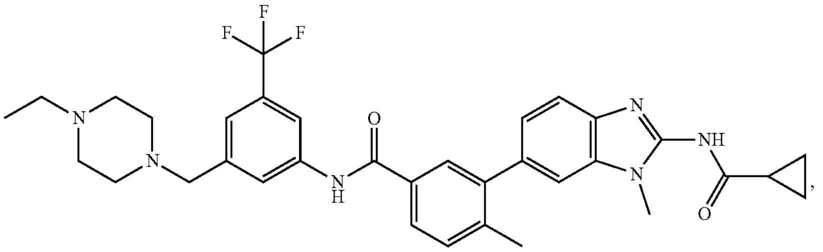
(I-26)
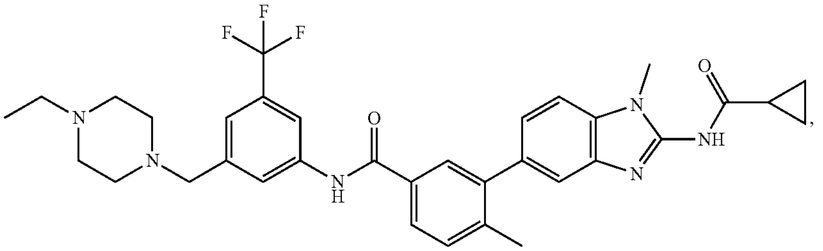
or
(I-27)
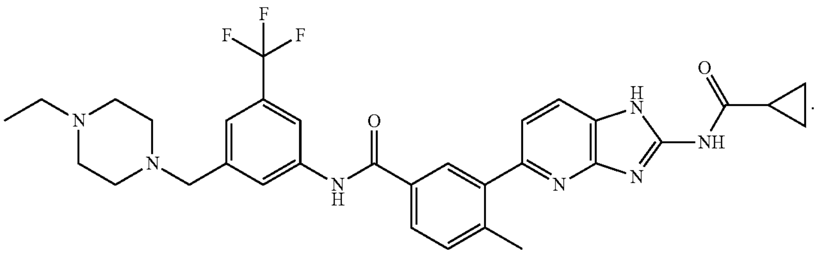

16. The compound of claim 1, or a pharmaceutically acceptable salt thereof.

17. A pharmaceutical composition comprising:

a compound of claim 1, or a pharmaceutically acceptable salt, solvate, hydrate, tautomer, or stereoisomer thereof; and a pharmaceutically acceptable excipient.

18. A kit comprising:

a compound of claim 1, or a pharmaceutically acceptable salt, solvate, hydrate, tautomer, or stereoisomer thereof, or a pharmaceutical composition thereof further comprising a pharmaceutically acceptable excipient; and instructions for using the compound, or a pharmaceutically acceptable salt, solvate, hydrate, tautomer, or stereoisomer thereof, or the pharmaceutical composition.

* * * * *